US011753639B2

(12) United States Patent
Pandolfi et al.

(10) Patent No.: US 11,753,639 B2
(45) Date of Patent: Sep. 12, 2023

(54) MICRO-RNA AND OBESITY

(71) Applicant: Beth Israel Deaconess Medical Center, Boston, MA (US)

(72) Inventors: Pier Paolo Pandolfi, Boston, MA (US); Riccardo Panella, Boston, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 284 days.

(21) Appl. No.: 16/979,777

(22) PCT Filed: Mar. 14, 2019

(86) PCT No.: PCT/US2019/022350

§ 371 (c)(1),
(2) Date: Sep. 10, 2020

(87) PCT Pub. No.: WO2019/178410

PCT Pub. Date: Sep. 19, 2019

(65) Prior Publication Data

US 2021/0017520 A1 Jan. 21, 2021

Related U.S. Application Data

(60) Provisional application No. 62/642,934, filed on Mar. 14, 2018.

(51) Int. Cl.
*C12N 15/113* (2010.01)
*A61K 31/713* (2006.01)

(52) U.S. Cl.
CPC .......... *C12N 15/113* (2013.01); *A61K 31/713* (2013.01); *C12N 2310/11* (2013.01); *C12N 2310/113* (2013.01); *C12N 2310/14* (2013.01); *C12N 2310/141* (2013.01); *C12N 2310/3231* (2013.01); *C12N 2310/344* (2013.01); *C12N 2320/50* (2013.01)

(58) Field of Classification Search
None
See application file for complete search history.

(56) References Cited

U.S. PATENT DOCUMENTS 9,453,224 B2 9/2016 Thibonnier
9,803,203 B2 10/2017 Thibonnier
9,822,358 B2 11/2017 Pandolfi et al.
10,131,905 B2 11/2018 Pandolfi et al.
10,253,319 B2 4/2019 Thibonnier
2010/0004320 A1 1/2010 Elmen et al.
2012/0148664 A1 6/2012 Dalby et al.
2014/0314833 A1 10/2014 Brown et al.
2018/0073025 A1 3/2018 Pandolfi et al.
2019/0127736 A1* 5/2019 Thibonnier ............ A61K 47/14
2021/0163929 A1* 6/2021 Wan ....................... A61K 47/46

FOREIGN PATENT DOCUMENTS

WO WO 2012/080459 A1 6/2012
WO WO 2017/187426 A1 11/2017
WO WO-2019053235 A1 * 3/2019
WO WO 2019/178411 A1 9/2019

OTHER PUBLICATIONS

Nassir et al. Gastroenterology & Hepatology vol. 11, pp. 167-175 (Year: 2015).*
Iliopoulos, et al., "Integrative MicroRNA and Proteomic Approaches Identify Novel Osteoarthritis Genes and Their Collaborative Metabolic and Inflammatory Networks," PLOS One, vol. vol. 3, No. 11, 10 pages, Nov. 2008.
Perri, et al., "MicroRNA Modulation in Obesity and Periodontitis," J Dent Res, vol. 91, No. 1, pp. 33-38, 2012.
International Search Report & Written Opinion, PCT Application No. PCT/US19/22350, dated Jun. 7, 2019, 11 pages.
Huang, "Preclinical and Clinical Advances of GalNAc-Decorated Nucleic Acid Therapeutics," Molecular Therapy-Nucleic Acids, vol. 16, pp. 116-132, Dec. 14, 2016.
PlaconÁ Diniz, et al., "Loss of microRNA-22 prevents high-fat diet induced dyslipidemia and increases energy expenditure without affecting cardiac hypertrophy," Clin. Sci (Lond), vol. 131, No. 24, pp. 2885-2900, Dec. 15, 2017.

* cited by examiner

*Primary Examiner* — Brian Whiteman
(74) *Attorney, Agent, or Firm* — Morgan, Lewis & Bockius LLP

(57) ABSTRACT

The present disclosure provides a method of treating or preventing metabolic disorders by administering agents that inhibit the activity of microRNAs that modulate metabolism.

18 Claims, 46 Drawing Sheets

Specification includes a Sequence Listing.

FIGURE 2 (Continued)
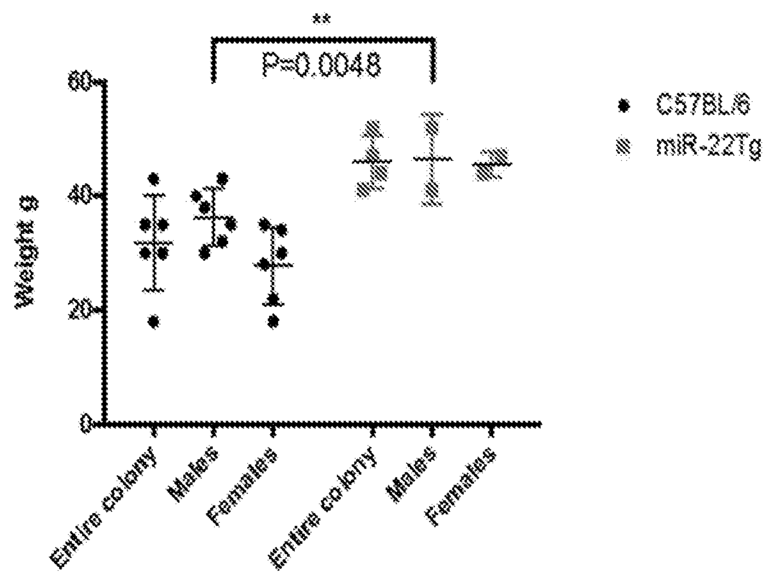
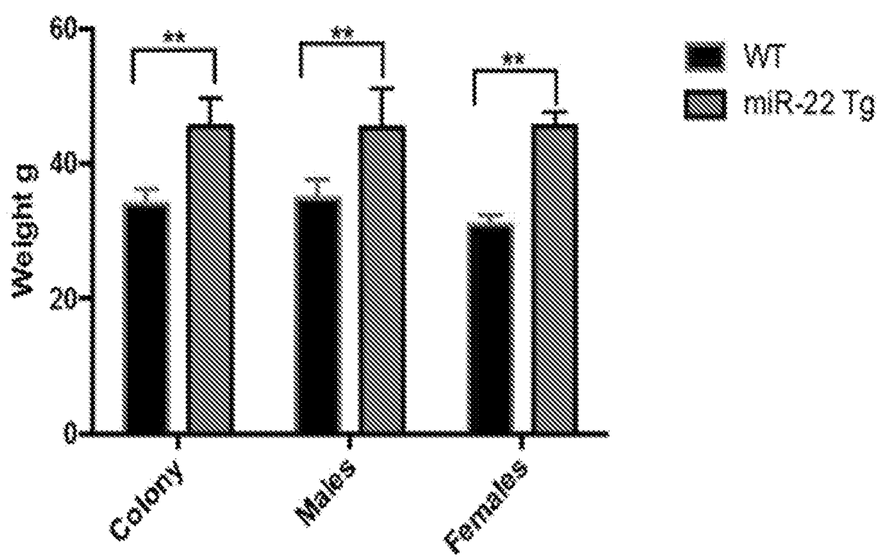

FIGURE 4
A
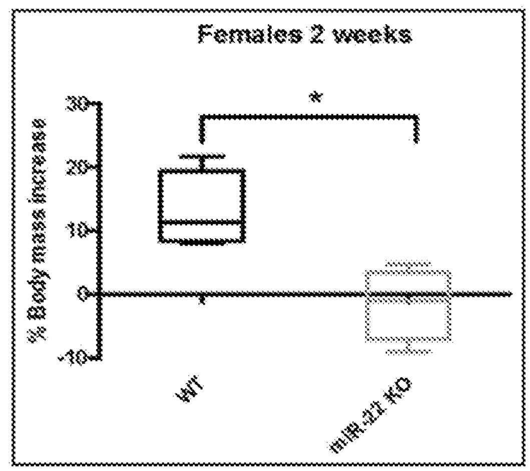
B
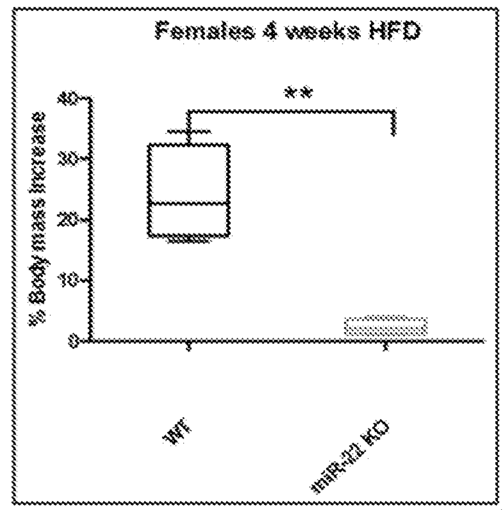
C
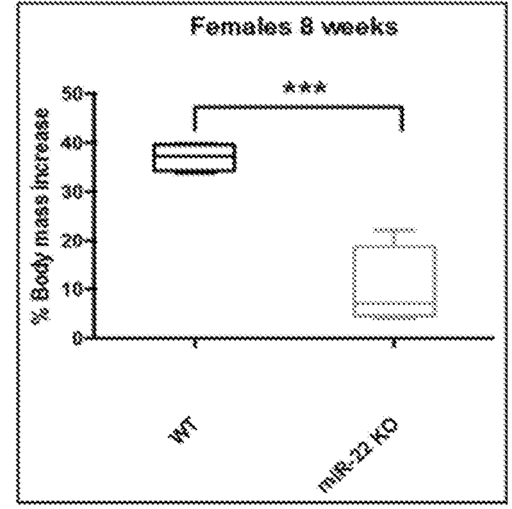

Oxygen Consumption(ml/kg/hr)

Day 0

VCO2 (ml/kg/hr) - measure of energy expenditure

Day 0

Respiratory Exchange Ratio ($VCO_2/VO_2$)

Day 0

Energy expenditure (kcal/hour)

Day 0

Locomotor Activity

Day 0

Food consumption (Kcal/4days)

Day 0

HFD 8 weeks

HFD
8 weeks

HFD
8 weeks

HFD
8 weeks

HFD
8 weeks

FIGURE 8

Design anti-miR-22 LNA

| | | | |
|---|---|---|---|
| hsa-miR-22 | 5' | AAGCUGCCAGUUGAAGAACUGU | 3' |
| CRM0008 | 3' | TCGACGGT | 5' |
| CRM0009 | | TCgAcGgtCAacTtC | |
| CRM0010 | | TCgACGgtCAacTTC | |
| CRM0011 | | TCgACGgtCaACTtCT | |
| CRM0012 | | TCgACGGtCaacTtCT | |
| CRM0013 | | TCgACGgTcaACTtCT | |
| CRM0014 | | TCgACGgTcaACTtcTT | |
| CRM0015 | | TCGaCGgtCaacTtctTG | |
| CRM0016 | | GCgATGatTgATAaGC | |
| CRM0017 | | GCgATGatTgATAaGC-FAM labelled | |

All anti-miR-22 oligos are designed with mix-mer strategy

Scramble

Capital Letter LNA
Lower case DNA

Food consumption mouse/week g of food/mice 20
15
10
5
0 ns
ns
ns

Vehicle
SCR
anti-miR-22

FIGURE 13B
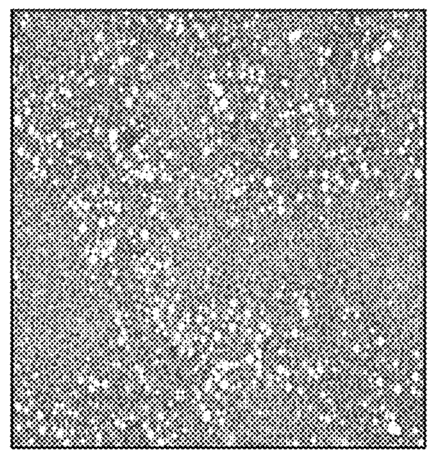
VHL treated
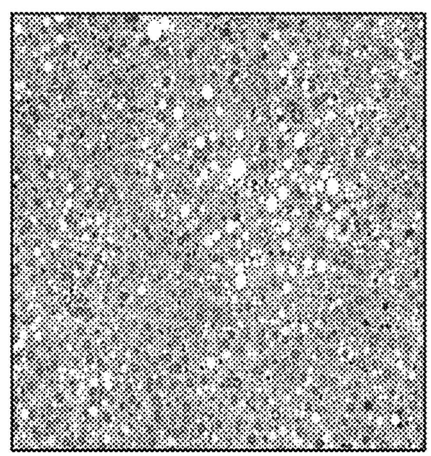
SCR treated
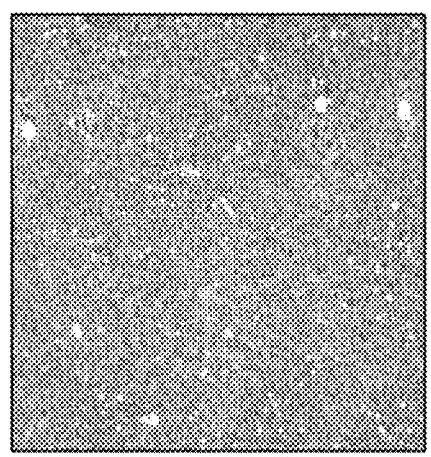
Anti-miR-22 treated LNAs are working FTO, CEBPα and PPARγ are downregulated LNAs are not working in BAT FTO, CEBPα and PPARγ are slightly downregulated CD36 and UCP1 are stable (CD36 and UCP1 are higly expressed in BAT

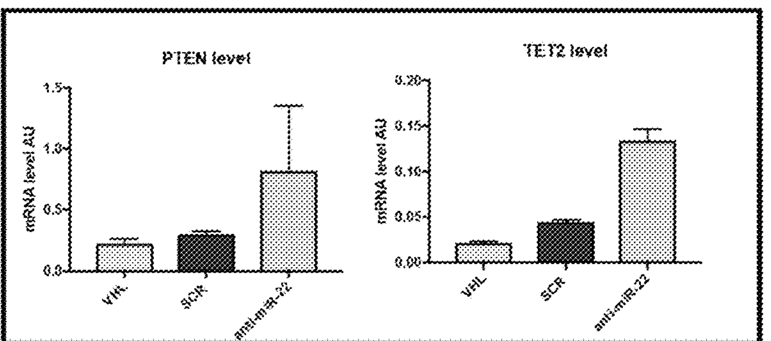
FIGURE 16A
LNAs are working
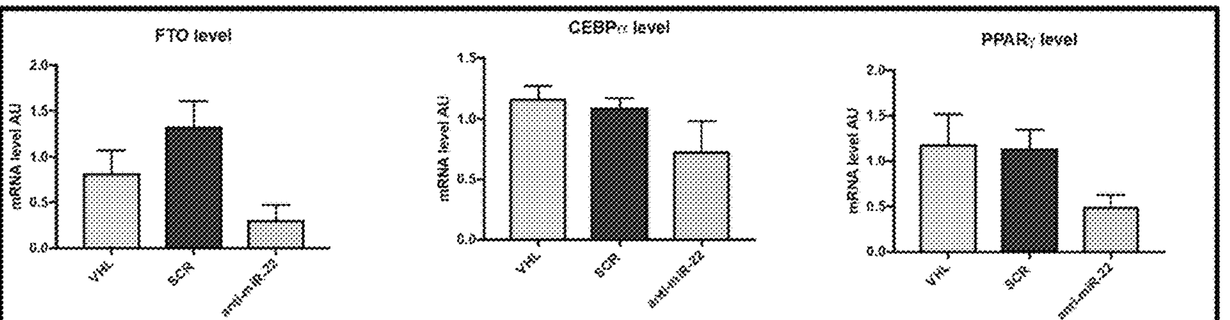
FIGURE 16B
FTO, CEBPα and PPARγ are downregulated
CD36 level
UCP1 level
CD36 and UCP1 are profoundly upregulated
FIGURE 16C

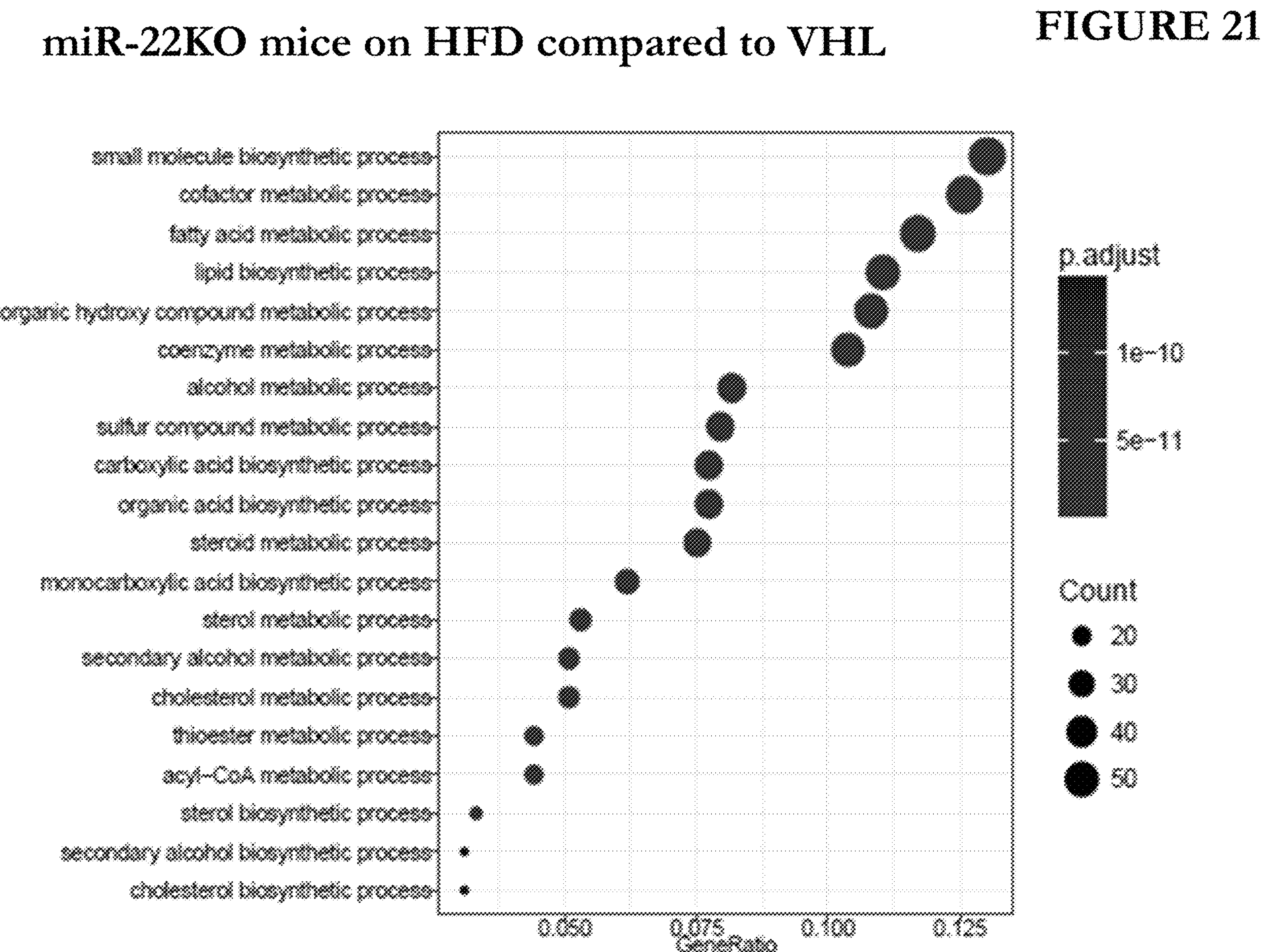
miR-22KO mice on HFD compared to VHL
FIGURE 21
small molecule biosynthetic process
cofactor metabolic process
fatty acid metabolic process
lipid biosynthetic process
organic hydroxy compound metabolic process
coenzyme metabolic process
alcohol metabolic process
sulfur compound metabolic process
carboxylic acid biosynthetic process
organic acid biosynthetic process
steroid metabolic process
monocarboxylic acid biosynthetic process
sterol metabolic process
secondary alcohol metabolic process
cholesterol metabolic process
thioester metabolic process
acyl−CoA metabolic process
sterol biosynthetic process
secondary alcohol biosynthetic process
cholesterol biosynthetic process
0.050
0.075
0.100
0.125
GeneRatio
p.adjust
1e−10
5e−11
Count
20
30
40
50

LNA anti miR-22 treated mice on HFD compared to VHL

A

LNA SCR

LNA #10

Oil-RedO staining

B

Human Mesenchymal Cells

Adipocite relative amount 1.2
1.0
0.8
0.6
0.4
0.2
0.0 ns

**

Normal media

Adipo Media

LNA#10

SCR

FIGURE 28A
RNA from Liver (n=7)
Colorimetric assay
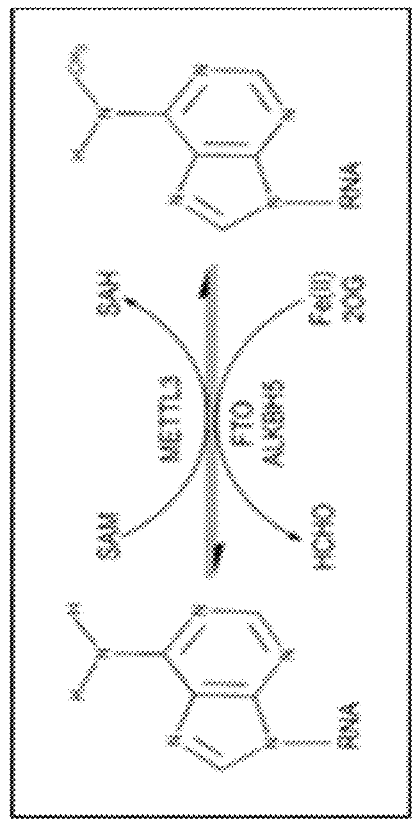
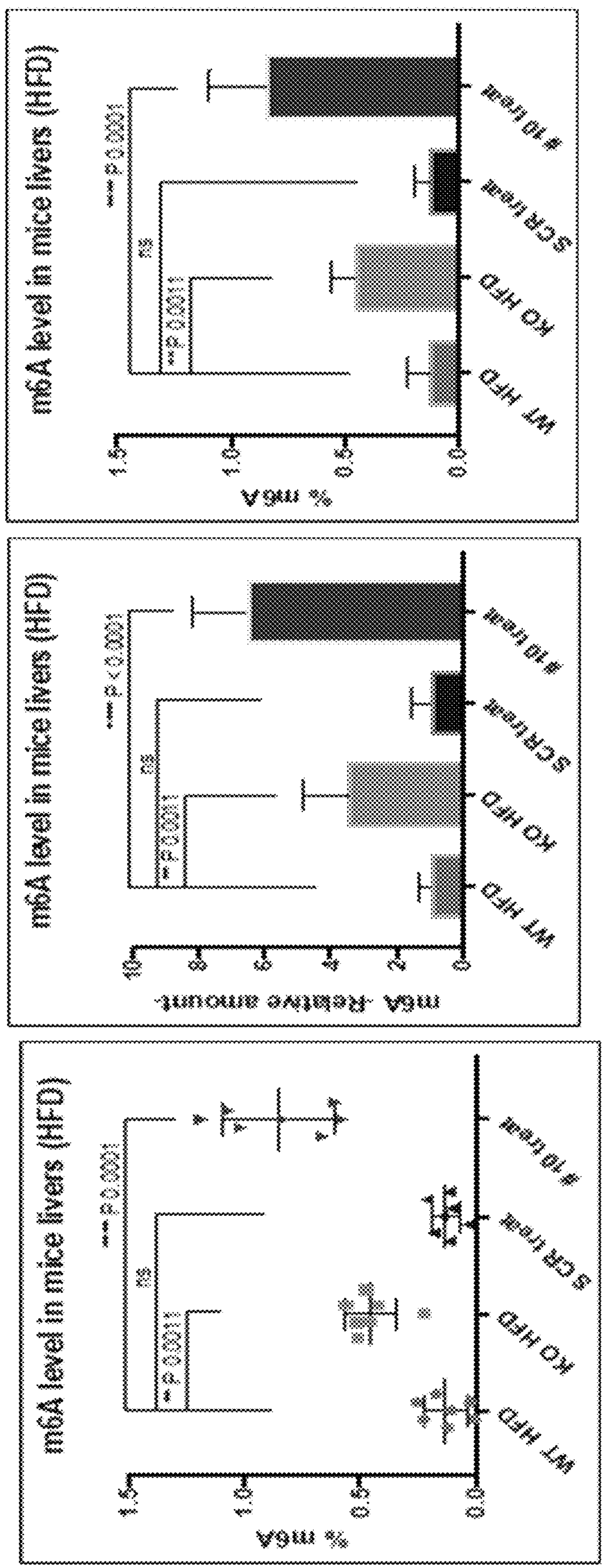
FIGURE 28B
FIGURE 28C
FIGURE 28D

MICRO-RNA AND OBESITY

PRIORITY

This application is a 371 a National Stage Entry of International Application No. PCT/US19/22350, filed Mar. 14, 2019, which claims the benefit of, and claims priority to, U.S. Provisional Application No. 62/642,934, filed Mar. 14, 2018, the contents of which is hereby incorporated by reference in its entirety.

FIELD OF THE DISCLOSURE

The disclosure relates to the treatment and prevention of metabolic disorders by administering agents that modulate the activity or expression of microRNAs.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: BID-005PC1_ST25.txt; date created: Mar. 14, 2019; file size: 323,976 bytes)

BACKGROUND

MicroRNAs (miRNA or miR) are nucleic acid molecules that regulate the expression of target genes. MiRNAs are typically short (typically 18-24 nucleotides) and act as repressors of target mRNAs by promoting their degradation, when their sequences are perfectly complementary, and/or by inhibiting translation, when their sequences contain mismatches. Functional analyses of miRNAs have revealed that these small non-coding RNAs contribute to different physiological and metabolic processes, including regulating genes associated with metabolic disorders. Metabolic disorders are characterized by one or more abnormalities in metabolic function in the body. Metabolic disorders are also characterized by obesity and weight gain, a deficiency in insulin production, or a deficiency in sensitivity to insulin. Some metabolic disorders are related to defects the body's use of blood glucose, resulting in abnormally high levels of blood glucose. Metabolic disorders affect millions of people worldwide, and can be life-threatening disorders. With the incidence of obesity on the rise in the United States, there is a critical need to develop more effective therapies to reduce the health risks and alleviate the symptoms associated with obesity, overeating, excessive bodyweight gain or excessive accumulation of fat. As such, there is a need for method and compositions to treat, prevent, or delay the onset of metabolic disorders.

SUMMARY

The present disclosure provides new methods for the treatment or prevention of metabolic disorders by administering agents that modulate the activity or expression of microRNAs, for example by inhibiting microRNA expression and/or activity. Such inhibition can be mediated by sequence specific chemically modified oligonucleotides, including for example, locked nucleic acid (LNA). Inhibitors based on LNA technology, among others, when directed at the metabolic gene regulating miRNAs disclosed herein provide for an effective method of treating or preventing metabolic disorders.

In one aspect, the present disclosure provides a method for treating or preventing a metabolic disorder, comprising administering an effective amount of an inhibitor of miR-22 to a subject in need thereof.

In some embodiments, the expression and/or activity of miR-22 is reduced in the subject following administration of the inhibitor.

In some embodiments, the inhibitor of miR-22 is an oligonucleotide-based inhibitor. In some embodiments, the oligonucleotide-based inhibitor comprises a sequence that is at least about 75%, about 80%, about 85%, about 90%, about 95%, about 96%, about 97%, about 98%, about 99%, or about 100% complementary to a mature sequence of miR-22. In some embodiments, the oligonucleotide-based inhibitor comprises deoxynucleotides or ribonucleotides. In some embodiments, the oligonucleotide-based inhibitor is single stranded. In some embodiments, wherein the oligonucleotide-based inhibitor is double stranded.

In some embodiments, the oligonucleotide-based inhibitor comprises one or more chemically modified nucleotides.

In some embodiments, the chemically modified nucleotides are locked nucleotides (LNAs).

In some embodiments, the oligonucleotide-based inhibitor comprises about 25, about 20, about 15, about 10, about 9, about 8, about 7, about 6, or about 5 or fewer nucleotides. In some embodiments, the oligonucleotide-based inhibitor is conjugated to one or more N-acetylgalactosamine (GalNAc) moieties.

In some embodiments, the oligonucleotide-based inhibitor is an antisense oligonucleotide inhibitor. In some embodiments, the oligonucleotide-based inhibitor is a small interfering RNA (siRNA). In some embodiments, the oligonucleotide-based inhibitor is an aptamer.

In some embodiments, the inhibitor of miR-22 is a peptide-based or protein-based inhibitor. In some embodiments, the protein-based inhibitor in an antibody or an antigen-binding portion thereof. In some embodiments, the inhibitor of miR-22 is a small molecule-based inhibitor.

In some embodiments, the metabolic disorder is obesity.

In some embodiments, the subject is suffering from Prader-Willi Syndrome.

In some embodiments, the subject is suffering from hypercholesterolemia.

In some embodiments, the subject harbors a fat mass and obesity-associated protein (FTO) variant and/or shows an upregulation of FTO expression and/or activity.

In some embodiments, the subject is obese and has a body mass index of greater than about 30. In some embodiments, the subject is overweight and has a body mass index of about 25-29.9.

In some embodiments, the method induces weight loss. In some embodiments, the method induces a total weight loss of about 1%, about 5%, about 10%, about 15%, about 20%, or about 25% or more in the subject. In some embodiments, the method prevents weight gain.

In some embodiments, the method reduces or prevents the growth of adipose tissue. In some embodiments, the method impairs adipocyte differentiation.

In some embodiments, the metabolic disorder is a fatty liver disease. In some embodiments, the fatty liver disease is selected from non-alcoholic fatty acid liver disease (NAFLD) or non-alcoholic steatohepatitis (NASH). In some embodiments, the method reduces or prevents liver steatosis.

In some embodiments, the method reduces or prevents liver fibrosis.

In some embodiments, the method reduces the activity and/or expression of FTO, ALKB Homologous 5

(ALKBH5), CCAAT/enhancer binding protein alpha (CEBPα), peroxisome proliferator activated receptor gamma (PPARγ), and/or ATP citrate lyase (ACLY).

In some embodiments, the method increases the activity and/or expression of phosphatase and tensin homolog (PTEN) and/or tet methylcytosine dioxygenase 2 (TET2).

In some embodiments, the method alters the activity and/or expression of PPARγ co-activator-α (PGC1-α), Specific Protein 1 (SP1), Fibroblast Grow Factor 21 (FGF-21), Uncoupled protein 1 (UCP1), DNA Damage Included Transcript 4 (DDIT-4, REDD1), tumor protein p63 (TP63), fibroblast growth factor 1 (FGF1), and/or Methyltransferase like 3 (METTL3). In some embodiments the method alters the level of DNA or RNA methylation, or affects the m6A level at RNA level.

Any aspect or embodiment described herein can be combined with any other aspect or embodiment as disclosed herein.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A is a schematic showing the position of miR-22 in in 3rd exon in non-coding transcript MGC14376.

FIG. 1B shows PTEN targeting miRNAs and FIG. 1C shows that miR-22 directly targets PTEN and TET to promote tumorigenesis and metastasis.

FIG. 2A is a picture showing the feeding regimen of Wild Type (WT) and Transgenic (Tg) mice. FIG. 2B is an immunohistochemical staining of WT liver and miR-22 Tg mice liver. FIG. 2C is a graph showing the average weight of WT versus miR-22 Tg mice and FIG. 2D is a bar graph showing the average weight of WT and miR-22 T mice colony. These data indicate that miR-22 overexpression affects weight of mice. The data in the right (red) bars in each data pair is for the with miR-2 Tg mice.

FIG. 3A shows the percentage of body mass increase the entire colony after 2 weeks on the HFD and FIG. 3B shows the percentage of body mass increase the entire colony after 4 weeks on the HFD. FIG. 3C shows the change in grams of KO vs WT from week 1 to 8 from the start of HFD.

FIG. 4A shows the percentage of body mass increase in female mice after 2 weeks on the HFD. FIG. 4B shows the percentage of body mass increase in female mice after 4 weeks on the HFD. FIG. 4C shows the percentage of body mass increase in female mice after 8 weeks on the HFD. FIG. 4D shows the change in grams in KO vs WT mice after 2 weeks. FIG. 4E shows the change in grams in KO vs WT mice after 4 weeks. FIG. 4F shows the change in grams in KO vs WT mice after 8 weeks.

FIG. 5A shows percentage of fat and lean mass (FIG. 5B), (% of total body mass) of miR-22 KO and WT mice pre (day 0) and post 8 weeks on HFD. miR-22 KO cohort has a statistically significant lower fat mass compared to WT after 8 weeks on HFD. Lean mass in miR-22 KO cohort is not affected by HFD, contrary top WT cohort that increase the % of fat mass and decrease the % of lean mass after HFD. FIGS. 5C and 5D show a series of parameters collected in metabolic cages. At steady state both miR-22KO and WT mice have the same metabolism. Once that mice are challenged with HFD miR-22KO cohort is able to not reduce its energy expenditure, while WT cohort does. Both VCO2 and VO2 are significant higher in miR-22KO cohort compared with WT, even if KO mice are less active than WT. The data in the right (red) bars in each bar graph of FIGS. 5C and 5D is for the with miR-22KO mice.

FIG. 7A is a bar graph showing adipocyte differentiation in MEFs, indicating that miR-22−/− MEFs show 27% less adipocytes than WT. FIG. 7B is an Oil-Red-O stain showing MEF from WT, miR-22$^{+/-}$ and miR-22$^{-/-}$, cultured in Adipo-differentiative media for 5 days.

FIG. 8 shows the design of anti-miR-22 LNA.

FIG. 11A shows the final percentage body increase. FIG. 11B shows in vivo silencing of miR-22 in DIO mice. In both figures, at the final time points, the order of data going from top to bottom is Vehicle (in green), SCR (in red), and anti-miR-22 (in blue).

FIG. 13A-B is a series of bar graphs (FIG. 13A) and immunohistochemical staining (FIG. 13B), showing that anti-miR-22 treatment doesn't affect liver lipid composition but profoundly suppresses liver steatosis.

FIG. 14A shows mRNA expression of TET2 and PTEN. FIG. 14B shows mRNA expression of FTO, FTO and CEBPa.

FIG. 15A shows mRNA expression of TET2 and PTEN. FIG. 15B shows mRNA expression of FTO, CEBPa and PPARg and FIG. 15C shows mRNA expression of UCP1 and CD36.

FIG. 16A-C is a series of bar graphs showing relative mRNA levels in White adipose tissue (WAT) of mice treated with VHL, SCR LNA or LNA anti-miR-22. FIG. 16A are bar graphs showing TET2 and PTEN mRNA expression levels. FIG. 16B are bar graphs showing FTO, CEBPa and PPARg mRNA expression levels and FIG. 16C are bar graphs showing, UCP1 and CD36 expression levels.

FIG. 19A shows fat pad from mice treated with VHL, FIG. 19B shows Fat pad from mice treated with anti-miR-22 and FIG. 19C shows fat pad from mice treated with SCR.

In FIG. 24B, the data in the right (red) bars in each bar graph is for the with LNA #10-treated cells.

FIG. 27A is a representation of the FTO gene and FIG. 27B is a bar graph showing FTO mRNA expression level under steady state and differentiation media conditions. In FIG. 27B, the order of data in the bar graphs, reading from left to right, is WT (in black), miR-22+/−(in grey), and miR-22−/−(in blue).

FIG. 28A-D shows that miR-22 down regulation (genetic or pharmacological) increase level of RNA m6A. FIG. 28A shows the chemical reaction. FIG. 28B, FIG. 28C and FIG. 28D are bar graphs showing the percentage and relative amount of m6A levels in mice on a HFD.

FIG. 33C shows FSP-1 positive cells in liver from mouse on a normal diet in WT and miR-22 Tg mice.

FIG. 34C shows FSP-1 positive cells in liver from mouse on a HFD in WT and miR-22+/− mice.

DETAILED DESCRIPTION OF THE DISCLOSURE

Figure 1A:
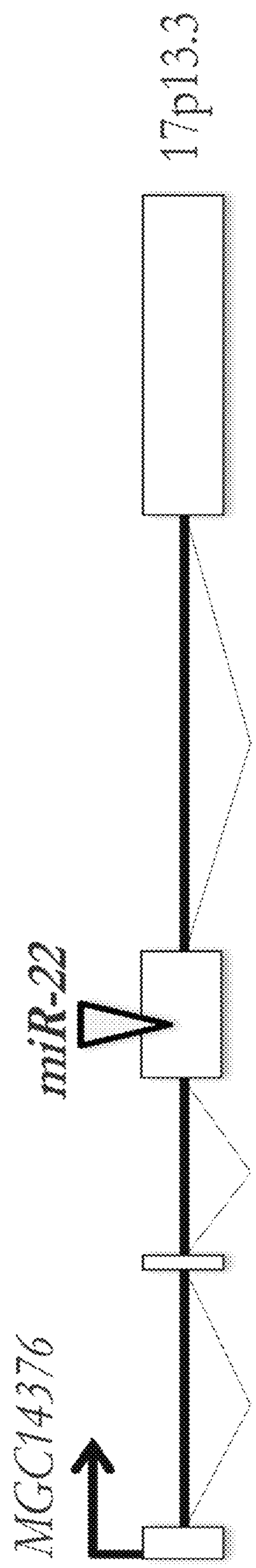
FIG. 1A-C are schematics showing the regulation profile of miR-22.
Figure 1B:
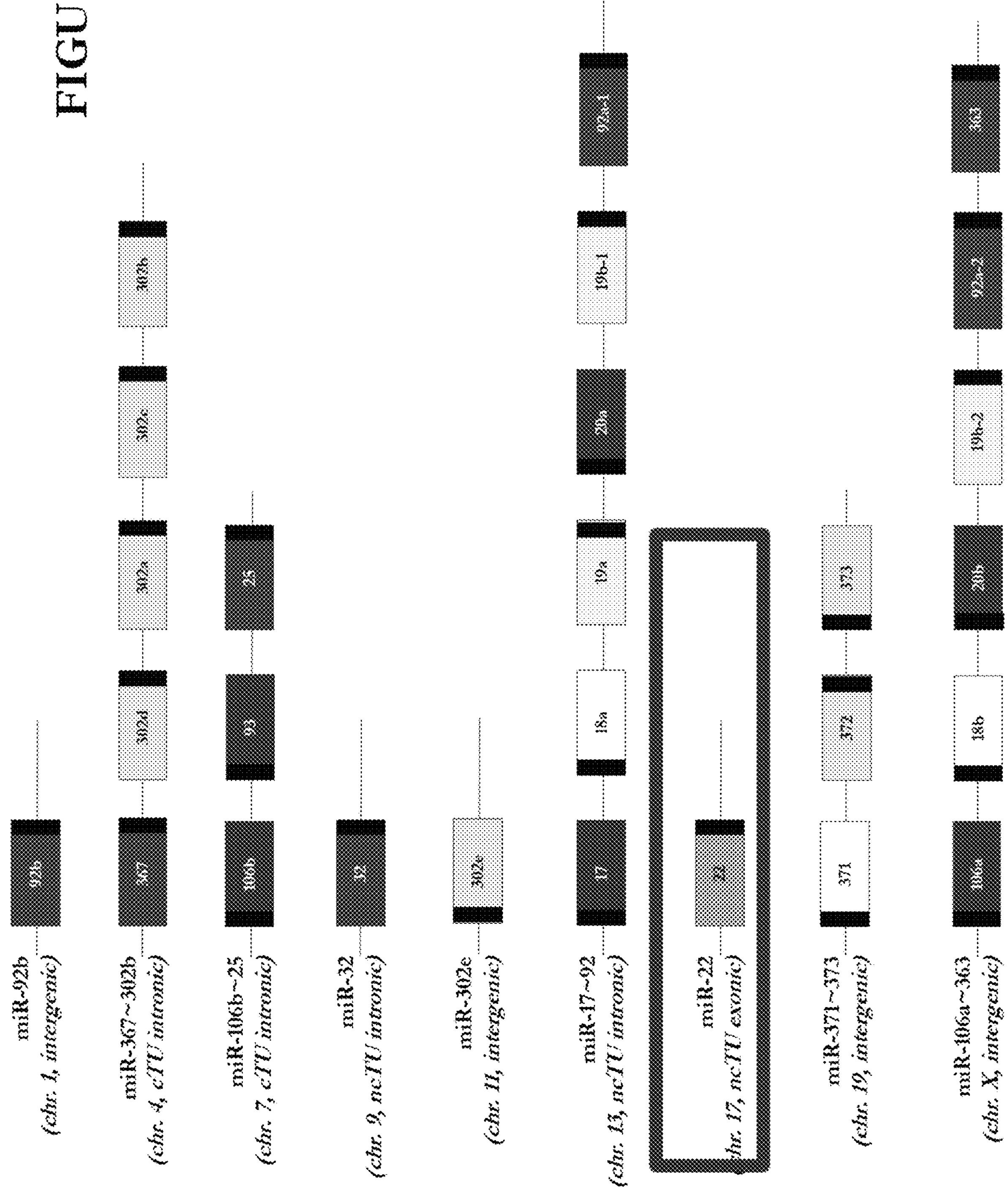
Figure 1C:
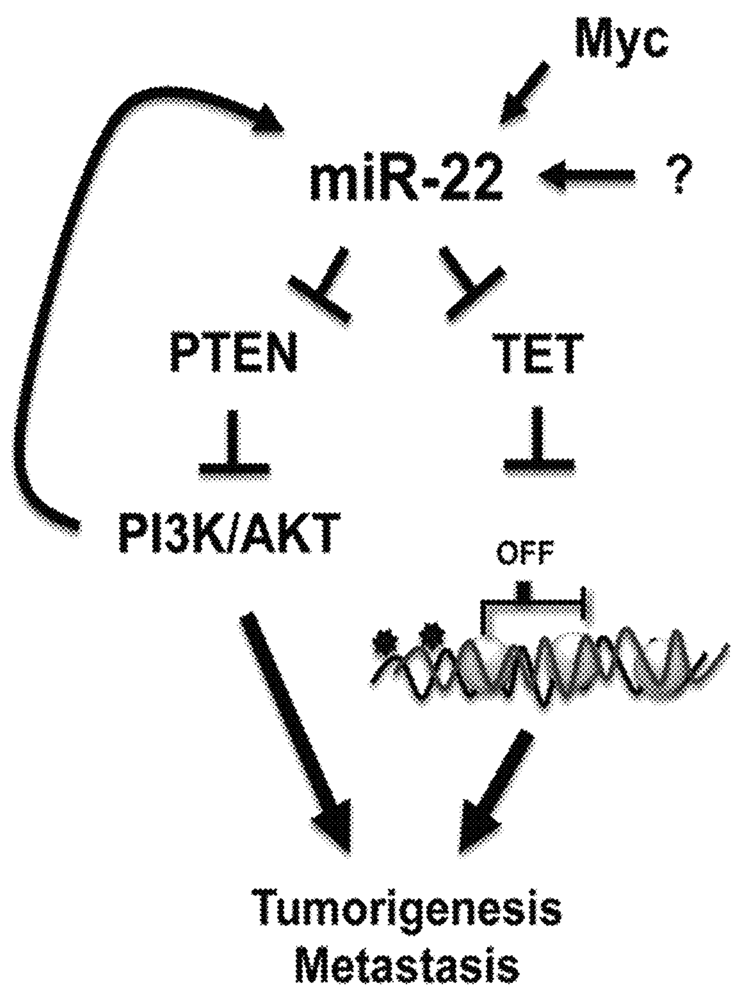
Figure 2:
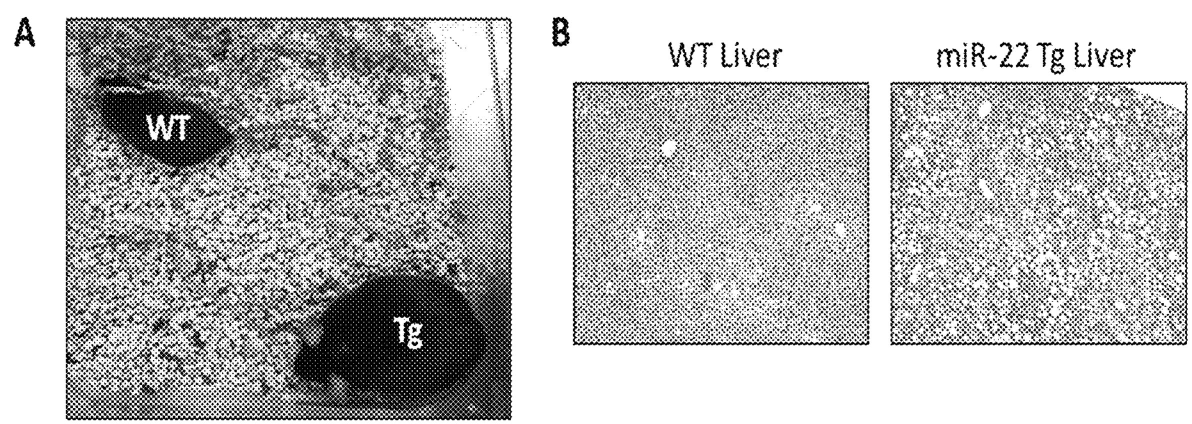
FIGS. 2A-D show that miR-22 overexpression affects weight of mice.
Figure 3:
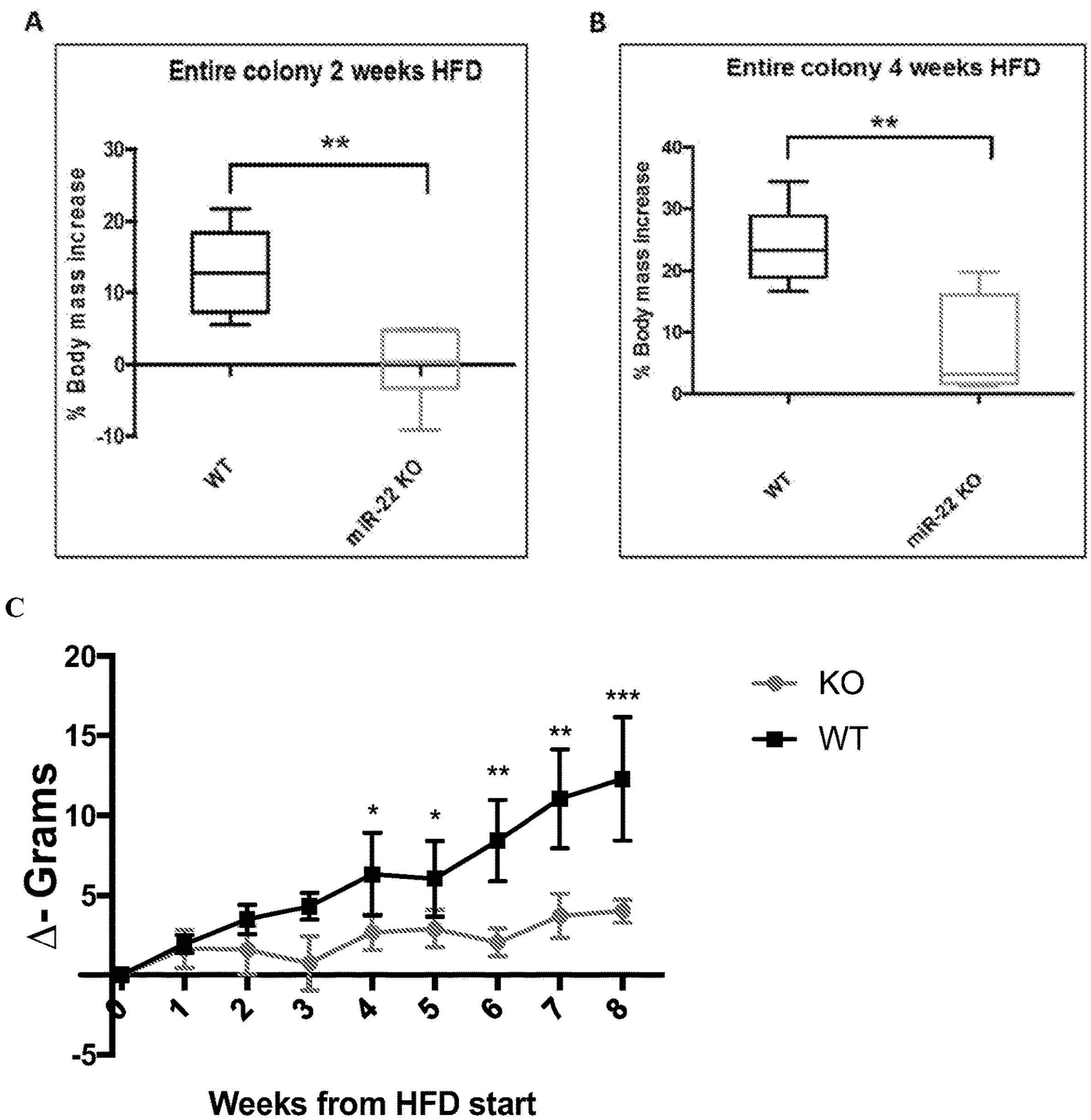
FIG. 3A-C are a pair of bar graphs and a line graph showing that miR-22 null mice fail to gain weight on High Fat Diet (HFD).
Figure 4:
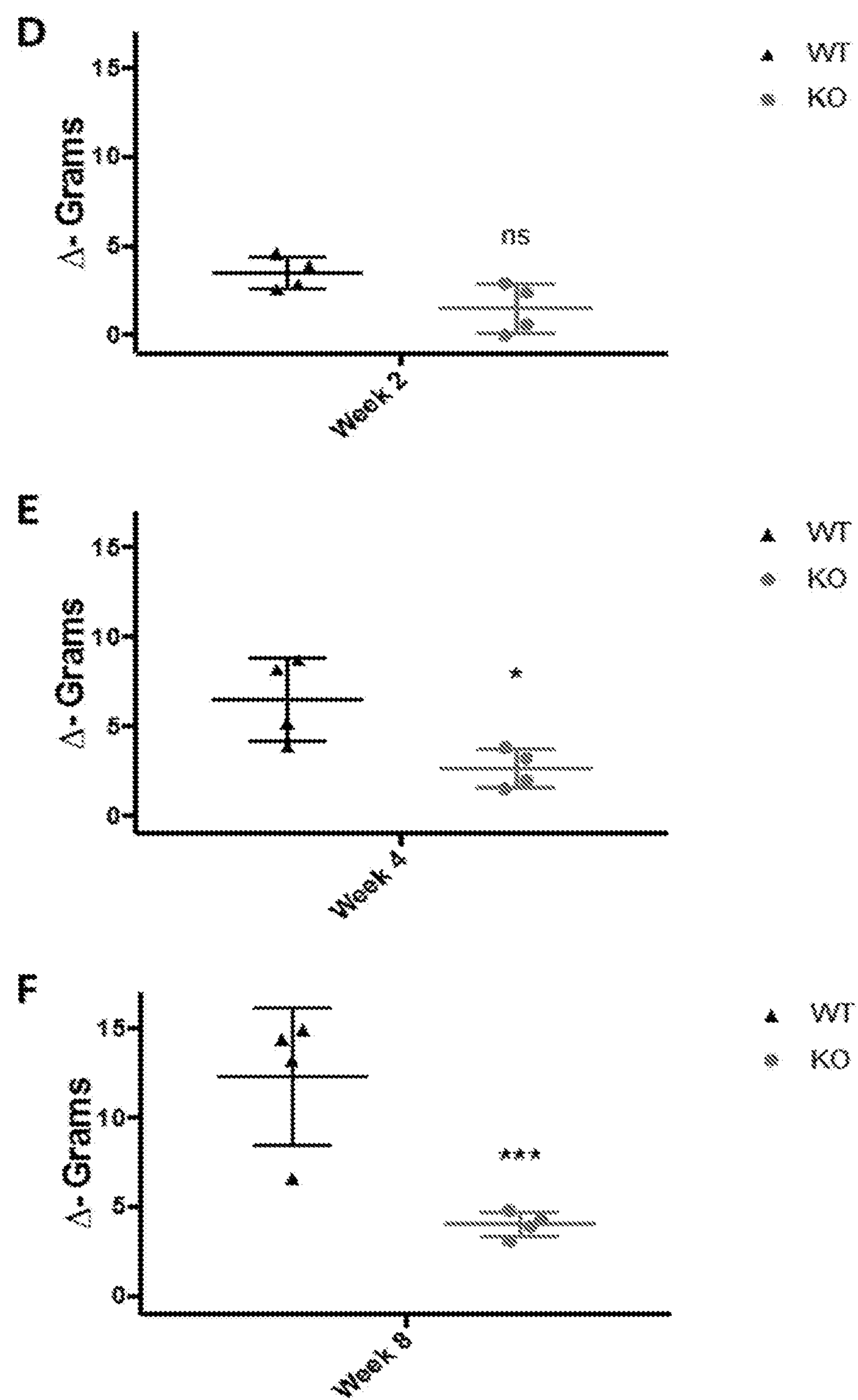
FIG. 4A-F are a series of bar graphs showing that miR-22 null mice fail to gain weight on HFD.
Figure 5:
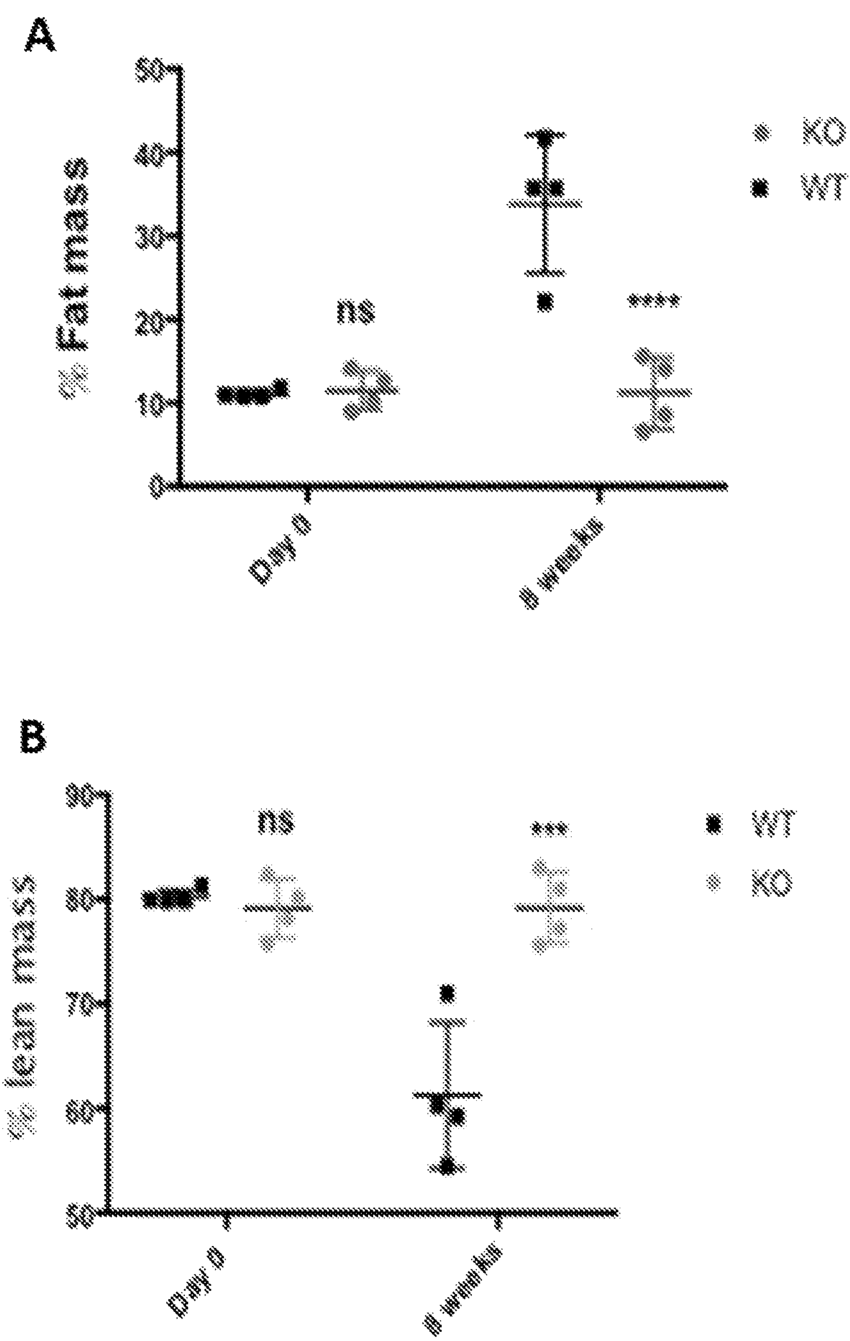
FIG. 5A-D are a series of graphs showing that miR-22 null mice show a different metabolism compared with WT when fed with HFD.
Figure 5C:
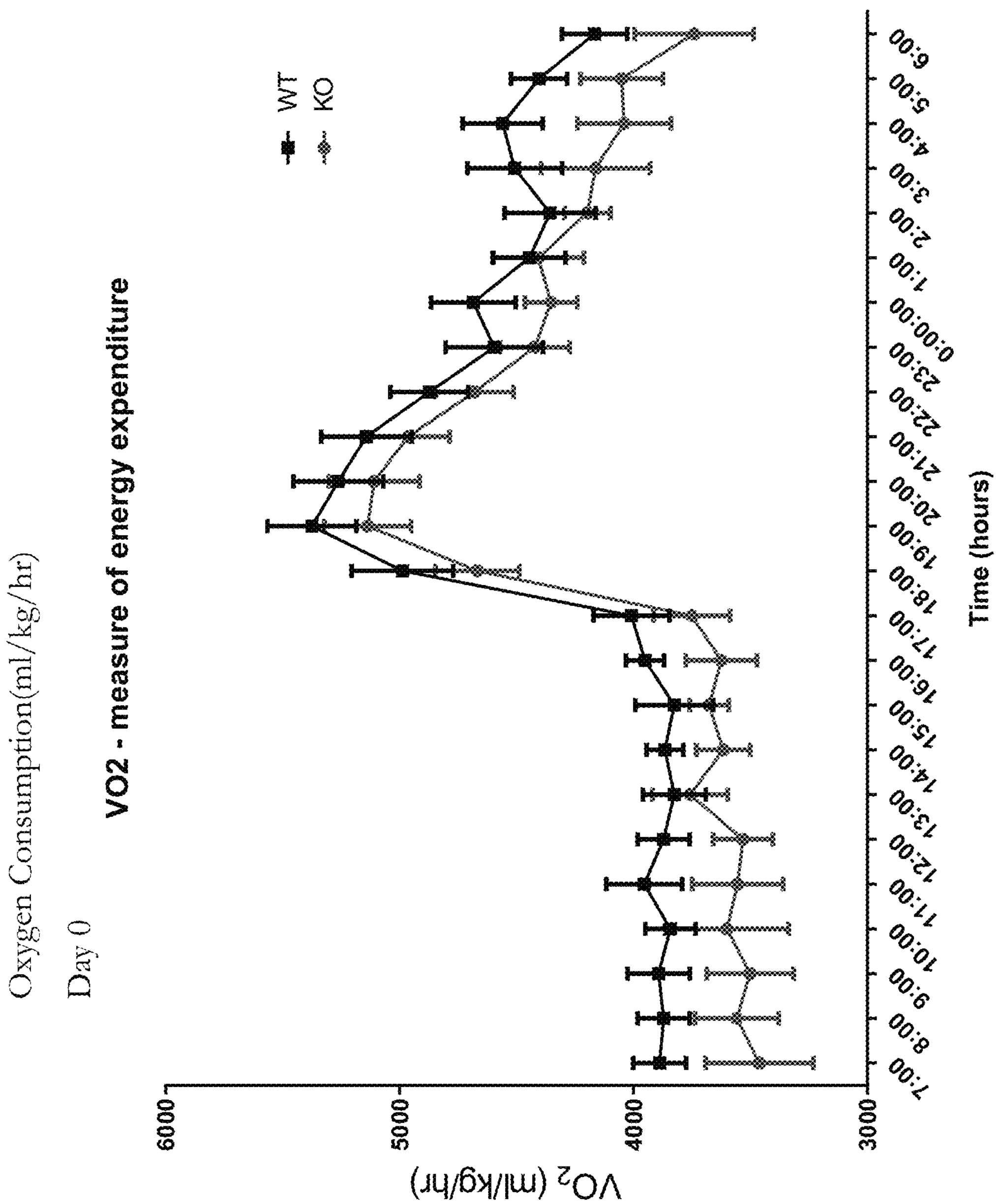
Figure 5C:
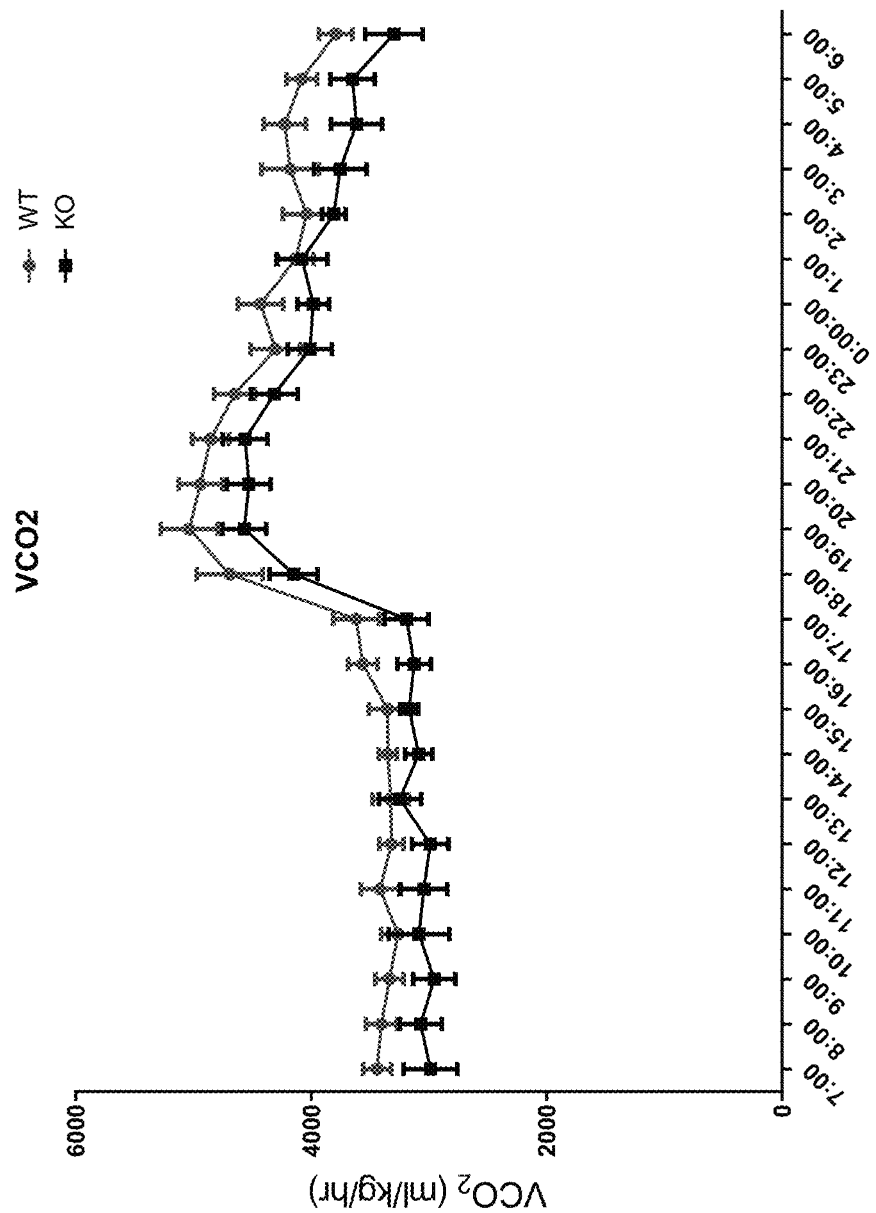
Figure 5C:
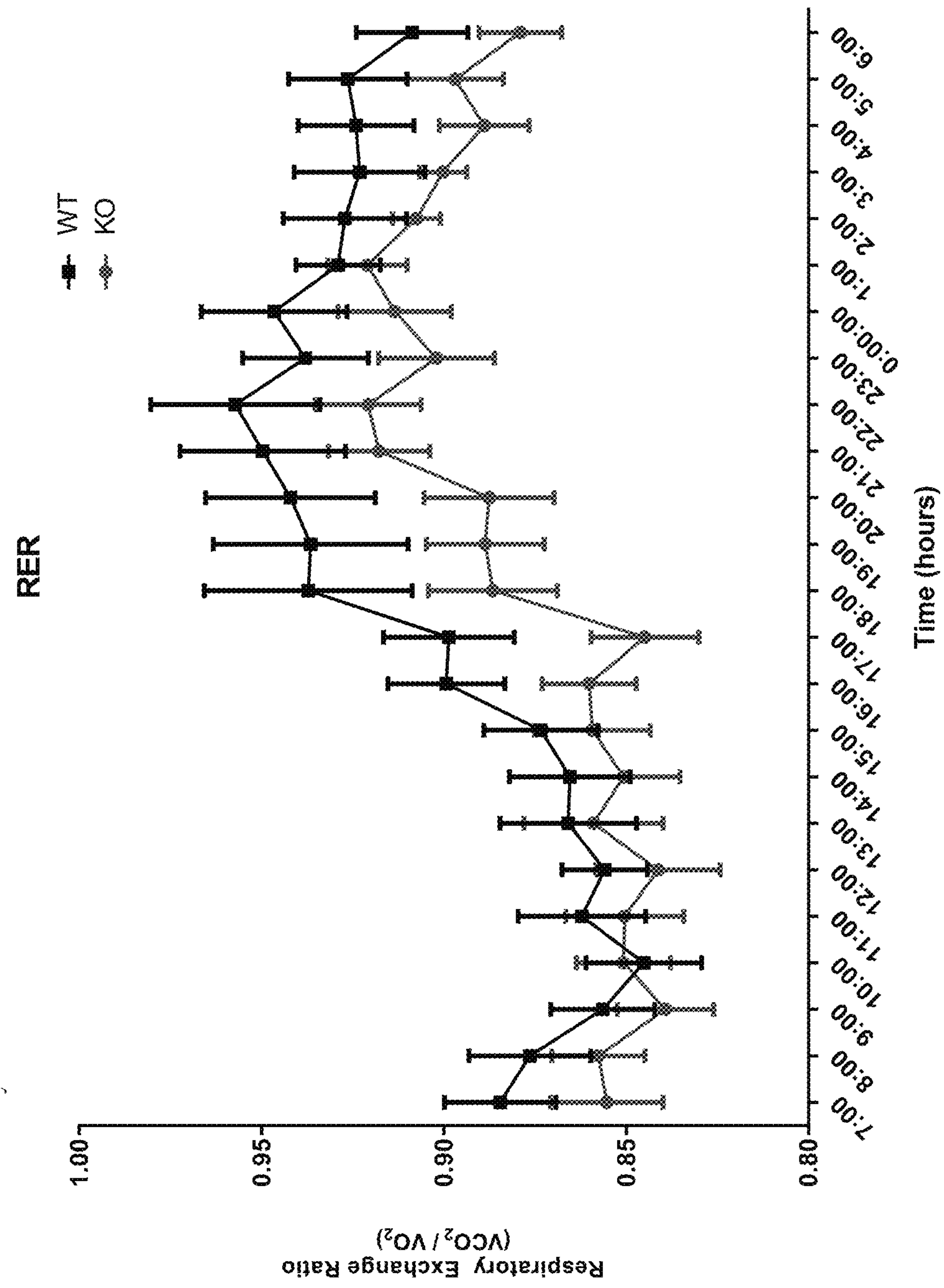
Figure 5C:
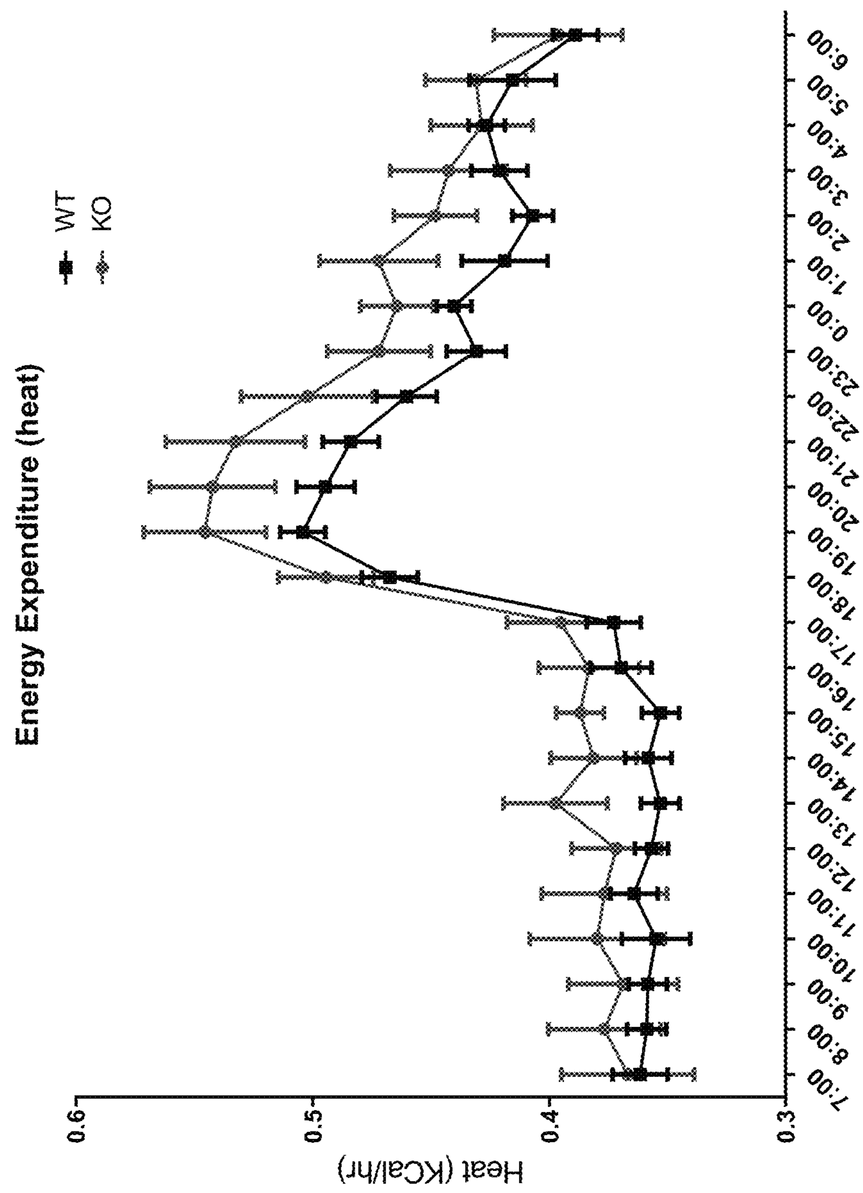
Figure 5C:
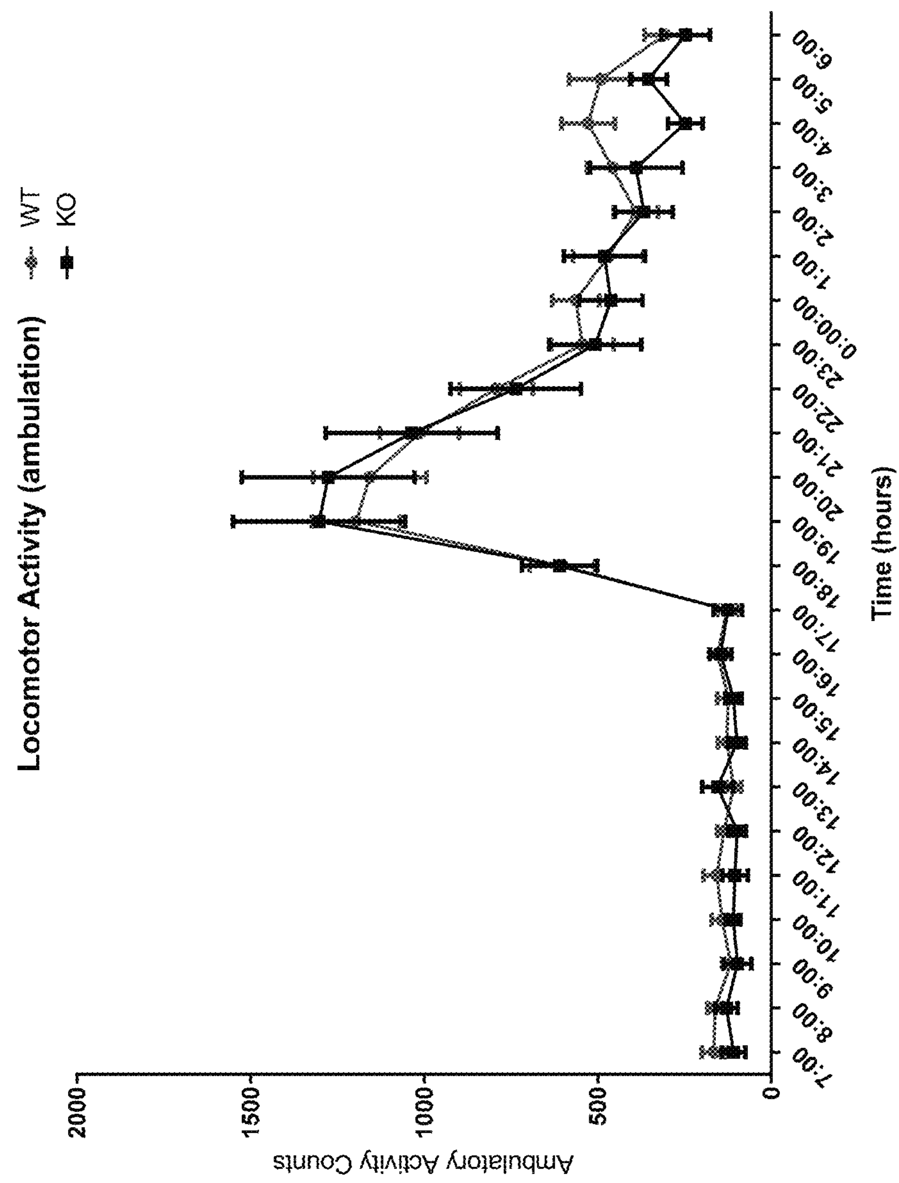
Figure 5C:
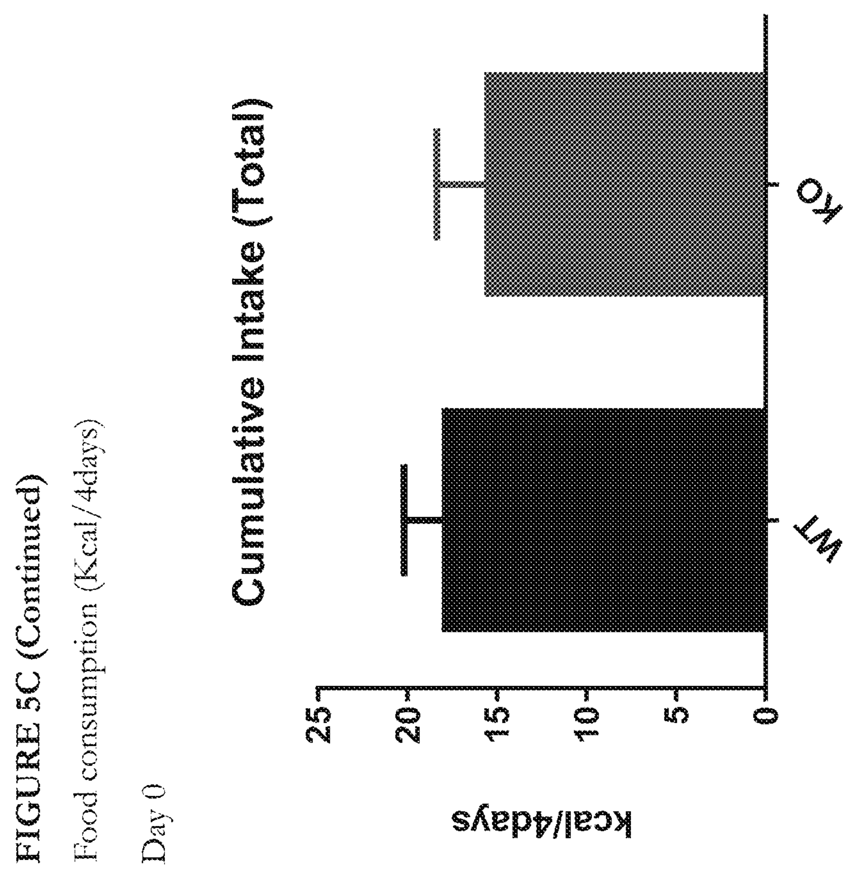
Figure 5D:
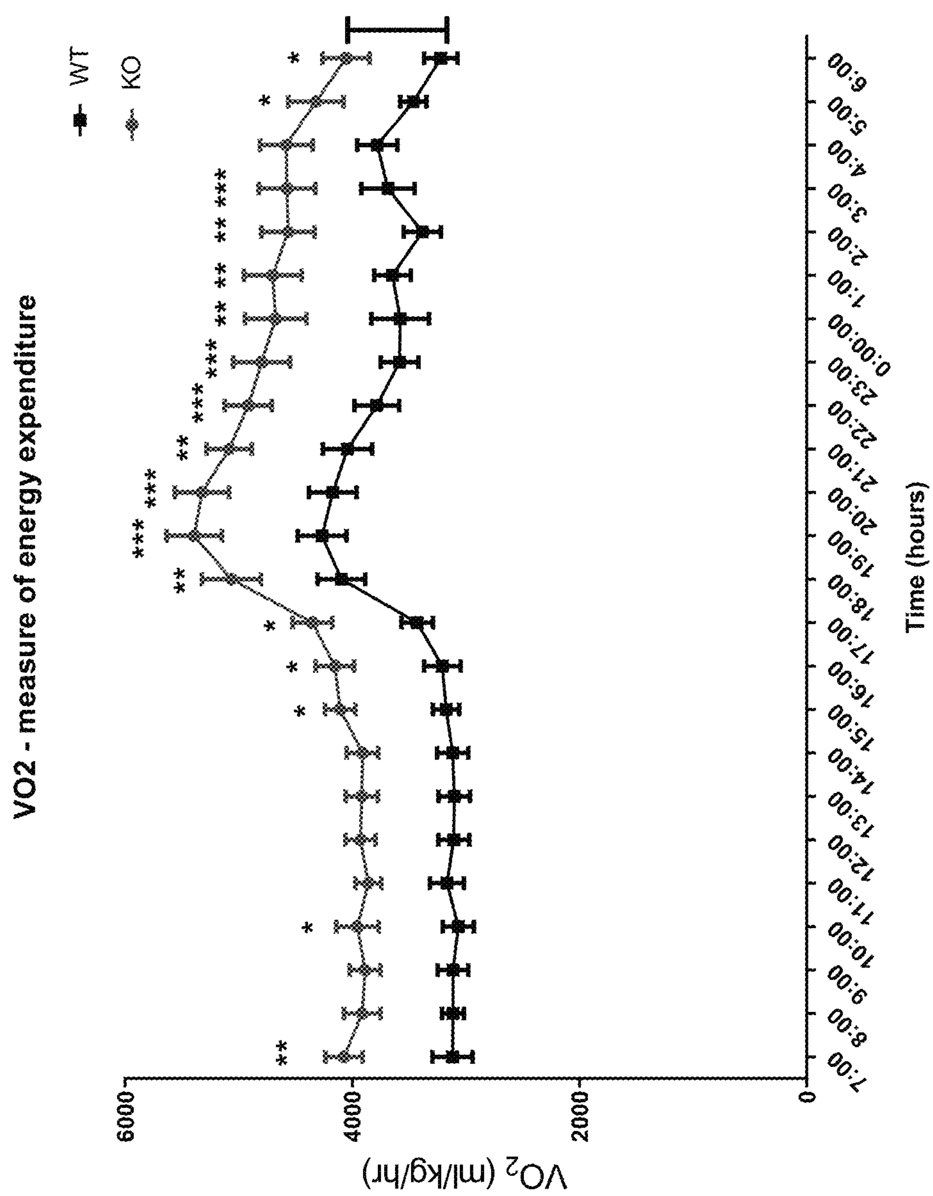
Figure 5D:
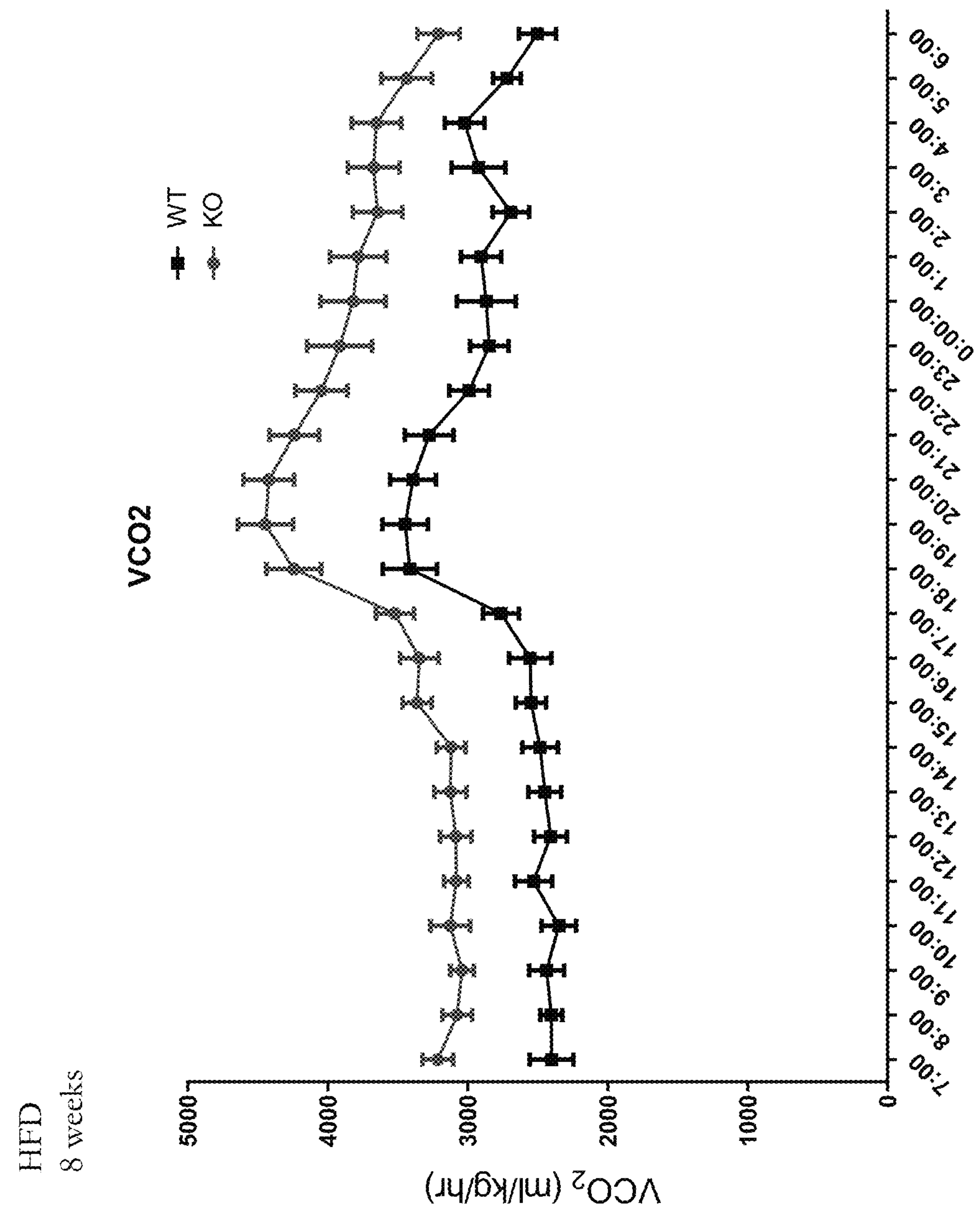
Figure 5D:
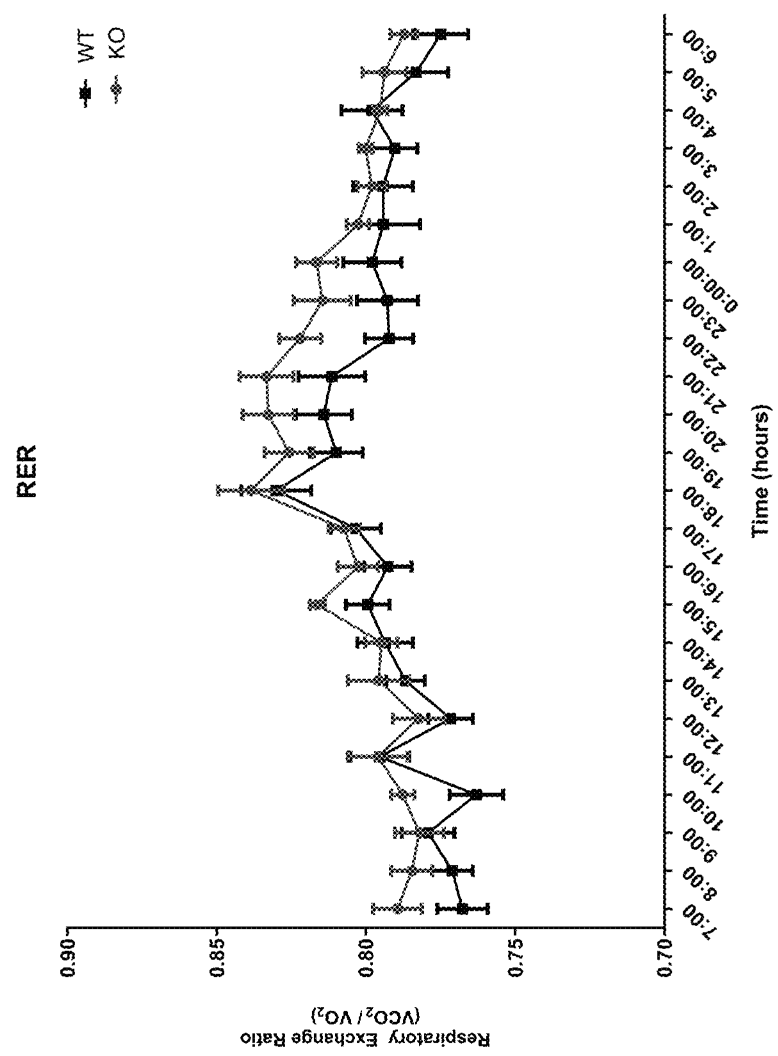
Figure 5D:
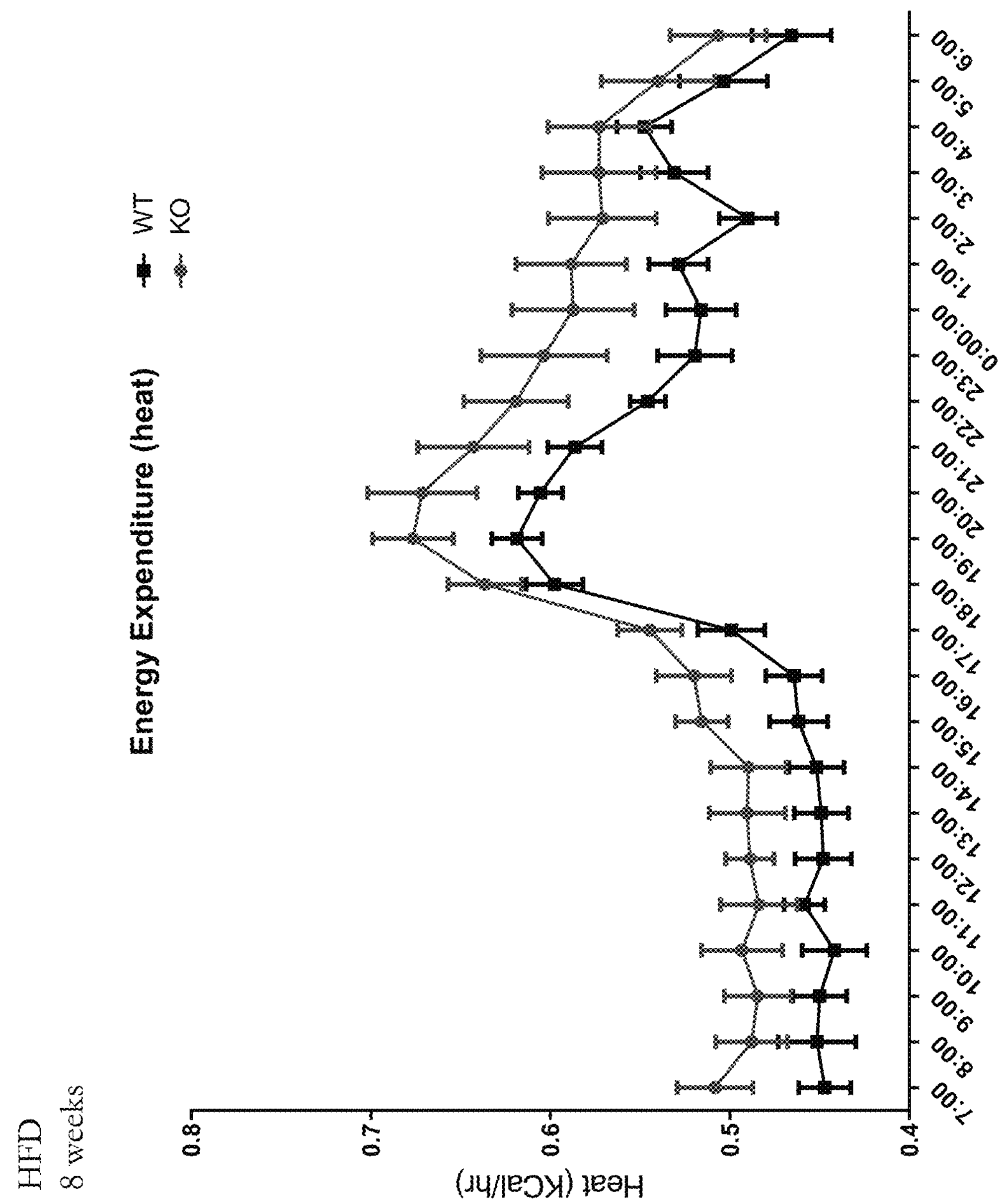
Figure 5D:
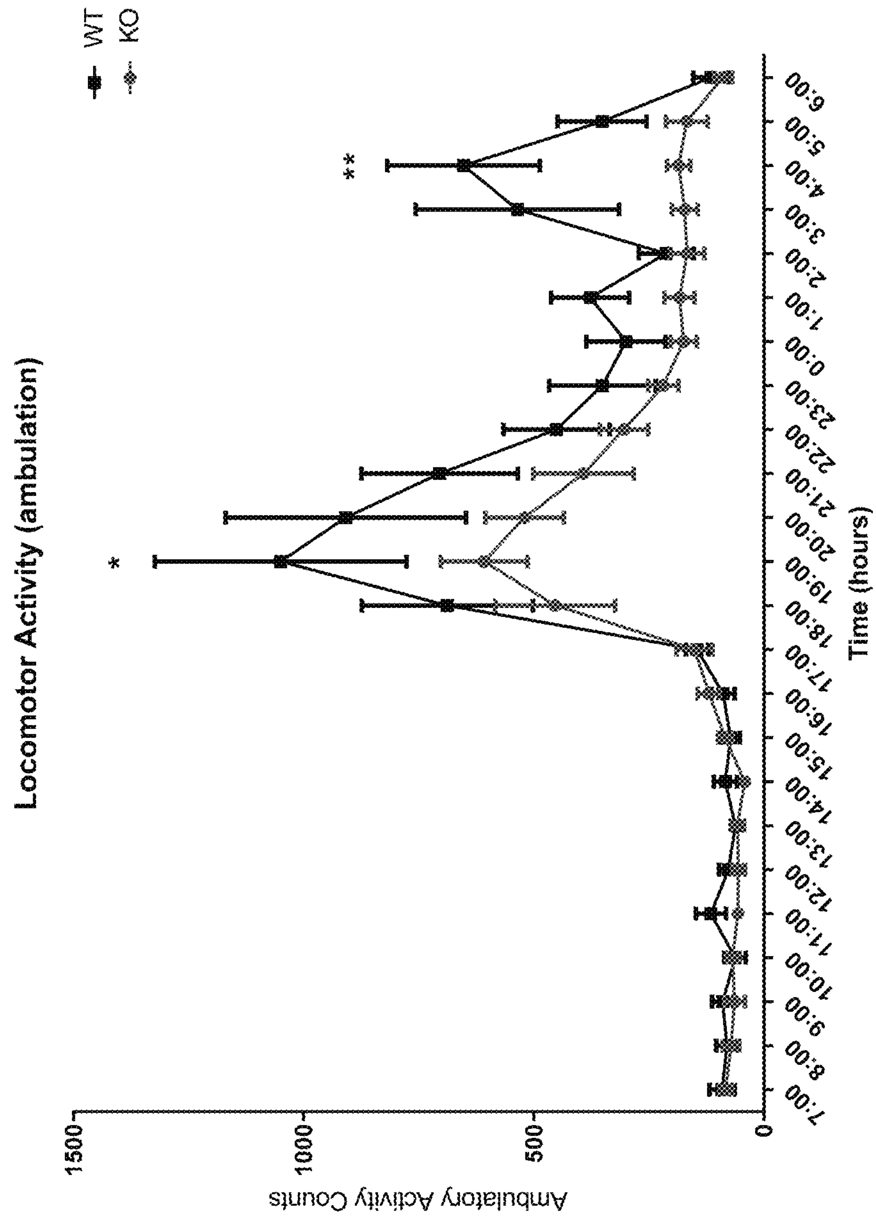
Figure 5D:
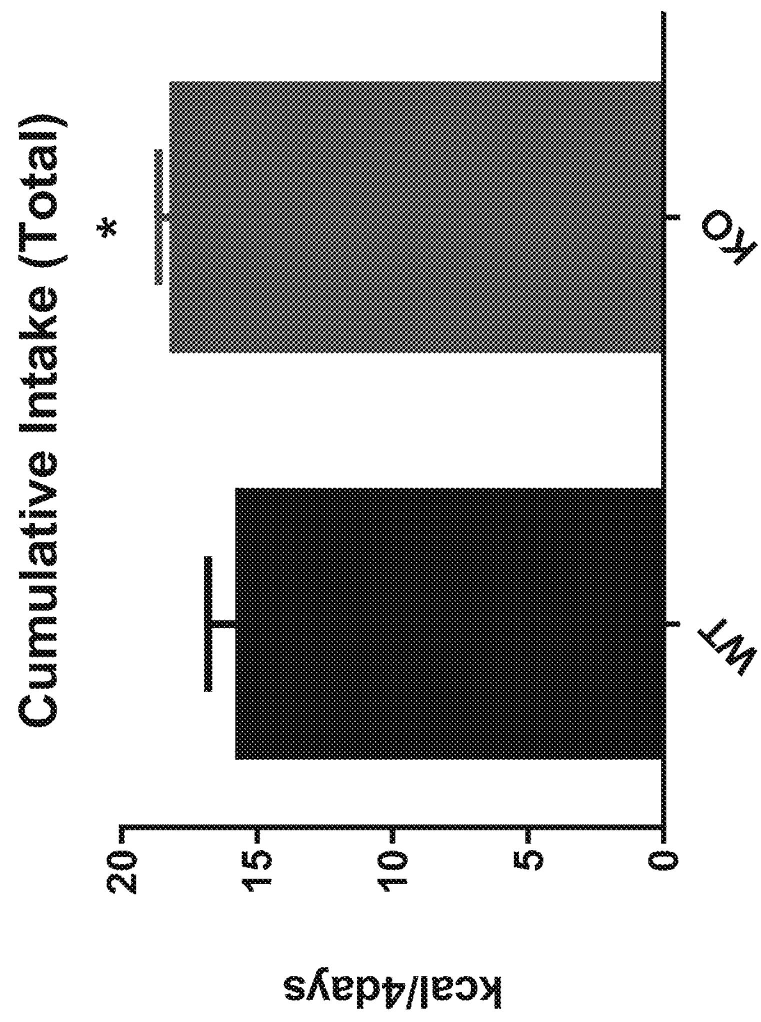
Figure 6:
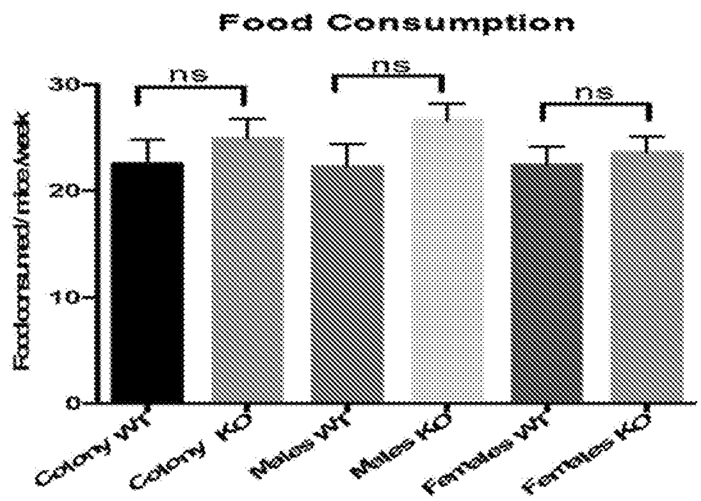
FIG. 6 is a bar graph showing no difference between WT and KO cohort in food consumption (HFD).
Figure 7:
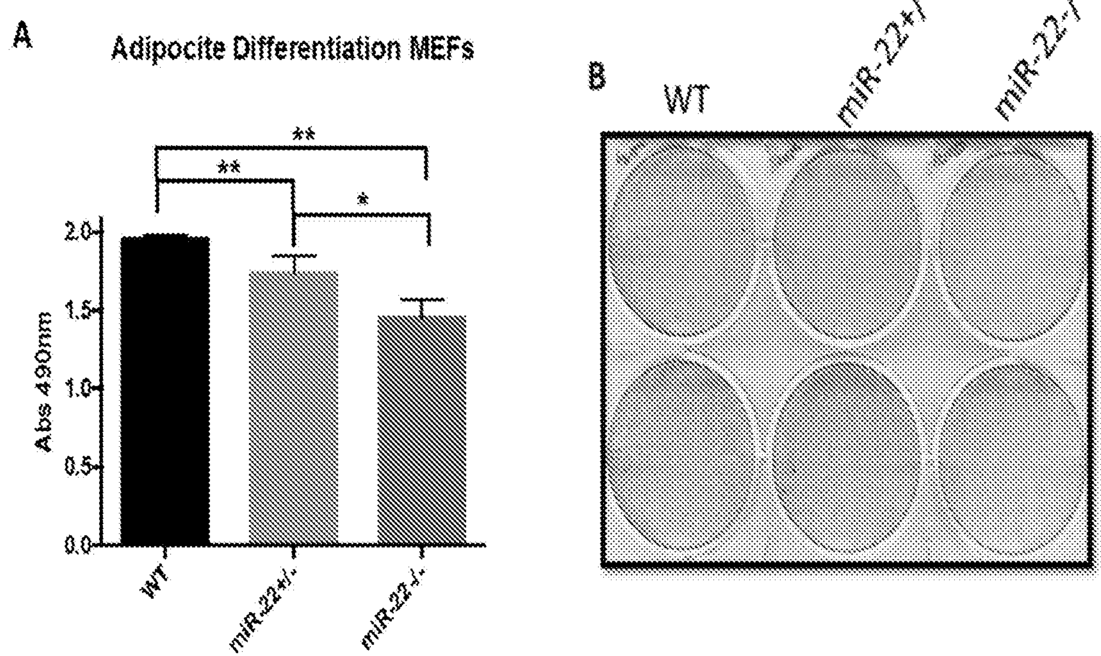
FIG. 7A-B is a bar graph and Oil-Red-O stain showing that down regulation of miR-22 impairs Mouse Embryonic Fibroblast (MEF) ability to differentiate in adipocytes.

The present disclosure is based on the discovery that miRNAs, including miR-22, can regulate targets that are linked to a variety of metabolic disorders, including Obesity, Prader-Willi Syndrome, Hypercholesterolemia, Fatty Liver Disease, Non-Fatty Acid Liver Disease (NAFLD) and/or Non-Alcoholic Steatohepatitis (NASH).

The present disclosure includes targeting miRNAs, including miR-22, with various inhibitors for the treatment and/or prevention of diseases the cause of which can be influenced by modulating the metabolism, for example, metabolic disorders, including Obesity, Prader-Willi Syndrome, Hypercholesterolemia, NAFLD and/or NASH.

MiR-22 directly targets phosphatase and tensin homolog (PTEN) and tet methylcytosine dioxygenase (TET) to promote tumorigenesis, metastasis and metabolic disorders. More than 60 PTEN-targeting miRNAs and no less than 30 new proto-oncogenic genetic loci are studied in human cancer. PTEN-targeting miRNAs are highly conserved evolutionarily among vertebrates and ubiquitously expressed in various tissues, (Lagos-Quintana et al., 2001, 2002; Neely et al., 2006). By targeting PTEN, miR-22 is remains metabolically relevant, as PTEN lowering or its elevation triggers a Warburg- or an anti-Warburg metabolic state respectively. In some embodiments, miR-22 targeting genes regulate metabolism and fatty acid oxidation or biogenesis.

In one aspect, the methods of the present disclosure provide a method for treating or preventing a metabolic disorder, comprising administering an effective amount of an inhibitor of miR-22 to a subject in need thereof.

For example, such inhibition could be mediated by sequence specific chemically modified oligonucleotides. An exemplary modification is a locked nucleic acid (LNA) in which the nucleic acid's ribose moiety is modified with an extra bridge connecting the 2' oxygen and 4' carbon, which locks the ribose in the 3'-endo conformation. The LNA inhibitors, among others, when directed at the metabolism gene-regulating miRNAs disclosed herein, provide for cost effective agents that can be delivered efficiently and possess sufficient bioavailability for the treatment and prevention of various metabolic disorders.

The present disclosure further provides uses of any methods or combinations described herein in the manufacture of a medicament for treating a disease. Such diseases include, for example, metabolic disorders or a disease influenced by modulating the metabolism (e.g., Fat related metabolism and synthesis pathway).

In some embodiments of the methods of the disclosure, miRNAs, including miR-22 regulate fat related metabolism and synthesis pathway targets and/or genes. In some embodiments, the fat related metabolism and synthesis genes include Fat mass and obesity-associated protein (FTO), CCAAT/enhancer binding protein alpha (CEBPa), peroxisome proliferator activated receptor gamma (PPARg), phosphatase and tensin homolog (PTEN), tet methylcytosine dioxygenase 2 (TET2), ATP citrate lyase (ACLY), bone morphogenetic protein 7 (BMP-7) and/or sirtuin 1 (SIRT-1).

In some embodiments, the fat related metabolism and synthesis genes include FTO. In some embodiments, the method reduces the activity and/or expression of fat mass and obesity-associated protein (FTO), CEBPα, and/or PPARγ.

In some embodiments, the method reduces the activity and/or expression of ALKB Homologous 5 (ALKBH5). In some embodiments, the method increases the activity and/or expression of PTEN and/or TET2.

In some embodiments, the method alters the activity and/or expression of PPARγ co-activator-α (PGC1-α), Specific Protein 1 (SP1), Fibroblast Grow Factor 21 (FGF-21), Uncoupled protein 1 (UCP1), DNA Damage Included Transcript 4 (DDIT-4, REDD1), Methyltransferase like 3 (METTL3), tumor protein p63 (TP63) and/or fibroblast growth factor 1 (FGF1).

In some embodiments the method alters the level of DNA or RNA methylation, or affects the m6A level at RNA level.

In some embodiments, the present disclosure treats or prevents metabolic disorders (by way of non-limiting example, Obesity, Prader-Willi Syndrome, Hypercholesterolemia, Fatty Liver Disease, NAFLD and/or NASH) in a subject through the inhibition of a miRNA. MiRNAs are short nucleic acid molecules that are able to regulate the expression of target genes. See review by Carrington et al., Science, Vol. 301(5631):336-338, 2003. MiRNAs are often between about 18 to 24 nucleotides in length. MiRNAs act as repressors of target mRNAs by promoting their degradation, when their sequences are perfectly complementary, and/or by inhibiting translation, when their sequences contain mismatches.

Without being bound by theory, mature miRNAs are believed to be generated by pol II or pol III and arise from initial transcripts termed pri-miRNAs. These pri-miRNAs are frequently several thousand bases long and are therefore processed to make much shorter mature miRNAs. These pri-miRNAs may be multicistronic and result from the transcription of several clustered sequences that organize what may develop into many miRNAs. The processing to yield miRNAs may be two-steps. First, pri-miRNAs may be processed in the nucleus by the RNase Drosha into about 70- to about 100-nucleotide hairpin-shaped precursors (pre-miRNAs). Second, after transposition to the cytoplasm, the hairpin pre-miRNAs may be further processed by the RNase Dicer to produce a double-stranded miRNA. The mature miRNA strand may then be incorporated into the RNA-induced silencing complex (RISC), where it may associate with its target mRNAs by base-pair complementarity and lead to suppression of protein expression. The other strand of the miRNA duplex that is not preferentially selected for entry into a RISC silencing complex is known as the passenger strand or minor miRNA or star (*) strand. This strand may be degraded. It is understood that, unless specified, as used herein a miRNA may refer to pri- and/or pre- and/or mature and/or minor (star) strand and/or duplex version of miRNA.

In some embodiments, miRNA genes may be located within introns of protein-coding genes or within introns or exons of noncoding transcriptional units. The expression of intronic miRNAs may coincide with that of the hosting transcriptional units because they are typically oriented in the same direction and are coordinately expressed with the pre-mRNAs in which they reside.

In some embodiments, miRNAs may bind to sequences within the 3' untranslated region (3'UTR) of target gene transcripts. In some embodiments, miRNAs may bind to sequences outside of the 3'UTR of target gene transcripts. In some embodiments, miRNAs may bind to both within and outside the 3'UTR of target gene transcripts.

In some embodiments, nucleotide pairing between the second and seventh nucleotides of the miRNA (the miRNA seed sequence) and the corresponding sequence along the target 3'UTR (seed match) may occur for target recognition. Accordingly, the binding between miRNA and target may comprise about a 5 nucleotide base pairing. Additionally, the binding between miRNA and target may comprise more than a 5 nucleotide base pairing. In some embodiments, the binding between an miRNA and the gene that it regulates may be mediated by the miRNA binding up to 2, up to 4, up to 6, up to 8, or up to 10 sites of the target nucleic acid.

MiRNAs of the present disclosure may regulate nucleic acids, including but not limited to metabolic-critical genes such as genes of a marker linked to a metabolic disorder etiology, by direct binding. This binding may be perfectly complementary to the target nucleic acid or contain mismatches. The effect of this binding may be to promote degradation and/or to inhibit translation of the target.

In some embodiments, the present invention treats or prevents metabolic disorder in a subject through the inhibition of miRNAs, such as miR-22. In some embodiments, the nucleic acid encoding mir-22 comprises or consists of AAGCUGCCAGUUGAAGAACUGU (SEQ ID NO: 1).

The predicted miR-22 hairpin precursor is contained entirely within exon 2 of a noncoding transcript, C17orf91, and the splicing pattern is generally conserved in human and mouse, despite the lack of protein-coding potential. See Rodriguez et al., Identification of mammalian microRNA host genes and transcription units. Genome Res. 2004 October; 14(10A):1902-10. Deletion of exon 2 of C17orf91 encompassing mir-22 in mouse models has revealed that miR-22 may play a role in cardiac hypertrophy and remodeling by targeting SIRT1 (NAD-dependent deacetylase sirtuin-1), HDAC4 (histone deacetylase 4), PURB (purine-rich element binding protein B) and PTEN. See Gurha et al., Targeted deletion of microRNA-22 promotes stress-induced cardiac dilation and contractile dysfunction. Circulation. 2012 Jun. 5; 125(22):2751-61; Huang et al., MicroRNA-22 regulates cardiac hypertrophy and remodeling in response to stress. Circ Res. 2013 Apr. 26; 112(9): 1234-43.

Additionally, it has been observed that AKT, a downstream target of PTEN, activated mir-22 transcription, suggesting a regulatory loop in the oncogenic PI3K/AKT signaling pathway. See Bar et al., miR-22 forms a regulatory loop in PTEN/AKT pathway and modulates signaling kinetics. PLoS One. 2010; 5(5): e10859.

The present invention, in some embodiments, shows that miR-22 may function as an epigenetic modifier and EMT promoter independently of its ability to target Pten. In some embodiments, the present disclosure includes treatment or prevention of metabolic disorder in a subject through the prevention of an increase and/or causing of a decrease in fat mass and obesity-associated protein (FTO) variant and/or shows a downregulation of FTO expression and/or activity. FTO is an enzyme that in humans is encoded by the FTO gene located on chromosome 16. As one homolog in the AlkB family proteins, it is the first mRNA demethylase that has been identified. Certain variants of the FTO gene are associated with obesity in humans.

In some embodiments, the sequence of the inhibitor is conserved across species. In some embodiments, the sequence of the inhibitor is taken, in part, from the sequence of a human transcript. In some embodiments, the inhibitor is selected to reduce the expression and/or activity of the target miRNA, by way of non-limiting example, miR-22, in a subject.

In some embodiments, an inhibitor of miRNA is an antisense oligonucleotide. Antisense oligonucleotides can include ribonucleotides or deoxyribonucleotides or a combination thereof. Antisense oligonucleotides may have at least one chemical modification (non-limiting examples are sugar or backbone modifications).

In some embodiments, the chemical modification is one or more of a phosphorothioate, 2'-0-Methyl, or 2'-O-Methoxyethyl, 2'-O-alkyl-RNA unit, 2'-OMe-RNA unit, 2'-amino-DNA unit, 2'-fluoro-DNA unit (including, but not limited to, a DNA analogue with a substitution to a fluorine at the 2' position (2' F)), LNA unit, PNA unit, HNA unit, INA unit, and a 2' MOE RNA unit.

Suitable antisense oligonucleotides can be comprised of one or more conformationally constrained or bicyclic sugar nucleoside modifications (BSN) that confer enhanced thermal stability to complexes formed between the oligonucleotide containing BSN and their complementary miRNA target strand. For example, in one embodiment, the antisense oligonucleotides contain at least one locked nucleic acid. Locked nucleic acids (LNAs) contain a 2'-0, 4'-C-methylene ribonucleoside (structure A) wherein the ribose sugar moiety is in a locked conformation. In another embodiment, the antisense oligonucleotides contain at least one 2', 4'-C-bridged 2' deoxyribonucleoside (CDNA, structure B). See, e.g., U.S. Pat. No. 6,403,566 and Wang et al., (1999) Bioorganic and Medicinal Chemistry Letters, Vol. 9: 1147-1150, both of which are herein incorporated by reference in their entireties. In yet another embodiment, the antisense oligonucleotides contain at least one modified nucleoside having the structure shown in structure C. The antisense oligonucleotides targeting miRNAs that regulate fat related metabolism and synthesis pathway targets can contain combinations of BSN (LNA, CDNA, and the like) or other modified nucleotides, and ribonucleotides or deoxyribonucleotides.

A.

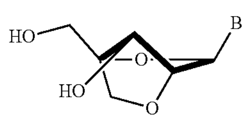

B.

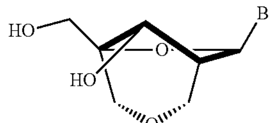

C.

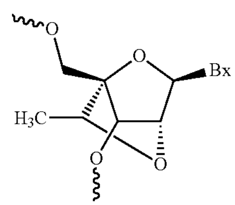

Alternatively, the antisense oligonucleotides can comprise peptide nucleic acids (PNAs), which contain a peptide-based backbone rather than a sugar-phosphate backbone. Other modified sugar or phosphodiester modifications to the antisense oligonucleotide are also contemplated. By way of non-limiting examples, other chemical modifications can include 2'-o-alkyl (e.g., 2'-0-methyl, 2'-o-methoxyethyl), 2'-fluoro, and 4'-thio modifications, and backbone modifications, such as one or more phosphorothioate, morpholino, or phosphonocarboxylate linkages (see, e.g., U.S. Pat. Nos. 6,693,187 and 7,067,641, which are herein incorporated by reference in their entireties). In one embodiment, antisense oligonucleotides targeting oncogenic miRNAs contain 2'-0-methyl sugar modifications on each base and are linked by phosphorothioate linkages. Antisense oligonucleotides, particularly those of shorter lengths (e.g., less than 16 nucleotides, 7-8 nucleotides) can comprise one or more affinity enhancing modifications, such as, but not limited to, LNAs, bicyclic nucleosides, phosphonoformates, 2' o-alkyl modifications, and the like. In some embodiments, suitable antisense oligonucleotides are 2'-0-methoxyethyl gapmers which contain 2'-O-methoxyethyl-modified ribonucleotides on both 5' and 3' ends with at least ten deoxyribonucleotides in the center. These gapmers are capable of triggering RNase H-dependent degradation mechanisms of RNA targets. Other modifications of antisense oligonucleotides to enhance stability and improve efficacy, such as those described in U.S. Pat. No. 6,838,283, which is herein incorporated by reference in its entirety, are known in the art and are suitable for use in the methods of the invention. For instance, and not intending to be limiting, to facilitate in vivo delivery and stability, the antisense oligonucleotide can be linked to a steroid, such as cholesterol moiety, a vitamin, a fatty acid, a carbohydrate or glycoside, a peptide, or other small molecule ligand at its 3' end.

In some embodiments, antisense oligonucleotides useful for inhibiting the activity of miRNAs, including, for example, miR-22, are about 5 to about 25 nucleotides in length, about 10 to about 30 nucleotides in length, or about 20 to about 25 nucleotides in length. In certain embodiments, antisense oligonucleotides targeting oncogenic miRNAs are about 8 to about 18 nucleotides in length, in other embodiments about 12 to about 16 nucleotides in length, and in other embodiments about 7 to about 8 nucleotides in length. Any 7-mer or longer complementary to an oncogenic miRNA may be used, i.e., any anti-miR complementary to the 5' end of the miRNA and progressing across the full complementary sequence of the miRNA. By way of non-limiting example, the antisense oligonucleotides targeting oncogenic miRNAs, including, for example, miR-22, are about 5, or about 6, or about 7, or about 8, or about 9, or about 10, or about 11, or about 12, or about 13, or about 14, or about 15, or about 16, or about 17, or about 18, or about 19, or about 20, or about 21, or about 22, or about 23, or about 24, or about 25, or about 26, or about 27, or about 28, or about 29, or about 30 nucleotides in length.

Antisense oligonucleotides can comprise a sequence that is at least partially complementary to a mature or minor (i.e. star) oncogenic miRNA sequence, e.g., at least about 75%, 80%, 85%, 90%, 95%, 96%, 97%, 98%, or 99% complementary to a mature or minor (i.e., star) oncogenic miRNA sequence. In some embodiments, the antisense oligonucleotide can be substantially complementary to a mature or minor oncogenic miRNA sequence, that is at least about 90%, 95%, 96%, 97%, 98%, or 99% complementary to a target polynucleotide sequence. In one embodiment, the antisense oligonucleotide comprises a sequence that is 100% complementary to a mature or minor oncogenic miRNA sequence.

As used herein, substantially complementary refers to a sequence that is at least about 95%, 96%, 97%, 98%, 99%, or 100% complementary to a target polynucleotide sequence (non-limiting examples are mature, minor, precursor miRNA, or pri-miRNA sequence of, for example, miR-22).

In some embodiments, the antisense oligonucleotides are antagomirs. Antagomirs are single-stranded, chemically-modified ribonucleotides that are at least partially complementary to miRNAs and therefore may silence them. See, e.g., Kriitzfeldt, et al., Nature (2005) 438 (7068): 685-9. Antagomirs may comprise one or more modified nucleotides, such as 2'-0-methyl-sugar modifications. In some embodiments, antagomirs comprise only modified nucleotides. Antagomirs can also comprise one or more phosphorothioate linkages resulting in a partial or full phosphorothioate backbone. To facilitate in vivo delivery and stability, the antagomir can be linked to a cholesterol or other moiety at its 3' end. Antagomirs suitable for inhibiting can be about 15 to about 50 nucleotides in length, about 18 to about 30 nucleotides in length, and about 20 to about 25 nucleotides in length. The antagomirs can be at least about 75%, 80%, 85%, 90%, 95%, 96%, 97%, 98%, or 99% complementary to a mature or minor oncogenic miRNA sequence. In some embodiments, the antagomir may be substantially complementary to a mature or minor oncogenic miRNA sequence, that is at least about 95%, 96%, 97%, 98%, or 99% complementary to a target polynucleotide sequence. In other embodiments, the antagomirs are 100% complementary to a mature or minor oncogenic miRNA sequence.

Antisense oligonucleotides or antagomirs may comprise a sequence that is substantially complementary to a precursor miRNA sequence (pre-miRNA) or primary miRNA sequence (pri-miRNA) of an oncogenic miRNA. In some embodiments, the antisense oligonucleotide comprises a sequence that is located outside the 3'-untranslated region of a target of that miRNA. In some embodiments, the antisense oligonucleotide comprises a sequence that is located inside the 3'-untranslated region of a target of that miRNA.

Any of the inhibitors or agonists of the oncogenic miRNAs described herein, including but not limited to, miR-22, can be delivered to a target cell by delivering to the cell an expression vector encoding the miRNA inhibitors or agonists. A vector is a composition of matter which can be used to deliver a nucleic acid of interest to the interior of a cell. Numerous vectors are known in the art, including, but not limited to, linear polynucleotides, polynucleotides associated with ionic or amphiphilic compounds, plasmids, and viruses. Thus, the term vector includes an autonomously replicating plasmid or a virus. Examples of viral vectors include, but are not limited to, adenoviral vectors, adeno-associated virus vectors, retroviral vectors, and the like. An expression construct can be replicated in a living cell, or it can be made synthetically. For purposes of this application, the terms expression construct, expression vector, and vector are used interchangeably to demonstrate the application of the invention in a general, illustrative sense, and are not intended to limit the invention.

In one embodiment, an expression vector for expressing an inhibitor of an oncogenic miRNA, e.g., miR-22, comprises a promoter operably linked to a polynucleotide encoding an antisense oligonucleotide. The sequence of the expressed antisense oligonucleotide may be partially or perfectly complementary to a mature or minor sequence of an oncogenic miRNA. The phrase operably linked or under transcriptional control as used herein means that the promoter is in the correct location and orientation in relation to a polynucleotide to control the initiation of transcription by RNA polymerase and expression of the polynucleotide.

As used herein, a promoter refers to a DNA sequence recognized by the synthetic machinery of the cell, or introduced synthetic machinery, required to initiate the specific transcription of a gene. Suitable promoters include, but are not limited to, RNA pol I, pol II, pol III, and viral promoters (e.g., human cytomegalovirus (CMV) immediate early gene promoter, the SV40 early promoter, and the Rous sarcoma virus long terminal repeat).

In certain embodiments, the promoter operably linked to a polynucleotide encoding a miRNA inhibitor or a polynucleotide encoding a metabolism gene regulating miRNA and/or miRNA targeting genes of markers linked to metabolic etiologies can be an inducible promoter. Inducible promoters are known in the art and include, but are not limited to, the tetracycline promoter, the metallothionein IIA promoter, the heat shock promoter, the steroid/thyroid hormone/retinoic acid response elements, the adenovirus late promoter, and the inducible mouse mammary tumor virus LTR.

Methods of delivering expression constructs and nucleic acids to cells are known in the art and can include, by way of non-limiting example, calcium phosphate co-precipitation, electroporation, microinjection, DEAE-dextran, lipofection, transfection employing polyamine transfection reagents, cell sonication, gene bombardment using high velocity microprojectiles, and receptor-mediated transfection.

The present invention also includes scavenging or clearing inhibitors of oncogenic miRNAs following treatment. Scavengers may include isolated nucleic acids that are complementary to miRNA inhibitors or vectors expressing the same. Therefore, they may bind to miRNA inhibitors or vectors expressing the same and, in doing so, prevent the binding between miRNA and target.

In some embodiments, the present disclosure provides a method of treating or preventing a metabolic disorder in a subject in need thereof. In some embodiments, the present disclosure provides a method of treating or preventing metabolic disorder, including Obesity, Prader-Willi Syndrome, Hypercholesterolemia, Fatty Liver Disease, Non Alcoholic Fatty Liver Disease (NAFLD) and/or Non-Alcoholic Steatohepatitis (NASH) in a subject.

Metabolic Disorders

The term "metabolic disorder" as used in context of this invention refers to a disease or condition that is impacted by the presence, level or activity of brown adipose tissue, plasma glucose concentration, plasma insulin level and/or body fat content. In some embodiments, the metabolic disorder or condition also includes, but is not limited to, Metabolic Syndrome, impaired glucose tolerance, elevated plasma insulin concentrations and insulin resistance, dyslipidemia, hyperglycemia, hyperlipidemia, hypertension, lipodystrophy, cardiovascular disease, respiratory problems or conditions. Metabolic disorders of particular interest are Obesity, Prader-Willi Syndrome, Hypercholesterolemia, Fatty Liver Disease, including Non-Fatty Acid Liver Disease (NAFLD) and/or Non-Alcoholic Steatohepatitis (NASH).

Obesity

In some embodiments, the present disclosure relates to obesity. Obesity is a chronic disease that is highly prevalent in modern society and is associated not only with a social stigma, but also with decreased life span and numerous medical problems, including diabetes mellitus, insulin resistance, hypertension, hypercholesterolemia, cholelithiasis, osteoarthritis, orthopedic injury, thromboembolic disease, cancer, and coronary heart disease. Rissanen et al., British Medical Journal, 301: 835-837 (1990). In some embodiments, Obesity can be calculated using the body mass index (BMI: body weight per height in meters squared). In some embodiments, obesity is defined as an otherwise healthy subject that has a BMI greater than or equal to 30 kg/m2, or a condition whereby a subject with at least one co-morbidity has a BMI greater than or equal to 27 kg/m2. In some embodiments of the method of the disclosure, the subject is obese and has a body mass index of greater than about 30. In some embodiments, the subject is overweight and has a body mass index of about 25-29.9. In some embodiments, the method induces weight loss. In some embodiments, the method prevents weight gain. In some embodiments, the method prevents the growth of adipose tissue and impair adipocyte differentiation.

In some embodiments, the present disclosure provides for methods of treatment comprising administering an inhibitor of miR-22 (and compounds related to miR-22) and/or uses of miR-22 (and compounds related to miR-22) in the treatment of, or manufacture of a medicament for, obesity and overweight, and related conditions. In some embodiments, the present disclosure provides a method for treating or preventing obesity, comprising administering an effective amount of miR-22 (and compounds related to inhibiting miR-22) to a patient in need thereof. In some aspects, the present disclosure provides a method for weight management, comprising administering an effective amount of an inhibitor of miR-22 (and compounds related to inhibiting miR-22) to induce weight loss and/or to prevent weight gain in a patient in need thereof.

In some embodiments, the present disclosure relates to a method for inducing weight loss or preventing weight gain (or treating or preventing obesity or inducing weight loss or preventing weight gain in a patient that does not substantially change caloric intake), comprising administering an effective amount of an inhibitor of miR-22 (and compounds related to miR-22) to a patient that: has undertaken or will undertake a surgery of the digestive system; is greater than about 80-100 pounds overweight; has a BMI of greater than about 35; or has a health problem related to obesity.

In some embodiments the surgery of the digestive system is one or more of those classified under ICD-9-CM: Operations on the Digestive System and therefore may include Operations on esophagus; Incision and excision of stomach; Other operations on stomach; Incision, excision, and anastomosis of intestine; Other operations on intestine; Operations on appendix; Operations on rectum, rectosigmoid and perirectal tissue; Operations on anus; Operations on liver; Operations on gallbladder and biliary tract; Operations on pancreas; Repair of hernia; and Other operations on abdominal region.

In some embodiments, the surgery of the digestive system is one or more of a restrictive surgery and/or malabsorptive procedure, including, for example, vertical banded gastroplasty (VBG, e.g., stomach stapling); gastric banding (e.g., LAP-BAND or REALIZE); sleeve gastrectomy; gastric bypass surgery (e.g., Roux-en-Y gastric bypass), biliopancreatic diversion and a cosmetic surgery (e.g., liposuction, such as, for example, suction-assisted liposuction (SAL); ultrasound-assisted liposuction (UAL); power-assisted liposuction (PAL); twin-cannula (assisted) liposuction (TCAL or TCL); external ultrasound-assisted liposuction (XUAL or EUAL); water-assisted liposuction (WAL); laser assisted liposuction; tumescent liposuction; and cryolipolysis).

In some embodiments, the health problem related to obesity is selected from cardiovascular diseases (e.g., high cholesterol, hypercholesterolemia, low HDL, high HDL, hypertension, coronary artery disease, heart failure), sleep apnea (including obstructive sleep apnea), osteoarthritis, thyroid problems, dementia, gout, asthma, gastroesophageal reflux disease, and chronic renal failure. In some embodiments, the health problem related to obesity is heart disease, sleep apnea, or high cholesterol.

In some aspects, the present disclosure provides for uses and methods for inducing weight loss or preventing weight gain, comprising administering an effective amount of an inhibitor of miR-22 (and compounds related to inhibiting miR-22) to a patient in need thereof; wherein the patient does not substantially change caloric intake. In some embodiments, the caloric intake is high, relative to guidelines, such as the USDA tables. In some embodiments, the patient's caloric intake is 2000-10000 calories/day, or greater than about 2000 calories/day, or about 2200 calories/day, or about 2400 calories/day, or about 2600 calories/day, or about 2800 calories/day, or about 3000 calories/day, or about 3200 calories/day, or about 3400 calories/day, or about 3600 calories/day, or about 3800 calories/day, or about 4000 calories/day, or about 5000 calories/day, or about 6000 calories/day. In some embodiments, the patient has a high caloric intake and does not gain weight or even loses weight. Therefore, the present disclosure provides for an effect without life style changes that often reduce patient adherence (e.g., failed dieting). In some embodiments, the patient's caloric intake is not restricted by more than about 20%, or not by more than about 10%, or not by more than about 5% of the patient's caloric intake at the start of treatment. In some embodiments, a high proportion of the patient's caloric intake is "empty calories," i.e. calories from solid fats and/or added sugars. In some embodiments, greater than about 15%, or 20%, or 25%, or 30%, or 35%, or 50% of the patient's caloric intake is empty calories. Even in these embodiments, a patient may not gain weight or even lose weight.

In some embodiments, the patient of the present disclosure is overweight or obese. In some embodiments, the patient of the present disclosure suffers from central obesity. In some embodiments, the obesity of one of simple obesity (alimentary obesity; usually resulting from consumption of more calories than the body can utilize), secondary obesity (usually resulting from an underlying medical condition, such as, for example, Cushing's syndrome and polycystic ovary syndrome), and childhood obesity. In some embodiments, the obesity is classified as: Class I, which includes a BMI between 30 and 34.99; Class II, which includes BMIs of 35 to 39.99; and Class III, which includes a BMI of over 40. Further, the present disclosure provides for obesity of any of classes I, II, or III that is further classified as severe, morbid, and super obesity. In some embodiments, the patient is at risk of further weight gain, as assessed by, for example, daily caloric intake.

In some embodiments, the weight management/weight loss/anti-obesity effects of an inhibitor of miR-22 (and compounds related to miR-22) can be assessed using various techniques and indices. In some embodiments, assessment before, during, and after treatment is undertaken. In some embodiments, body mass index (BMI), a measure of a person's weight taking into account height, may be used. In some embodiments, a patient described herein has a BMI that provides an "overweight" classification, i.e. 25-29.9, such as, for example, about 25, or about 25.5, or about 26, or about 26.5, or about 27, or about 27.5, or about 28, or about 28.5, or about 29, or about 29.5. In some embodiments, a patient described herein has a BMI that provides an "obese" classification, i.e. greater than 30, such as, for example, about 30, or about 31, or about 32, or about 33, or about 34, or about 35, or about 36, or about 37, or about 38, or about 39, or about 40, or about 50. In some embodiments, body volume index (BVI) is used. BVI uses 3D software to create a 31) image of a person so BVI can differentiate between people with the same BMI rating, but who have a different shape and different weight distribution. BVI measures where a person's weight and the fat are located on the body, rather than total weight or total fat content and places emphasis on the weight carried around the abdomen, commonly known as central obesity. In some embodiments, whole-body air displacement plethysmography (ADP) is used to assess the weight management/weight loss/anti-obesity effects of miR-22 (and compounds related to miR-22). In some embodiments, simple weighing is used in the present invention. In some embodiments, skinfold calipers or "pinch test," bioelectrical impedance analysis, hydrostatic weighing, or dual-energy X-ray absorptiometry (DEXA) may be used.

In some embodiments, simple circumferential measurement of the body may be used. In some embodiments, a patient of the present disclosure has a waist circumference exceeding about 35 inches, or about 36 inches, or about 37 inches, or about 38 inches, or about 39 inches, or about 40 inches, or about 41 inches, or about 42 inches, or about 43 inches, or about 44 inches, or about 45 inches, or about 46 inches, or about 47 inches, or about 48 inches, or about 50 inches, or about 55 inches, or about 60 inches. In some embodiments, the patient is male human with a waist circumference exceeding 40 inches. In some embodiments, the patient is a female human with a waist circumference exceeding 35 inches.

The methods of the disclosure may be used to treat humans having a body fat percentage above the recommended body fat percentage, i.e., at least in the "overweight" range, or at least in the "obese" range. The body fat percentage will differ between women and men. Specifically, for women, the methods of the disclosure may be used to treat a female human having a body fat percentage of at least about 25%, above 25%, at least about 32%, or above 32%. For men, the methods of the disclosure may be used to treat a male human having a body fat percentage of at least about 14%, above 14%, at least about 18%, above 18%, at least about 25%, or above 25%. Body fat percentage may be estimated using any method accepted in the art, including, for example, near infrared interactance, dual energy X-ray absorptiometry, body density measurement, bioelectrical impedance analysis, and the like.

The methods of the disclosure may be used to treat a patient who is a man that is greater than 100 pounds' overweight and/or has waist circumference exceeding 40 inches. The methods of the disclosure may be used to treat a patient who is a woman that is greater than 80 pounds' overweight and/or waist circumference exceeding 35 inches.

In some embodiments, the disclosure provides for an inhibitor of miR-22 (and compounds related to inhibiting miR-22) being used to treat and/or prevent certain disorders associated with being overweight. For example, miR-22 (and compounds related to miR-22) find use in cardiovascular diseases (e.g., high cholesterol, hypercholesterolemia, low HDL, high HDL, hypertension, coronary artery disease, heart failure), sleep apnea (including obstructive sleep apnea), osteoarthritis, thyroid problems, dementia, gout, asthma, gastroesophageal reflux disease, and chronic renal failure.

In some embodiments, the inhibitor of miR-22 (and compounds related to miR-22) administration and/or use prevents or reduces the growth of adipose tissue. In some embodiments. miR-22 (and compounds related to miR-22) effects one or more of white adipose tissue (WAT) and brown adipose tissue (BAT), including, for example, visceral adipose tissue (VAT), abdominal subcutaneous adipose tissue (ASAT), or ectopic fat. Such an effect may be assessed by, for example, using any of the techniques described herein (e.g., BMI, weight for-stature indexes, skinfold measures, electrical bioimpedance analysis, etc.), as well as various imaging techniques, including computed tomography (CT), magnetic-resonance imaging (MRI, including transverse body scans), dual energy X-ray absorptiometry (DXA).

miR-22 (and compounds related to miR-22) may also be used in combination with dietary therapy, behavioral therapy, physical therapy, exercise, and weight loss surgery, or a combination of two or more such therapies. In some embodiments, the subject is on a calorie restricted diet. In some embodiments, the subject engages in or is to engage in a physical exercise or physical therapy regimen. In some embodiments, the subject has undergone, or will undergo, weight loss surgery. In some embodiments, an inhibitor of miR-22 (and compounds related to inhibiting miR-22) may be in combination with additional agents or may be administered to patient undergoing treatment with various agents.

For example, including, but not limited to, embodiments pertaining to obesity and/or weight reduction/loss, the additional agents may include one or more of orlistat (e.g., ALLI, XENICAL), loracaserin (e.g., BELVIQ), phentermine-topiramate (e.g., QSYMIA), sibutramine (e.g., REDUCTIL or MERIDIA), rimonabant (ACOMPLIA), exenatide (e.g., BYETTA), pramlintide (e.g., SYMLIN) phentermine, benzphetamine, diethylpropion, phendimetrazine, bupropion, and metformin.

Agents that interfere with the body's ability to absorb specific nutrients in food are among the additional agents, e.g., orlistat (e.g., ALLI, XENICAL), glucomannan, and guar gum. Agents that suppress apetite are also among the additional agents, e.g. catecholamines and their derivatives (such as phentermine and other amphetamine-based drugs), various antidepressants and mood stabilizers (e.g., bupropion and topiramate), anorectics (e.g., dexedrine, digoxin). Agents that increase the body's metabolism are also among the additional agents.

In some embodiments, additional agents may be selected from among appetite suppressants, neurotransmitter reuptake inhibitors, dopaminergic agonists, serotonergic agonists, modulators of GABAcrgic signaling, anticonvulsants, antidepressants, monoamine oxidase inhibitors, substance P (NK1) receptor antagonists, melanocortin receptor agonists and antagonists, lipase inhibitors, inhibitors of fat absorption, regulators of energy intake or metabolism, cannabinoid receptor modulators, agents for treating addiction, agents for treating metabolic syndrome, peroxisome proliferator-activated receptor (PPAR) modulators; dipeptidyl peptidase 4 (DPP-4) antagonists, agents for treating cardiovascular disease, agents for treating elevated triglyceride levels, agents for treating low HDL, agents for treating hypercholesterolemia, and agents for treating hypertension. Some agents for cardiovascular disease include statins (e.g., lovastatin, atorvastatin, fluvastatin, rosuvastatin, simvastatin and pravastatin) and omega-3 agents (e.g., LOVAZA, EPANOVA, VASCEPA, esterified omega-3's in general, fish oils, krill oils, algal oils). In some embodiments, additional agents may be selected from among amphetamines, benzodiazepines, sulfonyl ureas, meglitinides, thiazolidinediones, biguanides, beta-blockers. ACE inhibitors, diuretics, nitrates, calcium channel blockers, phenlermine, sibutramine, lorcaserin, cetilistat, rimonabant, taranabant, topiramate, gabapentin, valproate, vigabatrin, bupropion, tiagabine, sertraline, fluoxetine, trazodone, zonisamide, methylphenidate, varenicline, naltrexone, diethylpropion, phendimetrazine, repaglinide, nateglinide, glimepiride, metformin, pioglitazone, rosiglilazone, and sitagliptin.

Prader-Willi Syndrome

In some embodiments, the method relates to Prader-Willi syndrome. Prader-Willi syndrome is a complex genetic condition that affects many parts of the body. In infancy, the condition is characterized by weak muscle tone (hypotonia), feeding difficulties, poor growth, and delayed development. Beginning in childhood, affected individuals develop an insatiable appetite, which leads to chronic overeating (hyperphagia) and obesity. In some embodiments, the subject is suffering from Prader-Willi syndrome. In some embodiments, Prader-Willi syndrome, particularly those with obesity, also develop type 2 diabetes mellitus.

Fatty Liver Disease

In some embodiments, the method of the disclosure relates to Fatty Liver Disease. A substantial fraction of the population is affected by fatty liver disease, also known as nonalcoholic steatohepatitis (NASH). NASH is often associated with obesity and diabetes. Hepatic steatosis, the presence of droplets of triglycerides with hepatocytes, predisposes the liver to chronic inflammation (detected in biopsy samples as infiltration of inflammatory leukocytes), which can lead to fibrosis and cirrhosis. Fatty liver disease is generally detected by observation of elevated serum levels of liver-specific enzymes such as the transaminases ALT and AST, which serve as indices of hepatocyte injury, as well as by presentation of symptoms which include fatigue and pain in the region of the liver, though definitive diagnosis often requires a biopsy. The anticipated benefit is a reduction in liver inflammation and fat content, resulting in attenuation, halting, or reversal of the progression of NASH toward fibrosis and cirrhosis. In some embodiments, the method reduces or prevents liver steatosis. In some embodiments, the method reduces or prevents liver fibrosis.

In some embodiments, the method is a method of treating NASH by administering the inhibitor of miR-22 described herein. The NASH patient can be a high risk NASH patient. A "high risk NASH patient" refers to characterization by one or more of: NAS≥4; baseline fibrosis stage 2 or 3; or baseline fibrosis stage 1 with a comorbidity (type 2 diabetes, BMI≥30 kg/m2 or ALT≥60 U/L).

In some embodiments, the inhibitor of miR-22 reduces one or more of steatosis, mixed acinar inflammation, and hepatocellular ballooning and/or pericellular fibrosis.

In some embodiments, the inhibitor of miR-22 reduces one or more of steatosis.

In some embodiments, the inhibitor of miR-22 treats mild, grade 1 NASH, or moderate, grade 2 NASH, or severe, grade 3 NASH, as described in Brunt, et al. Am. J. Gastroenterology, Vol. 94, No. 9 (1999), the entirety of which is incorporated by reference in its entirety:

| | |
|---|---|
| Mild, grade 1 | Steatosis (predominantly macrovesicular) involving up to 66% of biopsy; may see occasional ballooned zone 3 hepatocytes; scattered rate intra-acinar pmn's ± intra-acinar lymphocytes; no or mild portal chronic inflammation. |
| Moderate, grade 2 | Steatosis of any degree; ballooning of hepatocytes (predominantly zone 3) obvious; intra-acinar pmn's noted, may be associated with zone 3 pericellular fibrosis; portal and intra-acinar chronic inflammation noted, mild to moderate. |
| Severe, grade 3 | Panacinar steatosis; ballooning and disarray obvious, predominantly in zone 3; intra-acinar inflammation noted as scattered pmn's, pms's associated with ballooned hepatocytes ± mild chronic inflammation; portal chronic inflammation mild or moderate, not marked. |

In some embodiments, the inhibitor of miR-22 treats NASH of any of the following stages: Stage 0, No fibrosis; Stage 1, Zone 3 pericellular/sinusoidal fibrosis, focal or extensive; Stage 2, as in stage 1 plus portal fibrosis, focal or extensive; Stage 3, bridging fibrosis, focal or extensive; and Stage 4 cirrhosis (+/−residual pericellular fibrosis).

In some embodiments, the inhibitor of miR-22 treats NASH of any activity score (NAS), as described in Kleiner, et al., Hepatology, 2005. 41(6): p. 1313-21, the entirety of which is incorporated by reference in its entirety:

| Histological feature | Definition | Score |
|---|---|---|
| Steatosis | <5% | 0 |
| | 5-33% | 1 |
| | 33-66% | 2 |
| | >66% | 3 |
| Lobular inflammation* | None | 0 |
| | <2 foci | 1 |
| | 2-4 foci | 2 |
| | >4 foci | 3 |
| Ballooning** | None | 0 |
| | Few cells | 1 |
| | Prominent | 2 |

*The number of foci was counted per 200x field for lobular inflammation

**Few ballooned cells indicate rare but definite ballooned hepatocytes as well as cases that are diagnostically borderline In some embodiments, the inhibitor of miR-22 reduces the NASH to less than 8, or less than 7, or less than 6, or less than 5, or less than 4, or less than 3, or less than 2, or less than 1. In some embodiments, the AP-based reduces the NAS to about 7, or to about 6, or less than 5, or less than 4, or to about 3, to about 2, or to about 1.

In some embodiments, the inhibitor of miR-22 reduces steatosis by about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95%.

In some embodiments, the inhibitor of miR-22 reduces lobular inflammation to less than 4 foci, or less than 3 foci, or less than 2 foci, or less than 1 focus.

In some embodiments, the inhibitor of miR-22 reduces ballooning to a score of 0 or 1 per the scale above.

In some embodiments, the inhibitor of miR-22 treats a subject at risk for NASH, such as a subject suffering from various acquired metabolic diseases, such as obesity, diabetes (e.g., type 2), hypertriglyceridemia, rapid weight loss, and malnutrition. In some embodiments, the inhibitor of miR-22 treats a subject at risk for NASH, such as a subject suffering from various genetic metabolic diseases, such as Wilson disease, tyrosinemia, and abetalipoproteinemia. In some embodiments, the inhibitor of miR-22 treats a subject at risk for NASH, such as a subject suffering from various other factors such as lipodystrophy and jejunoileal bypass. In some embodiments, the inhibitor of miR-22 treats a subject at risk for NASH, such as a subject undergoing treatment with one or more of amiodarone, chemotherapeutic agents (e.g., irinotecan), tamoxifen, steroids, estrogens, diethylstilbestrol, methotrexate, calcium channel blockers (e.g., nifedipine, verapamil, and diltiazem).

In some embodiments, the present disclosure provides methods that reduce or prevent fibrosis. Direct markers of fibrosis include procollagen type (I, III, IV), matrix metalloproteinases, cytokines, and chemokines. In some embodiments, the present invention provides methods that reduce or prevent enhancement of extracellular matrix synthesis, e.g., by activated stellate cells. In some embodiments, the present invention provides methods that modulate levels of TIMP-1. In some embodiments, the present disclosure provides methods that reduce or prevent serum levels of hyaluronic acid.

In some embodiments, the effect of the inhibitor of miR-22 is monitored using tests that monitor one or more of combines hyaluronic acid, tissue inhibitor of a metalloproteinase-1 (TIMP-1), and alpha-2-macroglobulin (e.g., FIBROSpect II).

In some embodiments, the present invention provides methods that reduce or prevent cirrhosis.

In some embodiments, the present disclosure provides methods that modulate one or more of platelet count, prothrombin time, albumin, total bilirubin, and serum aminotransferase. In some embodiments, the present invention provides methods that modulate serum fibrotic markers, such as hyaluronic acid (HA) and alpha-2-macroglobulin.

Hypercholesterolemia

In some embodiments, the method of the disclosure relates to hypercholesterolemia. Hypercholesterolemia is a condition characterized by elevated serum cholesterol. Elevated serum cholesterol levels affect a substantial fraction of the population and are an important risk factor for atherosclerosis and myocardial infarction. Cholesterol-lowering drugs such as HMG-CoA reductase inhibitors (statins) can be administered to hypercholesterolemia patients in addition to agents of the invention, optionally incorporated into the same pharmaceutical. In some embodiments, the hypocholesterolemia is on-familial hypercholesterolemia which is a condition characterized by elevated serum cholesterol that is not the result of a single gene mutation. In some embodiments, the hypercholesterolemia is polygenic hypercholesterolemia which is a condition characterized by elevated cholesterol that results from the influence of a variety of genetic factors. In certain embodiments, polygenic hypercholesterolemia may be exacerbated by dietary intake of lipids. In some embodiments, the hypercholesterolemia is Familial hypercholesterolemia (FH) which is an autosomal dominant metabolic disorder characterized by a mutation in the LDL-receptor (LDL-R) gene, markedly elevated LDL-C and premature onset of atherosclerosis. A diagnosis of familial hypercholesterolemia is made when an individual meets one or more of the following criteria: genetic testing confirming 2 mutated LDL-receptor genes; genetic testing confirming one mutated LDL-receptor gene; document history of untreated serum LDL-cholesterol greater than 500 mg/dL; tendinous and/or cutaneous xanthoma prior to age 10 years; or, both parents have documented elevated serum LDL-cholesterol prior to lipid-lowering therapy consistent with heterozygous familial hypercholesterolemia. In some embodiments, the hypercholesterolemia is Homozygous familial hypercholesterolemia or HoFH which is a condition characterized by a mutation in both maternal and paternal LDL-R genes. In some embodiments, the hypercholesterolemia is Heterozygous familial hypercholesterolemia or HeFH which is a condition characterized by a mutation in either the maternal or paternal LDL-R gene.

In some embodiments of the methods of the disclosure, the wild type human FTO gene of the disclosure consists of or comprises the nucleic acid sequence (Genbank Accession number: NM_001080432.2; SEQ ID NO: 13).

In some embodiments of the methods of the disclosure, the wild type human FTO gene of the disclosure consists of or comprises the amino acid sequence (Genbank Accession number: NP 001073901.1; SEQ ID NO: 14).

In some embodiments of the methods of the disclosure, the wild type human CEBPa gene of the disclosure consists of or comprises the nucleic acid sequence (Genbank Accession number: NM_004364.4, transcript variant 1; SEQ ID NO: 15).

In some embodiments of the methods of the disclosure, the wild type human CEBPa gene of the disclosure consists of or comprises the amino acid sequence (Genbank Accession number: NP 004355.2, transcript variant 1; SEQ ID NO: 16).

In some embodiments of the methods of the disclosure, the wild type human CEBPa gene of the disclosure consists of or comprises the nucleic acid sequence (Genbank Accession number: NM_001285829.1, transcript variant 2; SEQ ID NO: 17).

In some embodiments of the methods of the disclosure, the wild type human CEBPa gene of the disclosure consists of or comprises the amino acid sequence (Genbank Accession number: NM_001285829.1, transcript variant 2; SEQ ID NO: 18).

In some embodiments of the methods of the disclosure, the wild type human CEBPa gene of the disclosure consists of or comprises the nucleic acid sequence (Genbank Accession number: NM_001287424.1, transcript variant 3; SEQ ID NO: 19).

In some embodiments of the methods of the disclosure, the wild type human CEBPa gene of the disclosure consists of or comprises the amino acid sequence (Genbank Accession number: NP_001274353.1, transcript variant 3; SEQ ID NO: 20).

In some embodiments of the methods of the disclosure, the wild type human CEBPa gene of the disclosure consists of or comprises the nucleic acid sequence (Genbank Accession number: NM_001287435.1, transcript variant 4; SEQ ID NO: 21).

In some embodiments of the methods of the disclosure, the wild type human CEBPa gene of the disclosure consists of or comprises the amino acid sequence (Genbank Accession number: NP_001274364.1, transcript variant 4; SEQ ID NO: 22).

In some embodiments of the methods of the disclosure, the wild type human PPARg gene of the disclosure consists of or comprises the nucleic acid sequence (Genbank Accession number: NM_138712.3, transcript variant 1; SEQ ID NO: 23).

In some embodiments of the methods of the disclosure, the wild type human PPARg gene of the disclosure consists of or comprises the amino acid sequence (Genbank Accession number: NP_619726.2, transcript variant 1; SEQ ID NO: 24).

In some embodiments of the methods of the disclosure, the wild type human PPARg gene of the disclosure consists of or comprises the nucleic acid sequence (Genbank Accession number: NM_015869.4, transcript variant 2; SEQ ID NO: 25).

In some embodiments of the methods of the disclosure, the wild type human PPARg gene of the disclosure consists of or comprises the amino acid sequence (Genbank Accession number: NP_056953.2, transcript variant 2; SEQ ID NO: 26).

In some embodiments of the methods of the disclosure, the wild type human PPARg gene of the disclosure consists of or comprises the nucleic acid sequence (Genbank Accession number: NM_138711.3, transcript variant 3; SEQ ID NO: 27).

In some embodiments of the methods of the disclosure, the wild type human PPARg gene of the disclosure consists of or comprises the amino acid sequence (Genbank Accession number: NP_619725.2, transcript variant 3; SEQ ID NO: 28).

In some embodiments of the methods of the disclosure, the wild type human PPARg gene of the disclosure consists of or comprises the nucleic acid sequence (Genbank Accession number: NM_005037.5, transcript variant 4; SEQ ID NO: 29).

In some embodiments of the methods of the disclosure, the wild type human PPARg gene of the disclosure consists of or comprises the amino acid sequence (Genbank Accession number: NP_005028.4, transcript variant 4; SEQ ID NO: 30).

In some embodiments of the methods of the disclosure, the wild type human PTEN gene of the disclosure consists of or comprises the nucleic acid sequence (Genbank Accession number: NM_000314.6, transcript variant 1; SEQ ID NO: 31).

In some embodiments of the methods of the disclosure, the wild type human PTEN gene of the disclosure consists of or comprises the amino acid sequence (Genbank Accession number: NP_000305.3, transcript variant 1; SEQ ID NO: 32).

In some embodiments of the methods of the disclosure, the wild type human PTEN gene of the disclosure consists of or comprises the nucleic acid sequence (Genbank Accession number: NM_001304717.2, transcript variant 1; SEQ ID NO: 33).

In some embodiments of the methods of the disclosure, the wild type human PTEN gene of the disclosure consists of or comprises the amino acid sequence (Genbank Accession number: NP_001291646.2, transcript variant 1; SEQ ID NO: 34).

In some embodiments of the methods of the disclosure, the wild type human PTEN gene of the disclosure consists of or comprises the nucleic acid sequence (Genbank Accession number: NM_001304718.1, transcript variant 2; SEQ ID NO: 35).

In some embodiments of the methods of the disclosure, the wild type human PTEN gene of the disclosure consists of or comprises the amino acid sequence (Genbank Accession number: NP_001291647.1, transcript variant 2; SEQ ID NO: 36).

In some embodiments of the methods of the disclosure, the wild type human TET2 gene of the disclosure consists of or comprises the nucleic acid sequence (Genbank Accession number: NM_001127208.2, transcript variant 1; SEQ ID NO: 37).

In some embodiments of the methods of the disclosure, the wild type human TET2 gene of the disclosure consists of or comprises the amino acid sequence (Genbank Accession number: NP_001120680.1, transcript variant 1; SEQ ID NO: 38).

In some embodiments of the methods of the disclosure, the wild type human TET2 gene of the disclosure consists of or comprises the nucleic acid sequence (Genbank Accession number: NM_017628.4, transcript variant 2; SEQ ID NO: 39).

In some embodiments of the methods of the disclosure, the wild type human TET2 gene of the disclosure consists of or comprises the amino acid sequence (Genbank Accession number: NP_060098.3, transcript variant 2; SEQ ID NO: 40).

In some embodiments of the methods of the disclosure, the wild type human BMP-7 gene of the disclosure consists of or comprises the nucleic acid sequence (Genbank Accession number: NM_001719.2, transcript variant 1; SEQ ID NO: 41).

In some embodiments of the methods of the disclosure, the wild type human BMP-7 gene of the disclosure consists of or comprises the amino acid sequence (Genbank Accession number: NP_001710.1, transcript variant 1; SEQ ID NO: 42).

In some embodiments of the methods of the disclosure, the wild type human SIRT-1 gene of the disclosure consists of or comprises the nucleic acid sequence (Genbank Accession number: NM_012238.4, transcript variant 1; SEQ ID NO: 43).

In some embodiments of the methods of the disclosure, the wild type human SIRT-1 gene of the disclosure consists of or comprises the amino acid sequence (Genbank Accession number: NP_036370.2, transcript variant 1; SEQ ID NO: 44).

In some embodiments of the methods of the disclosure, the wild type human SIRT-1 gene of the disclosure consists of or comprises the nucleic acid sequence (Genbank Accession number: NM_001142498.1, transcript variant 2; SEQ ID NO: 45).

In some embodiments of the methods of the disclosure, the wild type human SIRT-1 gene of the disclosure consists of or comprises the amino acid sequence (Genbank Accession number: NP_001135970.1, transcript variant 2; SEQ ID NO: 46).

In some embodiments of the methods of the disclosure, the wild type human SIRT-1 gene of the disclosure consists of or comprises the nucleic acid sequence (Genbank Accession number: NM_001314049.1, transcript variant 3; SEQ ID NO: 47).

In some embodiments of the methods of the disclosure, the wild type human SIRT-1 gene of the disclosure consists of or comprises the amino acid sequence (Genbank Accession number: NP_001300978.1, transcript variant 3; SEQ ID NO: 48).

In some embodiments of the methods of the disclosure, the wild type human PGC1-α gene of the disclosure consists of or comprises the nucleic acid sequence (Genbank Accession number NM_001330751, transcript variant 1; SEQ ID NO: 49).

In some embodiments of the methods of the disclosure, the wild type human PGC1a gene of the disclosure consists of or comprises the amino acid sequence (Genbank Accession number NP_001317680: transcript variant 2; SEQ ID NO: 50).

In some embodiments of the methods of the disclosure, the wild type human PGC1-α gene of the disclosure consists of or comprises the nucleic acid sequence (Genbank Accession number NM_013261, transcript variant 2; SEQ ID NO: 51).

In some embodiments of the methods of the disclosure, the wild type human PGC1a gene of the disclosure consists of or comprises the amino acid sequence (Genbank Accession number NP_037393: transcript variant 2; SEQ ID NO: 52).

In some embodiments of the methods of the disclosure, the wild type human PGC1-α gene of the disclosure consists of or comprises the nucleic acid sequence (Genbank Accession number NM_001330752.1, transcript variant 3; SEQ ID NO: 53).

In some embodiments of the methods of the disclosure, the wild type human PGC1a gene of the disclosure consists of or comprises the amino acid sequence (Genbank Accession number NP_001317681.1, transcript variant 3; SEQ ID NO: 54).

In some embodiments of the methods of the disclosure, the wild type human PGC1-α gene of the disclosure consists of or comprises the nucleic acid sequence (Genbank Accession number NM_001330753.1, transcript variant 4; SEQ ID NO: 55).

In some embodiments of the methods of the disclosure, the wild type human PGC1a gene of the disclosure consists of or comprises the amino acid sequence (Genbank Accession number NP_001317682, transcript variant 4; SEQ ID NO: 56).

In some embodiments of the methods of the disclosure, the wild type human SP-1 gene of the disclosure consists of or comprises the nucleic acid sequence (Genbank Accession number NM_138473.2; SEQ ID NO: 57).

In some embodiments of the methods of the disclosure, the wild type human SP-1 gene of the disclosure consists of or comprises the amino acid sequence (Genbank Accession number NP_612482; SEQ ID NO: 58).

In some embodiments of the methods of the disclosure, the wild type human FGF-21 gene of the disclosure consists of or comprises the nucleic acid sequence (Genbank Accession number NM_019113.3; SEQ ID NO: 59).

In some embodiments of the methods of the disclosure, the wild type human FGF-21 gene of the disclosure consists of or comprises the amino acid sequence (Genbank Accession number NP_061986.1; SEQ ID NO: 60).

In some embodiments of the methods of the disclosure, the wild type human UCP1 gene of the disclosure consists of or comprises the nucleic acid sequence (Genbank Accession number NM_021833.4; SEQ ID NO: 61).

In some embodiments of the methods of the disclosure, the wild type human UCP1 gene of the disclosure consists of or comprises the amino acid sequence (Genbank Accession number NP_068605.1; SEQ ID NO: 62).

In some embodiments of the methods of the disclosure, the wild type human DDIT-4 gene of the disclosure consists of or comprises the nucleic acid sequence (Genbank Accession number NM_019058.3; SEQ ID NO: 63).

In some embodiments of the methods of the disclosure, the wild type human DDIT-4 gene of the disclosure consists of or comprises the amino acid sequence (Genbank Accession number NP_061931.1; SEQ ID NO: 64).

In some embodiments of the methods of the disclosure, the wild type human METTL3 gene of the disclosure consists of or comprises the nucleic acid sequence (Genbank Accession number NM_019852.4; SEQ ID NO: 65).

In some embodiments of the methods of the disclosure, the wild type human METTL3 gene of the disclosure consists of or comprises the amino acid sequence (Genbank Accession number NP_062826.2; SEQ ID NO: 66).

In some embodiments of the methods of the disclosure, the wild type human FGF lgene of the disclosure consists of or comprises the nucleic acid sequence (Genbank Accession number NM_000800.4; SEQ ID NO: 67).

In some embodiments of the methods of the disclosure, the wild type human FGF1 gene of the disclosure consists of or comprises the amino acid sequence (Genbank Accession number NP_000791.1; SEQ ID NO: 68).

In some embodiments of the methods of the disclosure, the wild type human TP63 gene of the disclosure consists of or comprises the nucleic acid sequence (Genbank Accession number NM_001114978.1; SEQ ID NO: 69).

In some embodiments of the methods of the disclosure, the wild type human TP63 gene of the disclosure consists of or comprises the amino acid sequence (Genbank Accession number NP_001108450.1; SEQ ID NO: 70).

As used herein, the term subject or patient refers to any vertebrate including, without limitation, humans and other primates (e.g., chimpanzees and other apes and monkey species), farm animals (e.g., cattle, sheep, pigs, goats, and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some embodiments, the subject is a mammal. In some embodiments, the subject is a human.

Another embodiment of the present invention is a pharmaceutical composition, or use of pharmaceutical composition, comprising an inhibitor of a miRNA, such as miR-22, and a pharmaceutically acceptable carrier. Where clinical applications are contemplated, pharmaceutical compositions may be prepared in a form appropriate for the intended application. Generally, this will entail preparing compositions that are essentially free of pyrogens, as well as other impurities that could be harmful to humans or animals.

In one embodiment, a pharmaceutical composition comprises an effective dose of a miRNA inhibitor, by way of non-limiting example, an antisense oligonucleotide directed to miR-22, and a pharmaceutically acceptable carrier. An effective dose is an amount sufficient to affect a beneficial or desired clinical result. An effective dose of a miRNA inhibitor of the invention may be from about 1 mg/kg to about 100 mg/kg, about 2.5 mg/kg to about 50 mg/kg, or about 5 mg/kg to about 25 mg/kg. The precise determination of what would be considered an effective dose may be based on factors individual to each patient, including their size, age, type of metabolic disorder, and nature of inhibitor or agonist (non-limiting examples include antagomir, expression construct, antisense oligonucleotide, polynucleotide duplex, etc.). Therefore, dosages can be readily ascertained by those of ordinary skill in the art from this disclosure and the knowledge in the art. For example, doses may be determined with reference Physicians' Desk Reference, 66th Edition, PDR Network; 2012 Edition (Dec. 27, 2011), the contents of which are incorporated by reference in its entirety.

A beneficial or desired treatment result may include, inter alia, a reduction a body mass index, weight loss or a marker that is associated with the presence of metabolic disorder as compared to what is observed without administration of the inhibitor. A beneficial or desired treatment result may also include, inter alia, an increased or decreased presence of a marker or gene that is associated with a reduction of metabolic disorder as compared to what is observed without administration of the inhibitor. In some embodiments, the marker or gene is fat mass and obesity-associated protein (FTO), CEBPa, and/or PPARγ, ALKBH5, and ACLY. In some embodiments, there is a perturbation in activity and/or expression of FTO, CEBPa, PPARa, ACLY, SP-1, PGC1a, ALKBH5, SIRT-1, TP63, FGF1, and/or DDIT4. In some embodiments, the marker or gene is fat mass and obesity-associated protein (FTO).

Colloidal dispersion systems, such as macromolecule complexes, nanocapsules, microspheres, beads, and lipid-based systems including oil-in-water emulsions, micelles, mixed micelles, and liposomes, may be used as delivery vehicles for the oligonucleotide inhibitors of oncogenic miRNA function, polynucleotides encoding Fat related metabolism and synthesis pathway targets miRNA agonists, or constructs expressing particular miRNA inhibitors or agonists. Commercially available fat emulsions that are suitable for delivering the nucleic acids of the disclosure to adipose tissues (e.g., adipocytes) include INTRALIPIDO, LIPOSYN®, LIPOSYN® II, LIPOSYN® III, Nutrilipid, and other similar lipid emulsions. A colloidal system for use as a delivery vehicle in vivo is a liposome (i.e., an artificial membrane vesicle). The preparation and use of such systems is well known in the art. Exemplary formulations are also disclosed in U.S. Pat. Nos. 5,981,505; 6,217,900; 6,383,512; 5,783,565; 7,202,227; 6,379,965; 6,127,170; 5,837,533; 6,747,014; and WO03/093449, which are herein incorporated by reference in their entireties.

One will generally desire to employ appropriate salts and buffers to render delivery vehicles stable and allow for uptake by target cells. Aqueous compositions of the present invention comprise an effective amount of the delivery vehicle comprising the inhibitor polynucleotides (e.g., liposomes or other complexes or expression vectors) dissolved or dispersed in a pharmaceutically acceptable carrier or aqueous medium. The phrases pharmaceutically acceptable or pharmacologically acceptable refer to molecular entities and compositions that do not produce adverse, allergic, or other untoward reactions when administered to an animal or a human. As used herein, pharmaceutically acceptable carrier includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or polynucleotides of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection, or by direct injection into adipose tissue. The agents disclosed herein may also be administered by catheter systems. Such compositions would normally be administered as pharmaceutically acceptable compositions as described herein.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

Upon formulation, solutions may be administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic with, for example, sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion (see, e.g., Remington Pharmaceutical Sciences, 15th Edition, pages 1035-1038 and 1570-1580, the contents of which are hereby incorporated by reference). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by the FDA Office of Biologics standards.

In some embodiments, of the present disclosure includes a method of treating or preventing metabolic disorder in a subject in need thereof comprising administering to the subject: a first inhibitor of a first miRNA, wherein the miRNA is miR-22 and a second inhibitor of a second miRNA, wherein the miRNA is a regulator of a metabolism-related gene. In some embodiments, the second miRNA is a known miR inhibitor, including, by way of non-limiting example, those disclosed in International Patent Publication No. WO 2012/142313, the contents of which are hereby incorporated by reference in their entirety. In some embodiments, the first and second inhibitors may be administered in either order (e.g., first then second or second then first) or concurrently.

In some embodiments, of the present disclosure includes a method of treating or preventing metabolic disorder in a subject in need thereof comprising administering to the subject a first agent that is or comprises an inhibitor of miR-22 and a second agent that is or comprises at least one other metabolic disorder biologic, therapeutic or drug. In some embodiments, the first and second inhibitors may be administered in either order (e.g., first then second or second then first) or concurrently.

The invention also provides kits that can simplify the administration of any agent described herein, such as an inhibitor of an oncogenic miRNA, including antisense oligonucleotide directed to miR-22. An exemplary kit of the invention comprises any composition described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can further comprise one or more additional agent, such as a second inhibitor of an oncogenic miRNA, or a biologic, therapeutic, chemotherapeutic or drug described herein. In one embodiment, the kit comprises a container containing an effective amount of a composition of the invention and an effective amount of another composition, such those described herein.

EXAMPLES

In order that the invention disclosed herein may be more efficiently understood, examples are provided below. It should be understood that these examples are for illustrative purposes only and are not to be construed as limiting the invention in any manner.

Example 1: MiR-22 Role in Obesity miR-22 directly targets PTEN and TET to promote tumorigenesis, metastasis and other metabolic disorders. More than 60 PTEN-targeting miRNAs and no less than 30 new proto-oncogenic genetic loci were studied in human cancer. Highly conserved evolutionarily among vertebrates and ubiquitously expressed in various tissues, (Lagos-Quintana et al., 2001, 2002; Neely et al., 2006). By targeting PTEN, miR-22 is remains metabolically relevant, as PTEN lowering or its elevation triggers a Warburg- or an anti-Warburg metabolic state respectively. FIG. 2A-D shows that miR-22 overexpression affects weight of mice.

miR-22 Knockout Approach

To assess whether, the effect on a mouse's weight and fat accumulation is due to miR-22 overexpression and to evaluate the differential increase in mice weight during the time and differential consumption of food, 2 month old mice (start day), Wildtype (Wt) and miR-22 Transgenic (Tg) mice were placed on a High Fat (60%) Diet. Mice Weight was monitored 2 times/week and food usage monitored 1 time/week. (see FIG. 3A-C and FIG. 4A-F). Transgenic miR-22 (Tg) mice developed an obese phenotype on a Non-Diet (ND) while miR-22 Knockout mice (KO) mice failed to gain weight on HFD. Mouse Embryonic Fibroblast (MEF) miR-22 deficient cells showed an impaired ability to differentiate in adipocytes. This phenotype is correlated with a differential gene expression for a panel of different genes that are involved in adipocyte differentiation and generally in fat metabolism. Father, results indicate that the effect of miR-22 on weight gain is Leptin (or Leptin like) independent (see FIGS. 5A-D and FIG. 6).

Example 2: Inhibition of miR-22 as Therapy for Obesity

All the LNA anti-miR-22 are useful in both human and mouse. Host gene showed a 49% complementarity between human and mouse and LNA anti HG-miR-22 works predominately in human.

Design of Anti-miR-22 Locked Nucleic Acid (LNA)

LNA was designed to cover the seed sequence, contain between 8 nt and 20 nt in length, have a length-specific fraction of LNAs allowed and as high a binding affinity to miR-22 as possible.

Figure 33:
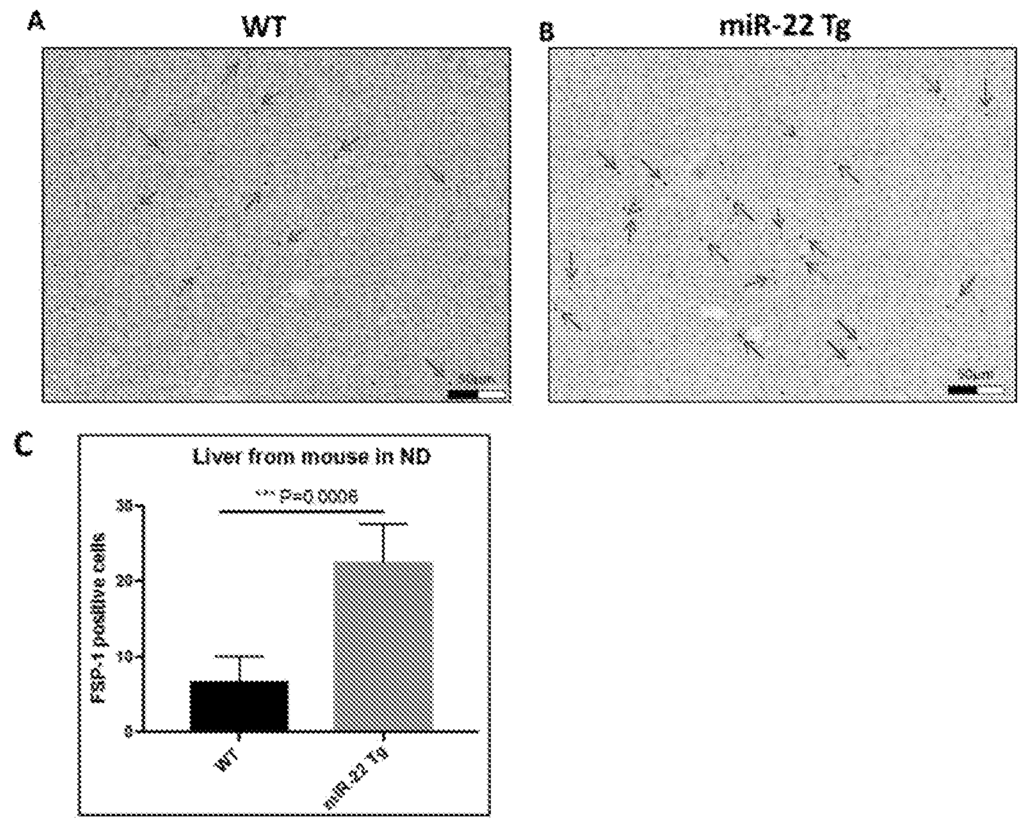
FIG. 33A-C shows that miR-22 Overexpression Affects Liver Function feed with normal chow: Fatty Liver and Fibrosis in WT-mice (FIG. 33A) and miR-22 Tg mice (FIG. 33B).
Figure 34:
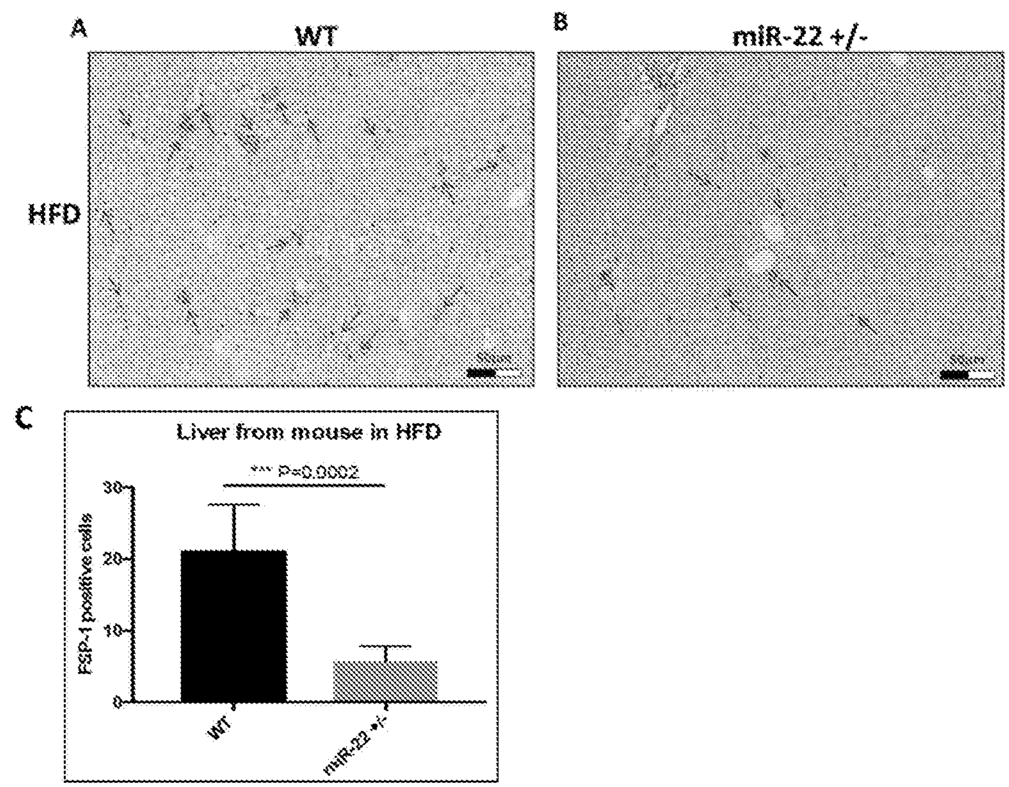
FIG. 34A-C show that miR-22 Overexpression Affects Liver Function: Fatty Liver and Fibrosis in WT-mice (FIG. 34A) and miR-22+/− mice (FIG. 34B).

The sequence was validated in an assay by optimization of protocol for LNA assisted uptake (Lipo200 transfection), an adherent cell line, FAM labeled LNA was used and the biological effect validated by Identifying the most potent anti-miR-22 in adherent cell line assisted and un-assisted uptake (analysis of miR-22 level pre and post treatment and TET2 activity and protein level). The aim was to use the anti-miR in a mouse model with the most potent anti-miR for use for in-vivo treatment, see FIG. 33A-C for confirmation results. In the below sequences, capital letters are LNA-modified and lower-case letters are unmodified; the orientations for the miR-22 (SEQ ID NO: 1) and for the anti-miR-22 oligonucleotides (SEQ ID NO: 2 to SEQ ID NO: 10) are orientated 5' to 3'. FIG. 8 shows the anti-miR-22 oligonucleotides orientated 3' to 5' as they would be when hybridizing to miR-22. The oligonucleotides of SEQ ID NO: 11 and SEQ ID NO: 12, orientated 5' to 3', are scrambled sequences and do not hybridize to the miR-22 (SEQ ID NO: 1).

```
hsa-miR-22
                                  (SEQ ID NO: 1)
AAGCUGCCAGUUGAAGAACUGU

CRM0008
                                  (SEQ ID NO: 2)
TGGCAGCT

CRM0009
                                  (SEQ ID NO: 4)
CtTcaACtgGcAgCT
```

-continued

CRM0010

(SEQ ID NO: 5)

CTTcaACtgGCAgCT

CRM0011

(SEQ ID NO: 6)

TCtTCAaCtgGCAgCT

CRM0012

(SEQ ID NO: 7)

TCtTcaaCtGGCAgCT

CRM0013

(SEQ ID NO: 8)

TCtTCAacTgGCAgCT

CRM0014

(SEQ ID NO: 9)

TTctTCAacTgGCAgCT

CRM0015

(SEQ ID NO: 10)

GTtctTcaaCtgGCaGCT

CRM0016

(SEQ ID NO: 11)

CGaATAgTtaGTAgCG

CRM0017

(SEQ ID NO: 12)

FAM labelled-CGaATAgTtaGTAgCG

Anti-miR-22 Therapy In-Vivo

Figures 9, 10:
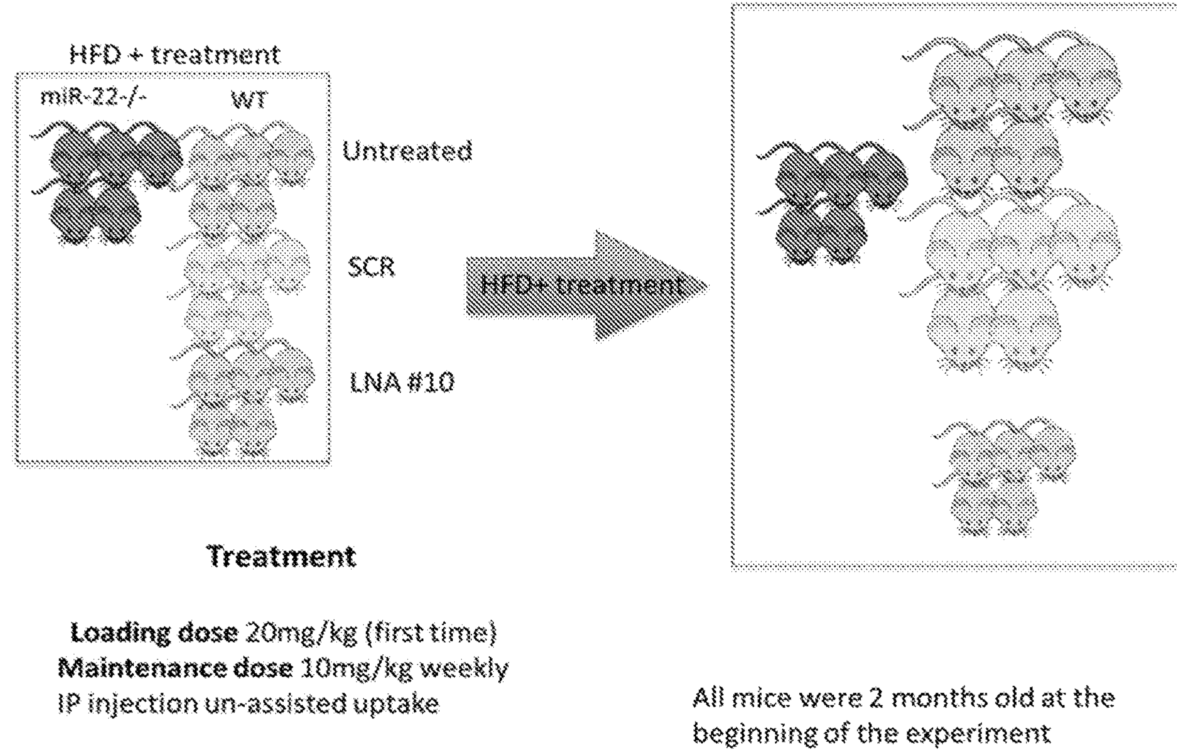
FIG. 9 is a pictorial showing the in vivo experimental planning and conditions for miR-22−/− and WT mice on HFD following transfection of Vehicle (VCH), Scramble Control RNA (SCR) and Locked Nucleic Acid (LNA).
FIG. 10 is a bar graph showing that there is no difference between treated and non-treated mice in food consumption for (Δ) Vehicle, (◇) SCR, (□) anti-miR-22.
Figure 11A:
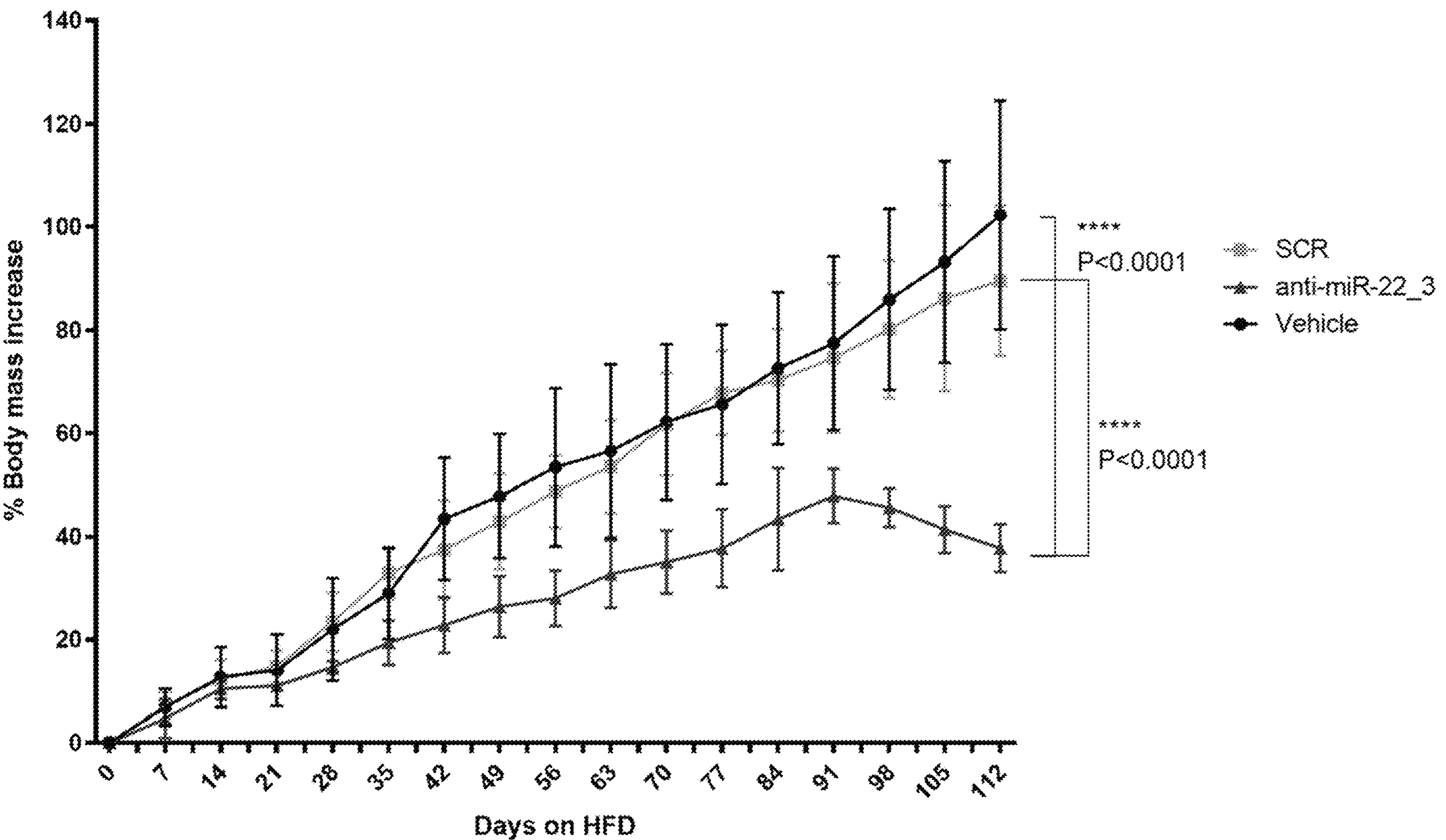
FIG. 11A-B are line graphs showing an in vivo pharmacological inhibition of miR-22 prevents mice from becoming obese.
Figure 11B:
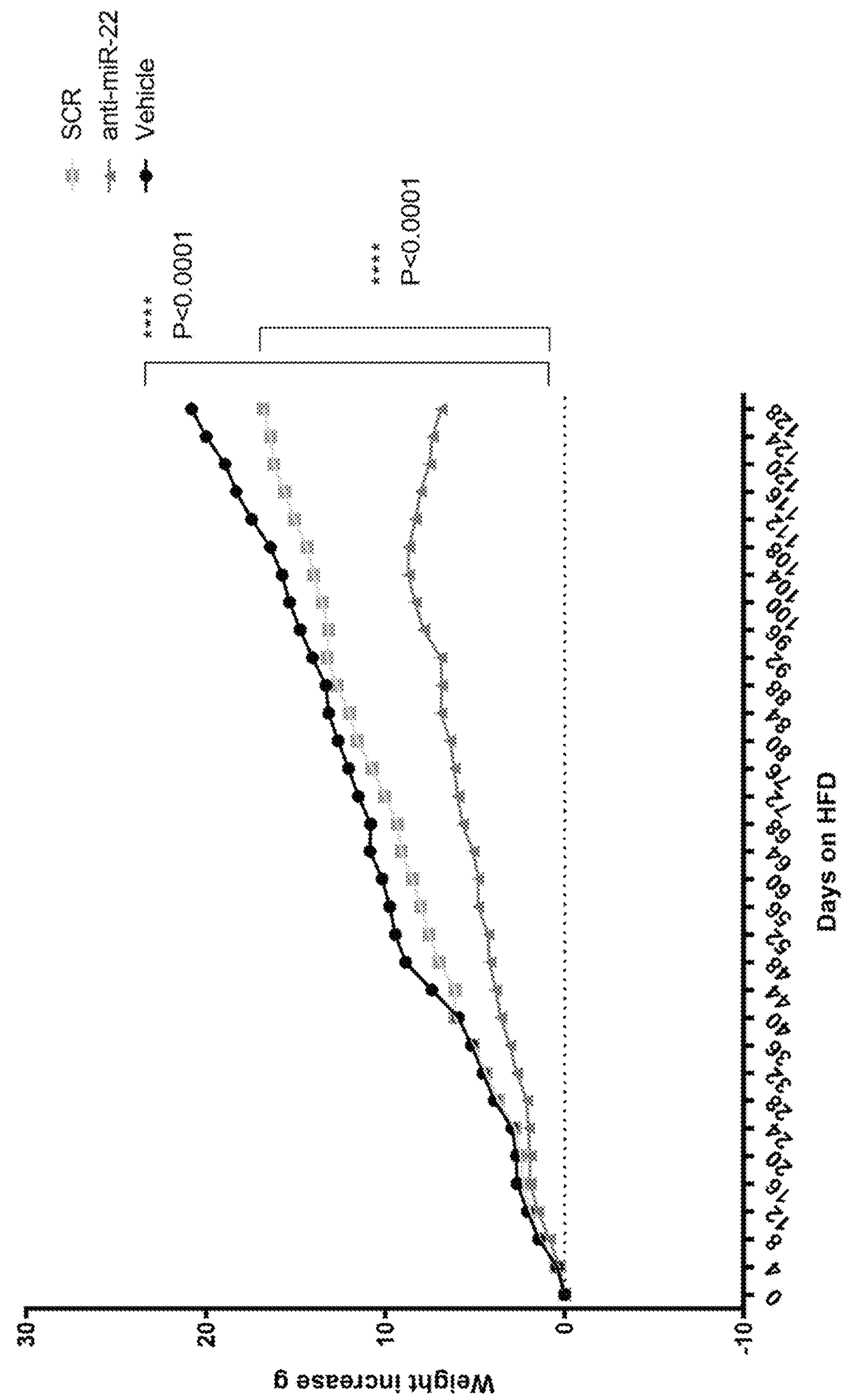

In an in vivo experimental planning for prevention, see FIG. 9, 2 months old miR-22−/− and WT on HFD were transfected with Vehicle (VCH), Scramble Control RNA (SCR) and Locked Nucleic Acid (LNA) and treated with a Loading dose 20 mg/kg (first time) and a Maintenance dose 10 mg/kg weekly IP injection un-assisted uptake. There was no difference between treated and non-treated mice in food consumption, see FIG. 10. In vivo pharmacological inhibition of miR-22 prevented mice from becoming obese and anti-miR-22 therapy in vivo was able to increase protein level of major miR-22 targets in the liver. Anti-miR-22 treatment did not affect liver lipid composition but profoundly suppressed liver steatosis.

Figure 12:
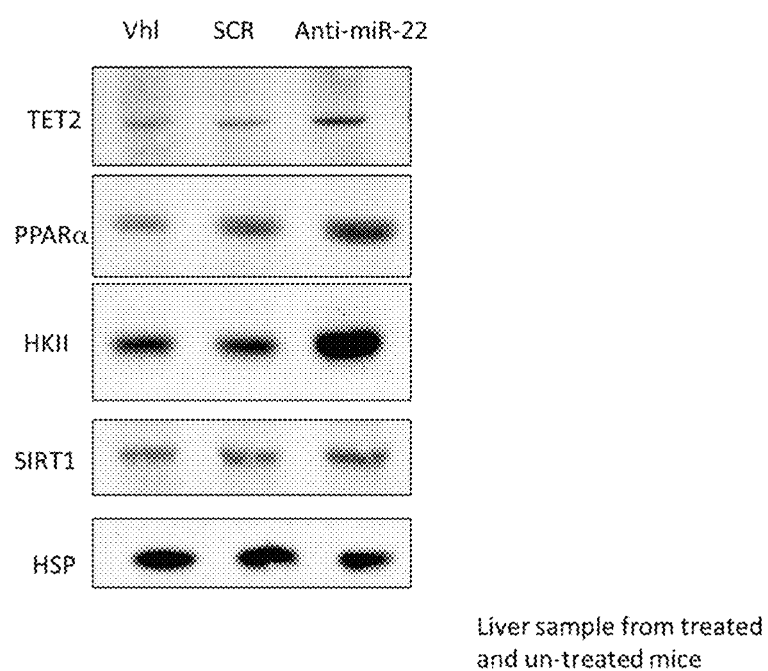
FIG. 12 is a western blot showing that anti-miR-22 therapy in-vivo is able to increase protein level of major miR-22 targets in the liver.
Figure 13A:
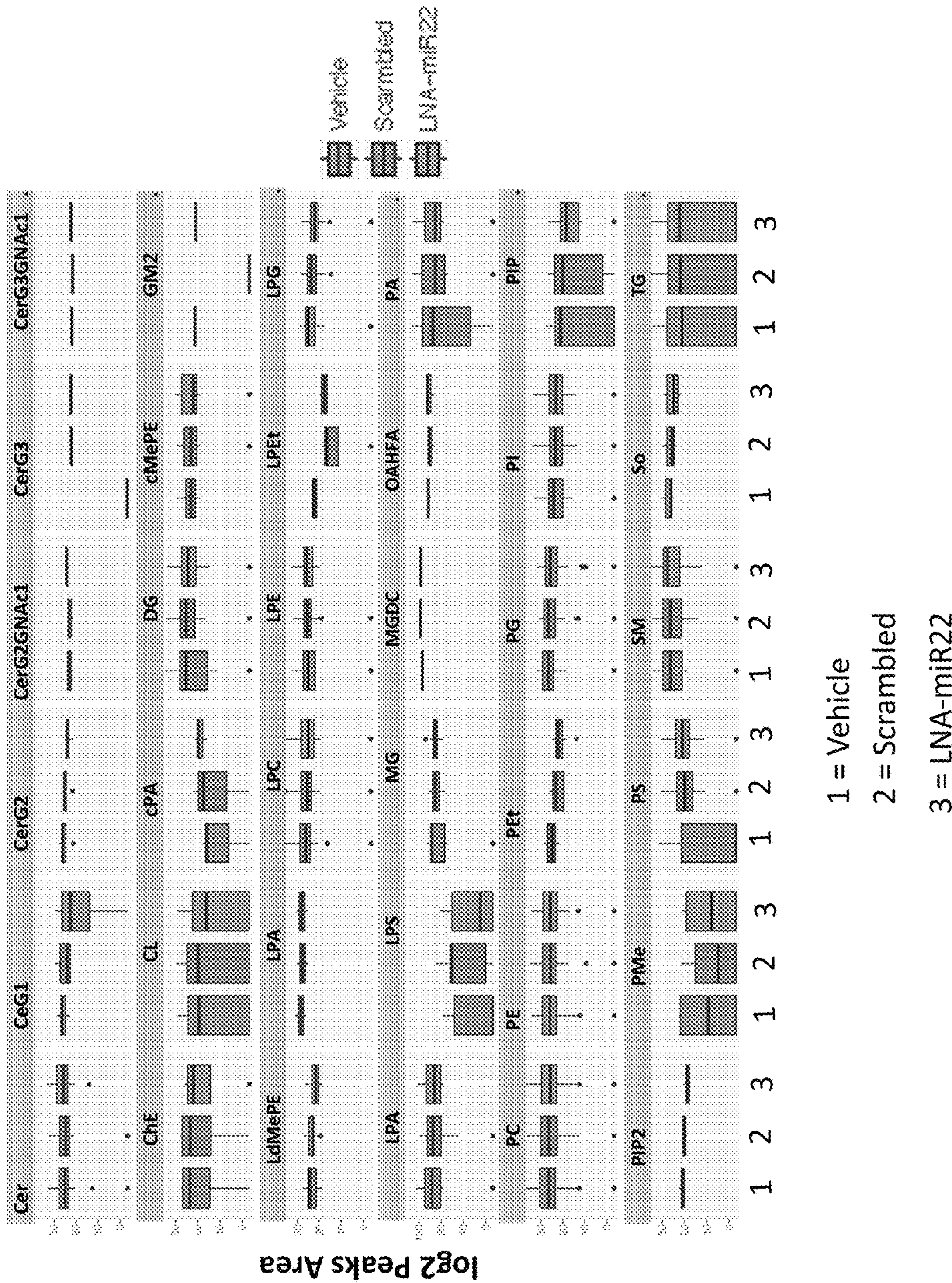
Figure 13A:
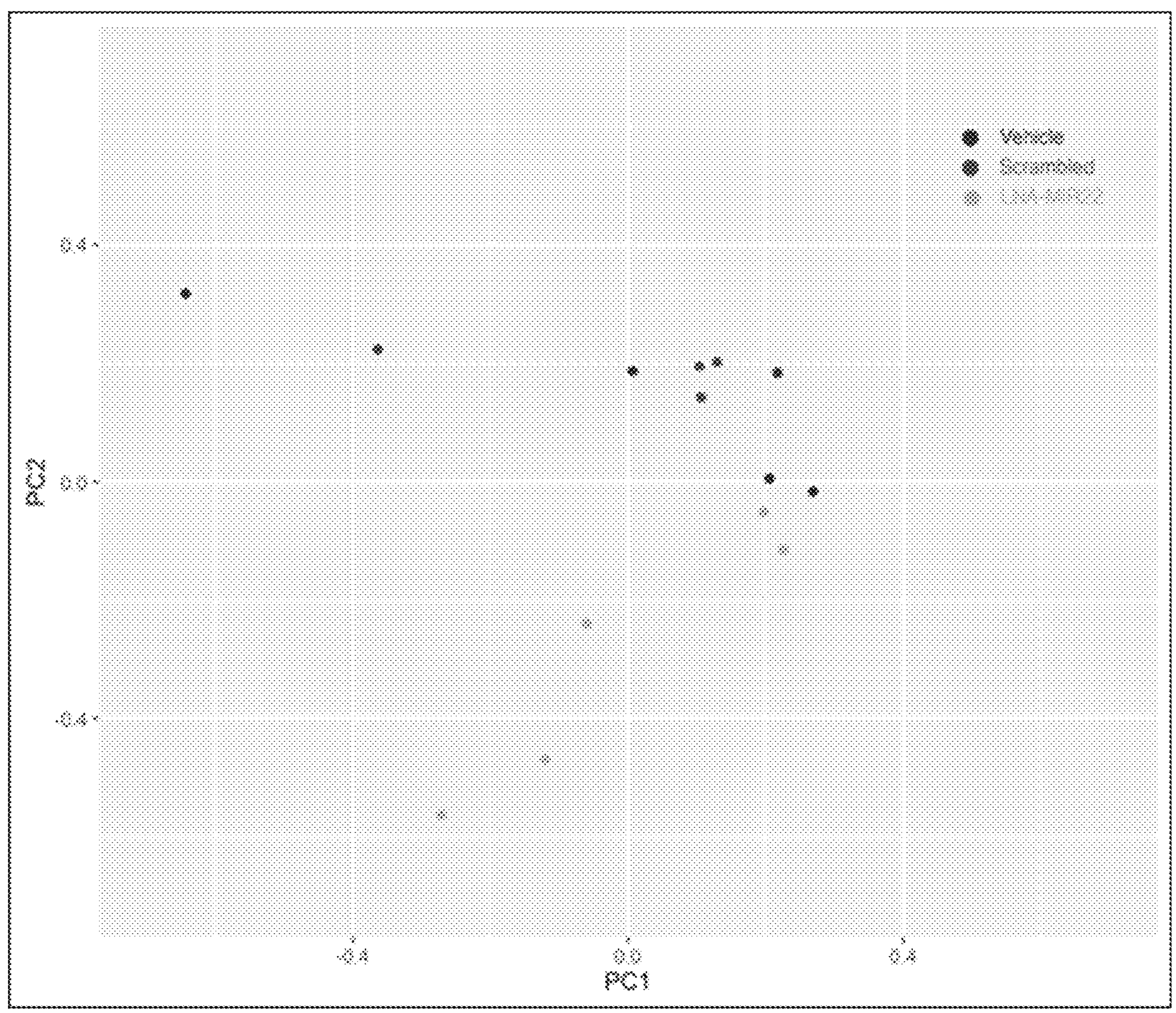
Figure 14A:
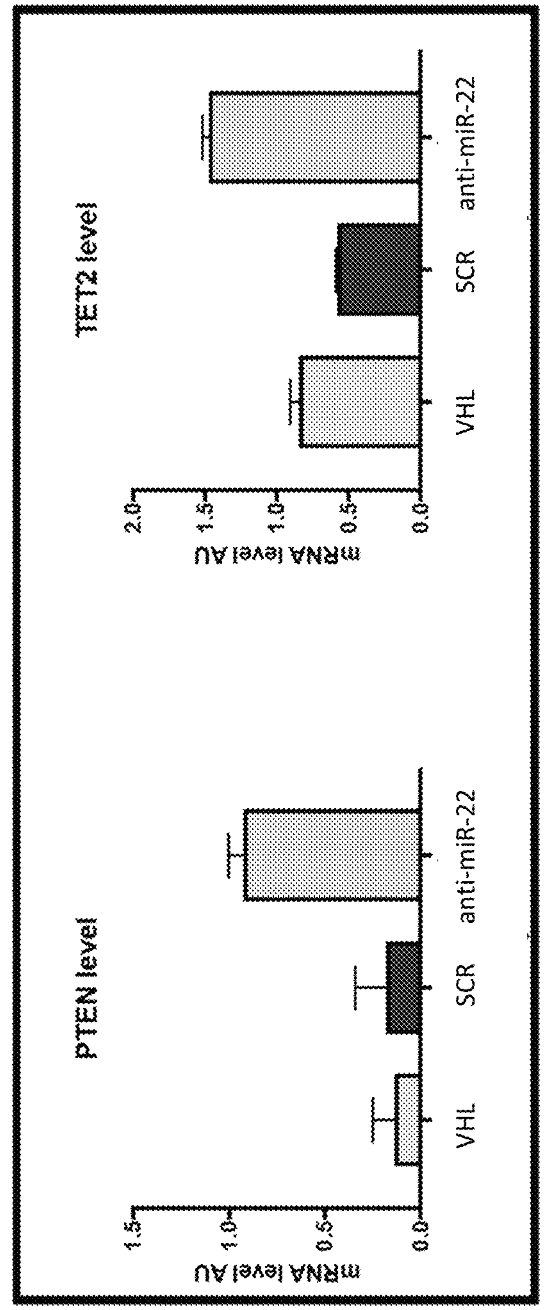
FIG. 14A-B is a series of bar graphs showing relative mRNA level in the liver of mice treated with VHL, SCR LNA or LNA anti-miR-22.
Figure 14B:
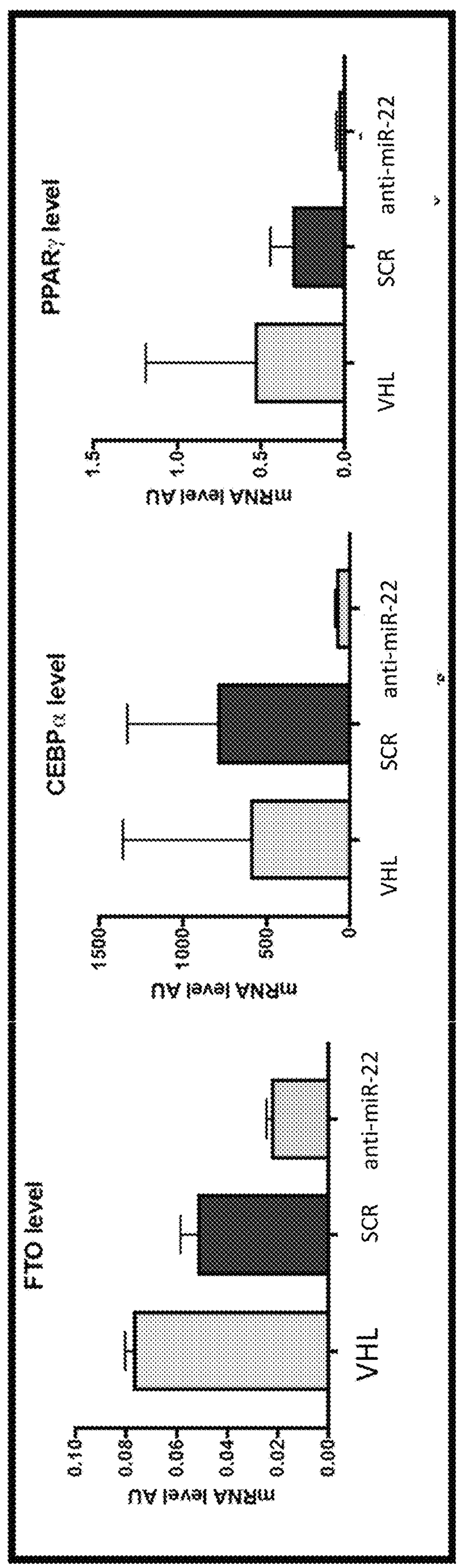
Figure 15A:
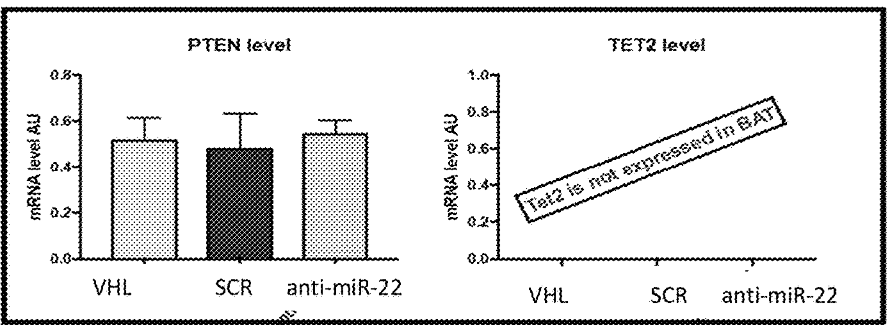
FIG. 15A-C is a series of bar graphs showing relative mRNA level in Brown adipose tissue (BAT) of mice treated with VHL, SCR LNA or LNA anti-miR-22.
Figure 15B:
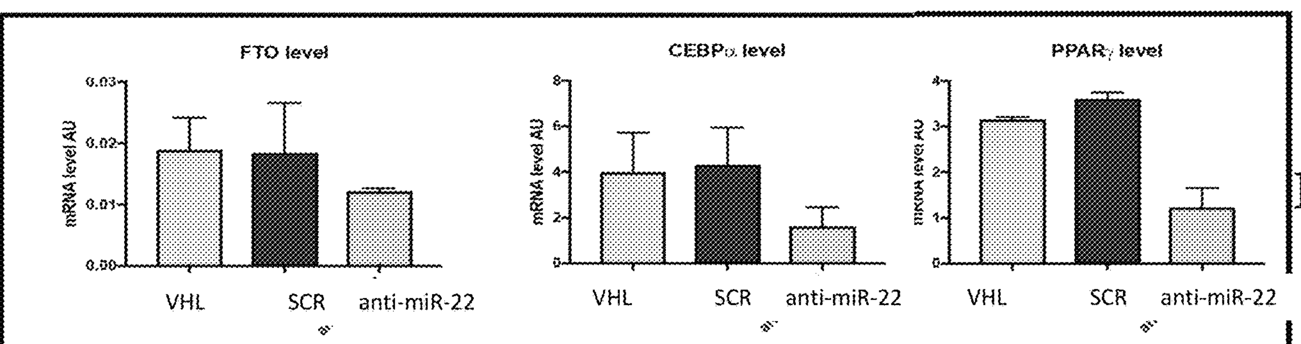
Figure 15C:
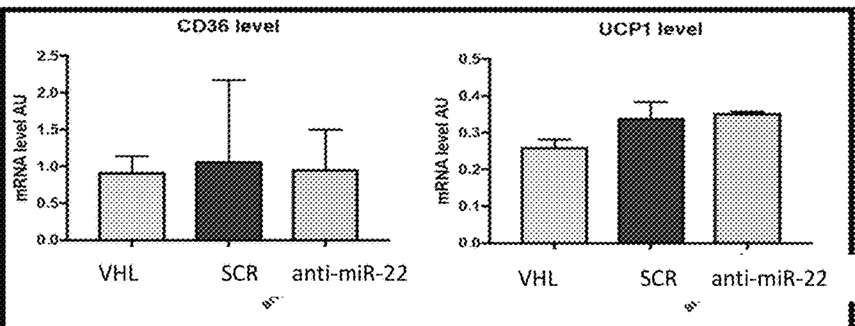
Figure 17:
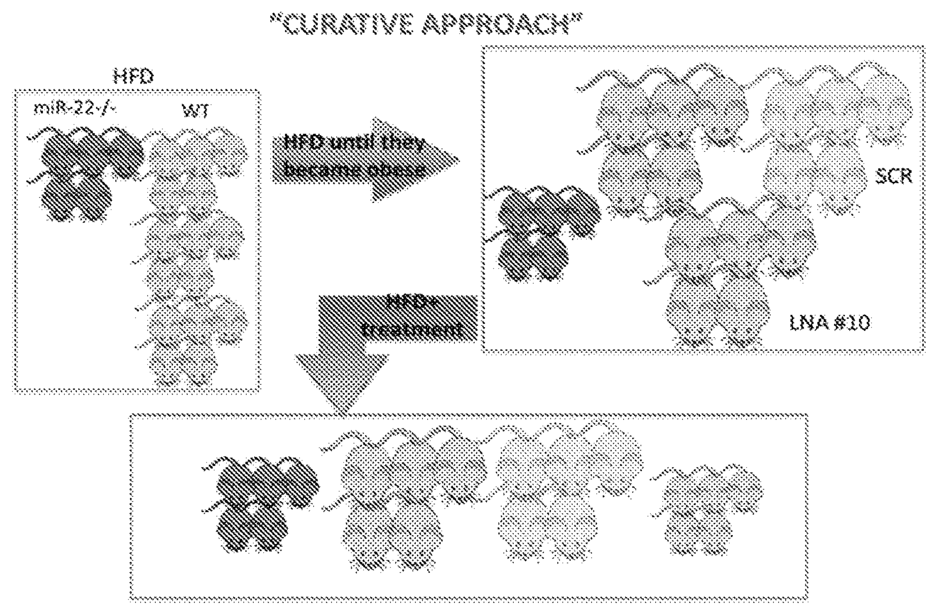
FIG. 17 is a pictorial of a curative approach showing miR-22−/− and WT mice on a HFD treated with an anti-miR-22-LNA, SCR and a VHL and placed on a second HFD regimen.

To evaluate potential gene expression of Fat metabolism, synthesis, differentiation in treated and untreated mice, RNAs from Livers, White adipose tissue (WAT) and Brown adipose tissue (BAT) were extracted from the mice treated with VHL, SCR LNA or LNA anti-miR-22 and mRNA expression of TET2, PTEN (Positive Control), FTO, CEBPa, PPARg which are involved in fat related metabolism and synthesis pathway and UCP1 and CD36 (as Brown marker) were a determined, (see FIG. 12).

Figure 18:
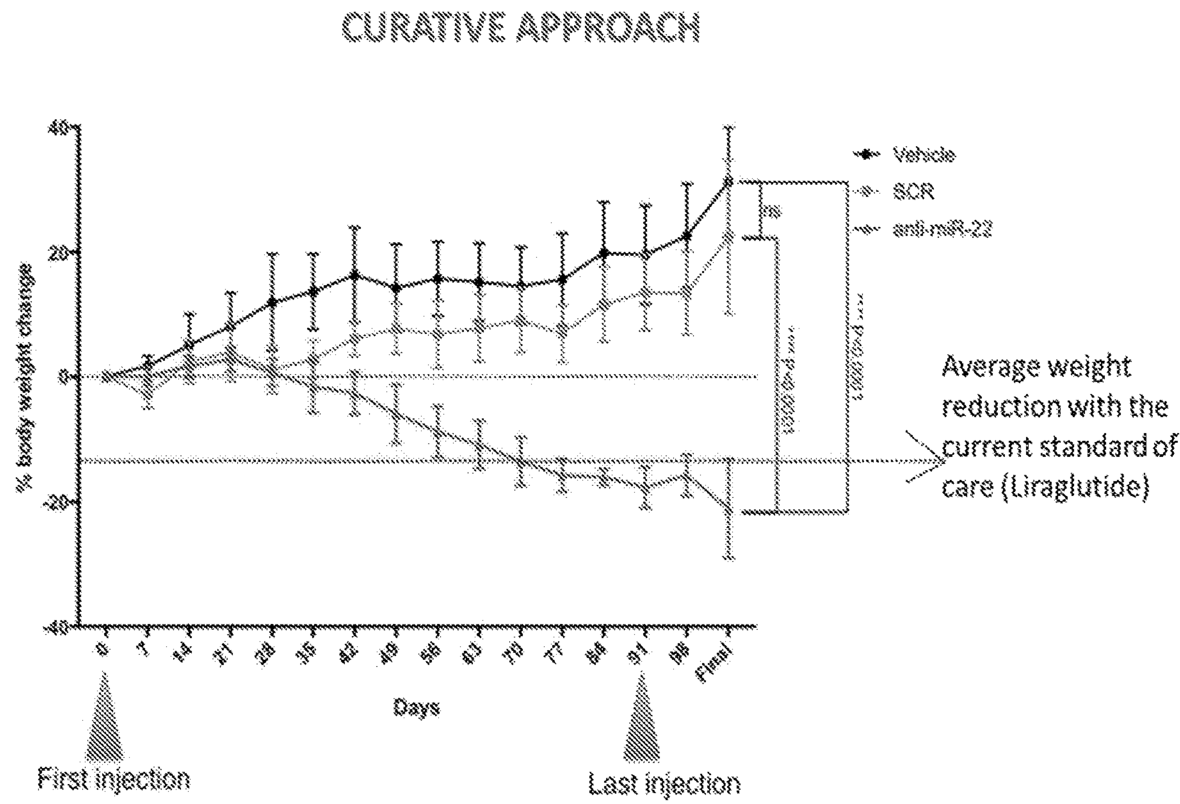
FIG. 18 is a line graph showing the results of the curative approach whereby there is a significant reduction in body weight in mice already obese and fed with a HFD. After 3½ months of treatment, a significant reduction in body weight was observed in obese mice (average weight >40 g) and fed with HFD. Mice were sacrificed, tissue collected, RNA from livers used for RNAseq.
Figure 19:
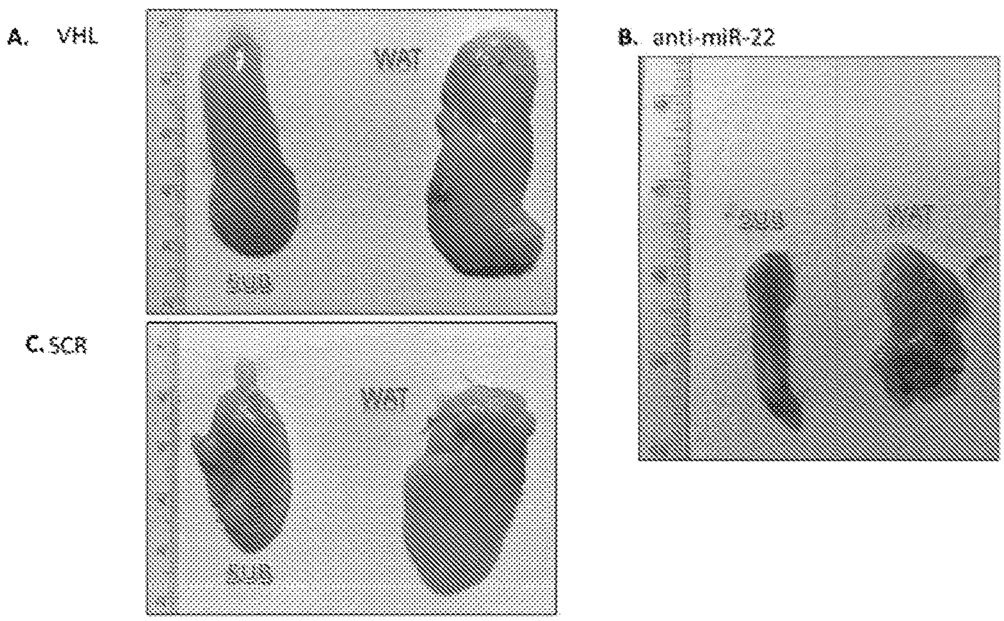
FIG. 19A-C are three pictures showing that miR-22 pharmacological inhibition reverts Obese phenotype in mice.
Figure 20:
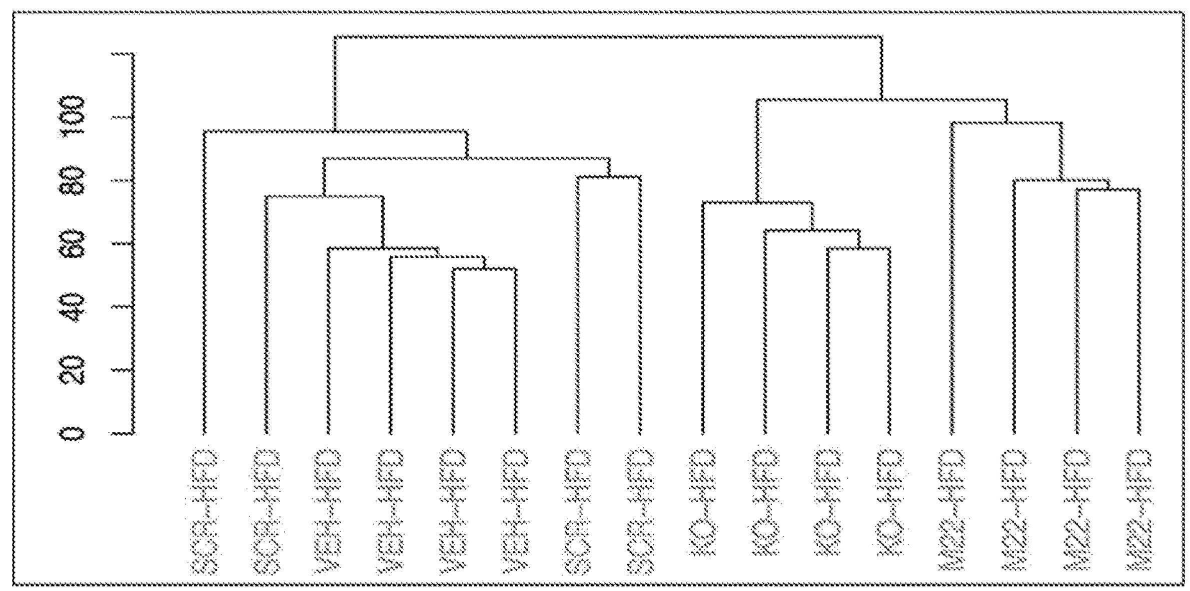
FIG. 20 is an RNA-seq plot showing the hierarchy cluster analysis from mice liver indicating that miR-22 pharmacological inhibition and genetic Knockout (KO) cluster together, indicating that the treatment is on target and that KO phenotype can be mimicked using LNA construct.
Figure 21:
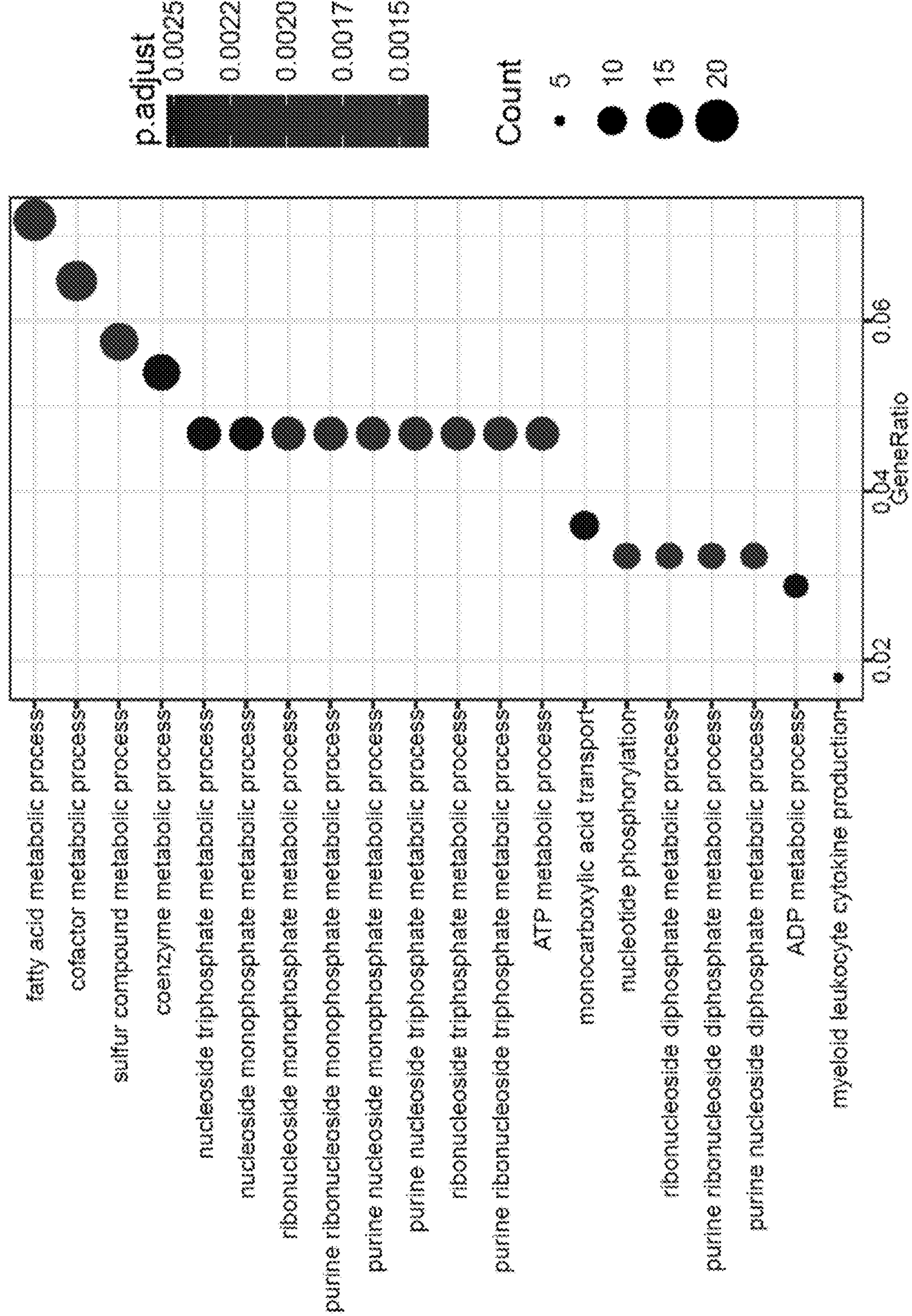
FIG. 21 is an RNA-Seq plot showing the gene ontology analysis in mice liver indicating that top down regulated pathway in KO and LNA treated mice are lipid metabolism and biosynthesis related.
Figure 22:
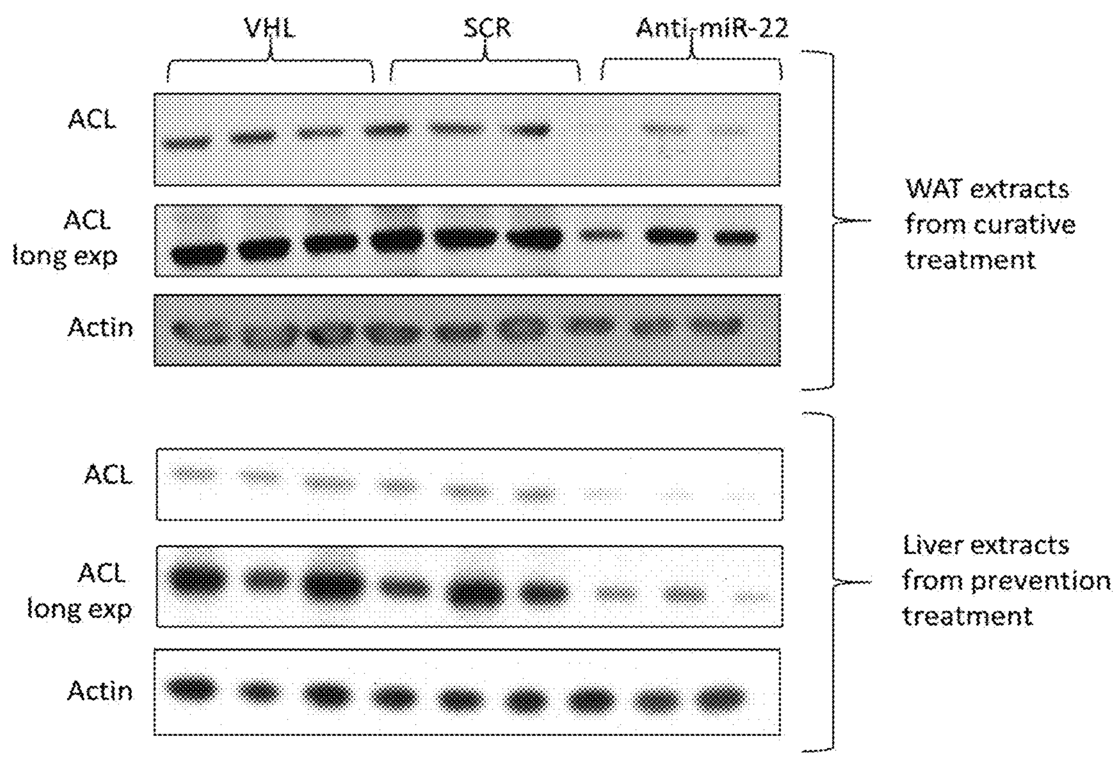
FIG. 22 is a western blot showing that anti-miR-22 therapy in-vivo strongly down regulate ATP-citrate lysase (ACL). Anti-miR-22 therapy in vivo strongly downregulates ACL.
Figures 23, 24:
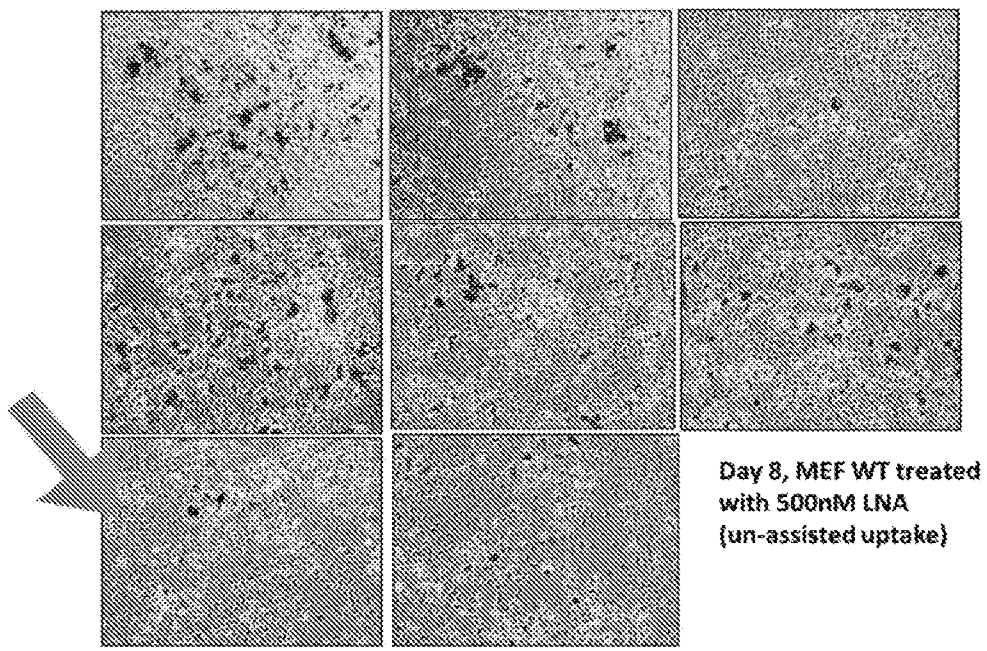
FIG. 23 is an Oil-Red-O staining showing that Pharmacological inhibition of miR-22 is effective in impairing MEFs adipocytic differentiation.
FIG. 24 is an Oil-Red O staining (FIG. 24A) and a bar graph (FIG. 24B) showing that anti-miR-22 treatment in Human Primary Mesenchymal cells cultured in Adipo differentiation media for 2 weeks with or without LNA anti-miR-22. Un-assisted uptake 500 nM (LNAs added every 2 days).
Figure 25:
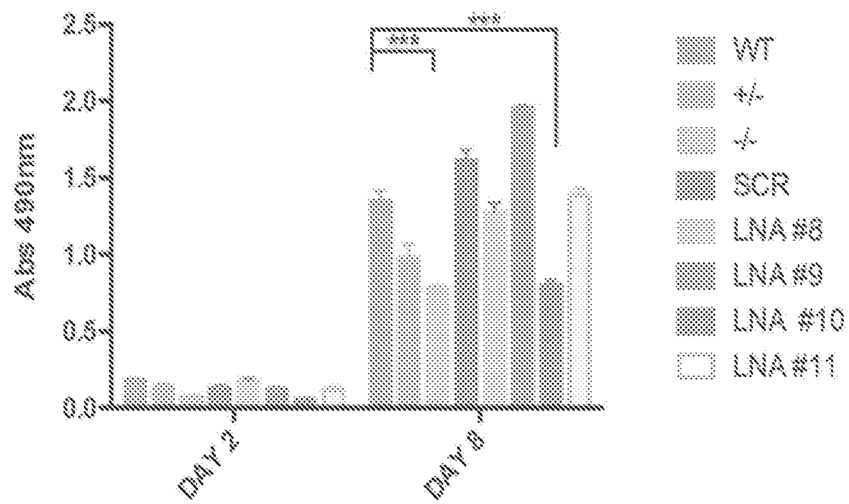
FIG. 25 is a bar graph showing that pharmacological inhibition of miR-22 is effective in impairing MEFs adipocytic differentiation. The order of data in the bar graphs, when reading from left to right corresponds with the legend (at the right of the graph) when reading from top to bottom.

In a curative approach, miR-22−/− and WT mice on a HFD treated with an anti-miR-22-LNA, SCR and a VHL and placed on a second HFD regimen. After 3.5 months of treatment there was a significant reduction in body weight in mice already obese (average weight >40 g) and fed with HFD. Mice were sacrificed, tissues collected, RNA from Livers used for RNAseq (FIGS. 16A-C, 17). miR-22 pharmacological inhibition was shown to revert Obese phenotype in mice (FIG. 18). FIG. 19A-C is an RNA-seq plot showing the hierarchy cluster analysis from mice liver indicating that miR-22 pharmacological inhibition and genetic Knockout (KO) cluster together, indicating that the treatment is on target and that KO phenotype can be mimicked using LNA construct and an RNA-Seq plot showing the gene ontology analysis in mice liver indicating that top down regulated pathway in KO and LNA treated mice are lipid metabolism and biosynthesis related is depicted in FIG. 20. Anti-miR-22 therapy in vivo strongly downregulated ACL and pharmacological inhibition of miR-22 was shown to be effective in impairing MEFs adipocytic differentiation.

Results indicate that anti-miR-22 therapy prevents mice from gaining weight when fed with HFD chow, reverses obese phenotype in obese mice fed with HFD chow, does not affect food consumption and efficiently target the liver and WAT in-vivo. Additionally, anti-miR-22 treatment affects the protein level of miR-22 target genes and does not affect any specific lipid class but is able to reduce the overall amount of total lipids in mice.

Figure 26:
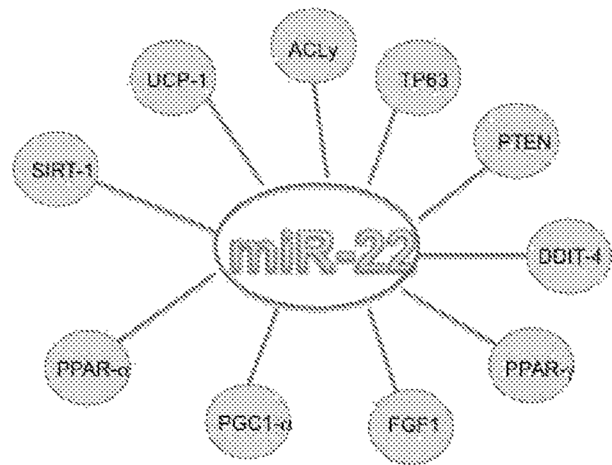
FIG. 26 Schematic representation of metabolic network that it is orchestrated by miR-22. miR-22 can target multiple metabolic player (directly or indirectly) at the same time.
Figure 27:
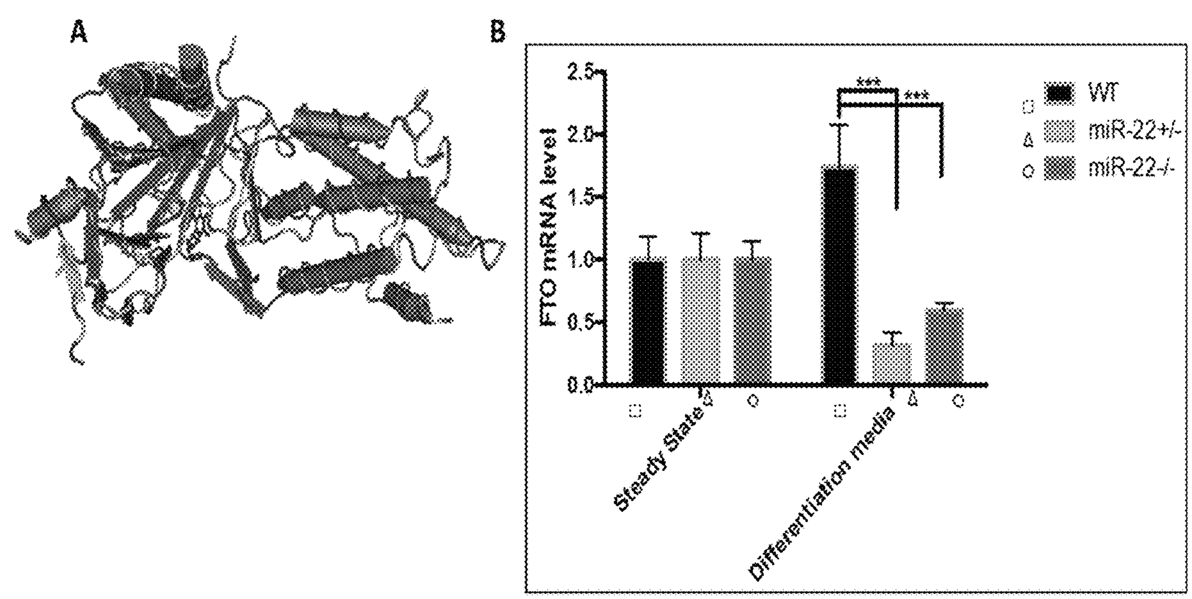
FIG. 27A-B show that, Fat Mass and Obesity-Associated protein (FTO) expression is profoundly down-regulated during adipose induced differentiation in miR-22 deficient MEF but not in WT MEF.
Figure 29:
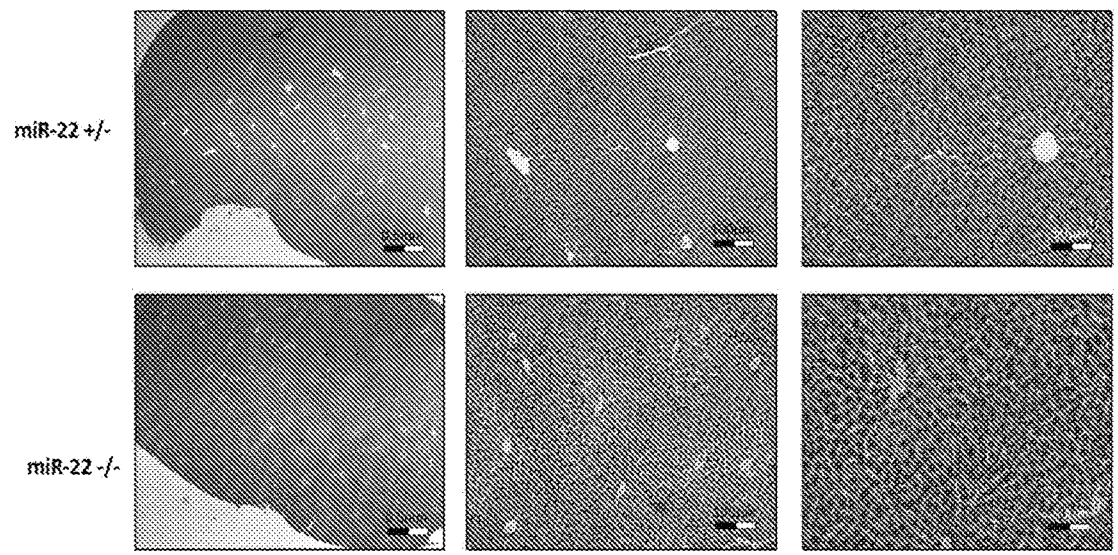
FIG. 29 are a series of immunohistochemical images showing that miR-22 genetic depletion doesn't affect liver function in 2-month old mice; n=8.
Figure 30:
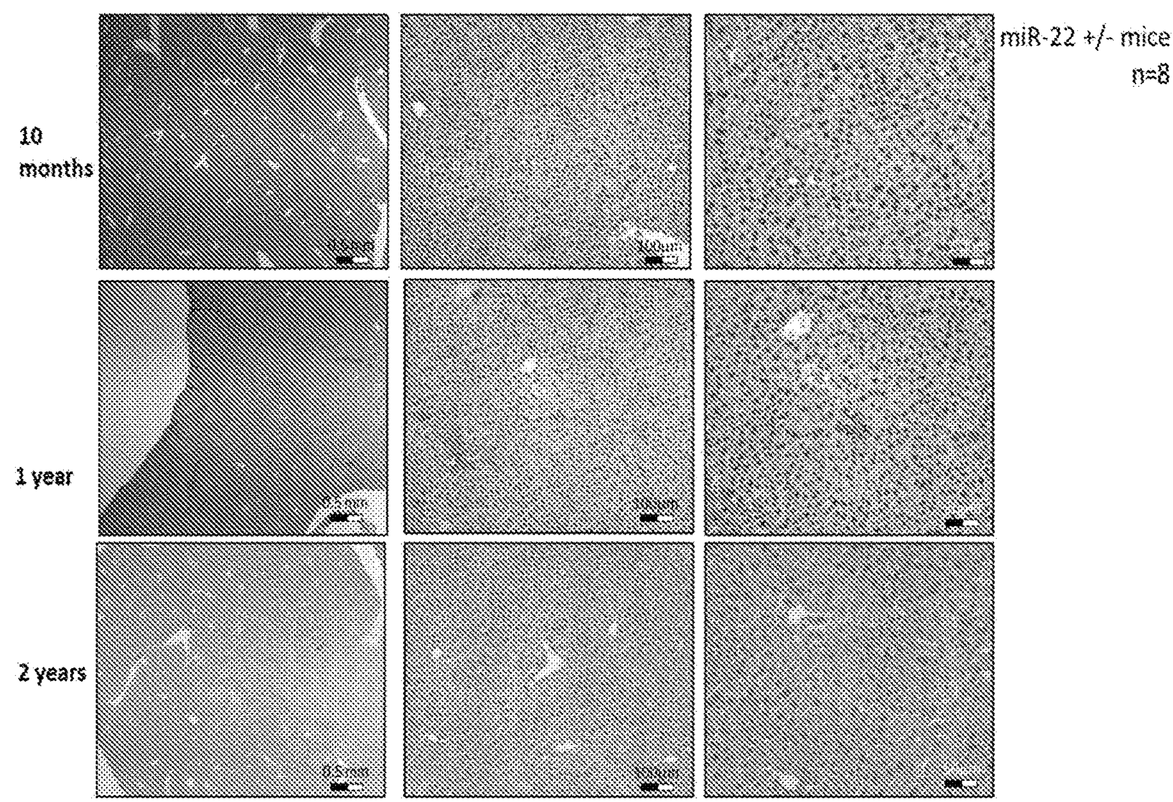
FIG. 30 are a series of immunohistochemical images showing that miR-22 genetic depletion doesn't affect liver function and that miR-22 KO mice do not show any liver related disease or dysfunction at old age.
Figure 31:
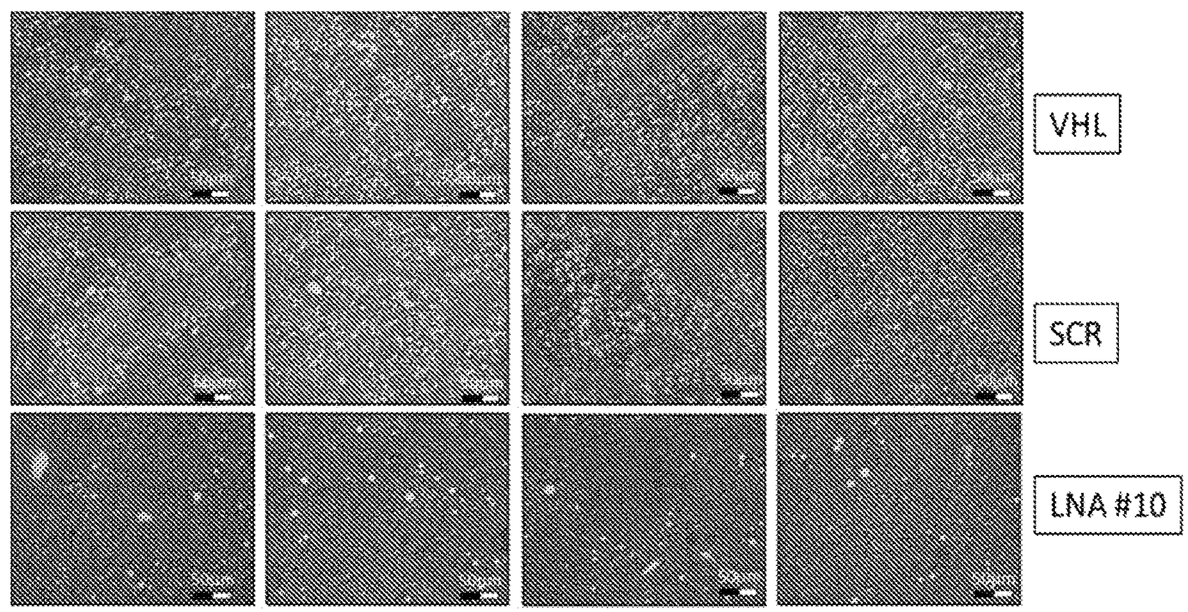
FIG. 31 are a series of immunohistochemical images showing that anti-miR-22 LNA treatment prevent liver steatosis in diet induced obese mice. Images are at 10× magnification.
Figure 32:
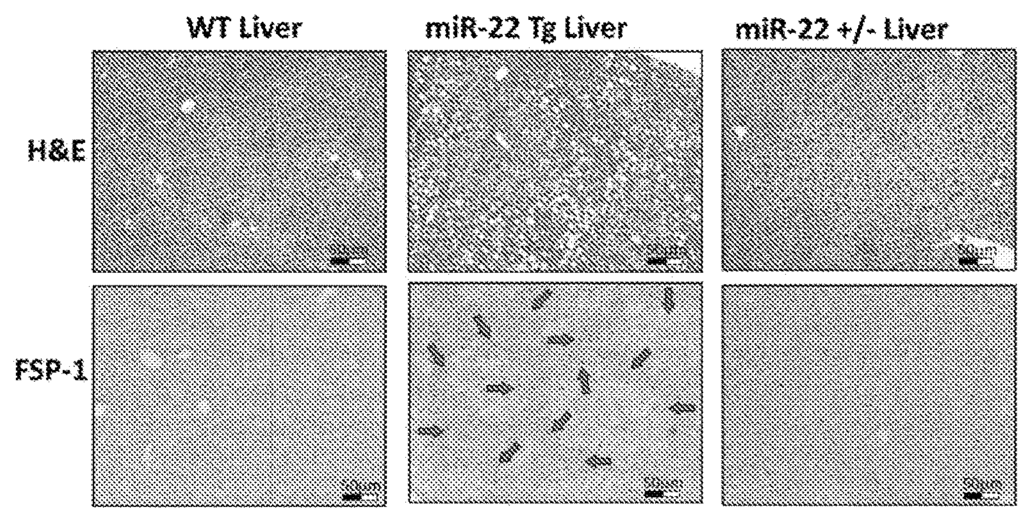
FIG. 32 are a series of immunohistochemical images showing the effects of miR-22 Overexpression and Under-expression on Liver Fibrosis.

Example 3: miR-22 Control Obesity and Fat Mass and Obesity-Associated Protein (FTO)

miR-22 directly targets PTEN and TET to promote tumorigenesis and metastasis. PTEN as many other miR-22 targeting genes are involved in metabolism and fatty acid oxidation or biogenesis including for example SIRT-1, BMP-7, PPAR-alpha, PPAR-γ, SP-1, PGC1a, FGF-21, UCP1, Methyltransferase like 3 and DDIT4. FTO expression was profoundly down-regulated during adipose induced differentiation in miR-22 deficient MEF but not in WT MEF (FIG. 26) and miR-22 down regulation (genetic or pharmacological) increased levels of RNA m6A (FIG. 27A-B). Mir-22 downregulation was shown to not affect liver function or show any liver related disease or dysfunction at old age (FIGS. 28A-B, 29).

To evaluate whether miR-22 Overexpression affects Liver function, Fatty Liver and Fibrosis, Mice between 8 and 10 months old were fed with normal diet. miR-22 OE was shown to lead to a fatty liver and increase the presence of FSP-1 positive cells FSP-1 identify a sub-population of macrophages in liver, associated with fibrosis.

Overall, miR-22 in an onco-miR (PTEN targeting, MEF transformation, EMT), miR-22 is 100% conserved in human and mouse, miR-22 OE leads to and obese phenotype in ND, miR-22 KO mice don't gain weight in HFD, miR-22 pharmacologically silencing impaired MEF and human MES to differentiate in adipocyte, LNA anti-miR-22 treatment prevent mice to become obese in a prevention setting, LNA anti-miR-22 treatment reverts obese phenotype in obese mice fed with HFD, miR-22 silencing doesn't show any liver toxicity, miR-22 silencing prevent liver from steatosis and fibrosis, miR-22 can target multiple genes related to metabolism and lipid biogenesis at the same time.

Other Embodiments

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any way.

What is claimed is:

1. A method for treating a metabolic disorder, comprising administering an effective amount of an inhibitor of miR-22 to a subject in need thereof, wherein the inhibitor of miR-22 is an oligonucleotide-based inhibitor complementary to miR-22 comprising one or more chemically modified nucleotides, said chemically modified nucleotides being locked nucleotides (LNAs), wherein the expression and/or activity of miR-22 is reduced in the subject following administration of the inhibitor, and wherein the metabolic disorder is liver steatosis.

2. The method of claim 1, wherein the oligonucleotide-based inhibitor comprises a sequence that is at least 75% complementary to a mature sequence of miR-22.

3. The method of claim 1, wherein the oligonucleotide-based inhibitor comprises 25 or fewer nucleotides.

4. The method of claim 1, wherein the oligonucleotide-based inhibitor is conjugated to one or more N-acetylgalactosamine (GalNAc) moieties.

5. The method of claim 1, wherein the oligonucleotide-based inhibitor is an antisense oligonucleotide inhibitor.

6. The method of claim 1, wherein the oligonucleotide-based inhibitor is a small interfering RNA (siRNA).

7. The method of claim 1, wherein the oligonucleotide-based inhibitor is an aptamer.

8. The method of claim 1, wherein the subject is obese.

9. The method of claim 8, wherein the subject is suffering from Prader-Willi Syndrome, or wherein the subject is suffering from hypercholesterolemia, or wherein the subject harbors a fat mass and obesity-associated protein (FTO) variant and/or shows an upregulation of FTO expression and/or activity.

10. The method of claim 8, wherein the subject is obese and has a body mass index of greater than about 30.

11. The method of claim 8, wherein the method induces weight loss, optionally wherein the method induces a total weight loss of 1% or more in the subject.

12. The method of claim 8, wherein the method reduces weight gain, reduces the growth of adipose tissue, or impairs adipocyte differentiation.

13. The method of claim 1, wherein the subject is overweight and has a body mass index of about 25-29.9.

14. The method of claim 1, wherein the method reduces liver steatosis, or reduces liver fibrosis.

15. The method of claim 1, wherein the method reduces the activity and/or expression of fat mass and obesity-associated protein (FTO), ALKB Homologous 5 (ALKBH5), CCAAT/enhancer binding protein alpha (CEBPα), peroxisome proliferator activated receptor gamma (PPARγ), peroxisome proliferator activated receptor alpha (PPARα), ATP citrate lyase (ACLY), PPARγ co-activator-α (PGC1-α), Specific Protein 1 (SP1), Fibroblast Grow Factor 21 (FGF-21), Uncoupled protein 1 (UCP1), DNA Damage Included Transcript 4 (DDIT-4, REDD1), tumor protein p63 (TP63), fibroblast growth factor 1 (FGF1), and/or Methyltransferase like 3 (METTL3).

16. The method of claim 1, wherein the method increases the activity and/or expression of phosphatase and tensin homolog (PTEN) and/or tet methylcytosine dioxygenase 2 (TET2).

17. The method of claim 1, wherein the inhibitor comprises a nucleic acid consisting of any one of SEQ ID Nos: 2, 4-12, wherein the capital letters are LNA (locked nucleic acid)-modified nucleotides, and the lower-case letters are unmodified nucleotides.

18. The method of claim 1, wherein the oligonucleotide-based inhibitor is CRM0010 CTTcaACtgGCAgCT (SEQ ID NO: 5).

* * * * *

SEQUENCE LISTING

<160> NUMBER OF SEQ ID NOS: 82

<210> SEQ ID NO 1
<211> LENGTH: 22
<212> TYPE: RNA
<213> ORGANISM: Artificial Sequence
<220> FEATURE:
<223> OTHER INFORMATION: Synthetic Polymer

<400> SEQUENCE: 1
aagcugccag uugaagaacu gu 22

<210> SEQ ID NO 2
<211> LENGTH: 10
<212> TYPE: DNA
<213> ORGANISM: Artificial Sequence
<220> FEATURE:
<223> OTHER INFORMATION: Synthetic Polymer
<220> FEATURE:
<221> NAME/KEY: misc_feature
<222> LOCATION: (1)..(1)
<223> OTHER INFORMATION: N-terminus, no nucleotide
<220> FEATURE:
<221> NAME/KEY: misc_feature
<222> LOCATION: (2)..(9)
<223> OTHER INFORMATION: Optionally LNA
<220> FEATURE:
<221> NAME/KEY: misc_feature
<222> LOCATION: (10)..(10)
<223> OTHER INFORMATION: C-terminus, no nucleotide

<400> SEQUENCE: 2 ntggcagctn 10

<210> SEQ ID NO 3

<400> SEQUENCE: 3

000

<210> SEQ ID NO 4
<211> LENGTH: 15
<212> TYPE: DNA
<213> ORGANISM: Artificial Sequence
<220> FEATURE:
<223> OTHER INFORMATION: Synthetic Polymer
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (3)..(3)
<223> OTHER INFORMATION: LNA
<220> FEATURE:
<221> NAME/KEY: misc_feature
<222> LOCATION: (6)..(7)
<223> OTHER INFORMATION: LNA
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (12)..(12)
<223> OTHER INFORMATION: LNA
<220> FEATURE:
<221> NAME/KEY: misc_feature
<222> LOCATION: (14)..(15)
<223> OTHER INFORMATION: LNA

<400> SEQUENCE: 4

```
cttcaactgg cagct                                                    15


<210> SEQ ID NO 5
<211> LENGTH: 15
<212> TYPE: DNA
<213> ORGANISM: Artificial Sequence
<220> FEATURE:
<223> OTHER INFORMATION: Synthetic Polymer
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (6)..(7)
<223> OTHER INFORMATION: LNA
<220> FEATURE:
<221> NAME/KEY: misc_feature
<222> LOCATION: (10)..(12)
<223> OTHER INFORMATION: LNA
<220> FEATURE:
<221> NAME/KEY: misc_feature
<222> LOCATION: (14)..(15)
<223> OTHER INFORMATION: LNA

<400> SEQUENCE: 5

tcgacggtca acttc                                                    15


<210> SEQ ID NO 6
<211> LENGTH: 16
<212> TYPE: DNA
<213> ORGANISM: Artificial Sequence
<220> FEATURE:
<223> OTHER INFORMATION: Synthetic Polymer
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (4)..(6)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (11)..(13)
<223> OTHER INFORMATION: LNA
<220> FEATURE:
<221> NAME/KEY: misc_feature
<222> LOCATION: (15)..(16)
<223> OTHER INFORMATION: LNA

<400> SEQUENCE: 6

tcgacggtca acttct                                                   16


<210> SEQ ID NO 7
<211> LENGTH: 16
<212> TYPE: DNA
<213> ORGANISM: Artificial Sequence
<220> FEATURE:
<223> OTHER INFORMATION: Synthetic Polymer
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (4)..(4)
<223> OTHER INFORMATION: LNA
<220> FEATURE:
<221> NAME/KEY: misc_feature
```

-continued

<222> LOCATION: (8)..(8)
<223> OTHER INFORMATION: LNA
<220> FEATURE:
<221> NAME/KEY: misc_feature
<222> LOCATION: (10)..(13)
<223> OTHER INFORMATION: LNA
<220> FEATURE:
<221> NAME/KEY: misc_feature
<222> LOCATION: (15)..(16)
<223> OTHER INFORMATION: LNA

<400> SEQUENCE: 7
tcgacggtca acttct 16

<210> SEQ ID NO 8
<211> LENGTH: 16
<212> TYPE: DNA
<213> ORGANISM: Artificial Sequence
<220> FEATURE:
<223> OTHER INFORMATION: Synthetic Polymer
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (4)..(6)
<223> OTHER INFORMATION: LNA
<220> FEATURE:
<221> NAME/KEY: misc_feature
<222> LOCATION: (9)..(9)
<223> OTHER INFORMATION: LNA
<220> FEATURE:
<221> NAME/KEY: misc_feature
<222> LOCATION: (11)..(13)
<223> OTHER INFORMATION: LNA
<220> FEATURE:
<221> NAME/KEY: misc_feature
<222> LOCATION: (15)..(16)
<223> OTHER INFORMATION: LNA

<400> SEQUENCE: 8
tcgacggtca acttct 16

<210> SEQ ID NO 9
<211> LENGTH: 17
<212> TYPE: DNA
<213> ORGANISM: Artificial Sequence
<220> FEATURE:
<223> OTHER INFORMATION: Synthetic Polymer
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (5)..(7)
<223> OTHER INFORMATION: LNA
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (12)..(14)
<223> OTHER INFORMATION: LNA
<220> FEATURE:
<221> NAME/KEY: misc_feature
<222> LOCATION: (16)..(17)
<223> OTHER INFORMATION: LNA

<400> SEQUENCE: 9
tcgacggtca acttctt 17

<210> SEQ ID NO 10
<211> LENGTH: 18
<212> TYPE: DNA
<213> ORGANISM: Artificial Sequence
<220> FEATURE:
<223> OTHER INFORMATION: Synthetic Polymer
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (6)..(6)
<223> OTHER INFORMATION: LNA
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (13)..(14)
<223> OTHER INFORMATION: LNA
<220> FEATURE:
<221> NAME/KEY: misc_feature
<222> LOCATION: (16)..(18)
<223> OTHER INFORMATION: LNA

<400> SEQUENCE: 10
tcgacggtca acttcttg 18

<210> SEQ ID NO 11
<211> LENGTH: 16
<212> TYPE: DNA
<213> ORGANISM: Artificial Sequence
<220> FEATURE:
<223> OTHER INFORMATION: Synthetic Polymer
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (4)..(6)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (11)..(13)
<223> OTHER INFORMATION: LNA
<220> FEATURE:
<221> NAME/KEY: misc_feature
<222> LOCATION: (15)..(16)
<223> OTHER INFORMATION: LNA

<400> SEQUENCE: 11
gcgatgattg ataagc 16

<210> SEQ ID NO 12
<211> LENGTH: 16
<212> TYPE: DNA
<213> ORGANISM: Artificial Sequence
<220> FEATURE:
<223> OTHER INFORMATION: Synthetic Polymer
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (4)..(6)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (11)..(13)
<223> OTHER INFORMATION: LNA
<220> FEATURE:
<221> NAME/KEY: misc_feature
<222> LOCATION: (15)..(16)
<223> OTHER INFORMATION: LNA

<400> SEQUENCE: 12
gcgatgattg ataagc 16

<210> SEQ ID NO 13
<211> LENGTH: 4313
<212> TYPE: DNA
<213> ORGANISM: Artificial Sequence
<220> FEATURE:
<223> OTHER INFORMATION: Synthetic Polymer

<400> SEQUENCE: 13
ctacgctctt ccagctgtcg gacctgggaa attctcctgt gctaaatccc gtggcgctcg 60
cgggtgtcgc cgcggtgcat cctgggagtt gtagtttttt ctactcagag ggagaatagc 120
tccagacggg agcaggacgc tgagagaact acatgcagga ggcggggtcc agggcgaggg 180
atctacgcag cttgcggtgg cgaaggcggc tttagtggca gcatgaagcg caccccgact 240
gccgaggaac gagagcgcga agctaagaaa ctgaggcttc ttgaagagct tgaagacact 300
tggctccctt atctgacccc caaagatgat gaattctatc agcagtggca gctgaaatat 360
cctaaactaa ttctccgaga agccagcagt gtatctgagg agctccataa agaggttcaa 420
gaagcctttc tcacactgca caagcatggc tgcttatttc gggacctggt taggatccaa 480
ggcaaagatc tgctcactcc ggtatctcgc atcctcattg gtaatccagg ctgcacctac 540
aagtacctga acaccaggct ctttacggtc ccctggccag tgaaagggtc taatataaaa 600
cacaccgagg ctgaaatagc cgctgcttgt gagaccttcc tcaagctcaa tgactacctg 660
cagatagaaa ccatccaggc tttggaagaa cttgctgcca aagagaaggc taatgaggat 720
gctgtgccat tgtgtatgtc tgcagatttc cccagggttg ggatgggttc atcctacaac 780
ggacaagatg aagtggacat taagagcaga gcagcataca acgtaacttt gctgaatttc 840
atggatcctc agaaaatgcc atacctgaaa gaggaacctt attttggcat ggggaaaatg 900
gcagtgagct ggcatcatga tgaaaatctg gtggacaggt cagcggtggc agtgtacagt 960
tatagctgtg aaggccctga agaggaaagt gaggatgact ctcatctcga aggcagggat 1020
cctgatattt ggcatgttgg ttttaagatc tcatgggaca tagagacacc tggtttggcg 1080
ataccccttc accaaggaga ctgctatttc atgcttgatg atctcaatgc cacccaccaa 1140
cactgtgttt tggccggttc acaacctcgg tttagttcca cccaccgagt ggcagagtgc 1200
tcaacaggaa ccttggatta tattttacaa cgctgtcagt tggctctgca gaatgtctgt 1260
gacgatgtgg acaatgatga tgtctctttg aaatcctttg agcctgcagt tttgaaacaa 1320
ggagaagaaa ttcataatga ggtcgagttt gagtggctga ggcagttttg gtttcaaggc 1380
aatcgataca gaaagtgcac tgactggtgg tgtcaaccca tggctcaact ggaagcactg 1440
tggaagaaga tggagggtgt gacaaatgct gtgcttcatg aagttaaaag agaggggctc 1500
cccgtggaac aaaggaatga aatcttgact gccatccttg cctcgctcac tgcacgccag 1560

-continued

```
aacctgagga gagaatggca tgccaggtgc cagtcacgaa ttgcccgaac attacctgct   1620
gatcagaagc cagaatgtcg gccatactgg gaaaaggatg atgcttcgat gcctctgccg   1680
tttgacctca cagacatcgt ttcagaactc agaggtcagc ttctggaagc aaaaccctag   1740
aaggagcaca agtctcaggc ggaggagaaa aagagatcgg cttttctcct ccaacgttgt   1800
catgggctta agcaagagca gtggagactt ctcttggccc ctagattgta gcacccgggt   1860
cccaatccaa aacagctagg aaatggtgcc catgaagttt taaatgtttt aaaatgaccc   1920
tgtgttatag tctgatttgg tgttaaacag gaccttcttc ccccaaaatt gttcagatta   1980
taaaatgtga gccattcagc cccaaggtc  cagggcaggc gacaggaacg agcccagcgt   2040
gtgacaaagc ctaacctact ttcctctttc ccaagctttt tcagagactc tggagtggac   2100
ccagccctct ggggaaagac agaacttaga gacatcccag ttactcacca cacccatagt   2160
gctgtccaat atggtagcca ctagctagct gtggctactt caatttaaat tcagttttaa   2220
ttttaattaa aaatgcagct cttcagtcgc cctggccaca tttcaagtgc ttaacagcct   2280
catgtggcta gtgactgctg tattggacgg tacagatatg gaacattttc atcatcgaag   2340
aaagtcctat tggacaacac ttctataaaa agtttgagag caggaattct catttccatt   2400
cgtctgtagc ttctatcccc aaaggcaaag aaactaaaag agaaatgact cattgaagat   2460
tggcctcttt cctttctcta agacaaacct aagtaaaagc ctgagctttg agtcctatgc   2520
tcagcacacg ggaaggagat gttaataatt aaaataaagt tgatatcctg tctttaggga   2580
gttcccttga tctcttgaaa gagacacagc cccatttaca ttatttcgtg gatttcacca   2640
gcatagtata gttttttttct gtaagtccct cattcttatg taataacagg tggaactgag   2700
gtttgaagaa cctcagtggc ccatcctgat gacattggag actcaaagag acaagagaga   2760
gtagggttta aaacctgagc tttaagactc ccactagctt cgtgtccttt ggcatgttaa   2820
cgtgcctcag tttcctcatc tgtataatgg ggatatatga aaggcaccag tcctaaggtg   2880
aacattaagt gagatgattc tagttacaga cttagaacaa tttccagcac atagttaaat   2940
atccaggaaa ttctggtact gttatgtgtg ggtgagctga cctggatgta gatgttttcc   3000
tctctcttgc tgacccctcc gccagttttg tcttgtgatg ccattaacac atctctccct   3060
ttctgacctg gctcctgccc attggtgtcc caagaaatcg tgagaatagt tagccccccg   3120
tctccccagc ctgttgcttt ctcgtgtagt tgttcacagt agttgagaag ttgaagagct   3180
tttgcctatt gaaggtgcac tgagaataaa ctctttcctg ccaccagaat tgcagtggtt   3240
cacggcctgc actcattccc atgaatgcag ttaatagcca cagaaatgtc acattaagca   3300
aagcagccag ggtctcatcg tgttgagact cgagtctctc agaccttgga ttcattccct   3360
ggtgtctttg agcctcagtt tcctcattgg taaaagagaa gtgaagcagt gtctcacagg   3420
gtcattacag agattaaatg aaataaatga aataacatag accaggaggg cgtggtgttt   3480
aaaagtcaca gatggggcac cctcgggcca tccagcccag tgttttcttt agcccctatg   3540
atgttcattt tttgttatat cccattaggt gcccatattt aaaaattggg agatttcaca   3600
taaaattaaa aggtctgcat tttctttttt cttttctttt tttttttttt tgagacacag   3660
tctcactctg tcaccaggct agagtgcagt ggcacgatct cagctcactg caacctctgc   3720
ctcccaggtt caagtaattc tcctgcctca gcctcccaag tagctgggac tacaggcacg   3780
tgccaccacg cccagctaat ttttgtattt ttagcagaga tggggtttca ccacattggc   3840
caggatggtc tcgatctcaa cctcgtgatc cacccacctc ggtctcccaa agcgctggga   3900
ttacaggcgt gagccaccgc gccaagccaa ggtctgcatt tttctttaga actcagaaca   3960
```

```
cccaatagtc ctaggccccc atcctcgcat ggcagcaagc taaataagca tcttcccact   4020

gcgagttggg gcatgaccca gcctatggtt tgccatactc cctctttttc tccgtttttt   4080

cattaattgt gaacctgacc tgcatcaccc tttcatgtca gtgctctcca aacctgcttg   4140

cttgcacccc tctagtcgaa atattttgtg cttaccccaa tatatgtgtg tgactattga   4200

actctattcg tagactgctt gtactaatgt catttgcatc ataaaatatt catatccaat   4260

aaacatatta aaaggatgag ataagaaacc gaaaaaaaaa aaaaaaaaaa aaa          4313
```

<210> SEQ ID NO 14
<211> LENGTH: 505
<212> TYPE: PRT
<213> ORGANISM: Artificial Sequence
<220> FEATURE:
<223> OTHER INFORMATION: Synthetic Polymer

<400> SEQUENCE: 14

```
Met Lys Arg Thr Pro Thr Ala Glu Glu Arg Glu Arg Glu Ala Lys Lys
1               5                   10                  15

Leu Arg Leu Leu Glu Glu Leu Glu Asp Thr Trp Leu Pro Tyr Leu Thr
            20                  25                  30

Pro Lys Asp Asp Glu Phe Tyr Gln Gln Trp Gln Leu Lys Tyr Pro Lys
        35                  40                  45

Leu Ile Leu Arg Glu Ala Ser Ser Val Ser Glu Glu Leu His Lys Glu
    50                  55                  60

Val Gln Glu Ala Phe Leu Thr Leu His Lys His Gly Cys Leu Phe Arg
65                  70                  75                  80

Asp Leu Val Arg Ile Gln Gly Lys Asp Leu Leu Thr Pro Val Ser Arg
                85                  90                  95

Ile Leu Ile Gly Asn Pro Gly Cys Thr Tyr Lys Tyr Leu Asn Thr Arg
            100                 105                 110

Leu Phe Thr Val Pro Trp Pro Val Lys Gly Ser Asn Ile Lys His Thr
        115                 120                 125

Glu Ala Glu Ile Ala Ala Ala Cys Glu Thr Phe Leu Lys Leu Asn Asp
    130                 135                 140

Tyr Leu Gln Ile Glu Thr Ile Gln Ala Leu Glu Glu Leu Ala Ala Lys
145                 150                 155                 160

Glu Lys Ala Asn Glu Asp Ala Val Pro Leu Cys Met Ser Ala Asp Phe
                165                 170                 175

Pro Arg Val Gly Met Gly Ser Ser Tyr Asn Gly Gln Asp Glu Val Asp
            180                 185                 190

Ile Lys Ser Arg Ala Ala Tyr Asn Val Thr Leu Leu Asn Phe Met Asp
        195                 200                 205

Pro Gln Lys Met Pro Tyr Leu Lys Glu Glu Pro Tyr Phe Gly Met Gly
    210                 215                 220

Lys Met Ala Val Ser Trp His His Asp Glu Asn Leu Val Asp Arg Ser
225                 230                 235                 240

Ala Val Ala Val Tyr Ser Tyr Ser Cys Glu Gly Pro Glu Glu Glu Ser
                245                 250                 255

Glu Asp Asp Ser His Leu Glu Gly Arg Asp Pro Asp Ile Trp His Val
            260                 265                 270

Gly Phe Lys Ile Ser Trp Asp Ile Glu Thr Pro Gly Leu Ala Ile Pro
        275                 280                 285

Leu His Gln Gly Asp Cys Tyr Phe Met Leu Asp Asp Leu Asn Ala Thr
    290                 295                 300
```

```
His Gln His Cys Val Leu Ala Gly Ser Gln Pro Arg Phe Ser Ser Thr
305                 310                 315                 320

His Arg Val Ala Glu Cys Ser Thr Gly Thr Leu Asp Tyr Ile Leu Gln
                325                 330                 335

Arg Cys Gln Leu Ala Leu Gln Asn Val Cys Asp Asp Val Asp Asn Asp
            340                 345                 350

Asp Val Ser Leu Lys Ser Phe Glu Pro Ala Val Leu Lys Gln Gly Glu
        355                 360                 365

Glu Ile His Asn Glu Val Glu Phe Glu Trp Leu Arg Gln Phe Trp Phe
    370                 375                 380

Gln Gly Asn Arg Tyr Arg Lys Cys Thr Asp Trp Trp Cys Gln Pro Met
385                 390                 395                 400

Ala Gln Leu Glu Ala Leu Trp Lys Lys Met Glu Gly Val Thr Asn Ala
                405                 410                 415

Val Leu His Glu Val Lys Arg Glu Gly Leu Pro Val Glu Gln Arg Asn
            420                 425                 430

Glu Ile Leu Thr Ala Ile Leu Ala Ser Leu Thr Ala Arg Gln Asn Leu
        435                 440                 445

Arg Arg Glu Trp His Ala Arg Cys Gln Ser Arg Ile Ala Arg Thr Leu
    450                 455                 460

Pro Ala Asp Gln Lys Pro Glu Cys Arg Pro Tyr Trp Glu Lys Asp Asp
465                 470                 475                 480

Ala Ser Met Pro Leu Pro Phe Asp Leu Thr Asp Ile Val Ser Glu Leu
                485                 490                 495

Arg Gly Gln Leu Leu Glu Ala Lys Pro
            500                 505

<210> SEQ ID NO 15
<211> LENGTH: 2631
<212> TYPE: DNA
<213> ORGANISM: Artificial Sequence
<220> FEATURE:
<223> OTHER INFORMATION: Synthetic Polymer

<400> SEQUENCE: 15

tataaaagct gggccggcgc gggccgggcc attcgcgacc cggaggtgcg cgggcgcggg      60

cgagcagggt ctccgggtgg gcggcggcga cgcccgcgc aggctggagg ccgccgaggc      120

tcgccatgcc gggagaactc taactccccc atggagtcgg ccgacttcta cgaggcggag     180

ccgcggcccc cgatgagcag ccacctgcag agccccccgc acgcgcccag cagcgccgcc     240

ttcggctttc cccggggcgc gggccccgcg cagcctcccg ccccacctgc cgccccggag     300

ccgctgggcg gcatctgcga gcacgagacg tccatcgaca tcagcgccta catcgacccg     360

gccgccttca acgacgagtt cctggccgac ctgttccagc acagccggca gcaggagaag     420

gccaaggcgg ccgtgggccc cacgggcggc ggcggcggcg gcgactttga ctacccgggc     480

gcgcccgcgg gccccggcgg cgccgtcatg cccgggggag cgcacgggcc cccgcccggc     540

tacggctgcg cggccgccgg ctacctggac ggcaggctgg agcccctgta cgagcgcgtc     600

ggggcgccgg cgctgcggcc gctggtgatc aagcaggagc cccgcgagga ggatgaagcc     660

aagcagctgg cgctggccgg cctcttccct taccagccgc cgccgccgcc gccgccctcg     720

cacccgcacc cgcacccgcc gcccgcgcac ctggccgccc cgcacctgca gttccagatc     780

gcgcactgcg gccagaccac catgcacctg cagcccggtc accccacgcc gccgcccacg     840

cccgtgccca gcccgcaccc cgcgcccgcg ctcggtgccg ccggcctgcc gggccctggc     900
```

```
agcgcgctca aggggctggg cgccgcgcac cccgacctcc gcgcgagtgg cggcagcggc    960

gcgggcaagg ccaagaagtc ggtggacaag aacagcaacg agtaccgggt gcggcgcgag   1020

cgcaacaaca tcgcggtgcg caagagccgc gacaaggcca agcagcgcaa cgtggagacg   1080

cagcagaagg tgctggagct gaccagtgac aatgaccgcc tgcgcaagcg ggtggaacag   1140

ctgagccgcg aactggacac gctgcggggc atcttccgcc agctgccaga gagctccttg   1200

gtcaaggcca tgggcaactg cgcgtgaggc gcgcggctgt gggaccgccc tgggccagcc   1260

tccggcgggg acccagggag tggtttgggg tcgccggatc tcgaggcttg cccgagccgt   1320

gcgagccagg actaggagat tccggtgcct cctgaaagcc tggcctgctc cgcgtgtccc   1380

ctcccttcct ctgcgccgga cttggtgcgt ctaagatgag gggccaggc ggtggcttct    1440

ccctgcgagg aggggagaat tcttggggct gagctgggag cccggcaact ctagtattta   1500

ggataacctt gtgccttgga aatgcaaact caccgctcca atgcctactg agtaggggga   1560

gcaaatcgtg ccttgtcatt ttatttggag gtttcctgcc tccttcccga ggctacagca   1620

gaccccccatg agagaaggag gggagcaggc ccgtggcagg aggagggctc agggagctga  1680

gatcccgaca agcccgccag ccccagccgc tcctccacgc ctgtccttag aaaggggtgg   1740

aaacataggg acttggggct tggaacctaa ggttgttccc ctagttctac atgaaggtgg   1800

agggtctcta gttccacgcc tctcccacct ccctccgcac acaccccacc ccagcctgct   1860

ataggctggg cttccccttg ggcggaact cactgcgatg ggggtcacca ggtgaccagt    1920

gggagccccc accccgagtc acaccagaaa gctaggtcgt gggtcagctc tgaggatgta   1980

taccccctggt gggagaggga gacctagaga tctggctgtg ggcgggcat gggggggtgaa  2040

gggccactgg gaccctcagc cttgtttgta ctgtatgcct tcagcattgc ctaggaacac   2100

gaagcacgat cagtccatcc cagagggacc ggagttatga caagctttcc aaatattttg   2160

ctttatcagc cgatatcaac acttgtatct ggcctctgtg ccccagcagt gccttgtgca   2220

atgtgaatgt gcgcgtctct gctaaaccac cattttattt ggtttttgtt ttgttttggt   2280

tttgctcgga tacttgccaa aatgagactc tccgtcggca gctgggggaa gggtctgaga   2340

ctcccttttcc ttttggtttt gggattactt ttgatcctgg gggaccaatg aggtgagggg  2400

ggttctcctt tgccctcagc tttccccagc ccctccggcc tgggctgccc acaaggcttg   2460

tcccccagag gccctggctc ctggtcggga agggaggtgg cctcccgcca acgcatcact   2520

ggggctggga gcagggaagg acggcttggt tctcttcttt tggggagaac gtagagtctc   2580

actctagatg ttttatgtat tatatctata atataaacat atcaaagtca a            2631
```

<210> SEQ ID NO 16
<211> LENGTH: 358
<212> TYPE: PRT
<213> ORGANISM: Artificial Sequence
<220> FEATURE:
<223> OTHER INFORMATION: Synthetic Polymer

<400> SEQUENCE: 16

```
Met Glu Ser Ala Asp Phe Tyr Glu Ala Glu Pro Arg Pro Pro Met Ser
1               5                   10                  15

Ser His Leu Gln Ser Pro Pro His Ala Pro Ser Ser Ala Ala Phe Gly
            20                  25                  30

Phe Pro Arg Gly Ala Gly Pro Ala Gln Pro Pro Ala Pro Pro Ala Ala
        35                  40                  45

Pro Glu Pro Leu Gly Gly Ile Cys Glu His Glu Thr Ser Ile Asp Ile
```

```
    50                  55                  60

Ser Ala Tyr Ile Asp Pro Ala Ala Phe Asn Asp Glu Phe Leu Ala Asp
65                  70                  75                  80

Leu Phe Gln His Ser Arg Gln Gln Glu Lys Ala Lys Ala Ala Val Gly
                85                  90                  95

Pro Thr Gly Gly Gly Gly Gly Gly Asp Phe Asp Tyr Pro Gly Ala Pro
            100                 105                 110

Ala Gly Pro Gly Gly Ala Val Met Pro Gly Gly Ala His Gly Pro Pro
        115                 120                 125

Pro Gly Tyr Gly Cys Ala Ala Ala Gly Tyr Leu Asp Gly Arg Leu Glu
    130                 135                 140

Pro Leu Tyr Glu Arg Val Gly Ala Pro Ala Leu Arg Pro Leu Val Ile
145                 150                 155                 160

Lys Gln Glu Pro Arg Glu Glu Asp Glu Ala Lys Gln Leu Ala Leu Ala
                165                 170                 175

Gly Leu Phe Pro Tyr Gln Pro Pro Pro Pro Pro Pro Pro Ser His Pro
            180                 185                 190

His Pro His Pro Pro Pro Ala His Leu Ala Ala Pro His Leu Gln Phe
        195                 200                 205

Gln Ile Ala His Cys Gly Gln Thr Thr Met His Leu Gln Pro Gly His
    210                 215                 220

Pro Thr Pro Pro Pro Thr Pro Val Pro Ser Pro His Pro Ala Pro Ala
225                 230                 235                 240

Leu Gly Ala Ala Gly Leu Pro Gly Pro Gly Ser Ala Leu Lys Gly Leu
                245                 250                 255

Gly Ala Ala His Pro Asp Leu Arg Ala Ser Gly Gly Ser Gly Ala Gly
            260                 265                 270

Lys Ala Lys Lys Ser Val Asp Lys Asn Ser Asn Glu Tyr Arg Val Arg
        275                 280                 285

Arg Glu Arg Asn Asn Ile Ala Val Arg Lys Ser Arg Asp Lys Ala Lys
    290                 295                 300

Gln Arg Asn Val Glu Thr Gln Gln Lys Val Leu Glu Leu Thr Ser Asp
305                 310                 315                 320

Asn Asp Arg Leu Arg Lys Arg Val Glu Gln Leu Ser Arg Glu Leu Asp
                325                 330                 335

Thr Leu Arg Gly Ile Phe Arg Gln Leu Pro Glu Ser Ser Leu Val Lys
            340                 345                 350

Ala Met Gly Asn Cys Ala
        355
```

```
<210> SEQ ID NO 17
<211> LENGTH: 2631
<212> TYPE: DNA
<213> ORGANISM: Artificial Sequence
<220> FEATURE:
<223> OTHER INFORMATION: Synthetic Polymer

<400> SEQUENCE: 17

tataaaagct gggccggcgc gggccgggcc attcgcgacc cggaggtgcg cgggcgcggg      60

cgagcagggt ctccgggtgg gcggcggcga cgccccgcgc aggctggagg ccgccgaggc     120

tcgccatgcc gggagaactc taactccccc atggagtcgg ccgacttcta cgaggcggag     180

ccgcggcccc cgatgagcag ccacctgcag agcccccgc acgcgcccag cagcgccgcc     240

ttcggctttc cccggggcgc gggccccgcg cagcctcccg ccccacctgc cgccccggag     300
```

```
ccgctgggcg gcatctgcga gcacgagacg tccatcgaca tcagcgccta catcgacccg    360
gccgccttca acgacgagtt cctggccgac ctgttccagc acagccggca gcaggagaag    420
gccaaggcgg ccgtgggccc cacgggcggc ggcggcggcg gcgactttga ctacccgggc    480
gcgcccgcgg gccccggcgg cgccgtcatg cccgggggag cgcacgggcc cccgcccggc    540
tacggctgcg cggccgccgg ctacctggac ggcaggctgg agcccctgta cgagcgcgtc    600
ggggcgccgg cgctgcggcc gctggtgatc aagcaggagc cccgcgagga ggatgaagcc    660
aagcagctgg cgctggccgg cctcttccct taccagccgc cgccgccgcc gccgccctcg    720
cacccgcacc cgcacccgcc gcccgcgcac ctggccgccc cgcacctgca gttccagatc    780
gcgcactgcg gccagaccac catgcacctg cagcccggtc accccacgcc gccgcccacg    840
cccgtgccca gcccgcaccc cgcgcccgcg ctcggtgccg ccggcctgcc gggccctggc    900
agcgcgctca aggggctggg cgccgcgcac cccgacctcc gcgcgagtgg cggcagcggc    960
gcgggcaagg ccaagaagtc ggtggacaag aacagcaacg agtaccgggt gcggcgcgag   1020
cgcaacaaca tcgcggtgcg caagagccgc gacaaggcca agcagcgcaa cgtggagacg   1080
cagcagaagg tgctggagct gaccagtgac aatgaccgcc tgcgcaagcg ggtggaacag   1140
ctgagccgcg aactggacac gctgcggggc atcttccgcc agctgccaga gagctccttg   1200
gtcaaggcca tgggcaactg cgcgtgaggc gcgcggctgt gggaccgccc tgggccagcc   1260
tccggcgggg acccagggag tggtttgggg tcgccggatc tcgaggcttg cccgagccgt   1320
gcgagccagg actaggagat tccggtgcct cctgaaagcc tggcctgctc cgcgtgtccc   1380
ctcccttcct ctgcgccgga cttggtgcgt ctaagatgag gggccaggc ggtggcttct    1440
ccctgcgagg aggggagaat tcttggggct gagctgggag cccggcaact ctagtattta   1500
ggataacctt gtgccttgga aatgcaaact caccgctcca atgcctactg agtaggggga   1560
gcaaatcgtg ccttgtcatt ttatttggag gtttcctgcc tccttcccga ggctacagca   1620
gaccccccatg agagaaggag gggagcaggc ccgtggcagg aggagggctc agggagctga   1680
gatcccgaca agcccgccag ccccagccgc tcctccacgc ctgtccttag aaaggggtgg   1740
aaacataggg acttggggct tggaacctaa ggttgttccc ctagttctac atgaaggtgg   1800
agggtctcta gttccacgcc tctcccacct ccctccgcac acaccccacc ccagcctgct   1860
ataggctggg cttccccttg gggcggaact cactgcgatg gggtcacca ggtgaccagt    1920
gggagccccc accccgagtc acaccagaaa gctaggtcgt gggtcagctc tgaggatgta   1980
tacccctggt gggagaggga gacctagaga tctggctgtg ggcgggcat ggggggtgaa    2040
gggccactgg gaccctcagc cttgtttgta ctgtatgcct tcagcattgc ctaggaacac   2100
gaagcacgat cagtccatcc cagagggacc ggagttatga caagctttcc aaatattttg   2160
ctttatcagc cgatatcaac acttgtatct ggcctctgtg ccccagcagt gccttgtgca   2220
atgtgaatgt gcgcgtctct gctaaaccac cattttattt ggtttttgtt ttgttttggt   2280
tttgctcgga tacttgccaa aatgagactc tccgtcggca gctgggggaa gggtctgaga   2340
ctccctttcc ttttggtttt gggattactt ttgatcctgg gggaccaatg aggtgagggg   2400
ggttctcctt tgccctcagc tttccccagc ccctccggcc tgggctgccc acaaggcttg   2460
tcccccagag gccctggctc ctggtcggga agggaggtgg cctcccgcca acgcatcact   2520
ggggctggga gcagggaagg acggcttggt tctcttcttt tggggagaac gtagagtctc   2580
actctagatg ttttatgtat tatatctata atataaacat atcaaagtca a            2631
```

<210> SEQ ID NO 18
<211> LENGTH: 239
<212> TYPE: PRT
<213> ORGANISM: Artificial Sequence
<220> FEATURE:
<223> OTHER INFORMATION: Synthetic Polymer

<400> SEQUENCE: 18

```
Met Pro Gly Gly Ala His Gly Pro Pro Pro Gly Tyr Gly Cys Ala Ala
1               5                   10                  15

Ala Gly Tyr Leu Asp Gly Arg Leu Glu Pro Leu Tyr Glu Arg Val Gly
            20                  25                  30

Ala Pro Ala Leu Arg Pro Leu Val Ile Lys Gln Glu Pro Arg Glu Glu
        35                  40                  45

Asp Glu Ala Lys Gln Leu Ala Leu Ala Gly Leu Phe Pro Tyr Gln Pro
    50                  55                  60

Pro Pro Pro Pro Pro Pro Ser His Pro His Pro His Pro Pro Pro Ala
65                  70                  75                  80

His Leu Ala Ala Pro His Leu Gln Phe Gln Ile Ala His Cys Gly Gln
                85                  90                  95

Thr Thr Met His Leu Gln Pro Gly His Pro Thr Pro Pro Pro Thr Pro
            100                 105                 110

Val Pro Ser Pro His Pro Ala Pro Ala Leu Gly Ala Ala Gly Leu Pro
        115                 120                 125

Gly Pro Gly Ser Ala Leu Lys Gly Leu Gly Ala Ala His Pro Asp Leu
    130                 135                 140

Arg Ala Ser Gly Gly Ser Gly Ala Gly Lys Ala Lys Lys Ser Val Asp
145                 150                 155                 160

Lys Asn Ser Asn Glu Tyr Arg Val Arg Arg Glu Arg Asn Asn Ile Ala
                165                 170                 175

Val Arg Lys Ser Arg Asp Lys Ala Lys Gln Arg Asn Val Glu Thr Gln
            180                 185                 190

Gln Lys Val Leu Glu Leu Thr Ser Asp Asn Asp Arg Leu Arg Lys Arg
        195                 200                 205

Val Glu Gln Leu Ser Arg Glu Leu Asp Thr Leu Arg Gly Ile Phe Arg
    210                 215                 220

Gln Leu Pro Glu Ser Ser Leu Val Lys Ala Met Gly Asn Cys Ala
225                 230                 235
```

<210> SEQ ID NO 19
<211> LENGTH: 2631
<212> TYPE: DNA
<213> ORGANISM: Artificial Sequence
<220> FEATURE:
<223> OTHER INFORMATION: Synthetic Polymer

<400> SEQUENCE: 19

```
tataaaagct gggccggcgc gggccgggcc attcgcgacc cggaggtgcg cgggcgcggg      60

cgagcagggt ctccgggtgg gcggcggcga cgccccgcgc aggctggagg ccgccgaggc     120

tcgccatgcc gggagaactc taactccccc atggagtcgg ccgacttcta cgaggcggag     180

ccgcggcccc cgatgagcag ccacctgcag agcccccgcc acgcgcccag cagcgccgcc     240

ttcggctttc cccggggcgc gggccccgcg cagcctcccg ccccacctgc cgccccggag     300

ccgctgggcg gcatctgcga gcacgagacg tccatcgaca tcagcgccta catcgacccg     360

gccgccttca acgacgagtt cctggccgac ctgttccagc acagccggca gcaggagaag     420

gccaaggcgg ccgtgggccc cacgggcggc ggcggcggcg gcgactttga ctacccgggc     480
```

```
gcgcccgcgg gccccggcgg cgccgtcatg cccgggggag cgcacgggcc cccgcccggc    540
tacggctgcg cggccgccgg ctacctggac ggcaggctgg agcccctgta cgagcgcgtc    600
ggggcgccgg cgctgcggcc gctggtgatc aagcaggagc cccgcgagga ggatgaagcc    660
aagcagctgg cgctggccgg cctcttccct taccagccgc cgccgccgcc gccgccctcg    720
cacccgcacc cgcacccgcc gcccgcgcac ctggccgccc cgcacctgca gttccagatc    780
gcgcactgcg gccagaccac catgcacctg cagcccggtc accccacgcc gccgcccacg    840
cccgtgccca gcccgcaccc cgcgcccgcg ctcggtgccg ccggcctgcc gggccctggc    900
agcgcgctca aggggctggg cgccgcgcac cccgacctcc gcgcgagtgg cggcagcggc    960
gcgggcaagg ccaagaagtc ggtggacaag aacagcaacg agtaccgggt gcggcgcgag   1020
cgcaacaaca tcgcggtgcg caagagccgc gacaaggcca agcagcgcaa cgtggagacg   1080
cagcagaagg tgctggagct gaccagtgac aatgaccgcc tgcgcaagcg ggtggaacag   1140
ctgagccgcg aactggacac gctgcggggc atcttccgcc agctgccaga gagctccttg   1200
gtcaaggcca tgggcaactg cgcgtgaggc gcgcggctgt gggaccgccc tgggccagcc   1260
tccggcgggg acccagggag tggtttgggg tcgccggatc tcgaggcttg cccgagccgt   1320
gcgagccagg actaggagat tccggtgcct cctgaaagcc tggcctgctc cgcgtgtccc   1380
ctcccttcct ctgcgccgga cttggtgcgt ctaagatgag ggggccaggc ggtggcttct   1440
ccctgcgagg aggggagaat tcttggggct gagctgggag cccggcaact ctagtattta   1500
ggataacctt gtgccttgga aatgcaaact caccgctcca atgcctactg agtagggga   1560
gcaaatcgtg ccttgtcatt ttatttggag gtttcctgcc tccttcccga ggctacagca   1620
gacccccatg agagaaggag gggagcaggc ccgtggcagg aggagggctc agggagctga   1680
gatcccgaca agcccgccag ccccagccgc tcctccacgc ctgtccttag aaaggggtgg   1740
aaacataggg acttggggct tggaacctaa ggttgttccc ctagttctac atgaaggtgg   1800
agggtctcta gttccacgcc tctcccacct ccctccgcac acaccccacc ccagcctgct   1860
ataggctggg cttccccttg gggcggaact cactgcgatg gggggtcacca ggtgaccagt   1920
gggagccccc accccgagtc acaccagaaa gctaggtcgt gggtcagctc tgaggatgta   1980
taccccctggt gggagaggga gacctagaga tctggctgtg gggcgggcat ggggggtgaa   2040
gggccactgg gaccctcagc cttgtttgta ctgtatgcct tcagcattgc ctaggaacac   2100
gaagcacgat cagtccatcc cagagggacc ggagttatga caagctttcc aaatattttg   2160
ctttatcagc cgatatcaac acttgtatct ggcctctgtg ccccagcagt gccttgtgca   2220
atgtgaatgt gcgcgtctct gctaaaccac cattttattt ggtttttgtt ttgttttggt   2280
tttgctcgga tacttgccaa aatgagactc tccgtcggca gctgggggaa gggtctgaga   2340
ctccctttcc ttttggtttt gggattactt ttgatcctgg gggaccaatg aggtgagggg   2400
ggttctcctt tgccctcagc tttccccagc ccctccggcc tggggctgccc acaaggcttg   2460
tcccccagag gccctggctc ctggtcggga agggaggtgg cctcccgcca acgcatcact   2520
ggggctggga gcagggaagg acggcttggt tctcttcttt tggggagaac gtagagtctc   2580
actctagatg ttttatgtat tatatctata atataaacat atcaaagtca a             2631
```

<210> SEQ ID NO 20
<211> LENGTH: 393
<212> TYPE: PRT
<213> ORGANISM: Artificial Sequence
<220> FEATURE:

```
<223> OTHER INFORMATION: Synthetic Polymer

<400> SEQUENCE: 20

Met Arg Gly Arg Gly Arg Ala Gly Ser Pro Gly Gly Arg Arg Arg Arg
1               5                   10                  15

Pro Ala Gln Ala Gly Gly Arg Arg Gly Ser Pro Cys Arg Glu Asn Ser
            20                  25                  30

Asn Ser Pro Met Glu Ser Ala Asp Phe Tyr Glu Ala Glu Pro Arg Pro
        35                  40                  45

Pro Met Ser Ser His Leu Gln Ser Pro Pro His Ala Pro Ser Ser Ala
    50                  55                  60

Ala Phe Gly Phe Pro Arg Gly Ala Gly Pro Ala Gln Pro Pro Ala Pro
65                  70                  75                  80

Pro Ala Ala Pro Glu Pro Leu Gly Gly Ile Cys Glu His Glu Thr Ser
                85                  90                  95

Ile Asp Ile Ser Ala Tyr Ile Asp Pro Ala Ala Phe Asn Asp Glu Phe
            100                 105                 110

Leu Ala Asp Leu Phe Gln His Ser Arg Gln Gln Glu Lys Ala Lys Ala
        115                 120                 125

Ala Val Gly Pro Thr Gly Gly Gly Gly Gly Gly Asp Phe Asp Tyr Pro
    130                 135                 140

Gly Ala Pro Ala Gly Pro Gly Gly Ala Val Met Pro Gly Gly Ala His
145                 150                 155                 160

Gly Pro Pro Pro Gly Tyr Gly Cys Ala Ala Ala Gly Tyr Leu Asp Gly
                165                 170                 175

Arg Leu Glu Pro Leu Tyr Glu Arg Val Gly Ala Pro Ala Leu Arg Pro
            180                 185                 190

Leu Val Ile Lys Gln Glu Pro Arg Glu Glu Asp Glu Ala Lys Gln Leu
        195                 200                 205

Ala Leu Ala Gly Leu Phe Pro Tyr Gln Pro Pro Pro Pro Pro Pro Pro
    210                 215                 220

Ser His Pro His Pro His Pro Pro Pro Ala His Leu Ala Ala Pro His
225                 230                 235                 240

Leu Gln Phe Gln Ile Ala His Cys Gly Gln Thr Thr Met His Leu Gln
                245                 250                 255

Pro Gly His Pro Thr Pro Pro Pro Thr Pro Val Pro Ser Pro His Pro
            260                 265                 270

Ala Pro Ala Leu Gly Ala Ala Gly Leu Pro Gly Pro Gly Ser Ala Leu
        275                 280                 285

Lys Gly Leu Gly Ala Ala His Pro Asp Leu Arg Ala Ser Gly Gly Ser
    290                 295                 300

Gly Ala Gly Lys Ala Lys Lys Ser Val Asp Lys Asn Ser Asn Glu Tyr
305                 310                 315                 320

Arg Val Arg Arg Glu Arg Asn Asn Ile Ala Val Arg Lys Ser Arg Asp
                325                 330                 335

Lys Ala Lys Gln Arg Asn Val Glu Thr Gln Gln Lys Val Leu Glu Leu
            340                 345                 350

Thr Ser Asp Asn Asp Arg Leu Arg Lys Arg Val Glu Gln Leu Ser Arg
        355                 360                 365

Glu Leu Asp Thr Leu Arg Gly Ile Phe Arg Gln Leu Pro Glu Ser Ser
    370                 375                 380

Leu Val Lys Ala Met Gly Asn Cys Ala
385                 390
```

<210> SEQ ID NO 21
<211> LENGTH: 2631
<212> TYPE: DNA
<213> ORGANISM: Artificial Sequence
<220> FEATURE:
<223> OTHER INFORMATION: Synthetic Polymer

<400> SEQUENCE: 21

```
tataaaagct gggccggcgc gggccgggcc attcgcgacc cggaggtgcg cgggcgcggg     60
cgagcagggt ctccgggtgg gcggcggcga cgccccgcgc aggctggagg ccgccgaggc    120
tcgccatgcc gggagaactc taactccccc atggagtcgg ccgacttcta cgaggcggag    180
ccgcggcccc cgatgagcag ccacctgcag agcccccgc acgcgcccag cagcgccgcc    240
ttcggctttc cccggggcgc gggccccgcg cagcctcccg ccccacctgc cgccccggag    300
ccgctgggcg gcatctgcga gcacgagacg tccatcgaca tcagcgccta catcgacccg    360
gccgccttca acgacgagtt cctggccgac ctgttccagc acagccggca gcaggagaag    420
gccaaggcgg ccgtgggccc cacgggcggc ggcggcggcg gcgactttga ctacccgggc    480
gcgcccgcgg gccccggcgg cgccgtcatg cccgggggag cgcacgggcc cccgcccggc    540
tacggctgcg cggccgccgg ctacctggac ggcaggctgg agcccctgta cgagcgcgtc    600
ggggcgccgg cgctgcggcc gctggtgatc aagcaggagc cccgcgagga ggatgaagcc    660
aagcagctgg cgctggccgg cctcttccct taccagccgc cgccgccgcc gccgccctcg    720
cacccgcacc cgcacccgcc gcccgcgcac ctggccgccc cgcacctgca gttccagatc    780
gcgcactgcg gccagaccac catgcacctg cagcccggtc accccacgcc gccgcccacg    840
cccgtgccca gcccgcaccc cgcgcccgcg ctcggtgccg ccggcctgcc gggccctggc    900
agcgcgctca aggggctggg cgccgcgcac cccgacctcc gcgcgagtgg cggcagcggc    960
gcgggcaagg ccaagaagtc ggtggacaag aacagcaacg agtaccgggt gcggcgcgag   1020
cgcaacaaca tcgcggtgcg caagagccgc gacaaggcca agcagcgcaa cgtggagacg   1080
cagcagaagg tgctggagct gaccagtgac aatgaccgcc tgcgcaagcg ggtggaacag   1140
ctgagccgcg aactggacac gctgcggggc atcttccgcc agctgccaga gagctccttg   1200
gtcaaggcca tgggcaactg cgcgtgaggc gcgcggctgt gggaccgccc tgggccagcc   1260
tccggcgggg acccagggag tggtttgggg tcgccggatc tcgaggcttg cccgagccgt   1320
gcgagccagg actaggagat tccggtgcct cctgaaagcc tggcctgctc cgcgtgtccc   1380
ctcccttcct ctgcgccgga cttggtgcgt ctaagatgag gggccaggc ggtggcttct   1440
ccctgcgagg aggggagaat tcttggggct gagctgggag cccggcaact ctagtattta   1500
ggataacctt gtgccttgga aatgcaaact caccgctcca atgcctactg agtaggggga   1560
gcaaatcgtg ccttgtcatt ttatttggag gtttcctgcc tccttcccga ggctacagca   1620
gacccccatg agagaaggag gggagcaggc ccgtggcagg aggagggctc agggagctga   1680
gatcccgaca agcccgccag ccccagccgc tcctccacgc ctgtccttag aaaggggtgg   1740
aaacataggg acttggggct tggaacctaa ggttgttccc ctagttctac atgaaggtgg   1800
agggtctcta gttccacgcc tctcccacct ccctccgcac acaccccacc ccagcctgct   1860
ataggctggg cttccccttg gggcggaact cactgcgatg gggtcacca ggtgaccagt    1920
gggagccccc accccgagtc acaccagaaa gctaggtcgt gggtcagctc tgaggatgta   1980
tacccctggt gggagaggga gacctagaga tctggctgtg gggcgggcat gggggtgaa    2040
gggccactgg gaccctcagc cttgtttgta ctgtatgcct tcagcattgc ctaggaacac   2100
```

-continued

```
gaagcacgat cagtccatcc cagagggacc ggagttatga caagctttcc aaatattttg   2160

ctttatcagc cgatatcaac acttgtatct ggcctctgtg ccccagcagt gccttgtgca   2220

atgtgaatgt gcgcgtctct gctaaaccac cattttattt ggtttttgtt ttgttttggt   2280

tttgctcgga tacttgccaa aatgagactc tccgtcggca gctgggggaa gggtctgaga   2340

ctccctttcc ttttggtttt gggattactt ttgatcctgg gggaccaatg aggtgagggg   2400

ggttctcctt tgccctcagc tttccccagc ccctccggcc tgggctgccc acaaggcttg   2460

tcccccagag gccctggctc ctggtcggga agggaggtgg cctcccgcca acgcatcact   2520

ggggctggga gcagggaagg acggcttggt tctcttcttt tggggagaac gtagagtctc   2580

actctagatg ttttatgtat tatatctata atataaacat atcaaagtca a            2631
```

```
<210> SEQ ID NO 22
<211> LENGTH: 344
<212> TYPE: PRT
<213> ORGANISM: Artificial Sequence
<220> FEATURE:
<223> OTHER INFORMATION: Synthetic Polymer

<400> SEQUENCE: 22

Met Ser Ser His Leu Gln Ser Pro Pro His Ala Pro Ser Ser Ala Ala
1               5                   10                  15

Phe Gly Phe Pro Arg Gly Ala Gly Pro Ala Gln Pro Pro Ala Pro Pro
            20                  25                  30

Ala Ala Pro Glu Pro Leu Gly Gly Ile Cys Glu His Glu Thr Ser Ile
        35                  40                  45

Asp Ile Ser Ala Tyr Ile Asp Pro Ala Ala Phe Asn Asp Glu Phe Leu
    50                  55                  60

Ala Asp Leu Phe Gln His Ser Arg Gln Gln Glu Lys Ala Lys Ala Ala
65                  70                  75                  80

Val Gly Pro Thr Gly Gly Gly Gly Gly Gly Asp Phe Asp Tyr Pro Gly
                85                  90                  95

Ala Pro Ala Gly Pro Gly Gly Ala Val Met Pro Gly Gly Ala His Gly
            100                 105                 110

Pro Pro Pro Gly Tyr Gly Cys Ala Ala Ala Gly Tyr Leu Asp Gly Arg
        115                 120                 125

Leu Glu Pro Leu Tyr Glu Arg Val Gly Ala Pro Ala Leu Arg Pro Leu
    130                 135                 140

Val Ile Lys Gln Glu Pro Arg Glu Glu Asp Glu Ala Lys Gln Leu Ala
145                 150                 155                 160

Leu Ala Gly Leu Phe Pro Tyr Gln Pro Pro Pro Pro Pro Pro Pro Ser
                165                 170                 175

His Pro His Pro His Pro Pro Pro Ala His Leu Ala Ala Pro His Leu
            180                 185                 190

Gln Phe Gln Ile Ala His Cys Gly Gln Thr Thr Met His Leu Gln Pro
        195                 200                 205

Gly His Pro Thr Pro Pro Pro Thr Pro Val Pro Ser Pro His Pro Ala
    210                 215                 220

Pro Ala Leu Gly Ala Ala Gly Leu Pro Gly Pro Gly Ser Ala Leu Lys
225                 230                 235                 240

Gly Leu Gly Ala Ala His Pro Asp Leu Arg Ala Ser Gly Gly Ser Gly
                245                 250                 255

Ala Gly Lys Ala Lys Lys Ser Val Asp Lys Asn Ser Asn Glu Tyr Arg
            260                 265                 270
```

```
Val Arg Arg Glu Arg Asn Asn Ile Ala Val Arg Lys Ser Arg Asp Lys
        275                 280                 285

Ala Lys Gln Arg Asn Val Glu Thr Gln Gln Lys Val Leu Glu Leu Thr
    290                 295                 300

Ser Asp Asn Asp Arg Leu Arg Lys Arg Val Glu Gln Leu Ser Arg Glu
305                 310                 315                 320

Leu Asp Thr Leu Arg Gly Ile Phe Arg Gln Leu Pro Glu Ser Ser Leu
                325                 330                 335

Val Lys Ala Met Gly Asn Cys Ala
            340


<210> SEQ ID NO 23
<211> LENGTH: 1892
<212> TYPE: DNA
<213> ORGANISM: Artificial Sequence
<220> FEATURE:
<223> OTHER INFORMATION: Synthetic Polymer

<400> SEQUENCE: 23

ggcgcccgcg cccgcccccg cgccgggccc ggctcggccc gacccggctc cgccgcgggc      60

aggcggggcc cagcgcactc ggagcccgag cccgagccgc agccgccgcc tggggcgctt     120

gggtcggcct cgaggacacc ggagaggggc gccacgccgc cgtggccgca gatttgaaag     180

aagccaacac taaaccacaa atatacaaca aggccatttt ctcaaacgag agtcagcctt     240

taacgaaatg accatggttg acacagagat gccattctgg cccaccaact ttgggatcag     300

ctccgtggat ctctccgtaa tggaagacca ctcccactcc tttgatatca agcccttcac     360

tactgttgac ttctccagca tttctactcc acattacgaa gacattccat tcacaagaac     420

agatccagtg gttgcagatt acaagtatga cctgaaactt caagagtacc aaagtgcaat     480

caaagtggag cctgcatctc caccttatta ttctgagaag actcagctct acaataagcc     540

tcatgaagag ccttccaact ccctcatggc aattgaatgt cgtgtctgtg gagataaagc     600

ttctggattt cactatggag ttcatgcttg tgaaggatgc aagggtttct tccggagaac     660

aatcagattg aagcttatct atgacagatg tgatcttaac tgtcggatcc acaaaaaaag     720

tagaaataaa tgtcagtact gtcggtttca gaaatgcctt gcagtgggga tgtctcataa     780

tgccatcagg tttgggcgga tgccacaggc cgagaaggag aagctgttgg cggagatctc     840

cagtgatatc gaccagctga atccagagtc cgctgacctc cgggccctgg caaaacattt     900

gtatgactca tacataaagt ccttcccgct gaccaaagca aaggcgaggg cgatcttgac     960

aggaaagaca acagacaaat caccattcgt tatctatgac atgaattcct taatgatggg    1020

agaagataaa atcaagttca aacacatcac ccccctgcag gagcagagca aagaggtggc    1080

catccgcatc tttcagggct gccagtttcg ctccgtggag gctgtgcagg agatcacaga    1140

gtatgccaaa agcattcctg gttttgtaaa tcttgacttg aacgaccaag taactctcct    1200

caaatatgga gtccacgaga tcatttacac aatgctggcc tccttgatga ataaagatgg    1260

ggttctcata tccgagggcc aaggcttcat gacaagggag tttctaaaga gcctgcgaaa    1320

gccttttggt gactttatgg agcccaagtt tgagtttgct gtgaagttca atgcactgga    1380

attagatgac agcgacttgg caatatttat tgctgtcatt attctcagtg gagaccgccc    1440

aggtttgctg aatgtgaagc ccattgaaga cattcaagac aacctgctac aagccctgga    1500

gctccagctg aagctgaacc accctgagtc ctcacagctg tttgccaagc tgctccagaa    1560

aatgacagac ctcagacaga ttgtcacgga acacgtgcag ctactgcagg tgatcaagaa    1620
```

```
gacggagaca gacatgagtc ttcacccgct cctgcaggag atctacaagg acttgtacta   1680

gcagagagtc ctgagccact gccaacattt cccttcttcc agttgcacta ttctgaggga   1740

aaatctgaca cctaagaaat ttactgtgaa aaagcatttt aaaaagaaaa ggttttagaa   1800

tatgatctat tttatgcata ttgtttataa agacacattt acaatttact tttaatatta   1860

aaaattacca tattatgaaa ttgctgatag ta                                 1892
```

```
<210> SEQ ID NO 24
<211> LENGTH: 477
<212> TYPE: PRT
<213> ORGANISM: Artificial Sequence
<220> FEATURE:
<223> OTHER INFORMATION: Synthetic Polymer

<400> SEQUENCE: 24

Met Thr Met Val Asp Thr Glu Met Pro Phe Trp Pro Thr Asn Phe Gly
1               5                   10                  15

Ile Ser Ser Val Asp Leu Ser Val Met Glu Asp His Ser His Ser Phe
            20                  25                  30

Asp Ile Lys Pro Phe Thr Thr Val Asp Phe Ser Ser Ile Ser Thr Pro
        35                  40                  45

His Tyr Glu Asp Ile Pro Phe Thr Arg Thr Asp Pro Val Val Ala Asp
    50                  55                  60

Tyr Lys Tyr Asp Leu Lys Leu Gln Glu Tyr Gln Ser Ala Ile Lys Val
65                  70                  75                  80

Glu Pro Ala Ser Pro Pro Tyr Tyr Ser Glu Lys Thr Gln Leu Tyr Asn
                85                  90                  95

Lys Pro His Glu Glu Pro Ser Asn Ser Leu Met Ala Ile Glu Cys Arg
            100                 105                 110

Val Cys Gly Asp Lys Ala Ser Gly Phe His Tyr Gly Val His Ala Cys
        115                 120                 125

Glu Gly Cys Lys Gly Phe Phe Arg Arg Thr Ile Arg Leu Lys Leu Ile
    130                 135                 140

Tyr Asp Arg Cys Asp Leu Asn Cys Arg Ile His Lys Lys Ser Arg Asn
145                 150                 155                 160

Lys Cys Gln Tyr Cys Arg Phe Gln Lys Cys Leu Ala Val Gly Met Ser
                165                 170                 175

His Asn Ala Ile Arg Phe Gly Arg Met Pro Gln Ala Glu Lys Glu Lys
            180                 185                 190

Leu Leu Ala Glu Ile Ser Ser Asp Ile Asp Gln Leu Asn Pro Glu Ser
        195                 200                 205

Ala Asp Leu Arg Ala Leu Ala Lys His Leu Tyr Asp Ser Tyr Ile Lys
    210                 215                 220

Ser Phe Pro Leu Thr Lys Ala Lys Ala Arg Ala Ile Leu Thr Gly Lys
225                 230                 235                 240

Thr Thr Asp Lys Ser Pro Phe Val Ile Tyr Asp Met Asn Ser Leu Met
                245                 250                 255

Met Gly Glu Asp Lys Ile Lys Phe Lys His Ile Thr Pro Leu Gln Glu
            260                 265                 270

Gln Ser Lys Glu Val Ala Ile Arg Ile Phe Gln Gly Cys Gln Phe Arg
        275                 280                 285

Ser Val Glu Ala Val Gln Glu Ile Thr Glu Tyr Ala Lys Ser Ile Pro
    290                 295                 300

Gly Phe Val Asn Leu Asp Leu Asn Asp Gln Val Thr Leu Leu Lys Tyr
```

```
305                 310                 315                 320

Gly Val His Glu Ile Ile Tyr Thr Met Leu Ala Ser Leu Met Asn Lys
                325                 330                 335

Asp Gly Val Leu Ile Ser Glu Gly Gln Gly Phe Met Thr Arg Glu Phe
            340                 345                 350

Leu Lys Ser Leu Arg Lys Pro Phe Gly Asp Phe Met Glu Pro Lys Phe
        355                 360                 365

Glu Phe Ala Val Lys Phe Asn Ala Leu Glu Leu Asp Asp Ser Asp Leu
    370                 375                 380

Ala Ile Phe Ile Ala Val Ile Ile Leu Ser Gly Asp Arg Pro Gly Leu
385                 390                 395                 400

Leu Asn Val Lys Pro Ile Glu Asp Ile Gln Asp Asn Leu Leu Gln Ala
                405                 410                 415

Leu Glu Leu Gln Leu Lys Leu Asn His Pro Glu Ser Ser Gln Leu Phe
            420                 425                 430

Ala Lys Leu Leu Gln Lys Met Thr Asp Leu Arg Gln Ile Val Thr Glu
        435                 440                 445

His Val Gln Leu Leu Gln Val Ile Lys Lys Thr Glu Thr Asp Met Ser
    450                 455                 460

Leu His Pro Leu Leu Gln Glu Ile Tyr Lys Asp Leu Tyr
465                 470                 475


<210> SEQ ID NO 25
<211> LENGTH: 1820
<212> TYPE: DNA
<213> ORGANISM: Artificial Sequence
<220> FEATURE:
<223> OTHER INFORMATION: Synthetic Polymer

<400> SEQUENCE: 25

ttcaagtctt tttcttttaa cggattgatc ttttgctaga tagagacaaa atatcagtgt      60

gaattacagc aaacccctat tccatgctgt tatgggtgaa actctgggag attctcctat     120

tgacccagaa agcgattcct tcactgatac actgtctgca aacatatcac aagaaatgac     180

catggttgac acagagatgc cattctggcc caccaacttt gggatcagct ccgtggatct     240

ctccgtaatg gaagaccact cccactcctt tgatatcaag cccttcacta ctgttgactt     300

ctccagcatt tctactccac attacgaaga cattccattc acaagaacag atccagtggt     360

tgcagattac aagtatgacc tgaaacttca agagtaccaa agtgcaatca aagtggagcc     420

tgcatctcca ccttattatt ctgagaagac tcagctctac aataagcctc atgaagagcc     480

ttccaactcc ctcatggcaa ttgaatgtcg tgtctgtgga gataaagctt ctggatttca     540

ctatggagtt catgcttgtg aaggatgcaa gggtttcttc cggagaacaa tcagattgaa     600

gcttatctat gacagatgtg atcttaactg tcggatccac aaaaaaagta gaaataaatg     660

tcagtactgt cggtttcaga aatgccttgc agtggggatg tctcataatg ccatcaggtt     720

tgggcggatg ccacaggccg agaaggagaa gctgttggcg gagatctcca gtgatatcga     780

ccagctgaat ccagagtccg ctgacctccg ggccctggca aaacatttgt atgactcata     840

cataaagtcc ttcccgctga ccaaagcaaa ggcgagggcg atcttgacag gaaagacaac     900

agacaaatca ccattcgtta tctatgacat gaattcctta atgatgggag aagataaaat     960

caagttcaaa cacatcaccc ccctgcagga gcagagcaaa gaggtggcca tccgcatctt    1020

tcagggctgc cagtttcgct ccgtggaggc tgtgcaggag atcacagagt atgccaaaag    1080

cattcctggt tttgtaaatc ttgacttgaa cgaccaagta actctcctca aatatggagt    1140
```

```
ccacgagatc atttacacaa tgctggcctc cttgatgaat aaagatgggg ttctcatatc   1200

cgagggccaa ggcttcatga caagggagtt tctaaagagc ctgcgaaagc cttttggtga   1260

ctttatggag cccaagtttg agtttgctgt gaagttcaat gcactggaat tagatgacag   1320

cgacttggca atatttattg ctgtcattat tctcagtgga gaccgcccag gtttgctgaa   1380

tgtgaagccc attgaagaca ttcaagacaa cctgctacaa gccctggagc tccagctgaa   1440

gctgaaccac cctgagtcct cacagctgtt tgccaagctg ctccagaaaa tgacagacct   1500

cagacagatt gtcacggaac acgtgcagct actgcaggtg atcaagaaga cggagacaga   1560

catgagtctt cacccgctcc tgcaggagat ctacaaggac ttgtactagc agagagtcct   1620

gagccactgc caacatttcc cttcttccag ttgcactatt ctgagggaaa atctgacacc   1680

taagaaattt actgtgaaaa agcattttaa aaagaaaagg ttttagaata tgatctattt   1740

tatgcatatt gtttataaag acacatttac aatttacttt taatattaaa aattaccata   1800

ttatgaaatt gctgatagta                                                1820
```

<210> SEQ ID NO 26
<211> LENGTH: 505
<212> TYPE: PRT
<213> ORGANISM: Artificial Sequence
<220> FEATURE:
<223> OTHER INFORMATION: Synthetic Polymer

<400> SEQUENCE: 26

```
Met Gly Glu Thr Leu Gly Asp Ser Pro Ile Asp Pro Glu Ser Asp Ser
1               5                   10                  15

Phe Thr Asp Thr Leu Ser Ala Asn Ile Ser Gln Glu Met Thr Met Val
            20                  25                  30

Asp Thr Glu Met Pro Phe Trp Pro Thr Asn Phe Gly Ile Ser Ser Val
        35                  40                  45

Asp Leu Ser Val Met Glu Asp His Ser His Ser Phe Asp Ile Lys Pro
    50                  55                  60

Phe Thr Thr Val Asp Phe Ser Ser Ile Ser Thr Pro His Tyr Glu Asp
65                  70                  75                  80

Ile Pro Phe Thr Arg Thr Asp Pro Val Val Ala Asp Tyr Lys Tyr Asp
                85                  90                  95

Leu Lys Leu Gln Glu Tyr Gln Ser Ala Ile Lys Val Glu Pro Ala Ser
            100                 105                 110

Pro Pro Tyr Tyr Ser Glu Lys Thr Gln Leu Tyr Asn Lys Pro His Glu
        115                 120                 125

Glu Pro Ser Asn Ser Leu Met Ala Ile Glu Cys Arg Val Cys Gly Asp
    130                 135                 140

Lys Ala Ser Gly Phe His Tyr Gly Val His Ala Cys Glu Gly Cys Lys
145                 150                 155                 160

Gly Phe Phe Arg Arg Thr Ile Arg Leu Lys Leu Ile Tyr Asp Arg Cys
                165                 170                 175

Asp Leu Asn Cys Arg Ile His Lys Lys Ser Arg Asn Lys Cys Gln Tyr
            180                 185                 190

Cys Arg Phe Gln Lys Cys Leu Ala Val Gly Met Ser His Asn Ala Ile
        195                 200                 205

Arg Phe Gly Arg Met Pro Gln Ala Glu Lys Glu Lys Leu Leu Ala Glu
    210                 215                 220

Ile Ser Ser Asp Ile Asp Gln Leu Asn Pro Glu Ser Ala Asp Leu Arg
225                 230                 235                 240
```

```
Ala Leu Ala Lys His Leu Tyr Asp Ser Tyr Ile Lys Ser Phe Pro Leu
            245                 250                 255

Thr Lys Ala Lys Ala Arg Ala Ile Leu Thr Gly Lys Thr Thr Asp Lys
            260                 265                 270

Ser Pro Phe Val Ile Tyr Asp Met Asn Ser Leu Met Met Gly Glu Asp
        275                 280                 285

Lys Ile Lys Phe Lys His Ile Thr Pro Leu Gln Glu Gln Ser Lys Glu
    290                 295                 300

Val Ala Ile Arg Ile Phe Gln Gly Cys Gln Phe Arg Ser Val Glu Ala
305                 310                 315                 320

Val Gln Glu Ile Thr Glu Tyr Ala Lys Ser Ile Pro Gly Phe Val Asn
                325                 330                 335

Leu Asp Leu Asn Asp Gln Val Thr Leu Leu Lys Tyr Gly Val His Glu
            340                 345                 350

Ile Ile Tyr Thr Met Leu Ala Ser Leu Met Asn Lys Asp Gly Val Leu
        355                 360                 365

Ile Ser Glu Gly Gln Gly Phe Met Thr Arg Glu Phe Leu Lys Ser Leu
    370                 375                 380

Arg Lys Pro Phe Gly Asp Phe Met Glu Pro Lys Phe Glu Phe Ala Val
385                 390                 395                 400

Lys Phe Asn Ala Leu Glu Leu Asp Asp Ser Asp Leu Ala Ile Phe Ile
                405                 410                 415

Ala Val Ile Ile Leu Ser Gly Asp Arg Pro Gly Leu Leu Asn Val Lys
            420                 425                 430

Pro Ile Glu Asp Ile Gln Asp Asn Leu Leu Gln Ala Leu Glu Leu Gln
        435                 440                 445

Leu Lys Leu Asn His Pro Glu Ser Ser Gln Leu Phe Ala Lys Leu Leu
    450                 455                 460

Gln Lys Met Thr Asp Leu Arg Gln Ile Val Thr Glu His Val Gln Leu
465                 470                 475                 480

Leu Gln Val Ile Lys Lys Thr Glu Thr Asp Met Ser Leu His Pro Leu
                485                 490                 495

Leu Gln Glu Ile Tyr Lys Asp Leu Tyr
            500                 505
```

<210> SEQ ID NO 27
<211> LENGTH: 1919
<212> TYPE: DNA
<213> ORGANISM: Artificial Sequence
<220> FEATURE:
<223> OTHER INFORMATION: Synthetic Polymer

<400> SEQUENCE: 27

```
ttggtggaag gtgggtgtgt agtcgtggta ctttacgcct cggtgtttag ggaggagcct      60

aaggtaagga gtcagaaacg gggagtaacc gagctgcggc ttttatataa ggtcagtggt     120

aggtaaggaa ggggccttaa cctctgctgg tgaccagaag cctgcatttc tgcattctgc     180

ttaattccct ttccttagat ttgaaagaag ccaacactaa accacaaata tacaacaagg     240

ccattttctc aaacgagagt cagcctttaa cgaaatgacc atggttgaca cagagatgcc     300

attctggccc accaactttg ggatcagctc cgtggatctc tccgtaatgg aagaccactc     360

ccactccttt gatatcaagc ccttcactac tgttgacttc tccagcattt ctactccaca     420

ttacgaagac attccattca caagaacaga tccagtggtt gcagattaca agtatgacct     480

gaaacttcaa gagtaccaaa gtgcaatcaa agtggagcct gcatctccac cttattattc     540
```

```
tgagaagact cagctctaca ataagcctca tgaagagcct tccaactccc tcatggcaat    600

tgaatgtcgt gtctgtggag ataaagcttc tggatttcac tatggagttc atgcttgtga    660

aggatgcaag ggtttcttcc ggagaacaat cagattgaag cttatctatg acagatgtga    720

tcttaactgt cggatccaca aaaaaagtag aaataaatgt cagtactgtc ggtttcagaa    780

atgccttgca gtggggatgt ctcataatgc catcaggttt gggcggatgc cacaggccga    840

gaaggagaag ctgttggcgg agatctccag tgatatcgac cagctgaatc cagagtccgc    900

tgacctccgg gccctggcaa aacatttgta tgactcatac ataaagtcct tcccgctgac    960

caaagcaaag gcgagggcga tcttgacagg aaagacaaca gacaaatcac cattcgttat   1020

ctatgacatg aattccttaa tgatgggaga agataaaatc aagttcaaac acatcacccc   1080

cctgcaggag cagagcaaag aggtggccat ccgcatcttt cagggctgcc agtttcgctc   1140

cgtggaggct gtgcaggaga tcacagagta tgccaaaagc attcctggtt ttgtaaatct   1200

tgacttgaac gaccaagtaa ctctcctcaa atatggagtc cacgagatca tttacacaat   1260

gctggcctcc ttgatgaata aagatggggt tctcatatcc gagggccaag gcttcatgac   1320

aagggagttt ctaaagagcc tgcgaaagcc ttttggtgac tttatggagc ccaagtttga   1380

gtttgctgtg aagttcaatg cactggaatt agatgacagc gacttggcaa tatttattgc   1440

tgtcattatt ctcagtggag accgcccagg tttgctgaat gtgaagccca ttgaagacat   1500

tcaagacaac ctgctacaag ccctggagct ccagctgaag ctgaaccacc ctgagtcctc   1560

acagctgttt gccaagctgc tccagaaaat gacagacctc agacagattg tcacggaaca   1620

cgtgcagcta ctgcaggtga tcaagaagac ggagacagac atgagtcttc acccgctcct   1680

gcaggagatc tacaaggact tgtactagca gagagtcctg agccactgcc aacatttccc   1740

ttcttccagt tgcactattc tgagggaaaa tctgacacct aagaaattta ctgtgaaaaa   1800

gcattttaaa aagaaaaggt tttagaatat gatctatttt atgcatattg tttataaaga   1860

cacatttaca atttactttt aatattaaaa attaccatat tatgaaattg ctgatagta    1919
```

<210> SEQ ID NO 28
<211> LENGTH: 477
<212> TYPE: PRT
<213> ORGANISM: Artificial Sequence
<220> FEATURE:
<223> OTHER INFORMATION: Synthetic Polymer

<400> SEQUENCE: 28

```
Met Thr Met Val Asp Thr Glu Met Pro Phe Trp Pro Thr Asn Phe Gly
1               5                   10                  15

Ile Ser Ser Val Asp Leu Ser Val Met Glu Asp His Ser His Ser Phe
            20                  25                  30

Asp Ile Lys Pro Phe Thr Thr Val Asp Phe Ser Ser Ile Ser Thr Pro
        35                  40                  45

His Tyr Glu Asp Ile Pro Phe Thr Arg Thr Asp Pro Val Val Ala Asp
    50                  55                  60

Tyr Lys Tyr Asp Leu Lys Leu Gln Glu Tyr Gln Ser Ala Ile Lys Val
65                  70                  75                  80

Glu Pro Ala Ser Pro Pro Tyr Tyr Ser Glu Lys Thr Gln Leu Tyr Asn
                85                  90                  95

Lys Pro His Glu Glu Pro Ser Asn Ser Leu Met Ala Ile Glu Cys Arg
            100                 105                 110

Val Cys Gly Asp Lys Ala Ser Gly Phe His Tyr Gly Val His Ala Cys
```

```
        115                 120                 125

Glu Gly Cys Lys Gly Phe Phe Arg Arg Thr Ile Arg Leu Lys Leu Ile
    130                 135                 140

Tyr Asp Arg Cys Asp Leu Asn Cys Arg Ile His Lys Lys Ser Arg Asn
145                 150                 155                 160

Lys Cys Gln Tyr Cys Arg Phe Gln Lys Cys Leu Ala Val Gly Met Ser
                165                 170                 175

His Asn Ala Ile Arg Phe Gly Arg Met Pro Gln Ala Glu Lys Glu Lys
            180                 185                 190

Leu Leu Ala Glu Ile Ser Ser Asp Ile Asp Gln Leu Asn Pro Glu Ser
        195                 200                 205

Ala Asp Leu Arg Ala Leu Ala Lys His Leu Tyr Asp Ser Tyr Ile Lys
    210                 215                 220

Ser Phe Pro Leu Thr Lys Ala Lys Ala Arg Ala Ile Leu Thr Gly Lys
225                 230                 235                 240

Thr Thr Asp Lys Ser Pro Phe Val Ile Tyr Asp Met Asn Ser Leu Met
                245                 250                 255

Met Gly Glu Asp Lys Ile Lys Phe Lys His Ile Thr Pro Leu Gln Glu
            260                 265                 270

Gln Ser Lys Glu Val Ala Ile Arg Ile Phe Gln Gly Cys Gln Phe Arg
        275                 280                 285

Ser Val Glu Ala Val Gln Glu Ile Thr Glu Tyr Ala Lys Ser Ile Pro
    290                 295                 300

Gly Phe Val Asn Leu Asp Leu Asn Asp Gln Val Thr Leu Leu Lys Tyr
305                 310                 315                 320

Gly Val His Glu Ile Ile Tyr Thr Met Leu Ala Ser Leu Met Asn Lys
                325                 330                 335

Asp Gly Val Leu Ile Ser Glu Gly Gln Gly Phe Met Thr Arg Glu Phe
            340                 345                 350

Leu Lys Ser Leu Arg Lys Pro Phe Gly Asp Phe Met Glu Pro Lys Phe
        355                 360                 365

Glu Phe Ala Val Lys Phe Asn Ala Leu Glu Leu Asp Asp Ser Asp Leu
    370                 375                 380

Ala Ile Phe Ile Ala Val Ile Ile Leu Ser Gly Asp Arg Pro Gly Leu
385                 390                 395                 400

Leu Asn Val Lys Pro Ile Glu Asp Ile Gln Asp Asn Leu Leu Gln Ala
                405                 410                 415

Leu Glu Leu Gln Leu Lys Leu Asn His Pro Glu Ser Ser Gln Leu Phe
            420                 425                 430

Ala Lys Leu Leu Gln Lys Met Thr Asp Leu Arg Gln Ile Val Thr Glu
        435                 440                 445

His Val Gln Leu Leu Gln Val Ile Lys Lys Thr Glu Thr Asp Met Ser
    450                 455                 460

Leu His Pro Leu Leu Gln Glu Ile Tyr Lys Asp Leu Tyr
465                 470                 475
```

<210> SEQ ID NO 29
<211> LENGTH: 1818
<212> TYPE: DNA
<213> ORGANISM: Artificial Sequence
<220> FEATURE:
<223> OTHER INFORMATION: Synthetic Polymer

<400> SEQUENCE: 29

```
ggcgcccgcg cccgcccccg cgccgggccc ggctcggccc gacccggctc cgccgcgggc     60
```

```
aggcggggcc cagcgcactc ggagcccgag cccgagccgc agccgccgcc tggggcgctt    120
gggtcggcct cgaggacacc ggagaggggc gccacgccgc cgtggccgca gaaatgacca    180
tggttgacac agagatgcca ttctggccca ccaactttgg gatcagctcc gtggatctct    240
ccgtaatgga agaccactcc cactcctttg atatcaagcc cttcactact gttgacttct    300
ccagcatttc tactccacat tacgaagaca ttccattcac aagaacagat ccagtggttg    360
cagattacaa gtatgacctg aaacttcaag agtaccaaag tgcaatcaaa gtggagcctg    420
catctccacc ttattattct gagaagactc agctctacaa taagcctcat gaagagcctt    480
ccaactccct catggcaatt gaatgtcgtg tctgtggaga taaagcttct ggatttcact    540
atggagttca tgcttgtgaa ggatgcaagg gtttcttccg gagaacaatc agattgaagc    600
ttatctatga cagatgtgat cttaactgtc ggatccacaa aaaaagtaga aataaatgtc    660
agtactgtcg gtttcagaaa tgccttgcag tggggatgtc tcataatgcc atcaggtttg    720
ggcggatgcc acaggccgag aaggagaagc tgttggcgga gatctccagt gatatcgacc    780
agctgaatcc agagtccgct gacctccggg ccctggcaaa acatttgtat gactcataca    840
taaagtcctt cccgctgacc aaagcaaagg cgagggcgat cttgacagga aagacaacag    900
acaaatcacc attcgttatc tatgacatga attccttaat gatgggagaa gataaaatca    960
agttcaaaca catcaccccc ctgcaggagc agagcaaaga ggtggccatc cgcatctttc   1020
agggctgcca gtttcgctcc gtggaggctg tgcaggagat cacagagtat gccaaaagca   1080
ttcctggttt tgtaaatctt gacttgaacg accaagtaac tctcctcaaa tatggagtcc   1140
acgagatcat ttacacaatg ctggcctcct tgatgaataa agatggggtt ctcatatccg   1200
agggccaagg cttcatgaca agggagtttc taaagagcct gcgaaagcct tttggtgact   1260
ttatggagcc caagtttgag tttgctgtga agttcaatgc actggaatta gatgacagcg   1320
acttggcaat atttattgct gtcattattc tcagtggaga ccgcccaggt ttgctgaatg   1380
tgaagcccat tgaagacatt caagacaacc tgctacaagc cctggagctc cagctgaagc   1440
tgaaccaccc tgagtcctca cagctgtttg ccaagctgct ccagaaaatg acagacctca   1500
gacagattgt cacggaacac gtgcagctac tgcaggtgat caagaagacg gagacagaca   1560
tgagtcttca cccgctcctg caggagatct acaaggactt gtactagcag agagtcctga   1620
gccactgcca acatttccct tcttccagtt gcactattct gagggaaaat ctgacaccta   1680
agaaatttac tgtgaaaaag cattttaaaa agaaaaggtt ttagaatatg atctatttta   1740
tgcatattgt ttataaagac acatttacaa tttactttta atattaaaaa ttaccatatt   1800
atgaaattgc tgatagta                                                 1818
```

<210> SEQ ID NO 30
<211> LENGTH: 477
<212> TYPE: PRT
<213> ORGANISM: Artificial Sequence
<220> FEATURE:
<223> OTHER INFORMATION: Synthetic Polymer

<400> SEQUENCE: 30

```
Met Thr Met Val Asp Thr Glu Met Pro Phe Trp Pro Thr Asn Phe Gly
1               5                   10                  15

Ile Ser Ser Val Asp Leu Ser Val Met Glu Asp His Ser His Ser Phe
            20                  25                  30

Asp Ile Lys Pro Phe Thr Thr Val Asp Phe Ser Ser Ile Ser Thr Pro
        35                  40                  45
```

```
His Tyr Glu Asp Ile Pro Phe Thr Arg Thr Asp Pro Val Val Ala Asp
    50                  55                  60

Tyr Lys Tyr Asp Leu Lys Leu Gln Glu Tyr Gln Ser Ala Ile Lys Val
65                  70                  75                  80

Glu Pro Ala Ser Pro Pro Tyr Tyr Ser Glu Lys Thr Gln Leu Tyr Asn
                85                  90                  95

Lys Pro His Glu Glu Pro Ser Asn Ser Leu Met Ala Ile Glu Cys Arg
            100                 105                 110

Val Cys Gly Asp Lys Ala Ser Gly Phe His Tyr Gly Val His Ala Cys
        115                 120                 125

Glu Gly Cys Lys Gly Phe Phe Arg Arg Thr Ile Arg Leu Lys Leu Ile
    130                 135                 140

Tyr Asp Arg Cys Asp Leu Asn Cys Arg Ile His Lys Lys Ser Arg Asn
145                 150                 155                 160

Lys Cys Gln Tyr Cys Arg Phe Gln Lys Cys Leu Ala Val Gly Met Ser
                165                 170                 175

His Asn Ala Ile Arg Phe Gly Arg Met Pro Gln Ala Glu Lys Glu Lys
            180                 185                 190

Leu Leu Ala Glu Ile Ser Ser Asp Ile Asp Gln Leu Asn Pro Glu Ser
        195                 200                 205

Ala Asp Leu Arg Ala Leu Ala Lys His Leu Tyr Asp Ser Tyr Ile Lys
    210                 215                 220

Ser Phe Pro Leu Thr Lys Ala Lys Ala Arg Ala Ile Leu Thr Gly Lys
225                 230                 235                 240

Thr Thr Asp Lys Ser Pro Phe Val Ile Tyr Asp Met Asn Ser Leu Met
                245                 250                 255

Met Gly Glu Asp Lys Ile Lys Phe Lys His Ile Thr Pro Leu Gln Glu
            260                 265                 270

Gln Ser Lys Glu Val Ala Ile Arg Ile Phe Gln Gly Cys Gln Phe Arg
        275                 280                 285

Ser Val Glu Ala Val Gln Glu Ile Thr Glu Tyr Ala Lys Ser Ile Pro
    290                 295                 300

Gly Phe Val Asn Leu Asp Leu Asn Asp Gln Val Thr Leu Leu Lys Tyr
305                 310                 315                 320

Gly Val His Glu Ile Ile Tyr Thr Met Leu Ala Ser Leu Met Asn Lys
                325                 330                 335

Asp Gly Val Leu Ile Ser Glu Gly Gln Gly Phe Met Thr Arg Glu Phe
            340                 345                 350

Leu Lys Ser Leu Arg Lys Pro Phe Gly Asp Phe Met Glu Pro Lys Phe
        355                 360                 365

Glu Phe Ala Val Lys Phe Asn Ala Leu Glu Leu Asp Asp Ser Asp Leu
    370                 375                 380

Ala Ile Phe Ile Ala Val Ile Ile Leu Ser Gly Asp Arg Pro Gly Leu
385                 390                 395                 400

Leu Asn Val Lys Pro Ile Glu Asp Ile Gln Asp Asn Leu Leu Gln Ala
                405                 410                 415

Leu Glu Leu Gln Leu Lys Leu Asn His Pro Glu Ser Ser Gln Leu Phe
            420                 425                 430

Ala Lys Leu Leu Gln Lys Met Thr Asp Leu Arg Gln Ile Val Thr Glu
        435                 440                 445

His Val Gln Leu Leu Gln Val Ile Lys Lys Thr Glu Thr Asp Met Ser
    450                 455                 460
```

Leu His Pro Leu Leu Gln Glu Ile Tyr Lys Asp Leu Tyr
465 470 475

<210> SEQ ID NO 31
<211> LENGTH: 8718
<212> TYPE: DNA
<213> ORGANISM: Artificial Sequence
<220> FEATURE:
<223> OTHER INFORMATION: Synthetic Polymer

<400> SEQUENCE: 31
cctcccctcg cccggcgcgg tcccgtccgc ctctcgctcg cctcccgcct cccctcggtc 60
ttccgaggcg cccgggctcc cggcgcggcg gcggaggggg cgggcaggcc ggcgggcggt 120
gatgtggcgg gactctttat gcgctgcggc aggatacgcg ctcggcgctg ggacgcgact 180
gcgctcagtt ctctcctctc ggaagctgca gccatgatgg aagtttgaga gttgagccgc 240
tgtgaggcga ggccgggctc aggcgaggga gatgagagac ggcggcggcc gcggcccgga 300
gcccctctca gcgcctgtga gcagccgcgg gggcagcgcc ctcggggagc cggccggcct 360
gcggcggcgg cagcggcggc gtttctcgcc tcctcttcgt cttttctaac cgtgcagcct 420
cttcctcggc ttctcctgaa agggaaggtg gaagccgtgg gctcgggcgg gagccggctg 480
aggcgcggcg gcggcggcgg cacctcccgc tcctggagcg gggggagaa gcggcggcgg 540 cggcggccgc ggcggctgca gctccaggga gggggtctga gtcgcctgtc accatttcca 600
gggctgggaa cgccggagag ttggtctctc cccttctact gcctccaaca cggcggcggc 660
ggcggcggca catccaggga cccgggccgg ttttaaacct cccgtccgcc gccgccgcac 720
cccccgtggc ccgggctccg gaggccgccg gcggaggcag ccgttcggag gattattcgt 780
cttctcccca ttccgctgcc gccgctgcca ggcctctggc tgctgaggag aagcaggccc 840
agtcgctgca accatccagc agccgccgca gcagccatta cccggctgcg gtccagagcc 900
aagcggcggc agagcgaggg gcatcagcta ccgccaagtc cagagccatt tccatcctgc 960
agaagaagcc ccgccaccag cagcttctgc catctctctc ctcctttttc ttcagccaca 1020
ggctcccaga catgacagcc atcatcaaag agatcgttag cagaaacaaa aggagatatc 1080
aagaggatgg attcgactta gacttgacct atatttatcc aaacattatt gctatgggat 1140
ttcctgcaga aagacttgaa ggcgtataca ggaacaatat tgatgatgta gtaaggtttt 1200
tggattcaaa gcataaaaac cattacaaga tatacaatct ttgtgctgaa agacattatg 1260
acaccgccaa atttaattgc agagttgcac aatatccttt tgaagaccat aacccaccac 1320
agctagaact tatcaaaccc ttttgtgaag atcttgacca atggctaagt gaagatgaca 1380
atcatgttgc agcaattcac tgtaaagctg gaaagggacg aactggtgta atgatatgtg 1440
catatttatt acatcggggc aaatttttaa aggcacaaga ggccctagat ttctatgggg 1500
aagtaaggac cagagacaaa aagggagtaa ctattcccag tcagaggcgc tatgtgtatt 1560
attatagcta cctgttaaag aatcatctgg attatagacc agtggcactg ttgtttcaca 1620
agatgatgtt tgaaactatt ccaatgttca gtggcggaac ttgcaatcct cagtttgtgg 1680
tctgccagct aaaggtgaag atatattcct ccaattcagg acccacacga cgggaagaca 1740
agttcatgta ctttgagttc cctcagccgt tacctgtgtg tggtgatatc aaagtagagt 1800
tcttccacaa acagaacaag atgctaaaaa aggacaaaat gtttcacttt tgggtaaata 1860
cattcttcat accaggacca gaggaaacct cagaaaaagt agaaaatgga agtctatgtg 1920
atcaagaaat cgatagcatt tgcagtatag agcgtgcaga taatgacaag gaatatctag 1980

```
tacttacttt aacaaaaaat gatcttgaca aagcaaataa agacaaagcc aaccgatact   2040
tttctccaaa ttttaaggtg aagctgtact tcacaaaaac agtagaggag ccgtcaaatc   2100
cagaggctag cagttcaact tctgtaacac cagatgttag tgacaatgaa cctgatcatt   2160
atagatattc tgacaccact gactctgatc cagagaatga accttttgat gaagatcagc   2220
atacacaaat tacaaaagtc tgaatttttt tttatcaaga gggataaaac accatgaaaa   2280
taaacttgaa taaactgaaa atggaccttt tttttttaa tggcaatagg acattgtgtc    2340
agattaccag ttataggaac aattctcttt tcctgaccaa tcttgtttta ccctatacat   2400
ccacagggtt ttgacacttg ttgtccagtt gaaaaaaggt tgtgtagctg tgtcatgtat   2460
ataccttttt gtgtcaaaag gacatttaaa attcaattag gattaataaa gatggcactt   2520
tcccgtttta ttccagtttt ataaaaagtg gagacagact gatgtgtata cgtaggaatt   2580
ttttcctttt gtgttctgtc accaactgaa gtggctaaag agctttgtga tatactggtt   2640
cacatcctac ccctttgcac ttgtggcaac agataagttt gcagttggct aagagaggtt   2700
tccgaagggt tttgctacat tctaatgcat gtattcgggt taggggaatg gagggaatgc   2760
tcagaaagga aataatttta tgctggactc tggaccatat accatctcca gctatttaca   2820
cacacctttc tttagcatgc tacagttatt aatctggaca ttcgaggaat tggccgctgt   2880
cactgcttgt tgtttgcgca ttttttttta aagcatattg gtgctagaaa aggcagctaa   2940
aggaagtgaa tctgtattgg ggtacaggaa tgaaccttct gcaacatctt aagatccaca   3000
aatgaaggga tataaaaata atgtcatagg taagaaacac agcaacaatg acttaaccat   3060
ataaatgtgg aggctatcaa caaagaatgg gcttgaaaca ttataaaaat tgacaatgat   3120
ttattaaata tgttttctca attgtaacga cttctccatc tcctgtgtaa tcaaggccag   3180
tgctaaaatt cagatgctgt tagtacctac atcagtcaac aacttacact tattttacta   3240
gttttcaatc ataatacctg ctgtggatgc ttcatgtgct gcctgcaagc ttcttttttc   3300
tcattaaata taaaatattt tgtaatgctg cacagaaatt ttcaatttga gattctacag   3360
taagcgtttt ttttctttga agatttatga tgcacttatt caatagctgt cagccgttcc   3420
accctttgga ccttacacat tctattacaa tgaattttgc agttttgcac attttttaaa   3480
tgtcattaac tgttagggaa ttttacttga atactgaata catataatgt ttatattaaa   3540
aaggacattt gtgttaaaaa ggaaattaga gttgcagtaa actttcaatg ctgcacacaa   3600
aaaaaagaca tttgattttt cagtagaaat tgtcctacat gtgctttatt gatttgctat   3660
tgaaagaata gggttttttt tttttttttt tttttttttt ttaaatgtgc agtgttgaat   3720
catttcttca tagtgctccc ccgagttggg actagggctt caatttcact tcttaaaaaa   3780
aatcatcata tatttgatat gcccagactg catacgattt taagcggagt acaactacta   3840
ttgtaaagct aatgtgaaga tattattaaa aaggtttttt tttccagaaa tttggtgtct   3900
tcaaattata ccttcacctt gacatttgaa tatccagcca ttttgtttct taatggtata   3960
aaattccatt ttcaataact tattggtgct gaaattgttc actagctgtg gtctgaccta   4020
gttaatttac aaatacagat tgaataggac ctactagagc agcatttata gagtttgatg   4080
gcaaatagat taggcagaac ttcatctaaa atattcttag taaataatgt tgacacgttt   4140
tccatacctt gtcagtttca ttcaacaatt tttaaatttt taacaaagct cttaggattt   4200
acacatttat atttaaacat tgatatatag agtattgatt gattgctcat aagttaaatt   4260
ggtaaagtta gagacaacta ttctaacacc tcaccattga aatttatatg ccaccttgtc   4320
tttcataaaa gctgaaaatt gttacctaaa atgaaaatca acttcatgtt ttgaagatag   4380
```

```
ttataaatat tgttctttgt tacaatttcg ggcaccgcat attaaaacgt aactttattg   4440
ttccaatatg taacatggag ggccaggtca taaataatga cattataatg ggcttttgca   4500
ctgttattat ttttcctttg gaatgtgaag gtctgaatga gggttttgat tttgaatgtt   4560
tcaatgtttt tgagaagcct tgcttacatt ttatggtgta gtcattggaa atggaaaaat   4620
ggcattatat atattatata tataaatata tattatacat actctcctta ctttatttca   4680
gttaccatcc ccatagaatt tgacaagaat tgctatgact gaaaggtttt cgagtcctaa   4740
ttaaaacttt atttatggca gtattcataa ttagcctgaa atgcattctg taggtaatct   4800
ctgagtttct ggaatatttt cttagacttt ttggatgtgc agcagcttac atgtctgaag   4860
ttacttgaag gcatcacttt taagaaagct tacagttggg ccctgtacca tcccaagtcc   4920
tttgtagctc ctcttgaaca tgtttgccat acttttaaaa gggtagttga ataaatagca   4980
tcaccattct ttgctgtggc acaggttata aacttaagtg gagtttaccg gcagcatcaa   5040
atgtttcagc tttaaaaaat aaaagtaggg tacaagttta atgtttagtt ctagaaattt   5100
tgtgcaatat gttcataacg atggctgtgg ttgccacaaa gtgcctcgtt tacctttaaa   5160
tactgttaat gtgtcatgca tgcagatgga aggggtggaa ctgtgcacta aagtgggggc   5220
tttaactgta gtatttggca gagttgcctt ctacctgcca gttcaaaagt tcaacctgtt   5280
ttcatataga atatatatac taaaaaattt cagtctgtta aacagcctta ctctgattca   5340
gcctcttcag atactcttgt gctgtgcagc agtggctctg tgtgtaaatg ctatgcactg   5400
aggatacaca aaaataccaa tatgatgtgt acaggataat gcctcatccc aatcagatgt   5460
ccatttgtta ttgtgtttgt taacaaccct ttatctctta gtgttataaa ctccacttaa   5520
aactgattaa agtctcattc ttgtcattgt gtgggtgttt tattaaatga gagtttataa   5580
ttcaaattgc ttaagtccat tgaagtttta attaatgggc agccaaatgt gaatacaaag   5640
ttttcagttt tttttttcc tgctgtcctt caaagcctac tgtttaaaaa aaaaaaaaaa   5700
aaaaaacatg gcctgagagt agagtatctg tctactcatg tttaattaag gaaaaacact   5760
tatttttagg gctttagtca tcacttcata aattgtataa gcacattaaa tagcgttcta   5820
gtcctgaaaa agtccaagat tcttagaaaa ttgtgcatat ttttattatg acagatgttt   5880
gaagataatt ccccagaatg gatttgatac tttagatttc aattttgtgg cttttgtcta   5940
ttattctgta ctctgccatc agcatatgga aagcttcatt tactcatcat gacttgtgcc   6000
atataaaaat tgatatttcg gaatagtcta aaggactttt tgtacttgaa tttaatcatg   6060
ttgtttctaa tattcttaaa agcttgaaga ctaaagcata tcctttcaac aaagcatagt   6120
aaggtaataa gaaagtgtag tttgtacaag tgttaaaaaa ataaagtaga caatgttaca   6180
gtgggactta ttatttcaag tttacatttt ctccatgtaa ttttttaaaa agtaaatgaa   6240
aaaatgtgca ataatgtaaa atatgaagtg tatgtgtaca cacattttat ttttcggtat   6300
cttgggtata cgtatggttg aaaactatac tggagtctaa aagtattcta atttataaga   6360
agacattttg gtgatgtttg aaaaatagaa atgtgctagt tttgttttta tatcatgtcc   6420
tttgtacgtt gtaatatgag ctggcttggt tcagtaaatg ccatcaccat ttccattgag   6480
aatttaaaac tcaccagtgt ttaatatgca ggcttccaaa ggcttatgaa aaaaatcaag   6540
acccttaaat ctagttaatt tgctgctaac atgaaactct ttggttcttt tatttttgcc   6600
agataattag acacacatct aaagcttagt cttaaatggc ttaagtgtag ctattgatta   6660
gtgctgttgc tagttcagaa agaaatgttt gtgaatggaa acaagaatat tcagtccaaa   6720
```

```
ctgttgtaag gacagtacct gaaaaccagg aaacaggata atggaaaaag tcttttaaag   6780

atgaaatgtt ggagccaact ttcttataga attaattgta tgtggctata gaaagcctaa   6840

tgattgttgc ttatttttga gagcatatta ttcttttatg accataatct tgctgttttt   6900

ccatcttcca aaagatcttc cttctaatat gtatatcaga atgtgggtag ccagtcagac   6960

aaattcatat tggttggtag ctttaaaaag tttgtaatgt gaagacagga aaggacaaaa   7020

tagtttgctt tggtggtagt actctggttg ttaagctagg tattttgaga ctacttcccc   7080

atcacaacaa caataaaata atcactcata atcctatcac ctggagacat agccatcgtt   7140

aatatgttag tgactataca atcatgtttt cttctgtata tccatgtata ttctttaaaa   7200

atgaaattta tactgtacct gatctcaaag ctttttagct tagtatatct gtcatgaatt   7260

tgtaggatgt tccattgcat cagaaaacgg acagtgattt gattactttc taatgccaca   7320

gatgcagatt acatgtagtt attgagaatc ctttcgaatt cagtggctta atcatgaatg   7380

tctaaatatt gttgacatta ggatgataca tgtaaattaa agttacattt gtttagcata   7440

gacaagctta acattgtaga tgtttctctt caaaaatcat cttaaacatt tgcatttgga   7500

attgtgttaa atagaatgtg tgaaacactg tattagtaaa cttcatcacc tttctacttc   7560

cttatagttt gaacttttca gtttttgtag ttcccaaaca gttgctcaat ttagagcaaa   7620

ttaatttaac acctgccaaa aaaaggctgc tgttggctta tcagttgtct ttaaattcaa   7680

atgctcatgt gacttttatc acatcaaaaa atatttcatt aatgattcac ctttagctct   7740

gaaaattacc gcgtttagta attatagtgg gcttataaaa acatgcaact ctttttgata   7800

gttatttgag aattttggtg aaaaatattt agctgagggc agtatagaac ttataaacca   7860

atatattgat atttttaaaa catttttaca tataagtaaa ctgccatctt tgagcataac   7920

tacatttaaa aataaagctg catattttta aatcaagtgt ttaacaagaa tttatatttt   7980

ttattttttta aaattaaaaa taatttatat ttcctctgtt gcatgaggat tctcatctgt   8040

gcttataatg gttagagatt ttatttgtgt ggaatgaagt gaggcttgta gtcatggttc   8100

tagtgtttca gtttgccaag tctgtttact gcagtgaaat tcatcaaatg tttcagtgtg   8160

gttttctgta gcctatcatt tactggctat ttttttatgt acacctttag gattttctgc   8220

ctactctatc cagttgtcca aatgatatcc tacattttac aaatgccctt tcagtttcta   8280

ttttcttttt ccattaaatt gccctcatgt cctaatgtgc agtttgtaag tgtgtgtgtg   8340

tgtgtctgtg tgtgtgtgaa tttgattttc aagagtgcta gacttccaat ttgagagatt   8400

aaataattta attcaggcaa acatttttca ttggaatttc acagttcatt gtaatgaaaa   8460

tgttaatcct ggatgacctt tgacatacag taatgaatct tggatattaa tgaatttgtt   8520

agtagcatct tgatgtgtgt tttaatgagt tattttcaaa gttgtgcatt aaaccaaagt   8580

tggcatactg gaagtgttta tatcaagttc catttggcta ctgatggaca aaaaatagaa   8640

atgccttcct atggagagta tttttccttt aaaaaattaa aaaggttaat tattttgact   8700

aaaaaaaaaa aaaaaaaa                                                 8718
```

<210> SEQ ID NO 32
<211> LENGTH: 403
<212> TYPE: PRT
<213> ORGANISM: Artificial Sequence
<220> FEATURE:
<223> OTHER INFORMATION: Synthetic Polymer

<400> SEQUENCE: 32

Met Thr Ala Ile Ile Lys Glu Ile Val Ser Arg Asn Lys Arg Arg Tyr

```
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
        115                 120                 125

Gly Arg Thr Gly Val Met Ile Cys Ala Tyr Leu Leu His Arg Gly Lys
    130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
        195                 200                 205

Gly Thr Cys Asn Pro Gln Phe Val Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
        275                 280                 285

Lys Val Glu Asn Gly Ser Leu Cys Asp Gln Glu Ile Asp Ser Ile Cys
    290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
            340                 345                 350

Glu Pro Ser Asn Pro Glu Ala Ser Ser Ser Thr Ser Val Thr Pro Asp
        355                 360                 365

Val Ser Asp Asn Glu Pro Asp His Tyr Arg Tyr Ser Asp Thr Thr Asp
    370                 375                 380

Ser Asp Pro Glu Asn Glu Pro Phe Asp Glu Asp Gln His Thr Gln Ile
385                 390                 395                 400

Thr Lys Val
```

<210> SEQ ID NO 33
<211> LENGTH: 8718

```
<212> TYPE: DNA
<213> ORGANISM: Artificial Sequence
<220> FEATURE:
<223> OTHER INFORMATION: Synthetic Polymer

<400> SEQUENCE: 33

cctcccctcg cccggcgcgg tcccgtccgc ctctcgctcg cctcccgcct cccctcggtc     60

ttccgaggcg cccgggctcc cggcgcggcg gcggaggggg cgggcaggcc ggcgggcggt    120

gatgtggcgg gactctttat gcgctgcggc aggatacgcg ctcggcgctg ggacgcgact    180

gcgctcagtt ctctcctctc ggaagctgca gccatgatgg aagtttgaga gttgagccgc    240

tgtgaggcga ggccgggctc aggcgaggga gatgagagac ggcggcggcc gcggcccgga    300

gcccctctca gcgcctgtga gcagccgcgg gggcagcgcc ctcggggagc cggccggcct    360

gcggcggcgg cagcggcggc gtttctcgcc tcctcttcgt cttttctaac cgtgcagcct    420

cttcctcggc ttctcctgaa agggaaggtg gaagccgtgg gctcgggcgg gagccggctg    480

aggcgcggcg gcggcggcgg cacctcccgc tcctggagcg gggggagaa gcggcggcgg     540

cggcggccgc ggcggctgca gctccaggga gggggtctga gtcgcctgtc accatttcca    600

gggctgggaa cgccggagag ttggtctctc cccttctact gcctccaaca cggcggcggc    660

ggcggcggca catccaggga cccgggccgg ttttaaacct cccgtccgcc gccgccgcac    720

cccccgtggc ccgggctccg gaggccgccg gcggaggcag ccgttcggag gattattcgt    780

cttctcccca ttccgctgcc gccgctgcca ggcctctggc tgctgaggag aagcaggccc    840

agtcgctgca accatccagc agccgccgca gcagccatta cccggctgcg gtccagagcc    900

aagcggcggc agagcgaggg gcatcagcta ccgccaagtc cagagccatt tccatcctgc    960

agaagaagcc ccgccaccag cagcttctgc catctctctc ctcctttttc ttcagccaca   1020

ggctcccaga catgacagcc atcatcaaag agatcgttag cagaaacaaa aggagatatc   1080

aagaggatgg attcgactta gacttgacct atatttatcc aaacattatt gctatgggat   1140

ttcctgcaga aagacttgaa ggcgtataca ggaacaatat tgatgatgta gtaaggtttt   1200

tggattcaaa gcataaaaac cattacaaga tatacaatct ttgtgctgaa agacattatg   1260

acaccgccaa atttaattgc agagttgcac aatatccttt tgaagaccat aacccaccac   1320

agctagaact tatcaaaccc ttttgtgaag atcttgacca atggctaagt gaagatgaca   1380

atcatgttgc agcaattcac tgtaaagctg gaaagggacg aactggtgta atgatatgtg   1440

catatttatt acatcggggc aaatttttaa aggcacaaga ggccctagat ttctatgggg   1500

aagtaaggac cagagacaaa aagggagtaa ctattcccag tcagaggcgc tatgtgtatt   1560

attatagcta cctgttaaag aatcatctgg attatagacc agtggcactg ttgtttcaca   1620

agatgatgtt tgaaactatt ccaatgttca gtggcggaac ttgcaatcct cagtttgtgg   1680

tctgccagct aaaggtgaag atatattcct ccaattcagg acccacacga cgggaagaca   1740

agttcatgta ctttgagttc cctcagccgt tacctgtgtg tggtgatatc aaagtagagt   1800

tcttccacaa acagaacaag atgctaaaaa aggacaaaat gtttcacttt tgggtaaata   1860

cattcttcat accaggacca gaggaaacct cagaaaaagt agaaaatgga agtctatgtg   1920

atcaagaaat cgatagcatt tgcagtatag agcgtgcaga taatgacaag gaatatctag   1980

tacttacttt aacaaaaaat gatcttgaca aagcaaataa agacaaagcc aaccgatact   2040

tttctccaaa ttttaaggtg aagctgtact tcacaaaaac agtagaggag ccgtcaaatc   2100

cagaggctag cagttcaact tctgtaacac cagatgttag tgacaatgaa cctgatcatt   2160
```

```
atagatattc tgacaccact gactctgatc cagagaatga accttttgat gaagatcagc   2220
atacacaaat tacaaaagtc tgaatttttt tttatcaaga gggataaaac accatgaaaa   2280
taaacttgaa taaactgaaa atggaccttt ttttttttaa tggcaatagg acattgtgtc   2340
agattaccag ttataggaac aattctcttt tcctgaccaa tcttgtttta ccctatacat   2400
ccacagggtt ttgacacttg ttgtccagtt gaaaaaaggt tgtgtagctg tgtcatgtat   2460
ataccttttt gtgtcaaaag gacatttaaa attcaattag gattaataaa gatggcactt   2520
tcccgtttta ttccagtttt ataaaaagtg gagacagact gatgtgtata cgtaggaatt   2580
ttttcctttt gtgttctgtc accaactgaa gtggctaaag agctttgtga tatactggtt   2640
cacatcctac ccctttgcac ttgtggcaac agataagttt gcagttggct aagagaggtt   2700
tccgaagggt tttgctacat tctaatgcat gtattcgggt taggggaatg gagggaatgc   2760
tcagaaagga aataatttta tgctggactc tggaccatat accatctcca gctatttaca   2820
cacacctttc tttagcatgc tacagttatt aatctggaca ttcgaggaat tggccgctgt   2880
cactgcttgt tgtttgcgca ttttttttta aagcatattg gtgctagaaa aggcagctaa   2940
aggaagtgaa tctgtattgg ggtacaggaa tgaaccttct gcaacatctt aagatccaca   3000
aatgaaggga tataaaaata atgtcatagg taagaaacac agcaacaatg acttaaccat   3060
ataaatgtgg aggctatcaa caaagaatgg gcttgaaaca ttataaaaat tgacaatgat   3120
ttattaaata tgttttctca attgtaacga cttctccatc tcctgtgtaa tcaaggccag   3180
tgctaaaatt cagatgctgt tagtacctac atcagtcaac aacttacact tattttacta   3240
gttttcaatc ataatacctg ctgtggatgc ttcatgtgct gcctgcaagc ttcttttttc   3300
tcattaaata taaaatattt tgtaatgctg cacagaaatt ttcaatttga gattctacag   3360
taagcgtttt ttttctttga agatttatga tgcacttatt caatagctgt cagccgttcc   3420
acccttttga ccttacacat tctattacaa tgaattttgc agttttgcac atttttttaaa   3480
tgtcattaac tgttagggaa ttttacttga atactgaata catataatgt ttatattaaa   3540
aaggacattt gtgttaaaaa ggaaattaga gttgcagtaa actttcaatg ctgcacacaa   3600
aaaaaagaca tttgattttt cagtagaaat tgtcctacat gtgctttatt gatttgctat   3660
tgaaagaata gggttttttt tttttttttt tttttttttt ttaaatgtgc agtgttgaat   3720
catttcttca tagtgctccc ccgagttggg actagggctt caatttcact tcttaaaaaa   3780
aatcatcata tatttgatat gcccagactg catacgattt taagcggagt acaactacta   3840
ttgtaaagct aatgtgaaga tattattaaa aaggtttttt tttccagaaa tttggtgtct   3900
tcaaattata ccttcacctt gacatttgaa tatccagcca ttttgtttct taatggtata   3960
aaattccatt ttcaataact tattggtgct gaaattgttc actagctgtg gtctgaccta   4020
gttaatttac aaatacagat tgaataggac ctactagagc agcatttata gagtttgatg   4080
gcaaatagat taggcagaac ttcatctaaa atattcttag taaataatgt tgacacgttt   4140
tccatacctt gtcagtttca ttcaacaatt tttaaatttt taacaaagct cttaggattt   4200
acacatttat atttaaacat tgatatatag agtattgatt gattgctcat aagttaaatt   4260
ggtaaagtta gagacaacta ttctaacacc tcaccattga aatttatatg ccaccttgtc   4320
tttcataaaa gctgaaaatt gttacctaaa atgaaaatca acttcatgtt ttgaagatag   4380
ttataaatat tgttctttgt tacaatttcg ggcaccgcat attaaaacgt aactttattg   4440
ttccaatatg taacatggag ggccaggtca taaataatga cattataatg ggcttttgca   4500
ctgttattat ttttcctttg gaatgtgaag gtctgaatga gggttttgat tttgaatgtt   4560
```

```
tcaatgtttt tgagaagcct tgcttacatt ttatggtgta gtcattggaa atggaaaaat   4620
ggcattatat atattatata tataaatata tattatacat actctcctta ctttatttca   4680
gttaccatcc ccatagaatt tgacaagaat tgctatgact gaaaggtttt cgagtcctaa   4740
ttaaaacttt atttatggca gtattcataa ttagcctgaa atgcattctg taggtaatct   4800
ctgagtttct ggaatatttt cttagacttt ttggatgtgc agcagcttac atgtctgaag   4860
ttacttgaag gcatcacttt taagaaagct tacagttggg ccctgtacca tcccaagtcc   4920
tttgtagctc ctcttgaaca tgtttgccat acttttaaaa gggtagttga ataaatagca   4980
tcaccattct ttgctgtggc acaggttata aacttaagtg gagtttaccg gcagcatcaa   5040
atgtttcagc tttaaaaaat aaaagtaggg tacaagttta atgtttagtt ctagaaattt   5100
tgtgcaatat gttcataacg atggctgtgg ttgccacaaa gtgcctcgtt tacctttaaa   5160
tactgttaat gtgtcatgca tgcagatgga aggggtggaa ctgtgcacta aagtgggggc   5220
tttaactgta gtatttggca gagttgcctt ctacctgcca gttcaaaagt tcaacctgtt   5280
ttcatataga atatatatac taaaaaattt cagtctgtta aacagcctta ctctgattca   5340
gcctcttcag atactcttgt gctgtgcagc agtggctctg tgtgtaaatg ctatgcactg   5400
aggatacaca aaaataccaa tatgatgtgt acaggataat gcctcatccc aatcagatgt   5460
ccatttgtta ttgtgtttgt taacaaccct ttatctctta gtgttataaa ctccacttaa   5520
aactgattaa agtctcattc ttgtcattgt gtgggtgttt tattaaatga gagtttataa   5580
ttcaaattgc ttaagtccat tgaagtttta attaatgggc agccaaatgt gaatacaaag   5640
ttttcagttt tttttttcc tgctgtcctt caaagcctac tgtttaaaaa aaaaaaaaaa   5700
aaaaaacatg gcctgagagt agagtatctg tctactcatg tttaattaag gaaaaacact   5760
tatttttagg gctttagtca tcacttcata aattgtataa gcacattaaa tagcgttcta   5820
gtcctgaaaa agtccaagat tcttagaaaa ttgtgcatat ttttattatg acagatgttt   5880
gaagataatt ccccagaatg gatttgatac tttagatttc aattttgtgg cttttgtcta   5940
ttattctgta ctctgccatc agcatatgga aagcttcatt tactcatcat gacttgtgcc   6000
atataaaaat tgatatttcg gaatagtcta aaggactttt tgtacttgaa tttaatcatg   6060
ttgtttctaa tattcttaaa agcttgaaga ctaaagcata tcctttcaac aaagcatagt   6120
aaggtaataa gaaagtgtag tttgtacaag tgttaaaaaa ataaagtaga caatgttaca   6180
gtgggactta ttatttcaag tttacatttt ctccatgtaa ttttttaaaa agtaaatgaa   6240
aaaatgtgca ataatgtaaa atatgaagtg tatgtgtaca cacattttat ttttcggtat   6300
cttgggtata cgtatggttg aaaactatac tggagtctaa aagtattcta atttataaga   6360
agacattttg gtgatgtttg aaaaatagaa atgtgctagt tttgttttta tatcatgtcc   6420
tttgtacgtt gtaatatgag ctggcttggt tcagtaaatg ccatcaccat ttccattgag   6480
aatttaaaac tcaccagtgt ttaatatgca ggcttccaaa ggcttatgaa aaaaatcaag   6540
acccttaaat ctagttaatt tgctgctaac atgaaactct ttggttcttt tatttttgcc   6600
agataattag acacacatct aaagcttagt cttaaatggc ttaagtgtag ctattgatta   6660
gtgctgttgc tagttcagaa agaaatgttt gtgaatggaa acaagaatat tcagtccaaa   6720
ctgttgtaag gacagtacct gaaaaccagg aaacaggata atggaaaaag tcttttaaag   6780
atgaaatgtt ggagccaact ttcttataga attaattgta tgtggctata gaaagcctaa   6840
tgattgttgc ttatttttga gagcatatta ttcttttatg accataatct tgctgttttt   6900
```

```
ccatcttcca aaagatcttc cttctaatat gtatatcaga atgtgggtag ccagtcagac   6960

aaattcatat tggttggtag ctttaaaaag tttgtaatgt gaagacagga aaggacaaaa   7020

tagtttgctt tggtggtagt actctggttg ttaagctagg tattttgaga ctacttcccc   7080

atcacaacaa caataaaata atcactcata atcctatcac ctggagacat agccatcgtt   7140

aatatgttag tgactataca atcatgtttt cttctgtata tccatgtata ttctttaaaa   7200

atgaaattta tactgtacct gatctcaaag ctttttagct tagtatatct gtcatgaatt   7260

tgtaggatgt tccattgcat cagaaaacgg acagtgattt gattactttc taatgccaca   7320

gatgcagatt acatgtagtt attgagaatc ctttcgaatt cagtggctta atcatgaatg   7380

tctaaatatt gttgacatta ggatgataca tgtaaattaa agttacattt gtttagcata   7440

gacaagctta acattgtaga tgtttctctt caaaaatcat cttaaacatt tgcatttgga   7500

attgtgttaa atagaatgtg tgaaacactg tattagtaaa cttcatcacc tttctacttc   7560

cttatagttt gaacttttca gtttttgtag ttcccaaaca gttgctcaat ttagagcaaa   7620

ttaatttaac acctgccaaa aaaaggctgc tgttggctta tcagttgtct ttaaattcaa   7680

atgctcatgt gacttttatc acatcaaaaa atatttcatt aatgattcac ctttagctct   7740

gaaaattacc gcgtttagta attatagtgg gcttataaaa acatgcaact ctttttgata   7800

gttatttgag aattttggtg aaaaatattt agctgagggc agtatagaac ttataaacca   7860

atatattgat atttttaaaa cattttttaca tataagtaaa ctgccatctt tgagcataac   7920

tacatttaaa aataaagctg catattttta aatcaagtgt ttaacaagaa tttatatttt   7980

ttatttttta aaattaaaaa taatttatat ttcctctgtt gcatgaggat tctcatctgt   8040

gcttataatg gttagagatt ttatttgtgt ggaatgaagt gaggcttgta gtcatggttc   8100

tagtgtttca gtttgccaag tctgtttact gcagtgaaat tcatcaaatg tttcagtgtg   8160

gttttctgta gcctatcatt tactggctat ttttttatgt acacctttag gatttttctgc   8220

ctactctatc cagttgtcca aatgatatcc tacattttac aaatgccctt tcagtttcta   8280

ttttcttttt ccattaaatt gccctcatgt cctaatgtgc agtttgtaag tgtgtgtgtg   8340

tgtgtctgtg tgtgtgtgaa tttgattttc aagagtgcta gacttccaat ttgagagatt   8400

aaataattta attcaggcaa acatttttca ttggaatttc acagttcatt gtaatgaaaa   8460

tgttaatcct ggatgacctt tgacatacag taatgaatct tggatattaa tgaatttgtt   8520

agtagcatct tgatgtgtgt tttaatgagt tattttcaaa gttgtgcatt aaaccaaagt   8580

tggcatactg gaagtgttta tatcaagttc catttggcta ctgatggaca aaaaatagaa   8640

atgccttcct atggagagta tttttccttt aaaaaattaa aaaggttaat tattttgact   8700

aaaaaaaaaa aaaaaaaa                                                 8718
```

<210> SEQ ID NO 34
<211> LENGTH: 576
<212> TYPE: PRT
<213> ORGANISM: Artificial Sequence
<220> FEATURE:
<223> OTHER INFORMATION: Synthetic Polymer

<400> SEQUENCE: 34

```
Leu Glu Arg Gly Gly Glu Ala Ala Ala Ala Ala Ala Ala Ala Ala Ala
1               5                   10                  15

Ala Pro Gly Arg Gly Ser Glu Ser Pro Val Thr Ile Ser Arg Ala Gly
            20                  25                  30

Asn Ala Gly Glu Leu Val Ser Pro Leu Leu Leu Pro Pro Thr Arg Arg
```

```
        35                  40                  45

Arg Arg Arg Arg His Ile Gln Gly Pro Gly Pro Val Leu Asn Leu Pro
    50                  55                  60

Ser Ala Ala Ala Ala Pro Pro Val Ala Arg Ala Pro Glu Ala Ala Gly
65                  70                  75                  80

Gly Gly Ser Arg Ser Glu Asp Tyr Ser Ser Ser Pro His Ser Ala Ala
                85                  90                  95

Ala Ala Ala Arg Pro Leu Ala Ala Glu Glu Lys Gln Ala Gln Ser Leu
            100                 105                 110

Gln Pro Ser Ser Ser Arg Arg Ser Ser His Tyr Pro Ala Ala Val Gln
        115                 120                 125

Ser Gln Ala Ala Ala Glu Arg Gly Ala Ser Ala Thr Ala Lys Ser Arg
    130                 135                 140

Ala Ile Ser Ile Leu Gln Lys Lys Pro Arg His Gln Gln Leu Leu Pro
145                 150                 155                 160

Ser Leu Ser Ser Phe Phe Phe Ser His Arg Leu Pro Asp Met Thr Ala
                165                 170                 175

Ile Ile Lys Glu Ile Val Ser Arg Asn Lys Arg Arg Tyr Gln Glu Asp
            180                 185                 190

Gly Phe Asp Leu Asp Leu Thr Tyr Ile Tyr Pro Asn Ile Ile Ala Met
        195                 200                 205

Gly Phe Pro Ala Glu Arg Leu Glu Gly Val Tyr Arg Asn Asn Ile Asp
    210                 215                 220

Asp Val Val Arg Phe Leu Asp Ser Lys His Lys Asn His Tyr Lys Ile
225                 230                 235                 240

Tyr Asn Leu Cys Ala Glu Arg His Tyr Asp Thr Ala Lys Phe Asn Cys
                245                 250                 255

Arg Val Ala Gln Tyr Pro Phe Glu Asp His Asn Pro Pro Gln Leu Glu
            260                 265                 270

Leu Ile Lys Pro Phe Cys Glu Asp Leu Asp Gln Trp Leu Ser Glu Asp
        275                 280                 285

Asp Asn His Val Ala Ala Ile His Cys Lys Ala Gly Lys Gly Arg Thr
    290                 295                 300

Gly Val Met Ile Cys Ala Tyr Leu Leu His Arg Gly Lys Phe Leu Lys
305                 310                 315                 320

Ala Gln Glu Ala Leu Asp Phe Tyr Gly Glu Val Arg Thr Arg Asp Lys
                325                 330                 335

Lys Gly Val Thr Ile Pro Ser Gln Arg Arg Tyr Val Tyr Tyr Tyr Ser
            340                 345                 350

Tyr Leu Leu Lys Asn His Leu Asp Tyr Arg Pro Val Ala Leu Leu Phe
        355                 360                 365

His Lys Met Met Phe Glu Thr Ile Pro Met Phe Ser Gly Gly Thr Cys
    370                 375                 380

Asn Pro Gln Phe Val Val Cys Gln Leu Lys Val Lys Ile Tyr Ser Ser
385                 390                 395                 400

Asn Ser Gly Pro Thr Arg Arg Glu Asp Lys Phe Met Tyr Phe Glu Phe
                405                 410                 415

Pro Gln Pro Leu Pro Val Cys Gly Asp Ile Lys Val Glu Phe Phe His
            420                 425                 430

Lys Gln Asn Lys Met Leu Lys Lys Asp Lys Met Phe His Phe Trp Val
        435                 440                 445

Asn Thr Phe Phe Ile Pro Gly Pro Glu Glu Thr Ser Glu Lys Val Glu
    450                 455                 460
```

```
Asn Gly Ser Leu Cys Asp Gln Glu Ile Asp Ser Ile Cys Ser Ile Glu
465                 470                 475                 480

Arg Ala Asp Asn Asp Lys Glu Tyr Leu Val Leu Thr Leu Thr Lys Asn
                485                 490                 495

Asp Leu Asp Lys Ala Asn Lys Asp Lys Ala Asn Arg Tyr Phe Ser Pro
            500                 505                 510

Asn Phe Lys Val Lys Leu Tyr Phe Thr Lys Thr Val Glu Glu Pro Ser
        515                 520                 525

Asn Pro Glu Ala Ser Ser Ser Thr Ser Val Thr Pro Asp Val Ser Asp
    530                 535                 540

Asn Glu Pro Asp His Tyr Arg Tyr Ser Asp Thr Thr Asp Ser Asp Pro
545                 550                 555                 560

Glu Asn Glu Pro Phe Asp Glu Asp Gln His Thr Gln Ile Thr Lys Val
                565                 570                 575


<210> SEQ ID NO 35
<211> LENGTH: 8833
<212> TYPE: DNA
<213> ORGANISM: Artificial Sequence
<220> FEATURE:
<223> OTHER INFORMATION: Synthetic Polymer

<400> SEQUENCE: 35

cctcccctcg cccggcgcgg tcccgtccgc ctctcgctcg cctcccgcct cccctcggtc     60

ttccgaggcg cccgggctcc cggcgcggcg gcggaggggg cgggcaggcc ggcgggcggt    120

gatgtggcgg gactctttat gcgctgcggc aggatacgcg ctcggcgctg ggacgcgact    180

gcgctcagtt ctctcctctc ggaagctgca gccatgatgg aagtttgaga gttgagccgc    240

tgtgaggcga ggccgggctc aggcgaggga gatgagagac ggcggcggcc gcggcccgga    300

gcccctctca gcgcctgtga gcagccgcgg gggcagcgcc ctcggggagc cggccggcct    360

gcggcggcgg cagcggcggc gtttctcgcc tcctcttcgt cttttctaac cgtgcagcct    420

cttcctcggc ttctcctgaa agggaaggtg gaagccgtgg gctcgggcgg gagccggctg    480

aggcgcggcg gcggcggcgg cacctcccgc tcctggagcg ggggggagaa gcggcggcgg    540

cggcggccgc ggcggctgca gctccaggga gggggtctga gtcgcctgtc accatttcca    600

gggctgggaa cgccggagag ttggtctctc cccttctact gcctccaaca cggcggcggc    660

ggcggcggca catccaggga cccgggccgg ttttaaacct cccgtccgcc gccgccgcac    720

cccccgtggc ccgggctccg gaggccgccg gcggaggcag ccgttcggag gattattcgt    780

cttctcccca ttccgctgcc gccgctgcca ggcctctggc tgctgaggag aagcaggccc    840

agtcgctgca accatccagc agccgccgca gcagccatta cccggctgcg gtccagagcc    900

aagcggcggc agagcgaggg gcatcagcta ccgccaagtc cagagccatt tccatcctgc    960

agaagaagcc ccgccaccag cagcttctgc catctctctc ctcctttttc ttcagccaca   1020

ggctcccaga catgacagcc atcatcaaag agatcgttag cagaaacaaa aggagatatc   1080

aagaggatgg attcgactta gacttgacct atatttatcc aaacattatt gctatgggat   1140

ttcctgcaga aagacttgaa ggcgtataca ggaacaatat tgatgatgta gtaagttgtg   1200

ctgaaagaca ttatgacacc gccaaattta attgcagagt tgcacaatat ccttttgaag   1260

accataaccc accacagcta gaacttatca aaccctttttg tgaagatctt gaccaatggc   1320

taagtgaaga tgacaatcat gttgcagcaa ttcactgtaa agctggaaag ggacgaactg   1380

gtgtaatgat atgtgcatat ttattacatc ggggcaaatt tttaaaggca caagaggccc   1440
```

```
tagatttcta tggggaagta aggaccagag acaaaaaggc agatcctaca ggaggtattc   1500
cagataaagg cattattgtc ataggagatg gcagctccat ggatgttatt gccccttaag   1560
accttccagt gggacaagat gtataggtgg aagacagtga tattgatgat cctgaccttg   1620
tagaggccaa ggctaaagga gtaactattc ccagtcagag gcgctatgtg tattattata   1680
gctacctgtt aaagaatcat ctggattata gaccagtggc actgttgttt cacaagatga   1740
tgtttgaaac tattccaatg ttcagtggcg gaacttgcaa tcctcagttt gtggtctgcc   1800
agctaaaggt gaagatatat tcctccaatt caggacccac acgacgggaa gacaagttca   1860
tgtactttga gttccctcag ccgttacctg tgtgtggtga tatcaaagta gagttcttcc   1920
acaaacagaa caagatgcta aaaaaggaca aaatgtttca cttttgggta aatacattct   1980
tcataccagg accagaggaa acctcagaaa aagtagaaaa tggaagtcta tgtgatcaag   2040
aaatcgatag catttgcagt atagagcgtg cagataatga caaggaatat ctagtactta   2100
ctttaacaaa aaatgatctt gacaaagcaa ataaagacaa agccaaccga tacttttctc   2160
caaattttaa ggtgaagctg tacttcacaa aaacagtaga ggagccgtca aatccagagg   2220
ctagcagttc aacttctgta acaccagatg ttagtgacaa tgaacctgat cattatagat   2280
attctgacac cactgactct gatccagaga atgaaccttt tgatgaagat cagcatacac   2340
aaattacaaa agtctgaatt tttttttatc aagagggata aaacaccatg aaaataaact   2400
tgaataaact gaaaatggac cttttttttt ttaatggcaa taggacattg tgtcagatta   2460
ccagttatag gaacaattct cttttcctga ccaatcttgt tttaccctat acatccacag   2520
ggttttgaca cttgttgtcc agttgaaaaa aggttgtgta gctgtgtcat gtatatacct   2580
ttttgtgtca aaaggacatt taaaattcaa ttaggattaa taaagatggc actttcccgt   2640
tttattccag ttttataaaa agtggagaca gactgatgtg tatacgtagg aatttttttcc  2700
ttttgtgttc tgtcaccaac tgaagtggct aaagagcttt gtgatatact ggttcacatc   2760
ctaccccttt gcacttgtgg caacagataa gtttgcagtt ggctaagaga ggtttccgaa   2820
gggttttgct acattctaat gcatgtattc gggttagggg aatggaggga atgctcagaa   2880
aggaaataat tttatgctgg actctggacc atataccatc tccagctatt tacacacacc   2940
tttctttagc atgctacagt tattaatctg gacattcgag gaattggccg ctgtcactgc   3000
ttgttgtttg cgcatttttt tttaaagcat attggtgcta gaaaaggcag ctaaaggaag   3060
tgaatctgta ttggggtaca ggaatgaacc ttctgcaaca tcttaagatc cacaaatgaa   3120
gggatataaa aataatgtca taggtaagaa acacagcaac aatgacttaa ccatataaat   3180
gtggaggcta tcaacaaaga atgggcttga aacattataa aaattgacaa tgatttatta   3240
aatatgtttt ctcaattgta acgacttctc catctcctgt gtaatcaagg ccagtgctaa   3300
aattcagatg ctgttagtac ctacatcagt caacaactta cacttatttt actagttttc   3360
aatcataata cctgctgtgg atgcttcatg tgctgcctgc aagcttcttt tttctcatta   3420
aatataaaat attttgtaat gctgcacaga aattttcaat ttgagattct acagtaagcg   3480
tttttttttct ttgaagattt atgatgcact tattcaatag ctgtcagccg ttccacccctt  3540
ttgaccttac acattctatt acaatgaatt ttgcagtttt gcacattttt taaatgtcat   3600
taactgttag ggaattttac ttgaatactg aatacatata atgtttatat taaaaaggac   3660
atttgtgtta aaaaggaaat tagagttgca gtaaactttc aatgctgcac acaaaaaaaa   3720
gacatttgat ttttcagtag aaattgtcct acatgtgctt tattgatttg ctattgaaag   3780
```

```
aatagggttt tttttttttt tttttttttt ttttttaaat gtgcagtgtt gaatcatttc   3840
ttcatagtgc tcccccgagt tgggactagg gcttcaattt cacttcttaa aaaaaatcat   3900
catatatttg atatgcccag actgcatacg attttaagcg gagtacaact actattgtaa   3960
agctaatgtg aagatattat taaaaaggtt tttttttcca gaaatttggt gtcttcaaat   4020
tataccttca ccttgacatt tgaatatcca gccattttgt ttcttaatgg tataaaattc   4080
cattttcaat aacttattgg tgctgaaatt gttcactagc tgtggtctga cctagttaat   4140
ttacaaatac agattgaata ggacctacta gagcagcatt tatagagttt gatggcaaat   4200
agattaggca gaacttcatc taaaatattc ttagtaaata atgttgacac gttttccata   4260
ccttgtcagt ttcattcaac aatttttaaa tttttaacaa agctcttagg atttacacat   4320
ttatatttaa acattgatat atagagtatt gattgattgc tcataagtta aattggtaaa   4380
gttagagaca actattctaa cacctcacca ttgaaattta tatgccacct tgtctttcat   4440
aaaagctgaa aattgttacc taaaatgaaa atcaacttca tgttttgaag atagttataa   4500
atattgttct ttgttacaat ttcgggcacc gcatattaaa acgtaacttt attgttccaa   4560
tatgtaacat ggagggccag gtcataaata atgacattat aatgggcttt tgcactgtta   4620
ttatttttcc tttggaatgt gaaggtctga atgagggttt tgattttgaa tgtttcaatg   4680
tttttgagaa gccttgctta cattttatgg tgtagtcatt ggaaatggaa aaatggcatt   4740
atatatatta tatatataaa tatatattat acatactctc cttactttat ttcagttacc   4800
atccccatag aatttgacaa gaattgctat gactgaaagg ttttcgagtc ctaattaaaa   4860
ctttatttat ggcagtattc ataattagcc tgaaatgcat tctgtaggta atctctgagt   4920
ttctggaata ttttcttaga ctttttggat gtgcagcagc ttacatgtct gaagttactt   4980
gaaggcatca cttttaagaa agcttacagt tgggccctgt accatcccaa gtcctttgta   5040
gctcctcttg aacatgtttg ccatactttt aaaagggtag ttgaataaat agcatcacca   5100
ttctttgctg tggcacaggt tataaactta agtggagttt accggcagca tcaaatgttt   5160
cagctttaaa aaataaaagt agggtacaag tttaatgttt agttctagaa attttgtgca   5220
atatgttcat aacgatggct gtggttgcca caaagtgcct cgtttacctt taaatactgt   5280
taatgtgtca tgcatgcaga tggaaggggt ggaactgtgc actaaagtgg gggctttaac   5340
tgtagtattt ggcagagttg ccttctacct gccagttcaa aagttcaacc tgttttcata   5400
tagaatatat atactaaaaa atttcagtct gttaaacagc cttactctga ttcagcctct   5460
tcagatactc ttgtgctgtg cagcagtggc tctgtgtgta aatgctatgc actgaggata   5520
cacaaaaata ccaatatgat gtgtacagga taatgcctca tcccaatcag atgtccattt   5580
gttattgtgt ttgttaacaa ccctttatct cttagtgtta taaactccac ttaaaactga   5640
ttaaagtctc attcttgtca ttgtgtgggt gttttattaa atgagagttt ataattcaaa   5700
ttgcttaagt ccattgaagt tttaattaat gggcagccaa atgtgaatac aaagttttca   5760
gttttttttt ttcctgctgt ccttcaaagc ctactgttta aaaaaaaaaa aaaaaaaaaa   5820
catggcctga gagtagagta tctgtctact catgtttaat taaggaaaaa cacttatttt   5880
tagggcttta gtcatcactt cataaattgt ataagcacat taaatagcgt tctagtcctg   5940
aaaaagtcca agattcttag aaaattgtgc atatttttat tatgacagat gtttgaagat   6000
aattccccag aatggatttg atactttaga tttcaatttt gtggcttttg tctattattc   6060
tgtactctgc catcagcata tggaaagctt catttactca tcatgacttg tgccatataa   6120
aaattgatat ttcggaatag tctaaaggac tttttgtact tgaatttaat catgttgttt   6180
```

```
ctaatattct taaaagcttg aagactaaag catatccttt caacaaagca tagtaaggta   6240
ataagaaagt gtagtttgta caagtgttaa aaaaataaag tagacaatgt tacagtggga   6300
cttattattt caagtttaca ttttctccat gtaatttttt aaaaagtaaa tgaaaaaatg   6360
tgcaataatg taaaatatga agtgtatgtg tacacacatt ttatttttcg gtatcttggg   6420
tatacgtatg gttgaaaact atactggagt ctaaaagtat tctaatttat aagaagacat   6480
tttggtgatg tttgaaaaat agaaatgtgc tagttttgtt tttatatcat gtcctttgta   6540
cgttgtaata tgagctggct tggttcagta aatgccatca ccatttccat tgagaattta   6600
aaactcacca gtgtttaata tgcaggcttc caaaggctta tgaaaaaaat caagacccct   6660
aaatctagtt aatttgctgc taacatgaaa ctctttggtt cttttatttt tgccagataa   6720
ttagacacac atctaaagct tagtcttaaa tggcttaagt gtagctattg attagtgctg   6780
ttgctagttc agaaagaaat gtttgtgaat ggaaacaaga atattcagtc caaactgttg   6840
taaggacagt acctgaaaac caggaaacag gataatggaa aaagtctttt aaagatgaaa   6900
tgttggagcc aactttctta tagaattaat tgtatgtggc tatagaaagc ctaatgattg   6960
ttgcttattt ttgagagcat attattcttt tatgaccata atcttgctgt ttttccatct   7020
tccaaaagat cttccttcta atatgtatat cagaatgtgg gtagccagtc agacaaattc   7080
atattggttg gtagctttaa aaagtttgta atgtgaagac aggaaaggac aaaatagttt   7140
gctttggtgg tagtactctg gttgttaagc taggtatttt gagactactt ccccatcaca   7200
acaacaataa aataatcact cataatccta tcacctggag acatagccat cgttaatatg   7260
ttagtgacta tacaatcatg ttttcttctg tatatccatg tatattcttt aaaaatgaaa   7320
tttatactgt acctgatctc aaagcttttt agcttagtat atctgtcatg aatttgtagg   7380
atgttccatt gcatcagaaa acggacagtg atttgattac tttctaatgc cacagatgca   7440
gattacatgt agttattgag aatcctttcg aattcagtgg cttaatcatg aatgtctaaa   7500
tattgttgac attaggatga tacatgtaaa ttaaagttac atttgtttag catagacaag   7560
cttaacattg tagatgtttc tcttcaaaaa tcatcttaaa catttgcatt tggaattgtg   7620
ttaaatagaa tgtgtgaaac actgtattag taaacttcat cacctttcta cttccttata   7680
gtttgaactt ttcagttttt gtagttccca aacagttgct caatttagag caaattaatt   7740
taacacctgc caaaaaaagg ctgctgttgg cttatcagtt gtctttaaat tcaaatgctc   7800
atgtgacttt tatcacatca aaaaatattt cattaatgat tcacctttag ctctgaaaat   7860
taccgcgttt agtaattata gtgggcttat aaaaacatgc aactcttttt gatagttatt   7920
tgagaatttt ggtgaaaaat atttagctga gggcagtata gaacttataa accaatatat   7980
tgatattttt aaaacatttt tacatataag taaactgcca tctttgagca taactacatt   8040
taaaaataaa gctgcatatt tttaaatcaa gtgtttaaca agaatttata ttttttattt   8100
tttaaaatta aaaataattt atatttcctc tgttgcatga ggattctcat ctgtgcttat   8160
aatggttaga gattttattt gtgtggaatg aagtgaggct tgtagtcatg gttctagtgt   8220
ttcagtttgc caagtctgtt tactgcagtg aaattcatca aatgtttcag tgtggttttc   8280
tgtagcctat catttactgg ctattttttt atgtacacct ttaggatttt ctgcctactc   8340
tatccagttg tccaaatgat atcctacatt ttacaaatgc cctttcagtt tctattttct   8400
ttttccatta aattgccctc atgtcctaat gtgcagtttg taagtgtgtg tgtgtgtgtc   8460
tgtgtgtgtg tgaatttgat tttcaagagt gctagacttc caatttgaga gattaaataa   8520
```

```
tttaattcag gcaaacattt ttcattggaa tttcacagtt cattgtaatg aaaatgttaa   8580

tcctggatga cctttgacat acagtaatga atcttggata ttaatgaatt tgttagtagc   8640

atcttgatgt gtgttttaat gagttatttt caaagttgtg cattaaacca aagttggcat   8700

actggaagtg tttatatcaa gttccatttg gctactgatg gacaaaaaat agaaatgcct   8760

tcctatggag agtatttttc ctttaaaaaa ttaaaaaggt taattatttt gactaaaaaa   8820

aaaaaaaaaa aaa                                                      8833
```

<210> SEQ ID NO 36
<211> LENGTH: 206
<212> TYPE: PRT
<213> ORGANISM: Artificial Sequence
<220> FEATURE:
<223> OTHER INFORMATION: Synthetic Polymer

<400> SEQUENCE: 36

```
Met Met Phe Glu Thr Ile Pro Met Phe Ser Gly Gly Thr Cys Asn Pro
1               5                   10                  15

Gln Phe Val Val Cys Gln Leu Lys Val Lys Ile Tyr Ser Ser Asn Ser
            20                  25                  30

Gly Pro Thr Arg Arg Glu Asp Lys Phe Met Tyr Phe Glu Phe Pro Gln
        35                  40                  45

Pro Leu Pro Val Cys Gly Asp Ile Lys Val Glu Phe Phe His Lys Gln
    50                  55                  60

Asn Lys Met Leu Lys Lys Asp Lys Met Phe His Phe Trp Val Asn Thr
65                  70                  75                  80

Phe Phe Ile Pro Gly Pro Glu Glu Thr Ser Glu Lys Val Glu Asn Gly
                85                  90                  95

Ser Leu Cys Asp Gln Glu Ile Asp Ser Ile Cys Ser Ile Glu Arg Ala
            100                 105                 110

Asp Asn Asp Lys Glu Tyr Leu Val Leu Thr Leu Thr Lys Asn Asp Leu
        115                 120                 125

Asp Lys Ala Asn Lys Asp Lys Ala Asn Arg Tyr Phe Ser Pro Asn Phe
    130                 135                 140

Lys Val Lys Leu Tyr Phe Thr Lys Thr Val Glu Glu Pro Ser Asn Pro
145                 150                 155                 160

Glu Ala Ser Ser Ser Thr Ser Val Thr Pro Asp Val Ser Asp Asn Glu
                165                 170                 175

Pro Asp His Tyr Arg Tyr Ser Asp Thr Thr Asp Ser Asp Pro Glu Asn
            180                 185                 190

Glu Pro Phe Asp Glu Asp Gln His Thr Gln Ile Thr Lys Val
        195                 200                 205
```

<210> SEQ ID NO 37
<211> LENGTH: 9796
<212> TYPE: DNA
<213> ORGANISM: Artificial Sequence
<220> FEATURE:
<223> OTHER INFORMATION: Synthetic Polymer

<400> SEQUENCE: 37

```
ggcagtggca gcggcgagag cttgggcggc cgccgccgcc tcctcgcgag cgccgcgcgc     60

ccgggtcccg ctcgcatgca agtcacgtcc gccccctcgg cgcggccgcc ccgagacgcc    120

ggccccgctg agtgatgaga acagacgtca aactgcctta tgaatattga tgcggaggct    180

aggctgcttt cgtagagaag cagaaggaag caagatggct gccctttagg atttgttaga    240
```

```
aaggagaccc gactgcaact gctggattgc tgcaaggctg agggacgaga acgaggctgg    300
caaacattca gcagcacacc ctctcaagat tgtttacttg cctttgctcc tgttgagtta    360
caacgcttgg aagcaggaga tgggctcagc agcagccaat aggacatgat ccaggaagag    420
cagtaaggga ctgagctgct gaattcaact agagggcagc cttgtggatg gccccgaagc    480
aagcctgatg gaacaggata gaaccaacca tgttgagggc aacagactaa gtccattcct    540
gataccatca cctcccattt gccagacaga acctctggct acaaagctcc agaatggaag    600
cccactgcct gagagagctc atccagaagt aaatggagac accaagtggc actctttcaa    660
aagttattat ggaataccct gtatgaaggg aagccagaat agtcgtgtga gtcctgactt    720
tacacaagaa agtagagggt attccaagtg tttgcaaaat ggaggaataa aacgcacagt    780
tagtgaacct tctctctctg ggctccttca gatcaagaaa ttgaaacaag accaaaaggc    840
taatggagaa agacgtaact tcggggtaag ccaagaaaga aatccaggtg aaagcagtca    900
accaaatgtc tccgatttga gtgataagaa agaatctgtg agttctgtag cccaagaaaa    960
tgcagttaaa gatttcacca gtttttcaac acataactgc agtgggcctg aaaatccaga   1020
gcttcagatt ctgaatgagc aggaggggaa aagtgctaat taccatgaca agaacattgt   1080
attacttaaa aacaaggcag tgctaatgcc taatggtgct acagtttctg cctcttccgt   1140
ggaacacaca catggtgaac tcctggaaaa aacactgtct caatattatc cagattgtgt   1200
ttccattgcg gtgcagaaaa ccacatctca cataaatgcc attaacagtc aggctactaa   1260
tgagttgtcc tgtgagatca ctcacccatc gcatacctca gggcagatca attccgcaca   1320
gacctctaac tctgagctgc ctccaaagcc agctgcagtg gtgagtgagg cctgtgatgc   1380
tgatgatgct gataatgcca gtaaactagc tgcaatgcta aatacctgtt cctttcagaa   1440
accagaacaa ctacaacaac aaaaatcagt ttttgagata tgcccatctc ctgcagaaaa   1500
taacatccag ggaaccacaa agctagcgtc tggtgaagaa ttctgttcag gttccagcag   1560
caatttgcaa gctcctggtg gcagctctga acggtattta aaacaaaatg aaatgaatgg   1620
tgcttacttc aagcaaagct cagtgttcac taaggattcc ttttctgcca ctaccacacc   1680
accaccacca tcacaattgc ttctttctcc ccctcctcct cttccacagg ttcctcagct   1740
tccttcagaa ggaaaaagca ctctgaatgg tggagtttta gaagaacacc accactaccc   1800
caaccaaagt aacacaacac ttttaaggga agtgaaaata gagggtaaac ctgaggcacc   1860
accttcccag agtcctaatc catctacaca tgtatgcagc ccttctccga tgctttctga   1920
aaggcctcag aataattgtg tgaacaggaa tgacatacag actgcaggga caatgactgt   1980
tccattgtgt tctgagaaaa caagaccaat gtcagaacac ctcaagcata acccaccaat   2040
ttttggtagc agtggagagc tacaggacaa ctgccagcag ttgatgagaa acaaagagca   2100
agagattctg aagggtcgag acaaggagca aacacgagat cttgtgcccc caacacagca   2160
ctatctgaaa ccaggatgga ttgaattgaa ggcccctcgt tttcaccaag cggaatccca   2220
tctaaaacgt aatgaggcat cactgccatc aattcttcag tatcaaccca atctctccaa   2280
tcaaatgacc tccaaacaat acactggaaa ttccaacatg cctggggggc tcccaaggca   2340
agcttacacc cagaaaacaa cacagctgga gcacaagtca caaatgtacc aagttgaaat   2400
gaatcaaggg cagtcccaag gtacagtgga ccaacatctc cagttccaaa aaccctcaca   2460
ccaggtgcac ttctccaaaa cagaccattt accaaaagct catgtgcagt cactgtgtgg   2520
cactagattt cattttcaac aaagagcaga ttcccaaact gaaaaactta tgtccccagt   2580
gttgaaacag cacttgaatc aacaggcttc agagactgag ccattttcaa actcacacct   2640
```

```
tttgcaacat aagcctcata aacaggcagc acaaacacaa ccatcccaga gttcacatct   2700
ccctcaaaac cagcaacagc agcaaaaatt acaaataaag aataaagagg aaatactcca   2760
gacttttcct cacccccaaa gcaacaatga tcagcaaaga gaaggatcat tctttggcca   2820
gactaaagtg gaagaatgtt ttcatggtga aaatcagtat tcaaaatcaa gcgagttcga   2880
gactcataat gtccaaatgg gactggagga agtacagaat ataaatcgta gaaattcccc   2940
ttatagtcag accatgaaat caagtgcatg caaaatacag gtttcttgtt caaacaatac   3000
acacctagtt tcagagaata aagaacagac tacacatcct gaactttttg caggaaacaa   3060
gacccaaaac ttgcatcaca tgcaatattt tccaaataat gtgatcccaa agcaagatct   3120
tcttcacagg tgctttcaag aacaggagca gaagtcacaa caagcttcag ttctacaggg   3180
atataaaaat agaaaccaag atatgtctgg tcaacaagct gcgcaacttg ctcagcaaag   3240
gtacttgata cataaccatg caaatgtttt tcctgtgcct gaccagggag gaagtcacac   3300
tcagacccct ccccagaagg acactcaaaa gcatgctgct ctaaggtggc atctcttaca   3360
gaagcaagaa cagcagcaaa cacagcaacc ccaaactgag tcttgccata gtcagatgca   3420
caggccaatt aaggtggaac ctggatgcaa gccacatgcc tgtatgcaca cagcaccacc   3480
agaaaacaaa acatggaaaa aggtaactaa gcaagagaat ccacctgcaa gctgtgataa   3540
tgtgcagcaa aagagcatca ttgagaccat ggagcagcat ctgaagcagt ttcacgccaa   3600
gtcgttattt gaccataagg ctcttactct caaatcacag aagcaagtaa aagttgaaat   3660
gtcagggcca gtcacagttt tgactagaca aaccactgct gcagaacttg atagccacac   3720
cccagcttta gagcagcaaa caacttcttc agaaaagaca ccaaccaaaa gaacagctgc   3780
ttctgttctc aataatttta tagagtcacc ttccaaatta ctagatactc ctataaaaaa   3840
tttattggat acacctgtca agactcaata tgatttccca tcttgcagat gtgtagagca   3900
aattattgaa aaagatgaag gtcctttttta tacccatcta ggagcaggtc ctaatgtggc   3960
agctattaga gaaatcatgg aagaaaggtt tggacagaag ggtaaagcta ttaggattga   4020
aagagtcatc tatactggta aagaaggcaa aagttctcag ggatgtccta ttgctaagtg   4080
ggtggttcgc agaagcagca gtgaagagaa gctactgtgt ttggtgcggg agcgagctgg   4140
ccacacctgt gaggctgcag tgattgtgat tctcatcctg gtgtgggaag gaatcccgct   4200
gtctctggct gacaaactct actcggagct taccgagacg ctgaggaaat acggcacgct   4260
caccaatcgc cggtgtgcct tgaatgaaga gagaacttgc gcctgtcagg ggctggatcc   4320
agaaacctgt ggtgcctcct tctcttttgg ttgttcatgg agcatgtact acaatggatg   4380
taagtttgcc agaagcaaga tcccaaggaa gtttaagctg cttggggatg acccaaaaga   4440
ggaagagaaa ctggagtctc atttgcaaaa cctgtccact cttatggcac caacatataa   4500
gaaacttgca cctgatgcat ataataatca gattgaatat gaacacagag caccagagtg   4560
ccgtctgggt ctgaaggaag gccgtccatt ctcaggggtc actgcatgtt tggacttctg   4620
tgctcatgcc cacagagact tgcacaacat gcagaatggc agcacattgg tatgcactct   4680
cactagagaa gacaatcgag aatttggagg aaaacctgag gatgagcagc ttcacgttct   4740
gcctttatac aaagtctctg acgtggatga gtttgggagt gtggaagctc aggaggagaa   4800
aaaacggagt ggtgccattc aggtactgag ttcttttcgg cgaaaagtca ggatgttagc   4860
agagccagtc aagacttgcc gacaaaggaa actagaagcc aagaaagctg cagctgaaaa   4920
gctttcctcc ctggagaaca gctcaaataa aaatgaaaag gaaaagtcag ccccatcacg   4980
```

```
tacaaaacaa actgaaaacg caagccaggc taaacagttg gcagaacttt tgcgactttc   5040
aggaccagtc atgcagcagt cccagcagcc ccagcctcta cagaagcagc caccacagcc   5100
ccagcagcag cagagacccc agcagcagca gccacatcac cctcagacag agtctgtcaa   5160
ctcttattct gcttctggat ccaccaatcc atacatgaga cggcccaatc cagttagtcc   5220
ttatccaaac tcttcacaca cttcagatat ctatggaagc accagcccta tgaacttcta   5280
ttccacctca tctcaagctg caggttcata tttgaattct tctaatccca tgaaccctta   5340
ccctgggctt ttgaatcaga atacccaata tccatcatat caatgcaatg gaaacctatc   5400
agtggacaac tgctccccat atctgggttc ctattctccc cagtctcagc cgatggatct   5460
gtataggtat ccaagccaag accctctgtc taagctcagt ctaccaccca tccatacact   5520
ttaccagcca aggtttggaa atagccagag ttttacatct aaatacttag gttatggaaa   5580
ccaaaatatg cagggagatg gtttcagcag ttgtaccatt agaccaaatg tacatcatgt   5640
agggaaattg cctccttatc ccactcatga gatggatggc cacttcatgg gagccacctc   5700
tagattacca cccaatctga gcaatccaaa catggactat aaaaatggtg aacatcattc   5760
accttctcac ataatccata actacagtgc agctccgggc atgttcaaca gctctcttca   5820
tgccctgcat ctccaaaaca aggagaatga catgctttcc cacacagcta atgggttatc   5880
aaagatgctt ccagctctta accatgatag aactgcttgt gtccaaggag gcttacacaa   5940
attaagtgat gctaatggtc aggaaaagca gccattggca ctagtccagg gtgtggcttc   6000
tggtgcagag gacaacgatg aggtctggtc agacagcgag cagagctttc tggatcctga   6060
cattggggga gtggccgtgg ctccaactca tgggtcaatt ctcattgagt gtgcaaagcg   6120
tgagctgcat gccacaaccc ctttaaagaa tcccaatagg aatcacccca ccaggatctc   6180
cctcgtcttt taccagcata agagcatgaa tgagccaaaa catggcttgg ctctttggga   6240
agccaaaatg gctgaaaaag cccgtgagaa agaggaagag tgtgaaaagt atggcccaga   6300
ctatgtgcct cagaaatccc atggcaaaaa agtgaaacgg gagcctgctg agccacatga   6360
aacttcagag cccacttacc tgcgtttcat caagtctctt gccgaaagga ccatgtccgt   6420
gaccacagac tccacagtaa ctacatctcc atatgccttc actcgggtca cagggcctta   6480
caacagatat atatgatatc accccctttt gttggttacc tcacttgaaa agaccacaac   6540
caacctgtca gtagtatagt tctcatgacg tgggcagtgg ggaaaggtca cagtattcat   6600
gacaaatgtg gtgggaaaaa cctcagctca ccagcaacaa aagaggttat cttaccatag   6660
cacttaattt tcactggctc ccaagtggtc acagatggca tctaggaaaa gaccaaagca   6720
ttctatgcaa aaagaaggtg gggaagaaag tgttccgcaa tttacatttt taaacactgg   6780
ttctattatt ggacgagatg atatgtaaat gtgatccccc ccccccgctt acaactctac   6840
acatctgtga ccacttttaa taatatcaag tttgcatagt catggaacac aaatcaaaca   6900
agtactgtag tattacagtg acaggaatct taaaatacca tctggtgctg aatatatgat   6960
gtactgaaat actggaatta tggctttttg aaatgcagtt tttactgtaa tcttaacttt   7020
tatttatcaa aatagctaca ggaaacatga atagcaggaa aacactgaat ttgtttggat   7080
gttctaagaa atggtgctaa gaaaatggtg tctttaatag ctaaaaattt aatgccttta   7140
tatcatcaag atgctatcag tgtactccag tgcccttgaa taataggggt accttttcat   7200
tcaagttttt atcataatta cctattctta cacaagctta gtttttaaaa tgtggacatt   7260
ttaaaggcct ctggattttg ctcatccagt gaagtccttg taggacaata aacgtatata   7320
tgtacatata tacacaaaca tgtatatgtg cacacacatg tatatgtata aatattttaa   7380
```

```
atggtgtttt agaagcactt tgtctaccta agctttgaca acttgaacaa tgctaaggta   7440
ctgagatgtt taaaaaacaa gtttactttc attttagaat gcaaagttga tttttttaag   7500
gaaacaaaga aagcttttaa aatatttttg cttttagcca tgcatctgct gatgagcaat   7560
tgtgtccatt tttaacacag ccagttaaat ccaccatggg gcttactgga ttcaagggaa   7620
tacgttagtc cacaaaacat gttttctggt gctcatctca catgctatac tgtaaaacag   7680
ttttatacaa aattgtatga caagttcatt gctcaaaaat gtacagtttt aagaattttc   7740
tattaactgc aggtaataat tagctgcatg ctgcagactc aacaaagcta gttcactgaa   7800
gcctatgcta ttttatggat cataggctct tcagagaact gaatggcagt ctgcctttgt   7860
gttgataatt atgtacattg tgacgttgtc atttcttagc ttaagtgtcc tctttaacaa   7920
gaggattgag cagactgatg cctgcataag atgaataaac agggttagtt ccatgtgaat   7980
ctgtcagtta aaaagaaaca aaaacaggca gctggtttgc tgtggtggtt ttaaatcatt   8040
aatttgtata aagaagtgaa agagttgtat agtaaattaa attgtaaaca aaactttttt   8100
aatgcaatgc tttagtattt tagtactgta aaaaaattaa atatatacat atatatatat   8160
atatatatat atatatatat gagtttgaag cagaattcac atcatgatgg tgctactcag   8220
cctgctacaa atatatcata atgtgagcta agaattcatt aaatgtttga gtgatgttcc   8280
tacttgtcat atacctcaac actagtttgg caataggata ttgaactgag agtgaaagca   8340
ttgtgtacca tcattttttt ccaagtcctt tttttattg ttaaaaaaaa aagcatacct   8400
tttttcaata cttgatttct tagcaagtat aacttgaact tcaacctttt tgttctaaaa   8460
attcagggat atttcagctc atgctctccc tatgccaaca tgtcacctgt gtttatgtaa   8520
aattgttgta ggttaataaa tatattcttt gtcagggatt taaccctttt attttgaatc   8580
ccttctattt tacttgtaca tgtgctgatg taactaaaac taattttgta aatctgttgg   8640
ctctttttat tgtaaagaaa agcattttaa aagtttgagg aatcttttga ctgtttcaag   8700
caggaaaaaa aaattacatg aaaatagaat gcactgagtt gataaaggga aaaattgtaa   8760
ggcaggagtt tggcaagtgg ctgttggcca gagacttact tgtaactctc taaatgaagt   8820
tttttgatc ctgtaatcac tgaaggtaca tactccatgt ggacttccct taaacaggca   8880
aacacctaca ggtatggtgt gcaacagatt gtacaattac attttggcct aaatacattt   8940
ttgcttacta gtatttaaaa taaattctta atcagaggag gcctttgggt tttattggtc   9000
aaatctttgt aagctggctt ttgtcttttt aaaaaatttc ttgaatttgt ggttgtgtcc   9060
aatttgcaaa catttccaaa aatgtttgct ttgcttacaa accacatgat tttaatgttt   9120
tttgtatacc ataatatcta gccccaaaca tttgattact acatgtgcat tggtgatttt   9180
gatcatccat tcttaatatt tgatttctgt gtcacctact gtcatttgtt aaactgctgg   9240
ccaacaagaa caggaagtat agtttggggg gttggggaga gtttacataa ggaagagaag   9300
aaattgagtg gcatattgta aatatcagat ctataattgt aaatataaaa cctgcctcag   9360
ttagaatgaa tggaaagcag atctacaatt tgctaatata ggaatatcag gttgactata   9420
tagccatact tgaaaatgct tctgagtggt gtcaacttta cttgaatgaa tttttcatct   9480
tgattgacgc acagtgatgt acagttcact tctgaagcta gtggttaact tgtgtaggaa   9540
acttttgcag tttgacacta agataacttc tgtgtgcatt tttctatgct tttttaaaaa   9600
ctagtttcat ttcattttca tgagatgttt ggtttataag atctgaggat ggttataaat   9660
actgtaagta ttgtaatgtt atgaatgcag gttatttgaa agctgtttat tattatatca   9720
```

ttcctgataa tgctatgtga gtgtttttaa taaaatttat atttatttaa tgcactctaa 9780
aaaaaaaaaa aaaaaa 9796

<210> SEQ ID NO 38
<211> LENGTH: 2002
<212> TYPE: PRT
<213> ORGANISM: Artificial Sequence
<220> FEATURE:
<223> OTHER INFORMATION: Synthetic Polymer

<400> SEQUENCE: 38

Met Glu Gln Asp Arg Thr Asn His Val Glu Gly Asn Arg Leu Ser Pro
1 5 10 15

Phe Leu Ile Pro Ser Pro Pro Ile Cys Gln Thr Glu Pro Leu Ala Thr
20 25 30

Lys Leu Gln Asn Gly Ser Pro Leu Pro Glu Arg Ala His Pro Glu Val
35 40 45

Asn Gly Asp Thr Lys Trp His Ser Phe Lys Ser Tyr Tyr Gly Ile Pro
50 55 60

Cys Met Lys Gly Ser Gln Asn Ser Arg Val Ser Pro Asp Phe Thr Gln
65 70 75 80

Glu Ser Arg Gly Tyr Ser Lys Cys Leu Gln Asn Gly Gly Ile Lys Arg
85 90 95

Thr Val Ser Glu Pro Ser Leu Ser Gly Leu Leu Gln Ile Lys Lys Leu
100 105 110

Lys Gln Asp Gln Lys Ala Asn Gly Glu Arg Arg Asn Phe Gly Val Ser
115 120 125

Gln Glu Arg Asn Pro Gly Glu Ser Ser Gln Pro Asn Val Ser Asp Leu
130 135 140

Ser Asp Lys Lys Glu Ser Val Ser Ser Val Ala Gln Glu Asn Ala Val
145 150 155 160

Lys Asp Phe Thr Ser Phe Ser Thr His Asn Cys Ser Gly Pro Glu Asn
165 170 175

Pro Glu Leu Gln Ile Leu Asn Glu Gln Glu Gly Lys Ser Ala Asn Tyr
180 185 190

His Asp Lys Asn Ile Val Leu Leu Lys Asn Lys Ala Val Leu Met Pro
195 200 205

Asn Gly Ala Thr Val Ser Ala Ser Ser Val Glu His Thr His Gly Glu
210 215 220

Leu Leu Glu Lys Thr Leu Ser Gln Tyr Tyr Pro Asp Cys Val Ser Ile
225 230 235 240

Ala Val Gln Lys Thr Thr Ser His Ile Asn Ala Ile Asn Ser Gln Ala
245 250 255

Thr Asn Glu Leu Ser Cys Glu Ile Thr His Pro Ser His Thr Ser Gly
260 265 270

Gln Ile Asn Ser Ala Gln Thr Ser Asn Ser Glu Leu Pro Pro Lys Pro
275 280 285

Ala Ala Val Val Ser Glu Ala Cys Asp Ala Asp Asp Ala Asp Asn Ala
290 295 300

Ser Lys Leu Ala Ala Met Leu Asn Thr Cys Ser Phe Gln Lys Pro Glu
305 310 315 320

Gln Leu Gln Gln Gln Lys Ser Val Phe Glu Ile Cys Pro Ser Pro Ala
325 330 335

Glu Asn Asn Ile Gln Gly Thr Thr Lys Leu Ala Ser Gly Glu Glu Phe
340 345 350

```
Cys Ser Gly Ser Ser Ser Asn Leu Gln Ala Pro Gly Gly Ser Ser Glu
        355                 360                 365

Arg Tyr Leu Lys Gln Asn Glu Met Asn Gly Ala Tyr Phe Lys Gln Ser
    370                 375                 380

Ser Val Phe Thr Lys Asp Ser Phe Ser Ala Thr Thr Thr Pro Pro Pro
385                 390                 395                 400

Pro Ser Gln Leu Leu Leu Ser Pro Pro Pro Pro Leu Pro Gln Val Pro
                405                 410                 415

Gln Leu Pro Ser Glu Gly Lys Ser Thr Leu Asn Gly Gly Val Leu Glu
            420                 425                 430

Glu His His His Tyr Pro Asn Gln Ser Asn Thr Thr Leu Leu Arg Glu
        435                 440                 445

Val Lys Ile Glu Gly Lys Pro Glu Ala Pro Pro Ser Gln Ser Pro Asn
    450                 455                 460

Pro Ser Thr His Val Cys Ser Pro Ser Pro Met Leu Ser Glu Arg Pro
465                 470                 475                 480

Gln Asn Asn Cys Val Asn Arg Asn Asp Ile Gln Thr Ala Gly Thr Met
                485                 490                 495

Thr Val Pro Leu Cys Ser Glu Lys Thr Arg Pro Met Ser Glu His Leu
            500                 505                 510

Lys His Asn Pro Pro Ile Phe Gly Ser Ser Gly Glu Leu Gln Asp Asn
        515                 520                 525

Cys Gln Gln Leu Met Arg Asn Lys Glu Gln Glu Ile Leu Lys Gly Arg
    530                 535                 540

Asp Lys Glu Gln Thr Arg Asp Leu Val Pro Pro Thr Gln His Tyr Leu
545                 550                 555                 560

Lys Pro Gly Trp Ile Glu Leu Lys Ala Pro Arg Phe His Gln Ala Glu
                565                 570                 575

Ser His Leu Lys Arg Asn Glu Ala Ser Leu Pro Ser Ile Leu Gln Tyr
            580                 585                 590

Gln Pro Asn Leu Ser Asn Gln Met Thr Ser Lys Gln Tyr Thr Gly Asn
        595                 600                 605

Ser Asn Met Pro Gly Gly Leu Pro Arg Gln Ala Tyr Thr Gln Lys Thr
    610                 615                 620

Thr Gln Leu Glu His Lys Ser Gln Met Tyr Gln Val Glu Met Asn Gln
625                 630                 635                 640

Gly Gln Ser Gln Gly Thr Val Asp Gln His Leu Gln Phe Gln Lys Pro
                645                 650                 655

Ser His Gln Val His Phe Ser Lys Thr Asp His Leu Pro Lys Ala His
            660                 665                 670

Val Gln Ser Leu Cys Gly Thr Arg Phe His Phe Gln Gln Arg Ala Asp
        675                 680                 685

Ser Gln Thr Glu Lys Leu Met Ser Pro Val Leu Lys Gln His Leu Asn
    690                 695                 700

Gln Gln Ala Ser Glu Thr Glu Pro Phe Ser Asn Ser His Leu Leu Gln
705                 710                 715                 720

His Lys Pro His Lys Gln Ala Ala Gln Thr Gln Pro Ser Gln Ser Ser
                725                 730                 735

His Leu Pro Gln Asn Gln Gln Gln Gln Gln Lys Leu Gln Ile Lys Asn
            740                 745                 750

Lys Glu Glu Ile Leu Gln Thr Phe Pro His Pro Gln Ser Asn Asn Asp
        755                 760                 765
```

```
Gln Gln Arg Glu Gly Ser Phe Phe Gly Gln Thr Lys Val Glu Glu Cys
    770                 775                 780

Phe His Gly Glu Asn Gln Tyr Ser Lys Ser Ser Glu Phe Glu Thr His
785                 790                 795                 800

Asn Val Gln Met Gly Leu Glu Glu Val Gln Asn Ile Asn Arg Arg Asn
                805                 810                 815

Ser Pro Tyr Ser Gln Thr Met Lys Ser Ser Ala Cys Lys Ile Gln Val
            820                 825                 830

Ser Cys Ser Asn Asn Thr His Leu Val Ser Glu Asn Lys Glu Gln Thr
        835                 840                 845

Thr His Pro Glu Leu Phe Ala Gly Asn Lys Thr Gln Asn Leu His His
    850                 855                 860

Met Gln Tyr Phe Pro Asn Asn Val Ile Pro Lys Gln Asp Leu Leu His
865                 870                 875                 880

Arg Cys Phe Gln Glu Gln Glu Gln Lys Ser Gln Gln Ala Ser Val Leu
                885                 890                 895

Gln Gly Tyr Lys Asn Arg Asn Gln Asp Met Ser Gly Gln Gln Ala Ala
            900                 905                 910

Gln Leu Ala Gln Gln Arg Tyr Leu Ile His Asn His Ala Asn Val Phe
        915                 920                 925

Pro Val Pro Asp Gln Gly Gly Ser His Thr Gln Thr Pro Pro Gln Lys
    930                 935                 940

Asp Thr Gln Lys His Ala Ala Leu Arg Trp His Leu Leu Gln Lys Gln
945                 950                 955                 960

Glu Gln Gln Gln Thr Gln Gln Pro Gln Thr Glu Ser Cys His Ser Gln
                965                 970                 975

Met His Arg Pro Ile Lys Val Glu Pro Gly Cys Lys Pro His Ala Cys
            980                 985                 990

Met His Thr Ala Pro Pro Glu Asn  Lys Thr Trp Lys Lys  Val Thr Lys
        995                 1000                1005

Gln Glu  Asn Pro Pro Ala Ser  Cys Asp Asn Val Gln  Gln Lys Ser
    1010                1015                1020

Ile Ile  Glu Thr Met Glu Gln  His Leu Lys Gln Phe  His Ala Lys
    1025                1030                1035

Ser Leu  Phe Asp His Lys Ala  Leu Thr Leu Lys Ser  Gln Lys Gln
    1040                1045                1050

Val Lys  Val Glu Met Ser Gly  Pro Val Thr Val Leu  Thr Arg Gln
    1055                1060                1065

Thr Thr  Ala Ala Glu Leu Asp  Ser His Thr Pro Ala  Leu Glu Gln
    1070                1075                1080

Gln Thr  Thr Ser Ser Glu Lys  Thr Pro Thr Lys Arg  Thr Ala Ala
    1085                1090                1095

Ser Val  Leu Asn Asn Phe Ile  Glu Ser Pro Ser Lys  Leu Leu Asp
    1100                1105                1110

Thr Pro  Ile Lys Asn Leu Leu  Asp Thr Pro Val Lys  Thr Gln Tyr
    1115                1120                1125

Asp Phe  Pro Ser Cys Arg Cys  Val Glu Gln Ile Ile  Glu Lys Asp
    1130                1135                1140

Glu Gly  Pro Phe Tyr Thr His  Leu Gly Ala Gly Pro  Asn Val Ala
    1145                1150                1155

Ala Ile  Arg Glu Ile Met Glu  Glu Arg Phe Gly Gln  Lys Gly Lys
    1160                1165                1170

Ala Ile  Arg Ile Glu Arg Val  Ile Tyr Thr Gly Lys  Glu Gly Lys
```

```
    1175                1180                1185

Ser Ser  Gln Gly Cys Pro Ile  Ala Lys Trp Val Val  Arg Arg Ser
    1190                1195                1200

Ser Ser  Glu Glu Lys Leu Leu  Cys Leu Val Arg Glu  Arg Ala Gly
    1205                1210                1215

His Thr  Cys Glu Ala Ala Val  Ile Val Ile Leu Ile  Leu Val Trp
    1220                1225                1230

Glu Gly  Ile Pro Leu Ser Leu  Ala Asp Lys Leu Tyr  Ser Glu Leu
    1235                1240                1245

Thr Glu  Thr Leu Arg Lys Tyr  Gly Thr Leu Thr Asn  Arg Arg Cys
    1250                1255                1260

Ala Leu  Asn Glu Glu Arg Thr  Cys Ala Cys Gln Gly  Leu Asp Pro
    1265                1270                1275

Glu Thr  Cys Gly Ala Ser Phe  Ser Phe Gly Cys Ser  Trp Ser Met
    1280                1285                1290

Tyr Tyr  Asn Gly Cys Lys Phe  Ala Arg Ser Lys Ile  Pro Arg Lys
    1295                1300                1305

Phe Lys  Leu Leu Gly Asp Asp  Pro Lys Glu Glu Glu  Lys Leu Glu
    1310                1315                1320

Ser His  Leu Gln Asn Leu Ser  Thr Leu Met Ala Pro  Thr Tyr Lys
    1325                1330                1335

Lys Leu  Ala Pro Asp Ala Tyr  Asn Asn Gln Ile Glu  Tyr Glu His
    1340                1345                1350

Arg Ala  Pro Glu Cys Arg Leu  Gly Leu Lys Glu Gly  Arg Pro Phe
    1355                1360                1365

Ser Gly  Val Thr Ala Cys Leu  Asp Phe Cys Ala His  Ala His Arg
    1370                1375                1380

Asp Leu  His Asn Met Gln Asn  Gly Ser Thr Leu Val  Cys Thr Leu
    1385                1390                1395

Thr Arg  Glu Asp Asn Arg Glu  Phe Gly Gly Lys Pro  Glu Asp Glu
    1400                1405                1410

Gln Leu  His Val Leu Pro Leu  Tyr Lys Val Ser Asp  Val Asp Glu
    1415                1420                1425

Phe Gly  Ser Val Glu Ala Gln  Glu Glu Lys Lys Arg  Ser Gly Ala
    1430                1435                1440

Ile Gln  Val Leu Ser Ser Phe  Arg Arg Lys Val Arg  Met Leu Ala
    1445                1450                1455

Glu Pro  Val Lys Thr Cys Arg  Gln Arg Lys Leu Glu  Ala Lys Lys
    1460                1465                1470

Ala Ala  Ala Glu Lys Leu Ser  Ser Leu Glu Asn Ser  Ser Asn Lys
    1475                1480                1485

Asn Glu  Lys Glu Lys Ser Ala  Pro Ser Arg Thr Lys  Gln Thr Glu
    1490                1495                1500

Asn Ala  Ser Gln Ala Lys Gln  Leu Ala Glu Leu Leu  Arg Leu Ser
    1505                1510                1515

Gly Pro  Val Met Gln Gln Ser  Gln Gln Pro Gln Pro  Leu Gln Lys
    1520                1525                1530

Gln Pro  Pro Gln Pro Gln Gln  Gln Gln Arg Pro Gln  Gln Gln Gln
    1535                1540                1545

Pro His  His Pro Gln Thr Glu  Ser Val Asn Ser Tyr  Ser Ala Ser
    1550                1555                1560

Gly Ser  Thr Asn Pro Tyr Met  Arg Arg Pro Asn Pro  Val Ser Pro
    1565                1570                1575
```

```
Tyr Pro  Asn Ser Ser His Thr  Ser Asp Ile Tyr Gly  Ser Thr Ser
    1580                 1585                 1590

Pro Met  Asn Phe Tyr Ser Thr  Ser Ser Gln Ala Ala  Gly Ser Tyr
    1595                 1600                 1605

Leu Asn  Ser Ser Asn Pro Met  Asn Pro Tyr Pro Gly  Leu Leu Asn
    1610                 1615                 1620

Gln Asn  Thr Gln Tyr Pro Ser  Tyr Gln Cys Asn Gly  Asn Leu Ser
    1625                 1630                 1635

Val Asp  Asn Cys Ser Pro Tyr  Leu Gly Ser Tyr Ser  Pro Gln Ser
    1640                 1645                 1650

Gln Pro  Met Asp Leu Tyr Arg  Tyr Pro Ser Gln Asp  Pro Leu Ser
    1655                 1660                 1665

Lys Leu  Ser Leu Pro Pro Ile  His Thr Leu Tyr Gln  Pro Arg Phe
    1670                 1675                 1680

Gly Asn  Ser Gln Ser Phe Thr  Ser Lys Tyr Leu Gly  Tyr Gly Asn
    1685                 1690                 1695

Gln Asn  Met Gln Gly Asp Gly  Phe Ser Ser Cys Thr  Ile Arg Pro
    1700                 1705                 1710

Asn Val  His His Val Gly Lys  Leu Pro Pro Tyr Pro  Thr His Glu
    1715                 1720                 1725

Met Asp  Gly His Phe Met Gly  Ala Thr Ser Arg Leu  Pro Pro Asn
    1730                 1735                 1740

Leu Ser  Asn Pro Asn Met Asp  Tyr Lys Asn Gly Glu  His His Ser
    1745                 1750                 1755

Pro Ser  His Ile Ile His Asn  Tyr Ser Ala Ala Pro  Gly Met Phe
    1760                 1765                 1770

Asn Ser  Ser Leu His Ala Leu  His Leu Gln Asn Lys  Glu Asn Asp
    1775                 1780                 1785

Met Leu  Ser His Thr Ala Asn  Gly Leu Ser Lys Met  Leu Pro Ala
    1790                 1795                 1800

Leu Asn  His Asp Arg Thr Ala  Cys Val Gln Gly Gly  Leu His Lys
    1805                 1810                 1815

Leu Ser  Asp Ala Asn Gly Gln  Glu Lys Gln Pro Leu  Ala Leu Val
    1820                 1825                 1830

Gln Gly  Val Ala Ser Gly Ala  Glu Asp Asn Asp Glu  Val Trp Ser
    1835                 1840                 1845

Asp Ser  Glu Gln Ser Phe Leu  Asp Pro Asp Ile Gly  Gly Val Ala
    1850                 1855                 1860

Val Ala  Pro Thr His Gly Ser  Ile Leu Ile Glu Cys  Ala Lys Arg
    1865                 1870                 1875

Glu Leu  His Ala Thr Thr Pro  Leu Lys Asn Pro Asn  Arg Asn His
    1880                 1885                 1890

Pro Thr  Arg Ile Ser Leu Val  Phe Tyr Gln His Lys  Ser Met Asn
    1895                 1900                 1905

Glu Pro  Lys His Gly Leu Ala  Leu Trp Glu Ala Lys  Met Ala Glu
    1910                 1915                 1920

Lys Ala  Arg Glu Lys Glu Glu  Glu Cys Glu Lys Tyr  Gly Pro Asp
    1925                 1930                 1935

Tyr Val  Pro Gln Lys Ser His  Gly Lys Lys Val Lys  Arg Glu Pro
    1940                 1945                 1950

Ala Glu  Pro His Glu Thr Ser  Glu Pro Thr Tyr Leu  Arg Phe Ile
    1955                 1960                 1965
```

```
Lys Ser  Leu Ala Glu Arg Thr  Met Ser Val Thr Thr  Asp Ser Thr
    1970                 1975                 1980

Val Thr  Thr Ser Pro Tyr Ala  Phe Thr Arg Val Thr  Gly Pro Tyr
    1985                 1990                 1995

Asn Arg  Tyr Ile
    2000
```

<210> SEQ ID NO 39
<211> LENGTH: 9236
<212> TYPE: DNA
<213> ORGANISM: Artificial Sequence
<220> FEATURE:
<223> OTHER INFORMATION: Synthetic Polymer

<400> SEQUENCE: 39

```
aaacagaagg tgggccgggg cggggagaaa cagaactcgg tcaatttccc agtttgtcgg     60

gtctttaaaa atacaggccc ctaaagcact aagggcatgc cctcggtgaa acaggggagc    120

gcttctgctg aatgagatta aagcgacaga aaagggaaag gagagcgcgg gcaacgggat    180

ctaaagggag atagagacgc gggcctctga gggctggcaa acattcagca gcacaccctc    240

tcaagattgt ttacttgcct ttgctcctgt tgagttacaa cgcttggaag caggagatgg    300

gctcagcagc agccaatagg acatgatcca ggaagagcag taagggactg agctgctgaa    360

ttcaactaga gggcagcctt gtggatggcc ccgaagcaag cctgatggaa caggatagaa    420

ccaaccatgt tgagggcaac agactaagtc cattcctgat accatcacct cccatttgcc    480

agacagaacc tctggctaca aagctccaga atggaagccc actgcctgag agagctcatc    540

cagaagtaaa tggagacacc aagtggcact ctttcaaaag ttattatgga ataccctgta    600

tgaagggaag ccagaatagt cgtgtgagtc ctgactttac acaagaaagt agagggtatt    660

ccaagtgttt gcaaaatgga ggaataaaac gcacagttag tgaaccttct ctctctgggc    720

tccttcagat caagaaattg aaacaagacc aaaaggctaa tggagaaaga cgtaacttcg    780

ggtaagcca agaaagaaat ccaggtgaaa gcagtcaacc aaatgtctcc gatttgagtg    840

ataagaaaga atctgtgagt tctgtagccc aagaaaatgc agttaaagat ttcaccagtt    900

tttcaacaca taactgcagt gggcctgaaa atccagagct tcagattctg aatgagcagg    960

aggggaaaag tgctaattac catgacaaga acattgtatt acttaaaaac aaggcagtgc   1020

taatgcctaa tggtgctaca gtttctgcct cttccgtgga acacacacat ggtgaactcc   1080

tggaaaaaac actgtctcaa tattatccag attgtgtttc cattgcggtg cagaaaacca   1140

catctcacat aaatgccatt aacagtcagg ctactaatga gttgtcctgt gagatcactc   1200

acccatcgca tacctcaggg cagatcaatt ccgcacagac ctctaactct gagctgcctc   1260

caaagccagc tgcagtggtg agtgaggcct gtgatgctga tgatgctgat aatgccagta   1320

aactagctgc aatgctaaat acctgttcct ttcagaaacc agaacaacta caacaacaaa   1380

aatcagtttt tgagatatgc ccatctcctg cagaaaataa catccaggga accacaaagc   1440

tagcgtctgg tgaagaattc tgttcaggtt ccagcagcaa tttgcaagct cctggtggca   1500

gctctgaacg gtatttaaaa caaaatgaaa tgaatggtgc ttacttcaag caaagctcag   1560

tgttcactaa ggattccttt tctgccacta ccacaccacc accaccatca caattgcttc   1620

tttctccccc tcctcctctt ccacaggttc ctcagcttcc ttcagaagga aaaagcactc   1680

tgaatggtgg agttttagaa gaacaccacc actaccccaa ccaaagtaac acaacacttt   1740

taagggaagt gaaaatagag ggtaaacctg aggcaccacc ttcccagagt cctaatccat   1800
```

```
ctacacatgt atgcagccct tctccgatgc tttctgaaag gcctcagaat aattgtgtga   1860
acaggaatga catacagact gcagggacaa tgactgttcc attgtgttct gagaaaacaa   1920
gaccaatgtc agaacacctc aagcataacc caccaatttt tggtagcagt ggagagctac   1980
aggacaactg ccagcagttg atgagaaaca aagagcaaga gattctgaag ggtcgagaca   2040
aggagcaaac acgagatctt gtgcccccaa cacagcacta tctgaaacca ggatggattg   2100
aattgaaggc ccctcgtttt caccaagcgg aatcccatct aaaacgtaat gaggcatcac   2160
tgccatcaat tcttcagtat caacccaatc tctccaatca aatgacctcc aaacaataca   2220
ctggaaattc caacatgcct ggggggctcc caaggcaagc ttacacccag aaaacaacac   2280
agctggagca caagtcacaa atgtaccaag ttgaaatgaa tcaagggcag tcccaaggta   2340
cagtggacca acatctccag ttccaaaaac cctcacacca ggtgcacttc tccaaaacag   2400
accatttacc aaaagctcat gtgcagtcac tgtgtggcac tagatttcat tttcaacaaa   2460
gagcagattc ccaaactgaa aaacttatgt ccccagtgtt gaaacagcac ttgaatcaac   2520
aggcttcaga gactgagcca ttttcaaact cacacctttt gcaacataag cctcataaac   2580
aggcagcaca aacacaacca tcccagagtt cacatctccc tcaaaaccag caacagcagc   2640
aaaaattaca aataaagaat aaagaggaaa tactccagac ttttcctcac ccccaaagca   2700
acaatgatca gcaaagagaa ggatcattct ttggccagac taaagtggaa gaatgttttc   2760
atggtgaaaa tcagtattca aaatcaagcg agttcgagac tcataatgtc caaatgggac   2820
tggaggaagt acagaatata aatcgtagaa attcccctta tagtcagacc atgaaatcaa   2880
gtgcatgcaa aatacaggtt tcttgttcaa acaatacaca cctagtttca gagaataaag   2940
aacagactac acatcctgaa ctttttgcag gaaacaagac ccaaaacttg catcacatgc   3000
aatattttcc aaataatgtg atcccaaagc aagatcttct tcacaggtgc tttcaagaac   3060
aggagcagaa gtcacaacaa gcttcagttc tacagggata taaaaataga aaccaagata   3120
tgtctggtca acaagctgcg caacttgctc agcaaaggta cttgatacat aaccatgcaa   3180
atgtttttcc tgtgcctgac cagggaggaa gtcacactca gacccctccc cagaaggaca   3240
ctcaaaagca tgctgctcta aggtggcatc tcttacagaa gcaagaacag cagcaaacac   3300
agcaacccca aactgagtct tgccatagtc agatgcacag gccaattaag gtggaacctg   3360
gatgcaagcc acatgcctgt atgcacacag caccaccaga aaacaaaaca tggaaaaagg   3420
taactaagca agagaatcca cctgcaagct gtgataatgt gcagcaaaag agcatcattg   3480
agaccatgga gcagcatctg aagcagtttc acgccaagtc gttatttgac cataaggctc   3540
ttactctcaa atcacagaag caagtaaaag ttgaaatgtc agggccagtc acagttttga   3600
ctagacaaac cactgctgca gaacttgata gccacacccc agctttagag cagcaaacaa   3660
cttcttcaga aaagacacca accaaaagaa cagctgcttc tgttctcaat aattttatag   3720
agtcaccttc caaattacta gatactccta taaaaaattt attggataca cctgtcaaga   3780
ctcaatatga tttcccatct tgcagatgtg taggtaagtg ccagaaatgt actgagacac   3840
atggcgttta tccagaatta gcaaatttat cttcagatat gggattttcc ttcttttttt   3900
aaatcttgag tctggcagca atttgtaaag gctcataaaa atctgaagct tacatttttt   3960
gtcaagttac cgatgcttgt gtcttgtgaa agagaacttc acttacatgc agtttttcca   4020
aaagaattaa ataatcgtgc atgtttattt ttccctctct tcagatcctg taaaatttga   4080
atgtatctgt tttagatcaa ttcgcctatt tagctctttg tatattatct cctggagaga   4140
cagctaggca gcaaaaaaac aatctattaa aatgagaaaa taacgaccat aggcagtcta   4200
```

```
atgtacgaac tttaaatatt ttttaattca aggtaaaata tattagtttc acaagatttc   4260
tggctaatag ggaaattatt atcttcagtc ttcatgagtt gggggaaatg ataatgctga   4320
cactcttagt gctcctaaag tttccttttc tccatttata catttggaat gttgtgattt   4380
atattcattt tgattccctt ttctctaaaa tttcatcttt ttgattaaaa aatatgatac   4440
aggcatacct cagagatatt gtgggtttgg ctccatacca caataaaatg aatattacaa   4500
taaagcaagt tgtaaggact ttttggtttc tcactgtatg taaaagttat ttatatacta   4560
tactgtaaca tactaagtgt gcaatagcat tgtgtctaaa aaatatatac tttaaaaata   4620
atttattgtt aaaaaaatgc caacaattat ctgggccttt agtgagtgct aatctttttg   4680
ctggtggagg gtcgtgcttc agtattgatc gctgtggact gatcatggtg gtagttgctg   4740
aaggttgctg ggatggctgt gtgtgtggca atttcttaaa ataagacaac agtgaagtgc   4800
tgtatcaatt gatttttcca ttcacaaaag atttctctgt agcatgcaat gctgtttgat   4860
agcatttaac ccacagcaga atttctttga aaattggact cagtcctctc aaactgtgct   4920
gctgctttat caactaagtt tttgtaattt tctgaatcct ttgttgtcat ttcagcagtt   4980
tacagcatct tcattggaag tatattccat ctcaaacatt ctttgttcat ccataagaag   5040
caacttctta tcaagttttt tcatgacatt gcagtaactc agccccatct tcaggctcta   5100
cttctaattc tggttctctt gctacatctc cctcatctgc agtgacctct ccacggaagt   5160
cttgaactcc tcaaagtaat ccatgagggt tggaatcaac ttctaaactc ctgttaatgt   5220
tgatatattg accccctccc atgaattatg aatgttctta ataacttcta aatggtgata   5280
cctttccaga aggctttcaa tgtactttgc ccggatccat cagaagacta tcttggcagc   5340
tgtagactaa caatatattt cttaaatgat aagacttgaa agtcaaaagt actccttaat   5400
ccataggctg cagaatcaat gttgtattaa caggcacgaa aacagcatta atcttgtgca   5460
tctccatcgg agctcttggg tgactaggtg ccttgagcag taatattttg aaaggaggtt   5520
ttggttttgt tttttgtttt tttttttgt tttttagcag taagtctcaa cactgggctt   5580
aaaatattca gtaaactatg ttgtaaaaag atgtgttatc atccagactt tgttgttcca   5640
ttactctaca caagcagggt acacttagca taattcttaa gggccttgga attttcagaa   5700
tggtaaatga gtatgggctt caacttaaaa tcatcaactg cattagcctg taacaagaga   5760
gtcagcctgt cctttgaagc aaggcattga cttctatcta tgaaagtctt agatggcacc   5820
ttgtttcaat agtaggctgt ttagtacagc caccttcatc agtgatctta gctagatctt   5880
ctgcataact tgctgcagct tctacatcag cacttgctgc ctcaccttgt cctttatgt    5940
tatagagaca gctgcgcttc ttaaacttta taaaccaact tctgctagct tccaacttct   6000
cttctgcagc ttcctcattc tcttcataga actgaaggga gtcaaggcct tgctctggat   6060
taagctttgg cttaaggaat gttgtggctg acgtgatctt ctatccagac cactaaagcg   6120
ctctccatat cagcaataag gccgttttgc tttcttacct ttcatgtgtt cactggagta   6180
atttccttca agaatttttc ctttacattc acaacttggc taactggcat gcaaggccta   6240
gctttcagcc tgtcttggct tttgacatgc cttcctcact tagctcgtca tatctagctt   6300
ttgatttaaa gtggcaggca tacaactctt cctttcactt gaacacttag aggccactgt   6360
agggttatta attggcctaa tttcaatatt gttgtgtttt agggaataga gaggcccagg   6420
gagagggaga gagcccaaac ggctggttga tagagcaggc agaatgcaca caacatttat   6480
cagattatgt ttgcaccatt taccagatta tgggtacggt ttgtggcacc ccccaaaaat   6540
```

-continued

```
tagaatagta acatcaaaga tcactgatca cagatcgcca taacataaat aataataaac   6600
tttaaaatac tgtgagaatt accaaaatgt gatacagaga catgaagtga gcacatgctg   6660
ttgaaaaaaa tgacactgat agacatactt aacacgtggg attgccacaa accttcagtt   6720
tgtaaaagtc acagtaactg tgactcacaa aagaacaaag cacaataaaa cgaggtatgc   6780
ctgtattttt aaaaaaagct ttttgttaaa attcaggata tgtaataggt ctgtaggaat   6840
agtgaaatat ttttgctgat ggatgtagat atatacgtgg atagagatga agatcttaat   6900
tatagctatg cagcatagat ttagtcaaag acatttgaaa agacaaatgt taaattagtg   6960
tggctaatga cctacccgtg ccatgttttc cctcttgcaa tgagataccc cacactgtgt   7020
agaaggatgg agggaggact cctactgtcc ctctttgcgt gtggttatta agttgcctca   7080
ctgggctaaa acaccacaca tctcatagat aatatttggt aagttgtaat cgtcttcact   7140
cttctcttat cacccacccc tatcttccca cttttccatc tttgttggtt tgcaacagcc   7200
ccttcttttt gcctgactct ccaggatttt ctctcatcat aaattgttct aaagtacata   7260
ctaatatggg tctggattga ctattcttat ttgcaaaaca gcaattaaat gttataggga   7320
agtaggaaga aaaaggggta tccttgacaa taaaccaagc aatattctgg gggtgggata   7380
gagcaggaaa ttttattttt aatcttttaa aatccaagta ataggtaggc ttccagttag   7440
ctttaaatgt tttttttttc cagctcaaaa aattggattg tagttgatac tacatataat   7500
acattctaat tccctcactg tattctttgt ttagtttcat ttatttggtt taaaataatt   7560
ttttatccca tatctgaaat gtaatatatt tttatccaac aaccagcatg tacatatact   7620
taattatgtg gcacattttc taatagatca gtccatcaat ctactcattt taaagaaaaa   7680
aaaattttaa agtcactttt agagccctta atgtgtagtt gggggttaag ctttgtggat   7740
gtagccttta tatttagtat aattgaggtc taaaataata atcttctatt atctcaacag   7800
agcaaattat tgaaaaagat gaaggtcctt tttataccca tctaggagca ggtcctaatg   7860
tggcagctat tagagaaatc atggaagaaa ggtaattaac gcaaaggcac agggcagatt   7920
aacgtttatc cttttgtata tgtcagaatt tttccagcct tcacacacaa agcagtaaac   7980
aattgtaaat tgagtaatta ttagtaggct tagctattct agggttgcca acactacaca   8040
ctgtgctatt caccagagag tcacaatatt tgacaggact aatagtctgc tagctggcac   8100
aggctgccca ctttgcgatg gatgccagaa aacccaggca tgaacaggaa tcggccagcc   8160
aggctgccag ccacaaggta ctggcacagg ctccaacgag aggtcccact ctggctttcc   8220
cacctgataa taaagtgtca aagcagaaag actggtaaag tgtggtataa gaaaagaacc   8280
actgaattaa attcacctag tgttgcaaat gagtacttat ctctaagttt tcttttacca   8340
taaaaagaga gcaagtgtga tatgttgaat agaaagagaa acatactatt tacagctgcc   8400
ttttttttt tttttcgcta tcaatcacag gtatacaagt acttgccttt actcctgcat   8460
gtagaagact cttatgagcg agataatgca gagaaggcct ttcatataaa tttatacagc   8520
tctgagctgt tcttcttcta gggtgccttt tcattaagag gtaggcagta ttattattaa   8580
agtacttagg atacattggg gcagctagga catattcagt atcattcttg ctccatttcc   8640
aaattattca tttctaaatt agcatgtaga agttcactaa ataatcatct agtggcctgg   8700
cagaaatagt gaatttccct aagtgccttt tttttgttgt ttttttgttt tgttttttaa   8760
acaagcagta ggtggtgctt tggtcataag ggaagatata gtctatttct aggactattc   8820
catattttcc atgtggctgg atactaacta tttgccagcc tccttttcta aattgtgaga   8880
cattcttgga ggaacagttc taactaaaat ctattatgac tccccaagtt ttaaaatagc   8940
```

```
taaatttagt aagggaaaaa atagtttatg ttttagaaga ctgaacttag caaactaacc   9000

tgaattttgt gctttgtgaa attttatatc gaaatgagct ttcccatttt cacccacatg   9060

taatttacaa aatagttcat tacaattatc tgtacatttt gatattgagg aaaaacaagg   9120

cttaaaaacc attatccagt ttgcttggcg tagacctgtt taaaaaataa taaaccgttc   9180

atttctcagg atgtggtcat agaataaagt tatgctcaaa tgttcaaata tttaaa       9236


<210> SEQ ID NO 40
<211> LENGTH: 1165
<212> TYPE: PRT
<213> ORGANISM: Artificial Sequence
<220> FEATURE:
<223> OTHER INFORMATION: Synthetic Polymer

<400> SEQUENCE: 40

Met Glu Gln Asp Arg Thr Asn His Val Glu Gly Asn Arg Leu Ser Pro
1               5                   10                  15

Phe Leu Ile Pro Ser Pro Pro Ile Cys Gln Thr Glu Pro Leu Ala Thr
            20                  25                  30

Lys Leu Gln Asn Gly Ser Pro Leu Pro Glu Arg Ala His Pro Glu Val
        35                  40                  45

Asn Gly Asp Thr Lys Trp His Ser Phe Lys Ser Tyr Tyr Gly Ile Pro
    50                  55                  60

Cys Met Lys Gly Ser Gln Asn Ser Arg Val Ser Pro Asp Phe Thr Gln
65                  70                  75                  80

Glu Ser Arg Gly Tyr Ser Lys Cys Leu Gln Asn Gly Gly Ile Lys Arg
                85                  90                  95

Thr Val Ser Glu Pro Ser Leu Ser Gly Leu Leu Gln Ile Lys Lys Leu
            100                 105                 110

Lys Gln Asp Gln Lys Ala Asn Gly Glu Arg Arg Asn Phe Gly Val Ser
        115                 120                 125

Gln Glu Arg Asn Pro Gly Glu Ser Ser Gln Pro Asn Val Ser Asp Leu
    130                 135                 140

Ser Asp Lys Lys Glu Ser Val Ser Ser Val Ala Gln Glu Asn Ala Val
145                 150                 155                 160

Lys Asp Phe Thr Ser Phe Ser Thr His Asn Cys Ser Gly Pro Glu Asn
                165                 170                 175

Pro Glu Leu Gln Ile Leu Asn Glu Gln Glu Gly Lys Ser Ala Asn Tyr
            180                 185                 190

His Asp Lys Asn Ile Val Leu Leu Lys Asn Lys Ala Val Leu Met Pro
        195                 200                 205

Asn Gly Ala Thr Val Ser Ala Ser Ser Val Glu His Thr His Gly Glu
    210                 215                 220

Leu Leu Glu Lys Thr Leu Ser Gln Tyr Tyr Pro Asp Cys Val Ser Ile
225                 230                 235                 240

Ala Val Gln Lys Thr Thr Ser His Ile Asn Ala Ile Asn Ser Gln Ala
                245                 250                 255

Thr Asn Glu Leu Ser Cys Glu Ile Thr His Pro Ser His Thr Ser Gly
            260                 265                 270

Gln Ile Asn Ser Ala Gln Thr Ser Asn Ser Glu Leu Pro Pro Lys Pro
        275                 280                 285

Ala Ala Val Val Ser Glu Ala Cys Asp Ala Asp Asp Ala Asp Asn Ala
    290                 295                 300

Ser Lys Leu Ala Ala Met Leu Asn Thr Cys Ser Phe Gln Lys Pro Glu
```

```
305                 310                 315                 320

Gln Leu Gln Gln Gln Lys Ser Val Phe Glu Ile Cys Pro Ser Pro Ala
                325                 330                 335

Glu Asn Asn Ile Gln Gly Thr Thr Lys Leu Ala Ser Gly Glu Glu Phe
            340                 345                 350

Cys Ser Gly Ser Ser Ser Asn Leu Gln Ala Pro Gly Gly Ser Ser Glu
        355                 360                 365

Arg Tyr Leu Lys Gln Asn Glu Met Asn Gly Ala Tyr Phe Lys Gln Ser
    370                 375                 380

Ser Val Phe Thr Lys Asp Ser Phe Ser Ala Thr Thr Thr Pro Pro Pro
385                 390                 395                 400

Pro Ser Gln Leu Leu Leu Ser Pro Pro Pro Pro Leu Pro Gln Val Pro
                405                 410                 415

Gln Leu Pro Ser Glu Gly Lys Ser Thr Leu Asn Gly Gly Val Leu Glu
            420                 425                 430

Glu His His His Tyr Pro Asn Gln Ser Asn Thr Thr Leu Leu Arg Glu
        435                 440                 445

Val Lys Ile Glu Gly Lys Pro Glu Ala Pro Pro Ser Gln Ser Pro Asn
    450                 455                 460

Pro Ser Thr His Val Cys Ser Pro Ser Pro Met Leu Ser Glu Arg Pro
465                 470                 475                 480

Gln Asn Asn Cys Val Asn Arg Asn Asp Ile Gln Thr Ala Gly Thr Met
                485                 490                 495

Thr Val Pro Leu Cys Ser Glu Lys Thr Arg Pro Met Ser Glu His Leu
            500                 505                 510

Lys His Asn Pro Pro Ile Phe Gly Ser Ser Gly Glu Leu Gln Asp Asn
        515                 520                 525

Cys Gln Gln Leu Met Arg Asn Lys Glu Gln Glu Ile Leu Lys Gly Arg
    530                 535                 540

Asp Lys Glu Gln Thr Arg Asp Leu Val Pro Pro Thr Gln His Tyr Leu
545                 550                 555                 560

Lys Pro Gly Trp Ile Glu Leu Lys Ala Pro Arg Phe His Gln Ala Glu
                565                 570                 575

Ser His Leu Lys Arg Asn Glu Ala Ser Leu Pro Ser Ile Leu Gln Tyr
            580                 585                 590

Gln Pro Asn Leu Ser Asn Gln Met Thr Ser Lys Gln Tyr Thr Gly Asn
        595                 600                 605

Ser Asn Met Pro Gly Gly Leu Pro Arg Gln Ala Tyr Thr Gln Lys Thr
    610                 615                 620

Thr Gln Leu Glu His Lys Ser Gln Met Tyr Gln Val Glu Met Asn Gln
625                 630                 635                 640

Gly Gln Ser Gln Gly Thr Val Asp Gln His Leu Gln Phe Gln Lys Pro
                645                 650                 655

Ser His Gln Val His Phe Ser Lys Thr Asp His Leu Pro Lys Ala His
            660                 665                 670

Val Gln Ser Leu Cys Gly Thr Arg Phe His Phe Gln Gln Arg Ala Asp
        675                 680                 685

Ser Gln Thr Glu Lys Leu Met Ser Pro Val Leu Lys Gln His Leu Asn
    690                 695                 700

Gln Gln Ala Ser Glu Thr Glu Pro Phe Ser Asn Ser His Leu Leu Gln
705                 710                 715                 720

His Lys Pro His Lys Gln Ala Ala Gln Thr Gln Pro Ser Gln Ser Ser
                725                 730                 735
```

```
His Leu Pro Gln Asn Gln Gln Gln Gln Gln Lys Leu Gln Ile Lys Asn
            740                 745                 750

Lys Glu Glu Ile Leu Gln Thr Phe Pro His Pro Gln Ser Asn Asn Asp
        755                 760                 765

Gln Gln Arg Glu Gly Ser Phe Phe Gly Gln Thr Lys Val Glu Glu Cys
    770                 775                 780

Phe His Gly Glu Asn Gln Tyr Ser Lys Ser Ser Glu Phe Glu Thr His
785                 790                 795                 800

Asn Val Gln Met Gly Leu Glu Glu Val Gln Asn Ile Asn Arg Arg Asn
                805                 810                 815

Ser Pro Tyr Ser Gln Thr Met Lys Ser Ser Ala Cys Lys Ile Gln Val
            820                 825                 830

Ser Cys Ser Asn Asn Thr His Leu Val Ser Glu Asn Lys Glu Gln Thr
        835                 840                 845

Thr His Pro Glu Leu Phe Ala Gly Asn Lys Thr Gln Asn Leu His His
    850                 855                 860

Met Gln Tyr Phe Pro Asn Asn Val Ile Pro Lys Gln Asp Leu Leu His
865                 870                 875                 880

Arg Cys Phe Gln Glu Gln Glu Gln Lys Ser Gln Gln Ala Ser Val Leu
                885                 890                 895

Gln Gly Tyr Lys Asn Arg Asn Gln Asp Met Ser Gly Gln Gln Ala Ala
            900                 905                 910

Gln Leu Ala Gln Gln Arg Tyr Leu Ile His Asn His Ala Asn Val Phe
        915                 920                 925

Pro Val Pro Asp Gln Gly Gly Ser His Thr Gln Thr Pro Pro Gln Lys
    930                 935                 940

Asp Thr Gln Lys His Ala Ala Leu Arg Trp His Leu Leu Gln Lys Gln
945                 950                 955                 960

Glu Gln Gln Gln Thr Gln Gln Pro Gln Thr Glu Ser Cys His Ser Gln
                965                 970                 975

Met His Arg Pro Ile Lys Val Glu Pro Gly Cys Lys Pro His Ala Cys
            980                 985                 990

Met His Thr Ala Pro Pro Glu Asn  Lys Thr Trp Lys Lys  Val Thr Lys
        995                 1000                1005

Gln Glu  Asn Pro Pro Ala Ser  Cys Asp Asn Val Gln  Gln Lys Ser
    1010                1015                1020

Ile Ile  Glu Thr Met Glu Gln  His Leu Lys Gln Phe  His Ala Lys
    1025                1030                1035

Ser Leu  Phe Asp His Lys Ala  Leu Thr Leu Lys Ser  Gln Lys Gln
    1040                1045                1050

Val Lys  Val Glu Met Ser Gly  Pro Val Thr Val Leu  Thr Arg Gln
    1055                1060                1065

Thr Thr  Ala Ala Glu Leu Asp  Ser His Thr Pro Ala  Leu Glu Gln
    1070                1075                1080

Gln Thr  Thr Ser Ser Glu Lys  Thr Pro Thr Lys Arg  Thr Ala Ala
    1085                1090                1095

Ser Val  Leu Asn Asn Phe Ile  Glu Ser Pro Ser Lys  Leu Leu Asp
    1100                1105                1110

Thr Pro  Ile Lys Asn Leu Leu  Asp Thr Pro Val Lys  Thr Gln Tyr
    1115                1120                1125

Asp Phe  Pro Ser Cys Arg Cys  Val Gly Lys Cys Gln  Lys Cys Thr
    1130                1135                1140
```

```
Glu Thr His Gly Val Tyr Pro Glu Leu Ala Asn Leu Ser Ser Asp
    1145                1150                1155

Met Gly Phe Ser Phe Phe Phe
    1160                1165


<210> SEQ ID NO 41
<211> LENGTH: 4049
<212> TYPE: DNA
<213> ORGANISM: Artificial Sequence
<220> FEATURE:
<223> OTHER INFORMATION: Synthetic Polymer

<400> SEQUENCE: 41

agcgcgtacc actctggcgc tcccgaggcg gcctcttgtg cgatccaggg cgcacaaggc      60

tgggagagcg ccccggggcc cctgctatcc gcgccggagg ttggaagagg gtgggttgcc     120

gccgcccgag ggcgagagcg ccagaggagc gggaagaagg agcgctcgcc cgcccgcctg     180

cctcctcgct gcctccccgg cgttggctct ctggactcct aggcttgctg gctgctcctc     240

ccacccgcgc ccgcctcctc actcgccttt tcgttcgccg gggctgcttt ccaagccctg     300

cggtgcgccc gggcgagtgc ggggcgaggg gcccggggcc agcaccgagc agggggcggg     360

ggtccgggca gagcgcggcc ggccggggag gggccatgtc tggcgcgggc gcagcgggggc    420

ccgtctgcag caagtgaccg agcggcgcgg acggccgcct gccccctctg ccacctgggg     480

cggtgcgggc ccggagcccg gagcccgggt agcgcgtaga gccggcgcga tgcacgtgcg     540

ctcactgcga gctgcggcgc cgcacagctt cgtggcgctc tgggcacccc tgttcctgct     600

gcgctccgcc ctggccgact tcagcctgga caacgaggtg cactcgagct tcatccaccg     660

gcgcctccgc agccaggagc ggcgggagat gcagcgcgag atcctctcca ttttgggctt     720

gccccaccgc ccgcgcccgc acctccaggg caagcacaac tcggcaccca tgttcatgct     780

ggacctgtac aacgccatgg cggtggagga gggcggcggg cccggcggcc agggcttctc     840

ctacccctac aaggccgtct tcagtaccca gggccccct ctggccagcc tgcaagatag     900

ccatttcctc accgacgccg acatggtcat gagcttcgtc aacctcgtgg aacatgacaa     960

ggaattcttc cacccacgct accaccatcg agagttccgg tttgatcttt ccaagatccc    1020

agaaggggaa gctgtcacgg cagccgaatt ccggatctac aaggactaca tccgggaacg    1080

cttcgacaat gagacgttcc ggatcagcgt ttatcaggtg ctccaggagc acttgggcag    1140

ggaatcggat ctcttcctgc tcgacagccg taccctctgg gcctcggagg agggctggct    1200

ggtgtttgac atcacagcca ccagcaacca ctgggtggtc aatccgcggc acaacctggg    1260

cctgcagctc tcggtggaga cgctggatgg gcagagcatc aaccccaagt tggcgggcct    1320

gattgggcgg cacgggcccc agaacaagca gcccttcatg gtggctttct tcaaggccac    1380

ggaggtccac ttccgcagca tccggtccac ggggagcaaa cagcgcagcc agaaccgctc    1440

caagacgccc aagaaccagg aagccctgcg gatggccaac gtggcagaga acagcagcag    1500

cgaccagagg caggcctgta agaagcacga gctgtatgtc agcttccgag acctgggctg    1560

gcaggactgg atcatcgcgc ctgaaggcta cgccgcctac tactgtgagg gggagtgtgc    1620

cttccctctg aactcctaca tgaacgccac caaccacgcc atcgtgcaga cgctggtcca    1680

cttcatcaac ccggaaacgg tgcccaagcc ctgctgtgcg cccacgcagc tcaatgccat    1740

ctccgtcctc tacttcgatg acagctccaa cgtcatcctg aagaaataca gaaacatggt    1800

ggtccgggcc tgtggctgcc actagctcct ccgagaattc agaccctttg gggccaagtt    1860

tttctggatc ctccattgct cgccttggcc aggaaccagc agaccaactg ccttttgtga    1920
```

```
gaccttcccc tccctatccc caactttaaa ggtgtgagag tattaggaaa catgagcagc   1980
atatggcttt tgatcagttt ttcagtggca gcatccaatg aacaagatcc tacaagctgt   2040
gcaggcaaaa cctagcagga aaaaaaaaca acgcataaag aaaaatggcc gggccaggtc   2100
attggctggg aagtctcagc catgcacgga ctcgtttcca gaggtaatta tgagcgccta   2160
ccagccaggc cacccagccg tgggaggaag ggggcgtggc aaggggtggg cacattggtg   2220
tctgtgcgaa aggaaaattg acccggaagt tcctgtaata aatgtcacaa taaaacgaat   2280
gaatgaaaat ggttaggacg ttacagatat attttcctaa acaatttatc cccatttctc   2340
ggtttatcct gatgcgtaaa cagaagctgt gtcaagtgga gggcggggag gtccctctcc   2400
attccctaca gttttcatcc tgaggcttgc agaggcccag tgtttaccga ggtttgccca   2460
aatccaagat ctagtgggag gggaaagagc aaatgtctgc tccgaggagg gcggtgtgtt   2520
gatctttgga ggaaaaatat gttctgttgt tcagctggat ttgccgtggc agaaatgaaa   2580
ctaggtgtgt gaaatacccg cagacatttg ggattggctt ttcacctcgc cccagtggta   2640
gtaaatccat gtgaaattgc agaggggaca aggacagcaa gtaggatgga acttgcaact   2700
caaccctgtt gttaagaagc accaatgggc cgggcacagt agctcccacc tgtaatccca   2760
gcactttggg aggctgaggt gggcggatca tttgaggtca ggagttcgag accagcctgg   2820
ccaacatggt gaaaccccat ctctactaaa aatacaaaaa ttagccgggc atggtggcac   2880
gcacctgtaa tcccagctac tctggaggct gaggcaggag aattgcttga accccagagg   2940
tggaggttgc agtgagccaa gatcgtccca ctgcactcca gcttgggtga caaaacaaga   3000
ctccatctca aaagaaaaaa aaaacagcac caatgaagcc tagttctcca cgggagtggg   3060
gtgagcagga gcactgcaca tcgccccagt ggaccctctg gtctttgtct gcagtggcat   3120
tccaaggctg ggccctggca agggcacccg tggctgtctc ttcatttgca gaccctgatc   3180
agaagtctct gcaaacaaat ttgctccttg aattaagggg gagatggcat aataggaggt   3240
ctgatgggtg caggatgtgc tggacttaca ttgcaaatag aagccttgtt gagggtgaca   3300
tcctaaccaa gtgtcccgat ttggaggtgg catttctgac gtggctcttg gtgtaagcct   3360
gccttgcctt ggctggtgag tcccataaat agtatgcact cagcctccgg ccacaaacac   3420
aaggcctagg ggagggctag actgtctgca aacgttttct gcatctgtaa agaaaacaag   3480
gtgatcgaaa actgtggcca tgtggaaccc ggtcttgtgg gggactgttt ctccatcttg   3540
actcagacag ttcctggaaa caccggggct ctgtttttat tttctttgat gtttttcttc   3600
tttagtagct tgggctgcag cctccactct ctagtcactg gggaggagta ttttttgtta   3660
tgtttggttt catttgctgg cagagctggg gctttttgtg tgatccctct tggtgtgagt   3720
tttctgaccc aaccagcctc tggttagcat catttgtaca tttaaacctg taaatagttg   3780
ttacaaagca aagagattat ttatttccat ccaaagctct tttgaacacc ccccccccctt   3840
taatccctcg ttcaggacga tgagcttgct ttccttcaac ctgtttgttt tcttatttaa   3900
gactatttat taatggttgg accaatgtac tcacagctgt tgcgtcgagc agtccttagt   3960
gaaaattctg tataaataga caaaatgaaa agggtttgac cttgcaataa aaggagacgt   4020
ttggttctgg caaaaaaaaa aaaaaaaaa                                     4049
```

<210> SEQ ID NO 42
<211> LENGTH: 431
<212> TYPE: PRT
<213> ORGANISM: Artificial Sequence
<220> FEATURE:

<223> OTHER INFORMATION: Synthetic Polymer

<400> SEQUENCE: 42

```
Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400
```

```
Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430
```

<210> SEQ ID NO 43
<211> LENGTH: 4110
<212> TYPE: DNA
<213> ORGANISM: Artificial Sequence
<220> FEATURE:
<223> OTHER INFORMATION: Synthetic Polymer

<400> SEQUENCE: 43

```
gtcgagcggg agcagaggag gcgagggagg agggccagag aggcagttgg aagatggcgg     60
acgaggcggc cctcgccctt cagcccggcg gctccccctc ggcggcgggg gccgacaggg    120
aggccgcgtc gtcccccgcc ggggagccgc tccgcaagag gccgcggaga gatggtcccg    180
gcctcgagcg gagcccgggc gagcccggtg gggcggcccc agagcgtgag gtgccggcgg    240
cggccagggg ctgcccgggt gcggcggcgg cggcgctgtg gcgggaggcg gaggcagagg    300
cggcggcggc aggcggggag caagaggccc aggcgactgc ggcggctggg gaaggagaca    360
atgggccggg cctgcagggc ccatctcggg agccaccgct ggccgacaac ttgtacgacg    420
aagacgacga cgacgagggc gaggaggagg aagaggcggc ggcggcggcg attgggtacc    480
gagataacct tctgttcggt gatgaaatta tcactaatgg ttttcattcc tgtgaaagtg    540
atgaggagga tagagcctca catgcaagct ctagtgactg gactccaagg ccacggatag    600
gtccatatac ttttgttcag caacatctta tgattggcac agatcctcga acaattctta    660
aagatttatt gccggaaaca atacctccac ctgagttgga tgatatgaca ctgtggcaga    720
ttgttattaa tatcctttca gaaccaccaa aaaggaaaaa aagaaaagat attaatacaa    780
ttgaagatgc tgtgaaatta ctgcaagagt gcaaaaaaat tatagttcta actggagctg    840
gggtgtctgt ttcatgtgga atacctgact tcaggtcaag ggatggtatt tatgctcgcc    900
ttgctgtaga cttcccagat cttccagatc ctcaagcgat gtttgatatt gaatatttca    960
gaaaagatcc aagaccattc ttcaagtttg caaaggaaat atatcctgga caattccagc   1020
catctctctg tcacaaattc atagccttgt cagataagga aggaaaacta cttcgcaact   1080
atacccagaa catagacacg ctggaacagg ttgcgggaat ccaaaggata attcagtgtc   1140
atggttcctt tgcaacagca tcttgcctga tttgtaaata caaagttgac tgtgaagctg   1200
tacgaggaga tatttttaat caggtagttc ctcgatgtcc taggtgccca gctgatgaac   1260
cgcttgctat catgaaacca gagattgtgt tttttggtga aaatttacca gaacagtttc   1320
atagagccat gaagtatgac aaagatgaag ttgacctcct cattgttatt gggtcttccc   1380
tcaaagtaag accagtagca ctaattccaa gttccatacc ccatgaagtg cctcagatat   1440
taattaatag agaacctttg cctcatctgc attttgatgt agagcttctt ggagactgtg   1500
atgtcataat taatgaattg tgtcataggt taggtggtga atatgccaaa ctttgctgta   1560
accctgtaaa gctttcagaa attactgaaa aacctccacg aacacaaaaa gaattggctt   1620
atttgtcaga gttgccaccc acacctcttc atgtttcaga agactcaagt tcaccagaaa   1680
gaacttcacc accagattct tcagtgattg tcacactttt agaccaagca gctaagagta   1740
atgatgattt agatgtgtct gaatcaaaag gttgtatgga agaaaaacca caggaagtac   1800
aaacttctag gaatgttgaa agtattgctg aacagatgga aaatccggat ttgaagaatg   1860
ttggttctag tactggggag aaaaatgaaa gaacttcagt ggctggaaca gtgagaaaat   1920
```

```
gctggcctaa tagagtggca aaggagcaga ttagtaggcg gcttgatggt aatcagtatc   1980
tgtttttgcc accaaatcgt tacattttcc atggcgctga ggtatattca gactctgaag   2040
atgacgtctt atcctctagt tcttgtggca gtaacagtga tagtgggaca tgccagagtc   2100
caagtttaga agaacccatg gaggatgaaa gtgaaattga agaattctac aatggcttag   2160
aagatgagcc tgatgttcca gagagagctg gaggagctgg atttgggact gatggagatg   2220
atcaagaggc aattaatgaa gctatatctg tgaaacagga agtaacagac atgaactatc   2280
catcaaacaa atcatagtgt aataattgtg caggtacagg aattgttcca ccagcattag   2340
gaactttagc atgtcaaaat gaatgtttac ttgtgaactc gatagagcaa ggaaaccaga   2400
aaggtgtaat atttataggt tggtaaaata gattgttttt catggataat ttttaacttc   2460
attatttctg tacttgtaca aactcaacac taactttttt ttttttaaaa aaaaaaaggt   2520
actaagtatc ttcaatcagc tgttggtcaa gactaacttt cttttaaagg ttcatttgta   2580
tgataaattc atatgtgtat atataatttt ttttgttttg tctagtgagt ttcaacattt   2640
ttaaagtttt caaaaagcca tcggaatgtt aaattaatgt aaagggaaca gctaatctag   2700
accaaagaat ggtattttca cttttctttg taacattgaa tggtttgaag tactcaaaat   2760
ctgttacgct aaacttttga ttctttaaca caattatttt taaacactgg cattttccaa   2820
aactgtggca gctaactttt taaaatctca aatgacatgc agtgtgagta gaaggaagtc   2880
aacaatatgt ggggagagca ctcggttgtc tttactttta aaagtaatac ttggtgctaa   2940
gaatttcagg attattgtat ttacgttcaa atgaagatgg cttttgtact tcctgtggac   3000
atgtagtaat gtctatattg gctcataaaa ctaacctgaa aaacaaataa atgctttgga   3060
aatgtttcag ttgctttaga aacattagtg cctgcctgga tccccttagt tttgaaatat   3120
ttgccattgt tgtttaaata cctatcactg tggtagagct tgcattgatc ttttccacaa   3180
gtattaaact gccaaaatgt gaatatgcaa agcctttctg aatctataat aatggtactt   3240
ctactgggga gagtgtaata ttttggactg ctgttttcca ttaatgagga gagcaacagg   3300
cccctgatta tacagttcca aagtaataag atgttaattg taattcagcc agaaagtaca   3360
tgtctcccat tgggaggatt tggtgttaaa taccaaactg ctagccctag tattatggag   3420
atgaacatga tgatgtaact tgtaatagca gaatagttaa tgaatgaaac tagttcttat   3480
aatttatctt tatttaaaag cttagcctgc cttaaaacta gagatcaact ttctcagctg   3540
caaaagcttc tagtctttca agaagttcat actttatgaa attgcacagt aagcatttat   3600
ttttcagacc atttttgaac atcactccta aattaataaa gtattcctct gttgctttag   3660
tatttattac aataaaaagg gtttgaaata tagctgttct ttatgcataa aacacccagc   3720
taggaccatt actgccagag aaaaaaatcg tattgaatgg ccatttccct acttataaga   3780
tgtctcaatc tgaatttatt tggctacact aaagaatgca gtatatttag ttttccattt   3840
gcatgatgtt tgtgtgctat agatgatatt ttaaattgaa aagtttgttt taaattattt   3900
ttacagtgaa gactgttttc agctcttttt atattgtaca tagtctttta tgtaatttac   3960
tggcatatgt tttgtagact gtttaatgac tggatatctt ccttcaactt ttgaaataca   4020
aaaccagtgt tttttacttg tacactgttt taaagtctat taaaattgtc atttgacttt   4080
tttctgttaa cttaaaaaaa aaaaaaaaaa                                    4110
```

<210> SEQ ID NO 44
<211> LENGTH: 747
<212> TYPE: PRT

```
<213> ORGANISM: Artificial Sequence
<220> FEATURE:
<223> OTHER INFORMATION: Synthetic Polymer

<400> SEQUENCE: 44

Met Ala Asp Glu Ala Ala Leu Ala Leu Gln Pro Gly Gly Ser Pro Ser
1               5                   10                  15

Ala Ala Gly Ala Asp Arg Glu Ala Ala Ser Ser Pro Ala Gly Glu Pro
            20                  25                  30

Leu Arg Lys Arg Pro Arg Arg Asp Gly Pro Gly Leu Glu Arg Ser Pro
        35                  40                  45

Gly Glu Pro Gly Gly Ala Ala Pro Glu Arg Glu Val Pro Ala Ala Ala
    50                  55                  60

Arg Gly Cys Pro Gly Ala Ala Ala Ala Ala Leu Trp Arg Glu Ala Glu
65                  70                  75                  80

Ala Glu Ala Ala Ala Ala Gly Gly Glu Gln Glu Ala Gln Ala Thr Ala
                85                  90                  95

Ala Ala Gly Glu Gly Asp Asn Gly Pro Gly Leu Gln Gly Pro Ser Arg
            100                 105                 110

Glu Pro Pro Leu Ala Asp Asn Leu Tyr Asp Glu Asp Asp Asp Asp Glu
        115                 120                 125

Gly Glu Glu Glu Glu Glu Ala Ala Ala Ala Ala Ile Gly Tyr Arg Asp
    130                 135                 140

Asn Leu Leu Phe Gly Asp Glu Ile Ile Thr Asn Gly Phe His Ser Cys
145                 150                 155                 160

Glu Ser Asp Glu Glu Asp Arg Ala Ser His Ala Ser Ser Ser Asp Trp
                165                 170                 175

Thr Pro Arg Pro Arg Ile Gly Pro Tyr Thr Phe Val Gln Gln His Leu
            180                 185                 190

Met Ile Gly Thr Asp Pro Arg Thr Ile Leu Lys Asp Leu Leu Pro Glu
        195                 200                 205

Thr Ile Pro Pro Pro Glu Leu Asp Asp Met Thr Leu Trp Gln Ile Val
    210                 215                 220

Ile Asn Ile Leu Ser Glu Pro Pro Lys Arg Lys Lys Arg Lys Asp Ile
225                 230                 235                 240

Asn Thr Ile Glu Asp Ala Val Lys Leu Leu Gln Glu Cys Lys Lys Ile
                245                 250                 255

Ile Val Leu Thr Gly Ala Gly Val Ser Val Ser Cys Gly Ile Pro Asp
            260                 265                 270

Phe Arg Ser Arg Asp Gly Ile Tyr Ala Arg Leu Ala Val Asp Phe Pro
        275                 280                 285

Asp Leu Pro Asp Pro Gln Ala Met Phe Asp Ile Glu Tyr Phe Arg Lys
    290                 295                 300

Asp Pro Arg Pro Phe Phe Lys Phe Ala Lys Glu Ile Tyr Pro Gly Gln
305                 310                 315                 320

Phe Gln Pro Ser Leu Cys His Lys Phe Ile Ala Leu Ser Asp Lys Glu
                325                 330                 335

Gly Lys Leu Leu Arg Asn Tyr Thr Gln Asn Ile Asp Thr Leu Glu Gln
            340                 345                 350

Val Ala Gly Ile Gln Arg Ile Ile Gln Cys His Gly Ser Phe Ala Thr
        355                 360                 365

Ala Ser Cys Leu Ile Cys Lys Tyr Lys Val Asp Cys Glu Ala Val Arg
    370                 375                 380

Gly Asp Ile Phe Asn Gln Val Val Pro Arg Cys Pro Arg Cys Pro Ala
```

```
385                 390                 395                 400

Asp Glu Pro Leu Ala Ile Met Lys Pro Glu Ile Val Phe Phe Gly Glu
                405                 410                 415

Asn Leu Pro Glu Gln Phe His Arg Ala Met Lys Tyr Asp Lys Asp Glu
            420                 425                 430

Val Asp Leu Leu Ile Val Ile Gly Ser Ser Leu Lys Val Arg Pro Val
        435                 440                 445

Ala Leu Ile Pro Ser Ser Ile Pro His Glu Val Pro Gln Ile Leu Ile
    450                 455                 460

Asn Arg Glu Pro Leu Pro His Leu His Phe Asp Val Glu Leu Leu Gly
465                 470                 475                 480

Asp Cys Asp Val Ile Ile Asn Glu Leu Cys His Arg Leu Gly Gly Glu
                485                 490                 495

Tyr Ala Lys Leu Cys Cys Asn Pro Val Lys Leu Ser Glu Ile Thr Glu
            500                 505                 510

Lys Pro Pro Arg Thr Gln Lys Glu Leu Ala Tyr Leu Ser Glu Leu Pro
        515                 520                 525

Pro Thr Pro Leu His Val Ser Glu Asp Ser Ser Ser Pro Glu Arg Thr
    530                 535                 540

Ser Pro Pro Asp Ser Ser Val Ile Val Thr Leu Leu Asp Gln Ala Ala
545                 550                 555                 560

Lys Ser Asn Asp Asp Leu Asp Val Ser Glu Ser Lys Gly Cys Met Glu
                565                 570                 575

Glu Lys Pro Gln Glu Val Gln Thr Ser Arg Asn Val Glu Ser Ile Ala
            580                 585                 590

Glu Gln Met Glu Asn Pro Asp Leu Lys Asn Val Gly Ser Ser Thr Gly
        595                 600                 605

Glu Lys Asn Glu Arg Thr Ser Val Ala Gly Thr Val Arg Lys Cys Trp
    610                 615                 620

Pro Asn Arg Val Ala Lys Glu Gln Ile Ser Arg Arg Leu Asp Gly Asn
625                 630                 635                 640

Gln Tyr Leu Phe Leu Pro Pro Asn Arg Tyr Ile Phe His Gly Ala Glu
                645                 650                 655

Val Tyr Ser Asp Ser Glu Asp Asp Val Leu Ser Ser Ser Ser Cys Gly
            660                 665                 670

Ser Asn Ser Asp Ser Gly Thr Cys Gln Ser Pro Ser Leu Glu Glu Pro
        675                 680                 685

Met Glu Asp Glu Ser Glu Ile Glu Glu Phe Tyr Asn Gly Leu Glu Asp
    690                 695                 700

Glu Pro Asp Val Pro Glu Arg Ala Gly Gly Ala Gly Phe Gly Thr Asp
705                 710                 715                 720

Gly Asp Asp Gln Glu Ala Ile Asn Glu Ala Ile Ser Val Lys Gln Glu
                725                 730                 735

Val Thr Asp Met Asn Tyr Pro Ser Asn Lys Ser
            740                 745
```

<210> SEQ ID NO 45
<211> LENGTH: 3604
<212> TYPE: DNA
<213> ORGANISM: Artificial Sequence
<220> FEATURE:
<223> OTHER INFORMATION: Synthetic Polymer

<400> SEQUENCE: 45

```
gcatctcctc ctccctctcc ccgggctcct actggcctga ggttgagggc ggctgggggc      60
```

```
tcggggcagg ctccgcggcg ttcccctccc caccccggcc ctccgttcag ccgcgctcct    120
ccggggctgc ggttcctact gcgcgagctg ccagtggatt cgctcttttc ctccgtccgt    180
ggcccgcctg ggcggccttg ttctttccgc agcagccaga taaccttctg ttcggtgatg    240
aaattatcac taatggtttt cattcctgtg aaagtgatga ggaggataga gcctcacatg    300
caagctctag tgactggact ccaaggccac ggataggtgt ctgtttcatg tggaatacct    360
gacttcaggt caagggatgg tatttatgct cgccttgctg tagacttccc agatcttcca    420
gatcctcaag cgatgtttga tattgaatat ttcagaaaag atccaagacc attcttcaag    480
tttgcaaagg aaatatatcc tggacaattc cagccatctc tctgtcacaa attcatagcc    540
ttgtcagata aggaaggaaa actacttcgc aactataccc agaacataga cacgctggaa    600
caggttgcgg gaatccaaag gataattcag tgtcatggtt cctttgcaac agcatcttgc    660
ctgatttgta aatacaaagt tgactgtgaa gctgtacgag gagatatttt taatcaggta    720
gttcctcgat gtcctaggtg cccagctgat gaaccgcttg ctatcatgaa accagagatt    780
gtgtttttgg gtgaaaattt accagaacag tttcatagag ccatgaagta tgacaaagat    840
gaagttgacc tcctcattgt tattgggtct tccctcaaag taagaccagt agcactaatt    900
ccaagttcca taccccatga agtgcctcag atattaatta atagagaacc tttgcctcat    960
ctgcattttg atgtagagct tcttggagac tgtgatgtca taattaatga attgtgtcat   1020
aggttaggtg gtgaatatgc caaactttgc tgtaaccctg taaagctttc agaaattact   1080
gaaaaacctc cacgaacaca aaaagaattg gcttatttgt cagagttgcc acccacacct   1140
cttcatgttt cagaagactc aagttcacca gaaagaactt caccaccaga ttcttcagtg   1200
attgtcacac ttttagacca agcagctaag agtaatgatg atttagatgt gtctgaatca   1260
aaaggttgta tggaagaaaa accacaggaa gtacaaactt ctaggaatgt tgaaagtatt   1320
gctgaacaga tggaaaatcc ggatttgaag aatgttggtt ctagtactgg ggagaaaaat   1380
gaaagaactt cagtggctgg aacagtgaga aaatgctggc ctaatagagt ggcaaaggag   1440
cagattagta ggcggcttga tggtaatcag tatctgtttt tgccaccaaa tcgttacatt   1500
ttccatggcg ctgaggtata ttcagactct gaagatgacg tcttatcctc tagttcttgt   1560
ggcagtaaca gtgatagtgg gacatgccag agtccaagtt tagaagaacc catggaggat   1620
gaaagtgaaa ttgaagaatt ctacaatggc ttagaagatg agcctgatgt tccagagaga   1680
gctggaggag ctggatttgg gactgatgga gatgatcaag aggcaattaa tgaagctata   1740
tctgtgaaac aggaagtaac agacatgaac tatccatcaa acaaatcata gtgtaataat   1800
tgtgcaggta caggaattgt tccaccagca ttaggaactt tagcatgtca aaatgaatgt   1860
ttacttgtga actcgataga gcaaggaaac cagaaaggtg taatatttat aggttggtaa   1920
aatagattgt ttttcatgga taatttttaa cttcattatt tctgtacttg tacaaactca   1980
acactaactt tttttttttt aaaaaaaaaa aggtactaag tatcttcaat cagctgttgg   2040
tcaagactaa ctttctttta aaggttcatt tgtatgataa attcatatgt gtatatataa   2100
tttttttttgt tttgtctagt gagtttcaac atttttaaag ttttcaaaaa gccatcggaa   2160
tgttaaatta atgtaaaggg aacagctaat ctagaccaaa gaatggtatt ttcacttttc   2220
tttgtaacat tgaatggttt gaagtactca aaatctgtta cgctaaactt ttgattcttt   2280
aacacaatta tttttaaaca ctggcatttt ccaaaactgt ggcagctaac tttttaaaat   2340
ctcaaatgac atgcagtgtg agtagaagga agtcaacaat atgtggggag agcactcggt   2400
```

```
tgtctttact tttaaaagta atacttggtg ctaagaattt caggattatt gtatttacgt   2460
tcaaatgaag atggcttttg tacttcctgt ggacatgtag taatgtctat attggctcat   2520
aaaactaacc tgaaaaacaa ataaatgctt tggaaatgtt tcagttgctt tagaaacatt   2580
agtgcctgcc tggatcccct tagttttgaa atatttgcca ttgttgttta aatacctatc   2640
actgtggtag agcttgcatt gatcttttcc acaagtatta aactgccaaa atgtgaatat   2700
gcaaagcctt tctgaatcta taataatggt acttctactg ggagagtgt aatattttgg    2760
actgctgttt tccattaatg aggagagcaa caggcccctg attatacagt tccaaagtaa   2820
taagatgtta attgtaattc agccagaaag tacatgtctc ccattgggag gatttggtgt   2880
taaataccaa actgctagcc ctagtattat ggagatgaac atgatgatgt aacttgtaat   2940
agcagaatag ttaatgaatg aaactagttc ttataattta tctttattta aaagcttagc   3000
ctgccttaaa actagagatc aactttctca gctgcaaaag cttctagtct ttcaagaagt   3060
tcatacttta tgaaattgca cagtaagcat ttatttttca gaccattttt gaacatcact   3120
cctaaattaa taaagtattc ctctgttgct ttagtattta ttacaataaa aagggtttga   3180
aatatagctg ttctttatgc ataaaacacc cagctaggac cattactgcc agagaaaaaa   3240
atcgtattga atggccattt ccctacttat aagatgtctc aatctgaatt tatttggcta   3300
cactaaagaa tgcagtatat ttagttttcc atttgcatga tgtttgtgtg ctatagatga   3360
tattttaaat tgaaaagttt gttttaaatt atttttacag tgaagactgt tttcagctct   3420
ttttatattg tacatagtct tttatgtaat ttactggcat atgttttgta gactgtttaa   3480
tgactggata tcttccttca acttttgaaa tacaaaacca gtgtttttta cttgtacact   3540
gttttaaagt ctattaaaat tgtcatttga ctttttctg ttaacttaaa aaaaaaaaaa    3600
aaaa                                                                3604
```

<210> SEQ ID NO 46
<211> LENGTH: 452
<212> TYPE: PRT
<213> ORGANISM: Artificial Sequence
<220> FEATURE:
<223> OTHER INFORMATION: Synthetic Polymer

<400> SEQUENCE: 46

```
Met Phe Asp Ile Glu Tyr Phe Arg Lys Asp Pro Arg Pro Phe Phe Lys
1               5                   10                  15

Phe Ala Lys Glu Ile Tyr Pro Gly Gln Phe Gln Pro Ser Leu Cys His
            20                  25                  30

Lys Phe Ile Ala Leu Ser Asp Lys Glu Gly Lys Leu Leu Arg Asn Tyr
        35                  40                  45

Thr Gln Asn Ile Asp Thr Leu Glu Gln Val Ala Gly Ile Gln Arg Ile
    50                  55                  60

Ile Gln Cys His Gly Ser Phe Ala Thr Ala Ser Cys Leu Ile Cys Lys
65                  70                  75                  80

Tyr Lys Val Asp Cys Glu Ala Val Arg Gly Asp Ile Phe Asn Gln Val
                85                  90                  95

Val Pro Arg Cys Pro Arg Cys Pro Ala Asp Glu Pro Leu Ala Ile Met
            100                 105                 110

Lys Pro Glu Ile Val Phe Phe Gly Glu Asn Leu Pro Glu Gln Phe His
        115                 120                 125

Arg Ala Met Lys Tyr Asp Lys Asp Glu Val Asp Leu Leu Ile Val Ile
    130                 135                 140
```

```
Gly Ser Ser Leu Lys Val Arg Pro Val Ala Leu Ile Pro Ser Ser Ile
145                 150                 155                 160

Pro His Glu Val Pro Gln Ile Leu Ile Asn Arg Glu Pro Leu Pro His
                165                 170                 175

Leu His Phe Asp Val Glu Leu Leu Gly Asp Cys Asp Val Ile Ile Asn
            180                 185                 190

Glu Leu Cys His Arg Leu Gly Gly Glu Tyr Ala Lys Leu Cys Cys Asn
        195                 200                 205

Pro Val Lys Leu Ser Glu Ile Thr Glu Lys Pro Pro Arg Thr Gln Lys
    210                 215                 220

Glu Leu Ala Tyr Leu Ser Glu Leu Pro Pro Thr Pro Leu His Val Ser
225                 230                 235                 240

Glu Asp Ser Ser Ser Pro Glu Arg Thr Ser Pro Pro Asp Ser Ser Val
                245                 250                 255

Ile Val Thr Leu Leu Asp Gln Ala Ala Lys Ser Asn Asp Asp Leu Asp
            260                 265                 270

Val Ser Glu Ser Lys Gly Cys Met Glu Glu Lys Pro Gln Glu Val Gln
        275                 280                 285

Thr Ser Arg Asn Val Glu Ser Ile Ala Glu Gln Met Glu Asn Pro Asp
    290                 295                 300

Leu Lys Asn Val Gly Ser Ser Thr Gly Glu Lys Asn Glu Arg Thr Ser
305                 310                 315                 320

Val Ala Gly Thr Val Arg Lys Cys Trp Pro Asn Arg Val Ala Lys Glu
                325                 330                 335

Gln Ile Ser Arg Arg Leu Asp Gly Asn Gln Tyr Leu Phe Leu Pro Pro
            340                 345                 350

Asn Arg Tyr Ile Phe His Gly Ala Glu Val Tyr Ser Asp Ser Glu Asp
        355                 360                 365

Asp Val Leu Ser Ser Ser Ser Cys Gly Ser Asn Ser Asp Ser Gly Thr
    370                 375                 380

Cys Gln Ser Pro Ser Leu Glu Glu Pro Met Glu Asp Glu Ser Glu Ile
385                 390                 395                 400

Glu Glu Phe Tyr Asn Gly Leu Glu Asp Glu Pro Asp Val Pro Glu Arg
                405                 410                 415

Ala Gly Gly Ala Gly Phe Gly Thr Asp Gly Asp Asp Gln Glu Ala Ile
            420                 425                 430

Asn Glu Ala Ile Ser Val Lys Gln Glu Val Thr Asp Met Asn Tyr Pro
        435                 440                 445

Ser Asn Lys Ser
    450
```

<210> SEQ ID NO 47
<211> LENGTH: 3393
<212> TYPE: DNA
<213> ORGANISM: Artificial Sequence
<220> FEATURE:
<223> OTHER INFORMATION: Synthetic Polymer

<400> SEQUENCE: 47

```
gtgtctgttt catgtggaat acctgacttc aggtcaaggg atggtattta tgctcgcctt     60

gctgtagact tcccagatct tccagatcct caagcgatgt ttgatattga atatttcaga    120

aaagatccaa gaccattctt caagtttgca aagaagaaac agcattgaag cattatttgg    180

ggggaaaaac acacacacaa aatccagcaa ctcagcattc atgagcaact ctatactata    240

ccagtatgtg cctgtgcagt ggaaggaaaa caattttgga aatatatcct ggacaattcc    300
```

```
agccatctct ctgtcacaaa ttcatagcct tgtcagataa ggaaggaaaa ctacttcgca    360
actataccca gaacatagac acgctggaac aggttgcggg aatccaaagg ataattcagt    420
gtcatggttc ctttgcaaca gcatcttgcc tgatttgtaa atacaaagtt gactgtgaag    480
ctgtacgagg agatattttt aatcaggtag ttcctcgatg tcctaggtgc ccagctgatg    540
aaccgcttgc tatcatgaaa ccagagattg tgttttttgg tgaaaattta ccagaacagt    600
ttcatagagc catgaagtat gacaaagatg aagttgacct cctcattgtt attgggtctt    660
ccctcaaagt aagaccagta gcactaattc caagttccat accccatgaa gtgcctcaga    720
tattaattaa tagagaacct ttgcctcatc tgcattttga tgtagagctt cttggagact    780
gtgatgtcat aattaatgaa ttgtgtcata ggttaggtgg tgaatatgcc aaactttgct    840
gtaaccctgt aaagctttca gaaattactg aaaaacctcc acgaacacaa aaagaattgg    900
cttatttgtc agagttgcca cccacacctc ttcatgtttc agaagactca agttcaccag    960
aaagaacttc accaccagat tcttcagtga ttgtcacact tttagaccaa gcagctaaga   1020
gtaatgatga tttagatgtg tctgaatcaa aaggttgtat ggaagaaaaa ccacaggaag   1080
tacaaacttc taggaatgtt gaaagtattg ctgaacagat ggaaaatccg gatttgaaga   1140
atgttggttc tagtactggg gagaaaaatg aaagaacttc agtggctgga acagtgagaa   1200
aatgctggcc taatagagtg gcaaaggagc agattagtag gcggcttgat ggtaatcagt   1260
atctgttttt gccaccaaat cgttacattt tccatggcgc tgaggtatat tcagactctg   1320
aagatgacgt cttatcctct agttcttgtg gcagtaacag tgatagtggg acatgccaga   1380
gtccaagttt agaagaaccc atggaggatg aaagtgaaat tgaagaattc tacaatggct   1440
tagaagatga gcctgatgtt ccagagagag ctggaggagc tggatttggg actgatggag   1500
atgatcaaga ggcaattaat gaagctatat ctgtgaaaca ggaagtaaca gacatgaact   1560
atccatcaaa caaatcatag tgtaataatt gtgcaggtac aggaattgtt ccaccagcat   1620
taggaacttt agcatgtcaa aatgaatgtt tacttgtgaa ctcgatagag caaggaaacc   1680
agaaaggtgt aatatttata ggttggtaaa atagattgtt tttcatggat aatttttaac   1740
ttcattattt ctgtacttgt acaaactcaa cactaacttt ttttttttta aaaaaaaaaa   1800
ggtactaagt atcttcaatc agctgttggt caagactaac tttcttttaa aggttcattt   1860
gtatgataaa ttcatatgtg tatatataat tttttttgtt ttgtctagtg agtttcaaca   1920
tttttaaagt tttcaaaaag ccatcggaat gttaaattaa tgtaaaggga acagctaatc   1980
tagaccaaag aatggtattt tcacttttct ttgtaacatt gaatggtttg aagtactcaa   2040
aatctgttac gctaaacttt tgattcttta acacaattat ttttaaacac tggcattttc   2100
caaaactgtg gcagctaact tttaaaaatc tcaaatgaca tgcagtgtga gtagaaggaa   2160
gtcaacaata tgtggggaga gcactcggtt gtctttactt ttaaaagtaa tacttggtgc   2220
taagaatttc aggattattg tatttacgtt caaatgaaga tggcttttgt acttcctgtg   2280
gacatgtagt aatgtctata ttggctcata aaactaacct gaaaaacaaa taaatgcttt   2340
ggaaatgttt cagttgcttt agaaacatta gtgcctgcct ggatcccctt agttttgaaa   2400
tatttgccat tgttgtttaa atacctatca ctgtggtaga gcttgcattg atcttttcca   2460
caagtattaa actgccaaaa tgtgaatatg caaagccttt ctgaatctat aataatggta   2520
cttctactgg ggagagtgta atattttgga ctgctgtttt ccattaatga ggagagcaac   2580
aggcccctga ttatacagtt ccaaagtaat aagatgttaa ttgtaattca gccagaaagt   2640
```

```
acatgtctcc cattgggagg atttggtgtt aaataccaaa ctgctagccc tagtattatg   2700

gagatgaaca tgatgatgta acttgtaata gcagaatagt taatgaatga aactagttct   2760

tataatttat ctttatttaa aagcttagcc tgccttaaaa ctagagatca actttctcag   2820

ctgcaaaagc ttctagtctt tcaagaagtt catactttat gaaattgcac agtaagcatt   2880

tatttttcag accattttg aacatcactc ctaaattaat aaagtattcc tctgttgctt   2940

tagtatttat tacaataaaa agggtttgaa atatagctgt tctttatgca taaaacaccc   3000

agctaggacc attactgcca gagaaaaaaa tcgtattgaa tggccatttc cctacttata   3060

agatgtctca atctgaattt atttggctac actaaagaat gcagtatatt tagttttcca   3120

tttgcatgat gtttgtgtgc tatagatgat attttaaatt gaaaagtttg ttttaaatta   3180

tttttacagt gaagactgtt ttcagctctt tttatattgt acatagtctt ttatgtaatt   3240

tactggcata tgttttgtag actgtttaat gactggatat cttccttcaa cttttgaaat   3300

acaaaaccag tgttttttac ttgtacactg ttttaaagtc tattaaaatt gtcatttgac   3360

tttttctgt taacttaaaa aaaaaaaaaa aaa                                 3393
```

```
<210> SEQ ID NO 48
<211> LENGTH: 444
<212> TYPE: PRT
<213> ORGANISM: Artificial Sequence
<220> FEATURE:
<223> OTHER INFORMATION: Synthetic Polymer

<400> SEQUENCE: 48

Met Cys Leu Cys Ser Gly Arg Lys Thr Ile Leu Glu Ile Tyr Pro Gly
1               5                   10                  15

Gln Phe Gln Pro Ser Leu Cys His Lys Phe Ile Ala Leu Ser Asp Lys
            20                  25                  30

Glu Gly Lys Leu Leu Arg Asn Tyr Thr Gln Asn Ile Asp Thr Leu Glu
        35                  40                  45

Gln Val Ala Gly Ile Gln Arg Ile Ile Gln Cys His Gly Ser Phe Ala
    50                  55                  60

Thr Ala Ser Cys Leu Ile Cys Lys Tyr Lys Val Asp Cys Glu Ala Val
65                  70                  75                  80

Arg Gly Asp Ile Phe Asn Gln Val Val Pro Arg Cys Pro Arg Cys Pro
                85                  90                  95

Ala Asp Glu Pro Leu Ala Ile Met Lys Pro Glu Ile Val Phe Phe Gly
            100                 105                 110

Glu Asn Leu Pro Glu Gln Phe His Arg Ala Met Lys Tyr Asp Lys Asp
        115                 120                 125

Glu Val Asp Leu Leu Ile Val Ile Gly Ser Ser Leu Lys Val Arg Pro
    130                 135                 140

Val Ala Leu Ile Pro Ser Ser Ile Pro His Glu Val Pro Gln Ile Leu
145                 150                 155                 160

Ile Asn Arg Glu Pro Leu Pro His Leu His Phe Asp Val Glu Leu Leu
                165                 170                 175

Gly Asp Cys Asp Val Ile Ile Asn Glu Leu Cys His Arg Leu Gly Gly
            180                 185                 190

Glu Tyr Ala Lys Leu Cys Cys Asn Pro Val Lys Leu Ser Glu Ile Thr
        195                 200                 205

Glu Lys Pro Pro Arg Thr Gln Lys Glu Leu Ala Tyr Leu Ser Glu Leu
    210                 215                 220

Pro Pro Thr Pro Leu His Val Ser Glu Asp Ser Ser Ser Pro Glu Arg
```

```
225                 230                 235                 240

Thr Ser Pro Pro Asp Ser Ser Val Ile Val Thr Leu Leu Asp Gln Ala
                245                 250                 255

Ala Lys Ser Asn Asp Asp Leu Asp Val Ser Glu Ser Lys Gly Cys Met
            260                 265                 270

Glu Glu Lys Pro Gln Glu Val Gln Thr Ser Arg Asn Val Glu Ser Ile
        275                 280                 285

Ala Glu Gln Met Glu Asn Pro Asp Leu Lys Asn Val Gly Ser Ser Thr
    290                 295                 300

Gly Glu Lys Asn Glu Arg Thr Ser Val Ala Gly Thr Val Arg Lys Cys
305                 310                 315                 320

Trp Pro Asn Arg Val Ala Lys Glu Gln Ile Ser Arg Arg Leu Asp Gly
                325                 330                 335

Asn Gln Tyr Leu Phe Leu Pro Pro Asn Arg Tyr Ile Phe His Gly Ala
            340                 345                 350

Glu Val Tyr Ser Asp Ser Glu Asp Asp Val Leu Ser Ser Ser Ser Cys
        355                 360                 365

Gly Ser Asn Ser Asp Ser Gly Thr Cys Gln Ser Pro Ser Leu Glu Glu
    370                 375                 380

Pro Met Glu Asp Glu Ser Glu Ile Glu Glu Phe Tyr Asn Gly Leu Glu
385                 390                 395                 400

Asp Glu Pro Asp Val Pro Glu Arg Ala Gly Gly Ala Gly Phe Gly Thr
                405                 410                 415

Asp Gly Asp Asp Gln Glu Ala Ile Asn Glu Ala Ile Ser Val Lys Gln
            420                 425                 430

Glu Val Thr Asp Met Asn Tyr Pro Ser Asn Lys Ser
        435                 440
```

<210> SEQ ID NO 49
<211> LENGTH: 6849
<212> TYPE: DNA
<213> ORGANISM: Artificial Sequence
<220> FEATURE:
<223> OTHER INFORMATION: Synthetic Polymer

<400> SEQUENCE: 49

```
gcggtctctc gctctgcgcg cacacaccac acacacgcac acgcacacac acgcgcgcac     60

acacgcagcc ggcacaggcg gcggcggcgg ctgcccaagt caggacgaac ctatctaggt    120

accgtcttga gaaggcggca gcggcggcgg cggcggcggc ggcggcagcc cgagcatccc    180

tcctctcccg gagagggagc accgccgaga gtttccgttc cctttgccat tcccttcccc    240

ctccttttct tttattttcg agagaatttc ttcttggctt attggtttaa tttgattttt    300

aaaattttgg gttgcttttg tgtatgtgtg cttttttttt ctttcctcat tttatttgca    360

tccagagcat ggcgggctgc gggctgtcgg aagacaccct cttctcttcc ttcttttaca    420

actacggctc ctcctgggaa accccttcca accaggtttt ttgcgaaaat cagtgaacta    480

atattggtaa aattggagcc ccatggatga agggtacttt tctgcccctg gactgccctg    540

gctgctgctt tggtaaaagc ttgcaaggag agagagtaac agccgctggc gaatccagtt    600

tgtgcaagca gcatcagcaa tggatgagac ctccccaagg ctggaagaag actggaaaaa    660

agtacttcag cgagaagcag gctggcagtg tgctgctctg gttggtgaag accagcctct    720

ttgcccagat cttcctgaac ttgatctttc tgaactagat gtgaacgact tggatacaga    780

cagctttctg ggtggactca agtggtgcag tgaccaatca gaaataatat ccaatcagta    840
```

```
caacaatgag ccttcaaaca tatttgagaa gatagatgaa gagaatgagg caaacttgct    900
agcagtcctc acagagacac tagacagtct ccctgtggat gaagacggat tgccctcatt    960
tgatgcgctg acagatggag acgtgaccac tgacaatgag gctagtcctt cctccatgcc   1020
tgacggcacc cctccacccc aggaggcaga agagccgtct ctacttaaga agctcttact   1080
ggcaccagcc aacactcagc taagttataa tgaatgcagt ggtctcagta cccagaacca   1140
tgcaaatcac aatcacagga tcagaacaaa ccctgcaatt gttaagactg agaattcatg   1200
gagcaataaa gcgaagagta tttgtcaaca gcaaaagcca caaagacgtc cctgctcgga   1260
gcttctcaaa tatctgacca caaacgatga ccctcctcac accaaaccca cagagaacag   1320
aaacagcagc agagacaaat gcacctccaa aaagaagtcc cacacacagt cgcagtcaca   1380
acacttacaa gccaaaccaa caactttatc tcttcctctg accccagagt caccaaatga   1440
ccccaagggt tccccatttg agaacaagac tattgaacgc accttaagtg tggaactctc   1500
tggaactgca ggcctaactc cacccaccac tcctcctcat aaagccaacc aagataaccc   1560
ttttagggct tctccaaagc tgaagtcctc ttgcaagact gtggtgccac caccatcaaa   1620
gaagcccagg tacagtgagt cttctggtac acaaggcaat aactccacca agaaagggcc   1680
ggagcaatcc gagttgtatg cacaactcag caagtcctca gtcctcactg gtggacacga   1740
ggaaaggaag accaagcggc ccagtctgcg gctgtttggt gaccatgact attgccagtc   1800
aattaattcc aaaacagaaa tactcattaa tatatcacag gagctccaag actctagaca   1860
actagaaaat aaagatgtct cctctgattg gcaggggcag atttgttctt ccacagattc   1920
agaccagtgc tacctgagag agactttgga ggcaagcaag caggtctctc cttgcagcac   1980
aagaaaacag ctccaagacc aggaaatccg agccgagctg aacaagcact tcggtcatcc   2040
cagtcaagct gtttttgacg acgaagcaga caagaccggt gaactgaggg acagtgattt   2100
cagtaatgaa caattctcca aactacctat gtttataaat tcaggactag ccatggatgg   2160
cctgtttgat gacagcgaag atgaaagtga taaactgagc taccccttggg atggcacgca   2220
atcctattca ttgttcaatg tgtctccttc ttgttcttct tttaactctc catgtagaga   2280
ttctgtgtca ccacccaaat ccttattttc tcaaagaccc caaaggatgc gctctcgttc   2340
aaggtccttt tctcgacaca ggtcgtgttc ccgatcacca tattccaggt caagatcaag   2400
gtctccaggc agtagatcct cttcaagatc ctgctattac tatgagtcaa gccactacag   2460
acaccgcacg caccgaaatt ctcccttgta tgtgagatca cgttcaagat cgccctacag   2520
ccgtcggccc aggtatgaca gctacgagga atatcagcac gagaggctga agagggaaga   2580
atatcgcaga gagtatgaga agcgagagtc tgagagggcc aagcaaaggg agaggcagag   2640
gcagaaggca attgaagagc gccgtgtgat ttatgtcggt aaaatcagac ctgacacaac   2700
acggacagaa ctgagggacc gttttgaagt tttggtgaa attgaggagt gcacagtaaa    2760
tctgcgggat gatggagaca gctatggttt cattacctac cgttatacct gtgatgcttt   2820
tgctgctctt gaaaatggat acactttgcg caggtcaaac gaaactgact ttgagctgta   2880
cttttgtgga cgcaagcaat tttcaagtc taactatgca gacctagatt caaactcaga    2940
tgactttgac cctgcttcca ccaagagcaa gtatgactct ctggattttg atagtttact   3000
gaaagaagct cagagaagct tgcgcaggta acatgttccc tagctgagga tgacagaggg   3060
atggcgaata cctcatggga cagcgcgtcc ttccctaaag actattgcaa gtcatactta   3120
ggaatttctc ctactttaca ctctctgtac aaaaacaaaa caaaacaaca acaatacaac   3180
aagaacaaca acaacaataa caacaatggt ttacatgaac acagctgctg aagaggcaag   3240
```

```
agacagaatg atatccagta agcacatgtt tattcatggg tgtcagcttt gcttttcctg   3300
gagtctcttg gtgatggagt gtgcgtgtgt gcatgtatgt gtgtgtgtat gtatgtgtgt   3360
ggtgtgtgtg cttggtttag gggaagtatg tgtgggtaca tgtgaggact gggggcacct   3420
gaccagaatg cgcaagggca aaccatttca aatggcagca gttccatgaa gacacgctta   3480
aaacctagaa cttcaaaatg ttcgtattct attcaaaagg aaatatatat atatatatat   3540
atatatatat atatatatat aaattaaaaa ggaaagaaaa ctaacaacca accaaccaac   3600
caaccaacca caaaccaccc taaaatgaca gccgctgatg tctgggcatc agcctttgta   3660
ctctgttttt ttaagaaagt gcagaatcaa cttgaagcaa gctttctctc ataacgtaat   3720
gattatatga caatcctgaa gaaaccacag gttccataga actaatatcc tgtctctctc   3780
tctctctctc tctctctctt ttttttttct ttttcctttt gccatggaat ctgggtggga   3840
gaggatactg cgggcaccag aatgctaaag tttcctaaca ttttgaagtt tctgtagttc   3900
atccttaatc ctgacaccca tgtaaatgtc caaaatgttg atcttccact gcaaatttca   3960
aaagccttgt caatggtcaa gcgtgcagct tgttcagcgg ttctttctga ggagcggaca   4020
ccgggttaca ttactaatga gagttgggta gaactctctg agatgtgttc agatagtgta   4080
attgctacat tctctgatgt agttaagtat ttacagatgt taaatggagt atttttattt   4140
tatgtatata ctatacaaca atgttctttt ttgttacagc tatgcactgt aaatgcagcc   4200
ttcttttcaa aactgctaaa tttttcttaa tcaagaatat tcaaatgtaa ttatgaggtg   4260
aaacaattat tgtacactaa catatttaga agctgaactt actgcttata tatatttgat   4320
tgtaaaaaca aaaagacagt gtgtgtgtct gttgagtgca acaagagcaa aatgatgctt   4380
tccgcacatc catcccttag gtgagcttca atctaagcat cttgtcaaga aatatcctag   4440
tcccctaaag gtattaacca cttctgcgat atttttccac attttcttgt cgcttgtttt   4500
tctttgaagt tttatacact ggatttgtta ggggaatgaa attttctcat ctaaaatttt   4560
tctagaagat atcatgattt tatgtaaagt ctctcaatgg gtaaccatta agaaatgttt   4620
ttattttctc tatcaacagt agttttgaaa ctagaagtca aaaatctttt taaaatgctg   4680
ttttgtttta atttttgtga ttttaatttg atacaaaatg ctgaggtaat aattatagta   4740
tgatttttac aataattaat gtgtgtctga agactatctt tgaagccagt atttctttcc   4800
cttggcagag tatgacgatg gtatttatct gtattttttta cagttatgca tcctgtataa   4860
atactgatat ttcattcctt tgtttactaa agagacatat ttatcagttg cagatagcct   4920
atttattata aattatgaga tgatgaaaat aataaagcca gtggaaattt tctacctagg   4980
atgcatgaca attgtcaggt tggagtgtaa gtgcttcatt tgggaaattc agcttttgca   5040
gaagcagtgt ttctacttgc actagcatgg cctctgacgt gaccatggtg ttgttcttga   5100
tgacattgct tctgctaaat ttaataaaaa cttcagaaaa acctccattt tgatcatcag   5160
gatttcatct gagtgtggag tccctggaat ggaattcagt aacatttgga gtgtgtattc   5220
aagtttctaa attgagattc gattactgtt tggctgacat gacttttctg gaagacatga   5280
tacacctact actcaattgt tcttttcctt tctctcgccc aacacgatct tgtaagatgg   5340
atttcacccc caggccaatg cagctaattt tgatagctgc attcatttat caccagcata   5400
ttgtgttctg agtgaatcca ctgtttgtcc tgtcggatgc ttgcttgatt ttttggcttc   5460
ttatttctaa gtagatagaa agcaataaaa atactatgaa atgaaagaac ttgttcacag   5520
gttctgcgtt acaacagtaa cacatcttta atccgcctaa ttcttgttgt tctgtaggtt   5580
```

```
aaatgcaggt attttaactg tgtgaacgcc aaactaaagt ttacagtctt tctttctgaa   5640

ttttgagtat cttctgttgt agaataataa taaaaagact attaagagca ataaattatt   5700

tttaagaaat cgagatttag taaatcctat tatgtgttca aggaccacat gtgttctcta   5760

ttttgccttt aaatttttgt gaaccaattt taaatacatt ctcctttttg ccctggattg   5820

ttgacatgag tggaatactt ggtttctttt cttacttatc aaaagacagc actacagata   5880

tcatattgag gattaattta tcccccctac ccccagcctg acaaatattg ttaccatgaa   5940

gatagttttc ctcaatggac ttcaaattgc atctagaatt agtggagctt ttgtatcttc   6000

tgcagacact gtgggtagcc catcaaaatg taagctgtgc tcctctcatt tttattttta   6060

ttttttgggg agagaatatt tcaaatgaac acgtgcaccc catcatcact ggaggcaaat   6120

ttcagcatag atctgtagga tttttagaag accgtgggcc attgccttca tgccgtggta   6180

agtaccacat ctacaatttt ggtaaccgaa ctggtgcttt agtaatgtgg attttttttct  6240

tttttaaaag agatgtagca gaataattct tccagtgcaa caaaatcaat tttttgctaa   6300

acgactccga gaacaacagt tgggctgtca acattcaaag cagcagagag ggaactttgc   6360

actattgggg tatgatgttt gggtcagttg ataaaaggaa accttttcat gcctttagat   6420

gtgagcttcc agtaggtaat gattatgtgt cctttcttga tggctgtaat gagaacttca   6480

atcactgtag tctaagacct gatctataga tgacctagaa tagccatgta ctataatgtg   6540

atgattctaa atttgtacct atgtgacaga cattttcaat aatgtgaact gctgatttga   6600

tggagctact ttaagatttg taggtgaaag tgtaatactg ttggttgaac tatgctgaag   6660

agggaaagtg agcgattagt tgagcccttg ccgggccttt tttccacctg ccaattctac   6720

atgtattgtt gtggttttat tcattgtatg aaaattcctg tgattttttt taaatgtgca   6780

gtacacatca gcctcactga gctaataaag ggaaacgaat gtttcaaatc taaaaaaaaa   6840

aaaaaaaaa                                                           6849
```

<210> SEQ ID NO 50
<211> LENGTH: 803
<212> TYPE: PRT
<213> ORGANISM: Artificial Sequence
<220> FEATURE:
<223> OTHER INFORMATION: Synthetic Polymer

<400> SEQUENCE: 50

```
Met Asp Glu Thr Ser Pro Arg Leu Glu Glu Asp Trp Lys Lys Val Leu
1               5                   10                  15

Gln Arg Glu Ala Gly Trp Gln Cys Ala Ala Leu Val Gly Glu Asp Gln
            20                  25                  30

Pro Leu Cys Pro Asp Leu Pro Glu Leu Asp Leu Ser Glu Leu Asp Val
        35                  40                  45

Asn Asp Leu Asp Thr Asp Ser Phe Leu Gly Gly Leu Lys Trp Cys Ser
    50                  55                  60

Asp Gln Ser Glu Ile Ile Ser Asn Gln Tyr Asn Asn Glu Pro Ser Asn
65                  70                  75                  80

Ile Phe Glu Lys Ile Asp Glu Glu Asn Glu Ala Asn Leu Leu Ala Val
                85                  90                  95

Leu Thr Glu Thr Leu Asp Ser Leu Pro Val Asp Glu Asp Gly Leu Pro
            100                 105                 110

Ser Phe Asp Ala Leu Thr Asp Gly Asp Val Thr Thr Asp Asn Glu Ala
        115                 120                 125

Ser Pro Ser Ser Met Pro Asp Gly Thr Pro Pro Pro Gln Glu Ala Glu
```

```
    130                 135                 140

Glu Pro Ser Leu Leu Lys Lys Leu Leu Leu Ala Pro Ala Asn Thr Gln
145                 150                 155                 160

Leu Ser Tyr Asn Glu Cys Ser Gly Leu Ser Thr Gln Asn His Ala Asn
                165                 170                 175

His Asn His Arg Ile Arg Thr Asn Pro Ala Ile Val Lys Thr Glu Asn
            180                 185                 190

Ser Trp Ser Asn Lys Ala Lys Ser Ile Cys Gln Gln Gln Lys Pro Gln
        195                 200                 205

Arg Arg Pro Cys Ser Glu Leu Leu Lys Tyr Leu Thr Thr Asn Asp Asp
    210                 215                 220

Pro Pro His Thr Lys Pro Thr Glu Asn Arg Asn Ser Ser Arg Asp Lys
225                 230                 235                 240

Cys Thr Ser Lys Lys Lys Ser His Thr Gln Ser Gln Ser Gln His Leu
                245                 250                 255

Gln Ala Lys Pro Thr Thr Leu Ser Leu Pro Leu Thr Pro Glu Ser Pro
            260                 265                 270

Asn Asp Pro Lys Gly Ser Pro Phe Glu Asn Lys Thr Ile Glu Arg Thr
        275                 280                 285

Leu Ser Val Glu Leu Ser Gly Thr Ala Gly Leu Thr Pro Pro Thr Thr
    290                 295                 300

Pro Pro His Lys Ala Asn Gln Asp Asn Pro Phe Arg Ala Ser Pro Lys
305                 310                 315                 320

Leu Lys Ser Ser Cys Lys Thr Val Val Pro Pro Pro Ser Lys Lys Pro
                325                 330                 335

Arg Tyr Ser Glu Ser Ser Gly Thr Gln Gly Asn Asn Ser Thr Lys Lys
            340                 345                 350

Gly Pro Glu Gln Ser Glu Leu Tyr Ala Gln Leu Ser Lys Ser Ser Val
        355                 360                 365

Leu Thr Gly Gly His Glu Glu Arg Lys Thr Lys Arg Pro Ser Leu Arg
    370                 375                 380

Leu Phe Gly Asp His Asp Tyr Cys Gln Ser Ile Asn Ser Lys Thr Glu
385                 390                 395                 400

Ile Leu Ile Asn Ile Ser Gln Glu Leu Gln Asp Ser Arg Gln Leu Glu
                405                 410                 415

Asn Lys Asp Val Ser Ser Asp Trp Gln Gly Gln Ile Cys Ser Ser Thr
            420                 425                 430

Asp Ser Asp Gln Cys Tyr Leu Arg Glu Thr Leu Glu Ala Ser Lys Gln
        435                 440                 445

Val Ser Pro Cys Ser Thr Arg Lys Gln Leu Gln Asp Gln Glu Ile Arg
    450                 455                 460

Ala Glu Leu Asn Lys His Phe Gly His Pro Ser Gln Ala Val Phe Asp
465                 470                 475                 480

Asp Glu Ala Asp Lys Thr Gly Glu Leu Arg Asp Ser Asp Phe Ser Asn
                485                 490                 495

Glu Gln Phe Ser Lys Leu Pro Met Phe Ile Asn Ser Gly Leu Ala Met
            500                 505                 510

Asp Gly Leu Phe Asp Asp Ser Glu Asp Glu Ser Asp Lys Leu Ser Tyr
        515                 520                 525

Pro Trp Asp Gly Thr Gln Ser Tyr Ser Leu Phe Asn Val Ser Pro Ser
    530                 535                 540

Cys Ser Ser Phe Asn Ser Pro Cys Arg Asp Ser Val Ser Pro Pro Lys
545                 550                 555                 560
```

Ser Leu Phe Ser Gln Arg Pro Gln Arg Met Arg Ser Arg Ser Arg Ser
565 570 575

Phe Ser Arg His Arg Ser Cys Ser Arg Ser Pro Tyr Ser Arg Ser Arg
580 585 590

Ser Arg Ser Pro Gly Ser Arg Ser Ser Ser Arg Ser Cys Tyr Tyr Tyr
595 600 605

Glu Ser Ser His Tyr Arg His Arg Thr His Arg Asn Ser Pro Leu Tyr
610 615 620

Val Arg Ser Arg Ser Arg Ser Pro Tyr Ser Arg Arg Pro Arg Tyr Asp
625 630 635 640

Ser Tyr Glu Glu Tyr Gln His Glu Arg Leu Lys Arg Glu Glu Tyr Arg
645 650 655

Arg Glu Tyr Glu Lys Arg Glu Ser Glu Arg Ala Lys Gln Arg Glu Arg
660 665 670

Gln Arg Gln Lys Ala Ile Glu Glu Arg Arg Val Ile Tyr Val Gly Lys
675 680 685

Ile Arg Pro Asp Thr Thr Arg Thr Glu Leu Arg Asp Arg Phe Glu Val
690 695 700

Phe Gly Glu Ile Glu Glu Cys Thr Val Asn Leu Arg Asp Asp Gly Asp
705 710 715 720

Ser Tyr Gly Phe Ile Thr Tyr Arg Tyr Thr Cys Asp Ala Phe Ala Ala
725 730 735

Leu Glu Asn Gly Tyr Thr Leu Arg Arg Ser Asn Glu Thr Asp Phe Glu
740 745 750

Leu Tyr Phe Cys Gly Arg Lys Gln Phe Phe Lys Ser Asn Tyr Ala Asp
755 760 765

Leu Asp Ser Asn Ser Asp Asp Phe Asp Pro Ala Ser Thr Lys Ser Lys
770 775 780

Tyr Asp Ser Leu Asp Phe Asp Ser Leu Leu Lys Glu Ala Gln Arg Ser
785 790 795 800

Leu Arg Arg

<210> SEQ ID NO 51
<211> LENGTH: 6335
<212> TYPE: DNA
<213> ORGANISM: Artificial Sequence
<220> FEATURE:
<223> OTHER INFORMATION: Synthetic Polymer

<400> SEQUENCE: 51
tagtaagaca ggtgccttca gttcactctc agtaaggggc tggttgcctg catgagtgtg 60
tgctctgtgt cactgtggat tggagttgaa aaagcttgac tggcgtcatt caggagctgg 120
atggcgtggg acatgtgcaa ccaggactct gagtctgtat ggagtgacat cgagtgtgct 180
gctctggttg gtgaagacca gcctctttgc ccagatcttc ctgaacttga tctttctgaa 240
ctagatgtga acgacttgga tacagacagc tttctgggtg gactcaagtg gtgcagtgac 300
caatcagaaa taatatccaa tcagtacaac aatgagcctt caaacatatt tgagaagata 360
gatgaagaga atgaggcaaa cttgctagca gtcctcacag agacactaga cagtctccct 420
gtggatgaag acggattgcc ctcatttgat gcgctgacag atggagacgt gaccactgac 480
aatgaggcta gtccttcctc catgcctgac ggcacccctc caccccagga ggcagaagag 540
ccgtctctac ttaagaagct cttactggca ccagccaaca ctcagctaag ttataatgaa 600
tgcagtggtc tcagtaccca gaaccatgca aatcacaatc acaggatcag aacaaaccct 660

```
gcaattgtta agactgagaa ttcatggagc aataaagcga agagtatttg tcaacagcaa    720
aagccacaaa gacgtccctg ctcggagctt ctcaaatatc tgaccacaaa cgatgaccct    780
cctcacacca aacccacaga gaacagaaac agcagcagag acaaatgcac ctccaaaaag    840
aagtcccaca cacagtcgca gtcacaacac ttacaagcca aaccaacaac tttatctctt    900
cctctgaccc cagagtcacc aaatgacccc aagggttccc catttgagaa caagactatt    960
gaacgcacct taagtgtgga actctctgga actgcaggcc taactccacc caccactcct   1020
cctcataaag ccaaccaaga taacccttt agggcttctc caaagctgaa gtcctcttgc    1080
aagactgtgg tgccaccacc atcaaagaag cccaggtaca gtgagtcttc tggtacacaa   1140
ggcaataact ccaccaagaa agggccggag caatccgagt tgtatgcaca actcagcaag   1200
tcctcagtcc tcactggtgg acacgaggaa aggaagacca agcggcccag tctgcggctg   1260
tttggtgacc atgactattg ccagtcaatt aattccaaaa cagaaatact cattaatata   1320
tcacaggagc tccaagactc tagacaacta gaaaataaag atgtctcctc tgattggcag   1380
gggcagattt gttcttccac agattcagac cagtgctacc tgagagagac tttggaggca   1440
agcaagcagg tctctccttg cagcacaaga aaacagctcc aagaccagga aatccgagcc   1500
gagctgaaca agcacttcgg tcatcccagt caagctgttt ttgacgacga agcagacaag   1560
accggtgaac tgagggacag tgatttcagt aatgaacaat tctccaaact acctatgttt   1620
ataaattcag gactagccat ggatggcctg tttgatgaca gcgaagatga aagtgataaa   1680
ctgagctacc cttgggatgg cacgcaatcc tattcattgt tcaatgtgtc tccttcttgt   1740
tcttctttta actctccatg tagagattct gtgtcaccac ccaaatcctt attttctcaa   1800
agaccccaaa ggatgcgctc tcgttcaagg tccttttctc gacacaggtc gtgttcccga   1860
tcaccatatt ccaggtcaag atcaaggtct ccaggcagta gatcctcttc aagatcctgc   1920
tattactatg agtcaagcca ctacagacac cgcacgcacc gaaattctcc cttgtatgtg   1980
agatcacgtt caagatcgcc ctacagccgt cggcccaggt atgacagcta cgaggaatat   2040
cagcacgaga ggctgaagag ggaagaatat cgcagagagt atgagaagcg agagtctgag   2100
agggccaagc aaagggagag gcagaggcag aaggcaattg aagagcgccg tgtgatttat   2160
gtcggtaaaa tcagacctga cacaacacgg acagaactga gggaccgttt tgaagttttt   2220
ggtgaaattg aggagtgcac agtaaatctg cgggatgatg gagacagcta tggtttcatt   2280
acctaccgtt atacctgtga tgcttttgct gctcttgaaa atggatacac tttgcgcagg   2340
tcaaacgaaa ctgactttga gctgtacttt tgtggacgca agcaattttt caagtctaac   2400
tatgcagacc tagattcaaa ctcagatgac tttgaccctg cttccaccaa gagcaagtat   2460
gactctctgg attttgatag tttactgaaa gaagctcaga gaagcttgcg caggtaacat   2520
gttccctagc tgaggatgac agagggatgg cgaatacctc atgggacagc gcgtccttcc   2580
ctaaagacta ttgcaagtca tacttaggaa tttctcctac tttacactct ctgtacaaaa   2640
acaaaacaaa acaacaacaa tacaacaaga acaacaacaa caataacaac aatggtttac   2700
atgaacacag ctgctgaaga ggcaagagac agaatgatat ccagtaagca catgtttatt   2760
catgggtgtc agctttgctt ttcctggagt ctcttggtga tggagtgtgc gtgtgtgcat   2820
gtatgtgtgt gtgtatgtat gtgtgtggtg tgtgtgcttg gtttagggga agtatgtgtg   2880
ggtacatgtg aggactgggg gcacctgacc agaatgcgca agggcaaacc atttcaaatg   2940
gcagcagttc catgaagaca cgcttaaaac ctagaacttc aaaatgttcg tattctattc   3000
```

-continued

```
aaaaggaaat atatatatat atatatatat atatatatat atatataaat taaaaaggaa   3060
agaaaactaa caaccaacca accaaccaac caaccacaaa ccaccctaaa atgacagccg   3120
ctgatgtctg ggcatcagcc tttgtactct gttttttaa gaaagtgcag aatcaacttg    3180
aagcaagctt tctctcataa cgtaatgatt atatgacaat cctgaagaaa ccacaggttc   3240
catagaacta atatcctgtc tctctctctc tctctctctc tctcttttt ttttcttttt    3300
ccttttgcca tggaatctgg gtgggagagg atactgcggg caccagaatg ctaaagtttc   3360
ctaacatttt gaagtttctg tagttcatcc ttaatcctga cacccatgta aatgtccaaa   3420
atgttgatct tccactgcaa atttcaaaag ccttgtcaat ggtcaagcgt gcagcttgtt   3480
cagcggttct ttctgaggag cggacaccgg gttacattac taatgagagt tgggtagaac   3540
tctctgagat gtgttcagat agtgtaattg ctacattctc tgatgtagtt aagtatttac   3600
agatgttaaa tggagtattt ttattttatg tatatactat acaacaatgt tctttttgt    3660
tacagctatg cactgtaaat gcagccttct tttcaaaact gctaaatttt tcttaatcaa   3720
gaatattcaa atgtaattat gaggtgaaac aattattgta cactaacata tttagaagct   3780
gaacttactg cttatatata tttgattgta aaaacaaaaa gacagtgtgt gtgtctgttg   3840
agtgcaacaa gagcaaaatg atgctttccg cacatccatc ccttaggtga gcttcaatct   3900
aagcatcttg tcaagaaata tcctagtccc ctaaaggtat taaccacttc tgcgatattt   3960
ttccacattt tcttgtcgct tgtttttctt tgaagtttta tacactggat ttgttagggg   4020
aatgaaattt tctcatctaa aatttttcta gaagatatca tgattttatg taaagtctct   4080
caatgggtaa ccattaagaa atgtttttat tttctctatc aacagtagtt ttgaaactag   4140
aagtcaaaaa tctttttaaa atgctgtttt gttttaattt ttgtgatttt aatttgatac   4200
aaaatgctga ggtaataatt atagtatgat ttttacaata attaatgtgt gtctgaagac   4260
tatctttgaa gccagtattt ctttcccttg gcagagtatg acgatggtat ttatctgtat   4320
tttttacagt tatgcatcct gtataaatac tgatatttca ttcctttgtt tactaaagag   4380
acatatttat cagttgcaga tagcctattt attataaatt atgagatgat gaaaataata   4440
aagccagtgg aaattttcta cctaggatgc atgacaattg tcaggttgga gtgtaagtgc   4500
ttcatttggg aaattcagct tttgcagaag cagtgtttct acttgcacta gcatggcctc   4560
tgacgtgacc atggtgttgt tcttgatgac attgcttctg ctaaatttaa taaaaacttc   4620
agaaaaacct ccattttgat catcaggatt tcatctgagt gtggagtccc tggaatggaa   4680
ttcagtaaca tttggagtgt gtattcaagt ttctaaattg agattcgatt actgtttggc   4740
tgacatgact tttctggaag acatgataca cctactactc aattgttctt ttcctttctc   4800
tcgcccaaca cgatcttgta agatggattt cacccccagg ccaatgcagc taattttgat   4860
agctgcattc atttatcacc agcatattgt gttctgagtg aatccactgt ttgtcctgtc   4920
ggatgcttgc ttgatttttt ggcttcttat ttctaagtag atagaaagca ataaaaatac   4980
tatgaaatga aagaacttgt tcacaggttc tgcgttacaa cagtaacaca tctttaatcc   5040
gcctaattct tgttgttctg taggttaaat gcaggtattt taactgtgtg aacgccaaac   5100
taaagtttac agtctttctt tctgaatttt gagtatcttc tgttgtagaa taataataaa   5160
aagactatta agagcaataa attattttta agaaatcgag atttagtaaa tcctattatg   5220
tgttcaagga ccacatgtgt tctctatttt gcctttaaat ttttgtgaac caattttaaa   5280
tacattctcc tttttgccct ggattgttga catgagtgga atacttggtt tcttttctta   5340
cttatcaaaa gacagcacta cagatatcat attgaggatt aatttatccc ccctaccccc   5400
```

```
agcctgacaa atattgttac catgaagata gttttcctca atggacttca aattgcatct   5460

agaattagtg gagcttttgt atcttctgca gacactgtgg gtagcccatc aaaatgtaag   5520

ctgtgctcct ctcattttta tttttatttt tttgggagag aatatttcaa atgaacacgt   5580

gcaccccatc atcactggag gcaaatttca gcatagatct gtaggatttt tagaagaccg   5640

tgggccattg ccttcatgcc gtggtaagta ccacatctac aattttggta accgaactgg   5700

tgctttagta atgtggattt ttttcttttt taaaagagat gtagcagaat aattcttcca   5760

gtgcaacaaa atcaattttt tgctaaacga ctccgagaac aacagttggg ctgtcaacat   5820

tcaaagcagc agagagggaa ctttgcacta ttggggtatg atgtttgggt cagttgataa   5880

aaggaaacct tttcatgcct ttagatgtga gcttccagta ggtaatgatt atgtgtcctt   5940

tcttgatggc tgtaatgaga acttcaatca ctgtagtcta agacctgatc tatagatgac   6000

ctagaatagc catgtactat aatgtgatga ttctaaattt gtacctatgt gacagacatt   6060

ttcaataatg tgaactgctg atttgatgga gctactttaa gatttgtagg tgaaagtgta   6120

atactgttgg ttgaactatg ctgaagaggg aaagtgagcg attagttgag cccttgccgg   6180

gccttttttc cacctgccaa ttctacatgt attgttgtgg ttttattcat tgtatgaaaa   6240

ttcctgtgat tttttttaaa tgtgcagtac acatcagcct cactgagcta ataaagggaa   6300

acgaatgttt caaatctaaa aaaaaaaaaa aaaaa                              6335
```

<210> SEQ ID NO 52
<211> LENGTH: 798
<212> TYPE: PRT
<213> ORGANISM: Artificial Sequence
<220> FEATURE:
<223> OTHER INFORMATION: Synthetic Polymer

<400> SEQUENCE: 52

```
Met Ala Trp Asp Met Cys Asn Gln Asp Ser Glu Ser Val Trp Ser Asp
1               5                   10                  15

Ile Glu Cys Ala Ala Leu Val Gly Glu Asp Gln Pro Leu Cys Pro Asp
            20                  25                  30

Leu Pro Glu Leu Asp Leu Ser Glu Leu Asp Val Asn Asp Leu Asp Thr
        35                  40                  45

Asp Ser Phe Leu Gly Gly Leu Lys Trp Cys Ser Asp Gln Ser Glu Ile
    50                  55                  60

Ile Ser Asn Gln Tyr Asn Asn Glu Pro Ser Asn Ile Phe Glu Lys Ile
65                  70                  75                  80

Asp Glu Glu Asn Glu Ala Asn Leu Leu Ala Val Leu Thr Glu Thr Leu
                85                  90                  95

Asp Ser Leu Pro Val Asp Glu Asp Gly Leu Pro Ser Phe Asp Ala Leu
            100                 105                 110

Thr Asp Gly Asp Val Thr Thr Asp Asn Glu Ala Ser Pro Ser Ser Met
        115                 120                 125

Pro Asp Gly Thr Pro Pro Pro Gln Glu Ala Glu Glu Pro Ser Leu Leu
    130                 135                 140

Lys Lys Leu Leu Leu Ala Pro Ala Asn Thr Gln Leu Ser Tyr Asn Glu
145                 150                 155                 160

Cys Ser Gly Leu Ser Thr Gln Asn His Ala Asn His Asn His Arg Ile
                165                 170                 175

Arg Thr Asn Pro Ala Ile Val Lys Thr Glu Asn Ser Trp Ser Asn Lys
            180                 185                 190
```

```
Ala Lys Ser Ile Cys Gln Gln Gln Lys Pro Gln Arg Arg Pro Cys Ser
        195                 200                 205

Glu Leu Leu Lys Tyr Leu Thr Thr Asn Asp Asp Pro Pro His Thr Lys
    210                 215                 220

Pro Thr Glu Asn Arg Asn Ser Ser Arg Asp Lys Cys Thr Ser Lys Lys
225                 230                 235                 240

Lys Ser His Thr Gln Ser Gln Ser Gln His Leu Gln Ala Lys Pro Thr
                245                 250                 255

Thr Leu Ser Leu Pro Leu Thr Pro Glu Ser Pro Asn Asp Pro Lys Gly
            260                 265                 270

Ser Pro Phe Glu Asn Lys Thr Ile Glu Arg Thr Leu Ser Val Glu Leu
        275                 280                 285

Ser Gly Thr Ala Gly Leu Thr Pro Pro Thr Thr Pro Pro His Lys Ala
    290                 295                 300

Asn Gln Asp Asn Pro Phe Arg Ala Ser Pro Lys Leu Lys Ser Ser Cys
305                 310                 315                 320

Lys Thr Val Val Pro Pro Pro Ser Lys Lys Pro Arg Tyr Ser Glu Ser
                325                 330                 335

Ser Gly Thr Gln Gly Asn Asn Ser Thr Lys Lys Gly Pro Glu Gln Ser
            340                 345                 350

Glu Leu Tyr Ala Gln Leu Ser Lys Ser Ser Val Leu Thr Gly Gly His
        355                 360                 365

Glu Glu Arg Lys Thr Lys Arg Pro Ser Leu Arg Leu Phe Gly Asp His
    370                 375                 380

Asp Tyr Cys Gln Ser Ile Asn Ser Lys Thr Glu Ile Leu Ile Asn Ile
385                 390                 395                 400

Ser Gln Glu Leu Gln Asp Ser Arg Gln Leu Glu Asn Lys Asp Val Ser
                405                 410                 415

Ser Asp Trp Gln Gly Gln Ile Cys Ser Ser Thr Asp Ser Asp Gln Cys
            420                 425                 430

Tyr Leu Arg Glu Thr Leu Glu Ala Ser Lys Gln Val Ser Pro Cys Ser
        435                 440                 445

Thr Arg Lys Gln Leu Gln Asp Gln Glu Ile Arg Ala Glu Leu Asn Lys
    450                 455                 460

His Phe Gly His Pro Ser Gln Ala Val Phe Asp Asp Glu Ala Asp Lys
465                 470                 475                 480

Thr Gly Glu Leu Arg Asp Ser Asp Phe Ser Asn Glu Gln Phe Ser Lys
                485                 490                 495

Leu Pro Met Phe Ile Asn Ser Gly Leu Ala Met Asp Gly Leu Phe Asp
            500                 505                 510

Asp Ser Glu Asp Glu Ser Asp Lys Leu Ser Tyr Pro Trp Asp Gly Thr
        515                 520                 525

Gln Ser Tyr Ser Leu Phe Asn Val Ser Pro Ser Cys Ser Ser Phe Asn
    530                 535                 540

Ser Pro Cys Arg Asp Ser Val Ser Pro Pro Lys Ser Leu Phe Ser Gln
545                 550                 555                 560

Arg Pro Gln Arg Met Arg Ser Arg Ser Arg Ser Phe Ser Arg His Arg
                565                 570                 575

Ser Cys Ser Arg Ser Pro Tyr Ser Arg Ser Arg Ser Arg Ser Pro Gly
            580                 585                 590

Ser Arg Ser Ser Ser Arg Ser Cys Tyr Tyr Tyr Glu Ser Ser His Tyr
        595                 600                 605

Arg His Arg Thr His Arg Asn Ser Pro Leu Tyr Val Arg Ser Arg Ser
```

```
    610                 615                 620

Arg Ser Pro Tyr Ser Arg Arg Pro Arg Tyr Asp Ser Tyr Glu Glu Tyr
625                 630                 635                 640

Gln His Glu Arg Leu Lys Arg Glu Glu Tyr Arg Arg Glu Tyr Glu Lys
                645                 650                 655

Arg Glu Ser Glu Arg Ala Lys Gln Arg Glu Arg Gln Arg Gln Lys Ala
            660                 665                 670

Ile Glu Glu Arg Arg Val Ile Tyr Val Gly Lys Ile Arg Pro Asp Thr
        675                 680                 685

Thr Arg Thr Glu Leu Arg Asp Arg Phe Glu Val Phe Gly Glu Ile Glu
    690                 695                 700

Glu Cys Thr Val Asn Leu Arg Asp Asp Gly Asp Ser Tyr Gly Phe Ile
705                 710                 715                 720

Thr Tyr Arg Tyr Thr Cys Asp Ala Phe Ala Ala Leu Glu Asn Gly Tyr
                725                 730                 735

Thr Leu Arg Arg Ser Asn Glu Thr Asp Phe Glu Leu Tyr Phe Cys Gly
            740                 745                 750

Arg Lys Gln Phe Phe Lys Ser Asn Tyr Ala Asp Leu Asp Ser Asn Ser
        755                 760                 765

Asp Asp Phe Asp Pro Ala Ser Thr Lys Ser Lys Tyr Asp Ser Leu Asp
    770                 775                 780

Phe Asp Ser Leu Leu Lys Glu Ala Gln Arg Ser Leu Arg Arg
785                 790                 795
```

<210> SEQ ID NO 53
<211> LENGTH: 6681
<212> TYPE: DNA
<213> ORGANISM: Artificial Sequence
<220> FEATURE:
<223> OTHER INFORMATION: Synthetic Polymer

<400> SEQUENCE: 53

```
gcggtctctc gctctgcgcg cacacaccac acacacgcac acgcacacac acgcgcgcac     60

acacgcagcc ggcacaggcg gcggcggcgg ctgcccaagt caggacgaac ctatctaggt    120

accgtcttga gaaggcggca gcggcggcgg cggcggcggc ggcggcagcc cgagcatccc    180

tcctctcccg gagagggagc accgccgaga gtttccgttc cctttgccat tcccttcccc    240

ctccttttct tttattttcg agagaatttc ttcttggctt attggtttaa tttgattttt    300

aaaattttgg gttgcttttg tgtatgtgtg cttttttttt ctttcctcat tttatttgca    360

tccagagcat ggcgggctgc gggctgtcgg aagacaccct cttctcttcc ttcttttaca    420

actacggctc ctcctgggaa accccttcca accaggtttt ttgcgaaaat cagtgaacta    480

atattggtaa aattggagcc ccatggatga agggtacttt tgtgctgctc tggttggtga    540

agaccagcct ctttgcccag atcttcctga acttgatctt tctgaactag atgtgaacga    600

cttggataca gacagctttc tgggtggact caagtggtgc agtgaccaat cagaaataat    660

atccaatcag tacaacaatg agccttcaaa catatttgag aagatagatg aagagaatga    720

ggcaaacttg ctagcagtcc tcacagagac actagacagt ctccctgtgg atgaagacgg    780

attgccctca tttgatgcgc tgacagatgg agacgtgacc actgacaatg aggctagtcc    840

ttcctccatg cctgacggca cccctccacc ccaggaggca gaagagccgt ctctacttaa    900

gaagctctta ctggcaccag ccaacactca gctaagttat aatgaatgca gtggtctcag    960

tacccagaac catgcaaatc acaatcacag gatcagaaca aaccctgcaa ttgttaagac   1020
```

```
tgagaattca tggagcaata aagcgaagag tatttgtcaa cagcaaaagc cacaaagacg   1080
tccctgctcg gagcttctca aatatctgac cacaaacgat gaccctcctc acaccaaacc   1140
cacagagaac agaaacagca gcagagacaa atgcacctcc aaaaagaagt cccacacaca   1200
gtcgcagtca caacacttac aagccaaacc aacaacttta tctcttcctc tgaccccaga   1260
gtcaccaaat gaccccaagg gttccccatt tgagaacaag actattgaac gcaccttaag   1320
tgtggaactc tctggaactg caggcctaac tccacccacc actcctcctc ataaagccaa   1380
ccaagataac ccttttaggg cttctccaaa gctgaagtcc tcttgcaaga ctgtggtgcc   1440
accaccatca aagaagccca ggtacagtga gtcttctggt acacaaggca ataactccac   1500
caagaaaggg ccggagcaat ccgagttgta tgcacaactc agcaagtcct cagtcctcac   1560
tggtggacac gaggaaagga agaccaagcg gcccagtctg cggctgtttg gtgaccatga   1620
ctattgccag tcaattaatt ccaaaacaga aatactcatt aatatatcac aggagctcca   1680
agactctaga caactagaaa ataaagatgt ctcctctgat tggcaggggc agatttgttc   1740
ttccacagat tcagaccagt gctacctgag agagactttg gaggcaagca agcaggtctc   1800
tccttgcagc acaagaaaac agctccaaga ccaggaaatc cgagccgagc tgaacaagca   1860
cttcggtcat cccagtcaag ctgtttttga cgacgaagca gacaagaccg gtgaactgag   1920
ggacagtgat ttcagtaatg aacaattctc caaactacct atgtttataa attcaggact   1980
agccatggat ggcctgtttg atgacagcga agatgaaagt gataaactga gctacccttg   2040
ggatggcacg caatcctatt cattgttcaa tgtgtctcct tcttgttctt cttttaactc   2100
tccatgtaga gattctgtgt caccacccaa atccttattt tctcaaagac cccaaaggat   2160
gcgctctcgt tcaaggtcct tttctcgaca caggtcgtgt tcccgatcac catattccag   2220
gtcaagatca aggtctccag gcagtagatc ctcttcaaga tcctgctatt actatgagtc   2280
aagccactac agacaccgca cgcaccgaaa ttctcccttg tatgtgagat cacgttcaag   2340
atcgccctac agccgtcggc ccaggtatga cagctacgag gaatatcagc acgagaggct   2400
gaagagggaa gaatatcgca gagagtatga gaagcgagag tctgagaggg ccaagcaaag   2460
ggagaggcag aggcagaagg caattgaaga gcgccgtgtg atttatgtcg gtaaaatcag   2520
acctgacaca acacggacag aactgaggga ccgttttgaa gtttttggtg aaattgagga   2580
gtgcacagta aatctgcggg atgatggaga cagctatggt ttcattacct accgttatac   2640
ctgtgatgct tttgctgctc ttgaaaatgg atacactttg cgcaggtcaa acgaaactga   2700
ctttgagctg tacttttgtg gacgcaagca atttttcaag tctaactatg cagacctaga   2760
ttcaaactca gatgactttg accctgcttc caccaagagc aagtatgact ctctggattt   2820
tgatagttta ctgaaagaag ctcagagaag cttgcgcagg taacatgttc cctagctgag   2880
gatgacagag ggatggcgaa tacctcatgg gacagcgcgt ccttccctaa agactattgc   2940
aagtcatact taggaatttc tcctacttta cactctctgt acaaaaacaa aacaaaacaa   3000
caacaataca acaagaacaa caacaacaat aacaacaatg gtttacatga acacagctgc   3060
tgaagaggca agagacagaa tgatatccag taagcacatg tttattcatg ggtgtcagct   3120
ttgcttttcc tggagtctct tggtgatgga gtgtgcgtgt gtgcatgtat gtgtgtgtgt   3180
atgtatgtgt gtggtgtgtg tgcttggttt aggggaagta tgtgtgggta catgtgagga   3240
ctgggggcac ctgaccagaa tgcgcaaggg caaaccattt caaatggcag cagttccatg   3300
aagacacgct taaaacctag aacttcaaaa tgttcgtatt ctattcaaaa ggaaatatat   3360
atatatatat atatatatat atatatatat ataaattaaa aaggaaagaa aactaacaac   3420
```

```
caaccaacca accaaccaac cacaaaccac cctaaaatga cagccgctga tgtctgggca   3480
tcagcctttg tactctgttt ttttaagaaa gtgcagaatc aacttgaagc aagctttctc   3540
tcataacgta atgattatat gacaatcctg aagaaaccac aggttccata gaactaatat   3600
cctgtctctc tctctctctc tctctctctc tttttttttt ctttttcctt ttgccatgga   3660
atctgggtgg gagaggatac tgcgggcacc agaatgctaa agtttcctaa cattttgaag   3720
tttctgtagt tcatccttaa tcctgacacc catgtaaatg tccaaaatgt tgatcttcca   3780
ctgcaaattt caaaagcctt gtcaatggtc aagcgtgcag cttgttcagc ggttctttct   3840
gaggagcgga caccgggtta cattactaat gagagttggg tagaactctc tgagatgtgt   3900
tcagatagtg taattgctac attctctgat gtagttaagt atttacagat gttaaatgga   3960
gtatttttat tttatgtata tactatacaa caatgttctt ttttgttaca gctatgcact   4020
gtaaatgcag ccttcttttc aaaactgcta aatttttctt aatcaagaat attcaaatgt   4080
aattatgagg tgaaacaatt attgtacact aacatattta gaagctgaac ttactgctta   4140
tatatatttg attgtaaaaa caaaaagaca gtgtgtgtgt ctgttgagtg caacaagagc   4200
aaaatgatgc tttccgcaca tccatccctt aggtgagctt caatctaagc atcttgtcaa   4260
gaaatatcct agtcccctaa aggtattaac cacttctgcg atatttttcc acattttctt   4320
gtcgcttgtt tttctttgaa gttttataca ctggatttgt taggggaatg aaattttctc   4380
atctaaaatt tttctagaag atatcatgat tttatgtaaa gtctctcaat gggtaaccat   4440
taagaaatgt ttttattttc tctatcaaca gtagttttga aactagaagt caaaaatctt   4500
tttaaaatgc tgttttgttt taatttttgt gattttaatt tgatacaaaa tgctgaggta   4560
ataattatag tatgattttt acaataatta atgtgtgtct gaagactatc tttgaagcca   4620
gtatttcttt cccttggcag agtatgacga tggtatttat ctgtattttt tacagttatg   4680
catcctgtat aaatactgat atttcattcc tttgtttact aaagagacat atttatcagt   4740
tgcagatagc ctatttatta taaattatga gatgatgaaa ataataaagc cagtggaaat   4800
tttctaccta ggatgcatga caattgtcag gttggagtgt aagtgcttca tttgggaaat   4860
tcagcttttg cagaagcagt gtttctactt gcactagcat ggcctctgac gtgaccatgg   4920
tgttgttctt gatgacattg cttctgctaa atttaataaa aacttcagaa aaacctccat   4980
tttgatcatc aggatttcat ctgagtgtgg agtccctgga atggaattca gtaacatttg   5040
gagtgtgtat tcaagtttct aaattgagat tcgattactg tttggctgac atgacttttc   5100
tggaagacat gatacaccta ctactcaatt gttcttttcc tttctctcgc ccaacacgat   5160
cttgtaagat ggatttcacc cccaggccaa tgcagctaat tttgatagct gcattcattt   5220
atcaccagca tattgtgttc tgagtgaatc cactgtttgt cctgtcggat gcttgcttga   5280
ttttttggct tcttatttct aagtagatag aaagcaataa aaatactatg aaatgaaaga   5340
acttgttcac aggttctgcg ttacaacagt aacacatctt taatccgcct aattcttgtt   5400
gttctgtagg ttaaatgcag gtattttaac tgtgtgaacg ccaaactaaa gtttacagtc   5460
tttctttctg aattttgagt atcttctgtt gtagaataat aataaaaaga ctattaagag   5520
caataaatta tttttaagaa atcgagattt agtaaatcct attatgtgtt caaggaccac   5580
atgtgttctc tattttgcct ttaaattttt gtgaaccaat tttaaataca ttctcctttt   5640
tgccctggat tgttgacatg agtggaatac ttggtttctt ttcttactta tcaaaagaca   5700
gcactacaga tatcatattg aggattaatt tatccccccct acccccagcc tgacaaatat   5760
```

```
tgttaccatg aagatagttt tcctcaatgg acttcaaatt gcatctagaa ttagtggagc   5820

ttttgtatct tctgcagaca ctgtgggtag cccatcaaaa tgtaagctgt gctcctctca   5880

tttttatttt tatttttttg ggagagaata tttcaaatga acacgtgcac cccatcatca   5940

ctggaggcaa atttcagcat agatctgtag gatttttaga agaccgtggg ccattgcctt   6000

catgccgtgg taagtaccac atctacaatt ttggtaaccg aactggtgct ttagtaatgt   6060

ggattttttt ctttttttaaa agagatgtag cagaataatt cttccagtgc aacaaaatca   6120

attttttgct aaacgactcc gagaacaaca gttgggctgt caacattcaa agcagcagag   6180

agggaacttt gcactattgg ggtatgatgt ttgggtcagt tgataaaagg aaaccttttc   6240

atgcctttag atgtgagctt ccagtaggta atgattatgt gtcctttctt gatggctgta   6300

atgagaactt caatcactgt agtctaagac ctgatctata gatgacctag aatagccatg   6360

tactataatg tgatgattct aaatttgtac ctatgtgaca gacattttca ataatgtgaa   6420

ctgctgattt gatggagcta ctttaagatt tgtaggtgaa agtgtaatac tgttggttga   6480

actatgctga agagggaaag tgagcgatta gttgagccct tgccgggcct tttttccacc   6540

tgccaattct acatgtattg ttgtggtttt attcattgta tgaaaattcc tgtgattttt   6600

tttaaatgtg cagtacacat cagcctcact gagctaataa agggaaacga atgtttcaaa   6660

tctaaaaaaa aaaaaaaaaa a                                             6681
```

<210> SEQ ID NO 54
<211> LENGTH: 786
<212> TYPE: PRT
<213> ORGANISM: Artificial Sequence
<220> FEATURE:
<223> OTHER INFORMATION: Synthetic Polymer

<400> SEQUENCE: 54

```
Met Asp Glu Gly Tyr Phe Cys Ala Ala Leu Val Gly Glu Asp Gln Pro
1               5                   10                  15

Leu Cys Pro Asp Leu Pro Glu Leu Asp Leu Ser Glu Leu Asp Val Asn
            20                  25                  30

Asp Leu Asp Thr Asp Ser Phe Leu Gly Gly Leu Lys Trp Cys Ser Asp
        35                  40                  45

Gln Ser Glu Ile Ile Ser Asn Gln Tyr Asn Asn Glu Pro Ser Asn Ile
    50                  55                  60

Phe Glu Lys Ile Asp Glu Glu Asn Glu Ala Asn Leu Leu Ala Val Leu
65                  70                  75                  80

Thr Glu Thr Leu Asp Ser Leu Pro Val Asp Glu Asp Gly Leu Pro Ser
                85                  90                  95

Phe Asp Ala Leu Thr Asp Gly Asp Val Thr Thr Asp Asn Glu Ala Ser
            100                 105                 110

Pro Ser Ser Met Pro Asp Gly Thr Pro Pro Pro Gln Glu Ala Glu Glu
        115                 120                 125

Pro Ser Leu Leu Lys Lys Leu Leu Leu Ala Pro Ala Asn Thr Gln Leu
    130                 135                 140

Ser Tyr Asn Glu Cys Ser Gly Leu Ser Thr Gln Asn His Ala Asn His
145                 150                 155                 160

Asn His Arg Ile Arg Thr Asn Pro Ala Ile Val Lys Thr Glu Asn Ser
                165                 170                 175

Trp Ser Asn Lys Ala Lys Ser Ile Cys Gln Gln Gln Lys Pro Gln Arg
            180                 185                 190

Arg Pro Cys Ser Glu Leu Leu Lys Tyr Leu Thr Thr Asn Asp Asp Pro
```

```
        195                 200                 205

Pro His Thr Lys Pro Thr Glu Asn Arg Asn Ser Ser Arg Asp Lys Cys
    210                 215                 220

Thr Ser Lys Lys Lys Ser His Thr Gln Ser Gln Ser Gln His Leu Gln
225                 230                 235                 240

Ala Lys Pro Thr Thr Leu Ser Leu Pro Leu Thr Pro Glu Ser Pro Asn
                245                 250                 255

Asp Pro Lys Gly Ser Pro Phe Glu Asn Lys Thr Ile Glu Arg Thr Leu
            260                 265                 270

Ser Val Glu Leu Ser Gly Thr Ala Gly Leu Thr Pro Pro Thr Thr Pro
        275                 280                 285

Pro His Lys Ala Asn Gln Asp Asn Pro Phe Arg Ala Ser Pro Lys Leu
    290                 295                 300

Lys Ser Ser Cys Lys Thr Val Val Pro Pro Pro Ser Lys Lys Pro Arg
305                 310                 315                 320

Tyr Ser Glu Ser Ser Gly Thr Gln Gly Asn Asn Ser Thr Lys Lys Gly
                325                 330                 335

Pro Glu Gln Ser Glu Leu Tyr Ala Gln Leu Ser Lys Ser Ser Val Leu
            340                 345                 350

Thr Gly Gly His Glu Glu Arg Lys Thr Lys Arg Pro Ser Leu Arg Leu
        355                 360                 365

Phe Gly Asp His Asp Tyr Cys Gln Ser Ile Asn Ser Lys Thr Glu Ile
    370                 375                 380

Leu Ile Asn Ile Ser Gln Glu Leu Gln Asp Ser Arg Gln Leu Glu Asn
385                 390                 395                 400

Lys Asp Val Ser Ser Asp Trp Gln Gly Gln Ile Cys Ser Ser Thr Asp
                405                 410                 415

Ser Asp Gln Cys Tyr Leu Arg Glu Thr Leu Glu Ala Ser Lys Gln Val
            420                 425                 430

Ser Pro Cys Ser Thr Arg Lys Gln Leu Gln Asp Gln Glu Ile Arg Ala
        435                 440                 445

Glu Leu Asn Lys His Phe Gly His Pro Ser Gln Ala Val Phe Asp Asp
    450                 455                 460

Glu Ala Asp Lys Thr Gly Glu Leu Arg Asp Ser Asp Phe Ser Asn Glu
465                 470                 475                 480

Gln Phe Ser Lys Leu Pro Met Phe Ile Asn Ser Gly Leu Ala Met Asp
                485                 490                 495

Gly Leu Phe Asp Asp Ser Glu Asp Glu Ser Asp Lys Leu Ser Tyr Pro
            500                 505                 510

Trp Asp Gly Thr Gln Ser Tyr Ser Leu Phe Asn Val Ser Pro Ser Cys
        515                 520                 525

Ser Ser Phe Asn Ser Pro Cys Arg Asp Ser Val Ser Pro Pro Lys Ser
    530                 535                 540

Leu Phe Ser Gln Arg Pro Gln Arg Met Arg Ser Arg Ser Arg Ser Phe
545                 550                 555                 560

Ser Arg His Arg Ser Cys Ser Arg Ser Pro Tyr Ser Arg Ser Arg Ser
                565                 570                 575

Arg Ser Pro Gly Ser Arg Ser Ser Ser Arg Ser Cys Tyr Tyr Tyr Glu
            580                 585                 590

Ser Ser His Tyr Arg His Arg Thr His Arg Asn Ser Pro Leu Tyr Val
        595                 600                 605

Arg Ser Arg Ser Arg Ser Pro Tyr Ser Arg Arg Pro Arg Tyr Asp Ser
    610                 615                 620
```

Tyr Glu Glu Tyr Gln His Glu Arg Leu Lys Arg Glu Glu Tyr Arg Arg
625 630 635 640

Glu Tyr Glu Lys Arg Glu Ser Glu Arg Ala Lys Gln Arg Glu Arg Gln
645 650 655

Arg Gln Lys Ala Ile Glu Glu Arg Arg Val Ile Tyr Val Gly Lys Ile
660 665 670

Arg Pro Asp Thr Thr Arg Thr Glu Leu Arg Asp Arg Phe Glu Val Phe
675 680 685

Gly Glu Ile Glu Glu Cys Thr Val Asn Leu Arg Asp Asp Gly Asp Ser
690 695 700

Tyr Gly Phe Ile Thr Tyr Arg Tyr Thr Cys Asp Ala Phe Ala Ala Leu
705 710 715 720

Glu Asn Gly Tyr Thr Leu Arg Arg Ser Asn Glu Thr Asp Phe Glu Leu
725 730 735

Tyr Phe Cys Gly Arg Lys Gln Phe Phe Lys Ser Asn Tyr Ala Asp Leu
740 745 750

Asp Ser Asn Ser Asp Asp Phe Asp Pro Ala Ser Thr Lys Ser Lys Tyr
755 760 765

Asp Ser Leu Asp Phe Asp Ser Leu Leu Lys Glu Ala Gln Arg Ser Leu
770 775 780

Arg Arg
785

<210> SEQ ID NO 55
<211> LENGTH: 6545
<212> TYPE: DNA
<213> ORGANISM: Artificial Sequence
<220> FEATURE:
<223> OTHER INFORMATION: Synthetic Polymer

<400> SEQUENCE: 55
agaagccact ttaaaaaaca aagcaaaagg ctcagaggta acagcctcca gtgaatctga 60
tccatgtgta aggaaaacag gatgcgtccc tggaccggct ggtagcaaga tttatgtttc 120
agaatattgc aacataactt ccttccctct gttgcctttg tgcattgttt gaaggaggag 180
aataaaggac tacttttgca gcacagcagt ctgtaaagat ggatggcatg gggttagttt 240
aaatagcata ttggcctttc tgggtcactg tgggcaacct tgtccctggt ttattttaac 300
acctgcttta atgcctccat gatacaactg aatgggcatc tttcattcat tcgtctgtta 360
cttctgaatg aagctacttg ggttcgtta gaatgatggc aagtgagaat gcagtcgtct 420
ctaggtcatt acttgtaata cgttctgagg actgcctttg ctgatggggg gagaaggact 480
ctcacagctg tagccagcgt tcatgtttgg tcattgctgg aactctcagg aagcctgaaa 540
ctgtgaactt tgtagcagaa aaggaagata gatgaagaga atgaggcaaa cttgctagca 600
gtcctcacag agacactaga cagtctccct gtggatgaag acggattgcc ctcatttgat 660
gcgctgacag atggagacgt gaccactgac aatgaggcta gtccttcctc catgcctgac 720
ggcacccctc caccccagga ggcagaagag ccgtctctac ttaagaagct cttactggca 780
ccagccaaca ctcagctaag ttataatgaa tgcagtggtc tcagtaccca gaaccatgca 840
aatcacaatc acaggatcag aacaaaccct gcaattgtta agactgagaa ttcatggagc 900
aataaagcga agagtatttg tcaacagcaa aagccacaaa gacgtccctg ctcggagctt 960
ctcaaatatc tgaccacaaa cgatgaccct cctcacacca aacccacaga gaacagaaac 1020
agcagcagag acaaatgcac ctccaaaaag aagtcccaca cacagtcgca gtcacaacac 1080

```
ttacaagcca aaccaacaac tttatctctt cctctgaccc cagagtcacc aaatgacccc   1140
aagggttccc catttgagaa caagactatt gaacgcacct taagtgtgga actctctgga   1200
actgcaggcc taactccacc caccactcct cctcataaag ccaaccaaga taaccctttt   1260
agggcttctc caaagctgaa gtcctcttgc aagactgtgg tgccaccacc atcaaagaag   1320
cccaggtaca gtgagtcttc tggtacacaa ggcaataact ccaccaagaa agggccggag   1380
caatccgagt tgtatgcaca actcagcaag tcctcagtcc tcactggtgg acacgaggaa   1440
aggaagacca agcggcccag tctgcggctg tttggtgacc atgactattg ccagtcaatt   1500
aattccaaaa cagaaatact cattaatata tcacaggagc tccaagactc tagacaacta   1560
gaaaataaag atgtctcctc tgattggcag gggcagattt gttcttccac agattcagac   1620
cagtgctacc tgagagagac tttggaggca agcaagcagg tctctccttg cagcacaaga   1680
aaacagctcc aagaccagga aatccgagcc gagctgaaca agcacttcgg tcatcccagt   1740
caagctgttt ttgacgacga agcagacaag accggtgaac tgagggacag tgatttcagt   1800
aatgaacaat tctccaaact acctatgttt ataaattcag gactagccat ggatggcctg   1860
tttgatgaca gcgaagatga aagtgataaa ctgagctacc cttgggatgg cacgcaatcc   1920
tattcattgt tcaatgtgtc tccttcttgt tcttctttta actctccatg tagagattct   1980
gtgtcaccac ccaaatcctt attttctcaa agaccccaaa ggatgcgctc tcgttcaagg   2040
tccttttctc gacacaggtc gtgttcccga tcaccatatt ccaggtcaag atcaaggtct   2100
ccaggcagta gatcctcttc aagatcctgc tattactatg agtcaagcca ctacagacac   2160
cgcacgcacc gaaattctcc cttgtatgtg agatcacgtt caagatcgcc ctacagccgt   2220
cggcccaggt atgacagcta cgaggaatat cagcacgaga ggctgaagag ggaagaatat   2280
cgcagagagt atgagaagcg agagtctgag agggccaagc aaagggagag gcagaggcag   2340
aaggcaattg aagagcgccg tgtgatttat gtcggtaaaa tcagacctga cacaacacgg   2400
acagaactga gggaccgttt tgaagttttt ggtgaaattg aggagtgcac agtaaatctg   2460
cgggatgatg gagacagcta tggtttcatt acctaccgtt atacctgtga tgcttttgct   2520
gctcttgaaa atggatacac tttgcgcagg tcaaacgaaa ctgactttga gctgtacttt   2580
tgtggacgca agcaattttt caagtctaac tatgcagacc tagattcaaa ctcagatgac   2640
tttgaccctg cttccaccaa gagcaagtat gactctctgg attttgatag tttactgaaa   2700
gaagctcaga gaagcttgcg caggtaacat gttccctagc tgaggatgac agagggatgg   2760
cgaatacctc atgggacagc gcgtccttcc ctaaagacta ttgcaagtca tacttaggaa   2820
tttctcctac tttacactct ctgtacaaaa acaaaacaaa acaacaacaa tacaacaaga   2880
acaacaacaa caataacaac aatggtttac atgaacacag ctgctgaaga ggcaagagac   2940
agaatgatat ccagtaagca catgtttatt catgggtgtc agctttgctt ttcctggagt   3000
ctcttggtga tggagtgtgc gtgtgtgcat gtatgtgtgt gtgtatgtat gtgtgtggtg   3060
tgtgtgcttg gtttagggga agtatgtgtg ggtacatgtg aggactgggg gcacctgacc   3120
agaatgcgca agggcaaacc atttcaaatg gcagcagttc catgaagaca cgcttaaaac   3180
ctagaacttc aaaatgttcg tattctattc aaaaggaaat atatatatat atatatatat   3240
atatatatat atatataaat taaaaaggaa agaaaactaa caaccaacca accaaccaac   3300
caaccacaaa ccaccctaaa atgacagccg ctgatgtctg ggcatcagcc tttgtactct   3360
gttttttttaa gaaagtgcag aatcaacttg aagcaagctt tctctcataa cgtaatgatt   3420
```

```
atatgacaat cctgaagaaa ccacaggttc catagaacta atatcctgtc tctctctctc   3480
tctctctctc tctctttttt ttttcttttt ccttttgcca tggaatctgg gtgggagagg   3540
atactgcggg caccagaatg ctaaagtttc ctaacatttt gaagtttctg tagttcatcc   3600
ttaatcctga cacccatgta aatgtccaaa atgttgatct tccactgcaa atttcaaaag   3660
ccttgtcaat ggtcaagcgt gcagcttgtt cagcggttct ttctgaggag cggacaccgg   3720
gttacattac taatgagagt tgggtagaac tctctgagat gtgttcagat agtgtaattg   3780
ctacattctc tgatgtagtt aagtatttac agatgttaaa tggagtattt ttattttatg   3840
tatatactat acaacaatgt tcttttttgt tacagctatg cactgtaaat gcagccttct   3900
tttcaaaact gctaaatttt tcttaatcaa gaatattcaa atgtaattat gaggtgaaac   3960
aattattgta cactaacata tttagaagct gaacttactg cttatatata tttgattgta   4020
aaaacaaaaa gacagtgtgt gtgtctgttg agtgcaacaa gagcaaaatg atgctttccg   4080
cacatccatc ccttaggtga gcttcaatct aagcatcttg tcaagaaata tcctagtccc   4140
ctaaaggtat taaccacttc tgcgatattt ttccacattt tcttgtcgct tgtttttctt   4200
tgaagtttta tacactggat ttgttagggg aatgaaattt tctcatctaa aatttttcta   4260
gaagatatca tgattttatg taaagtctct caatgggtaa ccattaagaa atgtttttat   4320
tttctctatc aacagtagtt ttgaaactag aagtcaaaaa tctttttaaa atgctgtttt   4380
gttttaattt ttgtgatttt aatttgatac aaaatgctga ggtaataatt atagtatgat   4440
ttttacaata attaatgtgt gtctgaagac tatctttgaa gccagtattt ctttcccttg   4500
gcagagtatg acgatggtat ttatctgtat tttttacagt tatgcatcct gtataaatac   4560
tgatatttca ttcctttgtt tactaaagag acatatttat cagttgcaga tagcctattt   4620
attataaatt atgagatgat gaaaataata aagccagtgg aaattttcta cctaggatgc   4680
atgacaattg tcaggttgga gtgtaagtgc ttcatttggg aaattcagct tttgcagaag   4740
cagtgtttct acttgcacta gcatggcctc tgacgtgacc atggtgttgt tcttgatgac   4800
attgcttctg ctaaatttaa taaaaacttc agaaaaacct ccattttgat catcaggatt   4860
tcatctgagt gtggagtccc tggaatggaa ttcagtaaca tttggagtgt gtattcaagt   4920
ttctaaattg agattcgatt actgtttggc tgacatgact tttctggaag acatgataca   4980
cctactactc aattgttctt ttcctttctc tcgcccaaca cgatcttgta agatggattt   5040
cacccccagg ccaatgcagc taattttgat agctgcattc atttatcacc agcatattgt   5100
gttctgagtg aatccactgt ttgtcctgtc ggatgcttgc ttgatttttt ggcttcttat   5160
ttctaagtag atagaaagca ataaaaatac tatgaaatga aagaacttgt tcacaggttc   5220
tgcgttacaa cagtaacaca tctttaatcc gcctaattct tgttgttctg taggttaaat   5280
gcaggtattt taactgtgtg aacgccaaac taaagtttac agtctttctt tctgaatttt   5340
gagtatcttc tgttgtagaa taataataaa aagactatta agagcaataa attattttta   5400
agaaatcgag atttagtaaa tcctattatg tgttcaagga ccacatgtgt tctctatttt   5460
gcctttaaat ttttgtgaac caattttaaa tacattctcc tttttgccct ggattgttga   5520
catgagtgga atacttggtt tcttttctta cttatcaaaa gacagcacta cagatatcat   5580
attgaggatt aatttatccc ccctaccccc agcctgacaa atattgttac catgaagata   5640
gttttcctca atggacttca aattgcatct agaattagtg gagcttttgt atcttctgca   5700
gacactgtgg gtagcccatc aaaatgtaag ctgtgctcct ctcattttta tttttatttt   5760
tttgggagag aatatttcaa atgaacacgt gcaccccatc atcactggag gcaaatttca   5820
```

```
gcatagatct gtaggatttt tagaagaccg tgggccattg ccttcatgcc gtggtaagta   5880
ccacatctac aattttggta accgaactgg tgctttagta atgtggattt ttttcttttt   5940
taaaagagat gtagcagaat aattcttcca gtgcaacaaa atcaattttt tgctaaacga   6000
ctccgagaac aacagttggg ctgtcaacat tcaaagcagc agagagggaa ctttgcacta   6060
ttggggtatg atgtttgggt cagttgataa aaggaaacct tttcatgcct ttagatgtga   6120
gcttccagta ggtaatgatt atgtgtcctt tcttgatggc tgtaatgaga acttcaatca   6180
ctgtagtcta agacctgatc tatagatgac ctagaatagc catgtactat aatgtgatga   6240
ttctaaattt gtacctatgt gacagacatt ttcaataatg tgaactgctg atttgatgga   6300
gctactttaa gatttgtagg tgaaagtgta atactgttgg ttgaactatg ctgaagaggg   6360
aaagtgagcg attagttgag cccttgccgg gcctttttc cacctgccaa ttctacatgt   6420
attgttgtgg ttttattcat tgtatgaaaa ttcctgtgat tttttttaaa tgtgcagtac   6480
acatcagcct cactgagcta ataaagggaa acgaatgttt caaatctaaa aaaaaaaaaa   6540
aaaaa                                                                6545
```

<210> SEQ ID NO 56
<211> LENGTH: 671
<212> TYPE: PRT
<213> ORGANISM: Artificial Sequence
<220> FEATURE:
<223> OTHER INFORMATION: Synthetic Polymer

<400> SEQUENCE: 56

```
Met Pro Asp Gly Thr Pro Pro Pro Gln Glu Ala Glu Glu Pro Ser Leu
1               5                   10                  15

Leu Lys Lys Leu Leu Leu Ala Pro Ala Asn Thr Gln Leu Ser Tyr Asn
            20                  25                  30

Glu Cys Ser Gly Leu Ser Thr Gln Asn His Ala Asn His Asn His Arg
        35                  40                  45

Ile Arg Thr Asn Pro Ala Ile Val Lys Thr Glu Asn Ser Trp Ser Asn
    50                  55                  60

Lys Ala Lys Ser Ile Cys Gln Gln Gln Lys Pro Gln Arg Arg Pro Cys
65                  70                  75                  80

Ser Glu Leu Leu Lys Tyr Leu Thr Thr Asn Asp Asp Pro Pro His Thr
                85                  90                  95

Lys Pro Thr Glu Asn Arg Asn Ser Ser Arg Asp Lys Cys Thr Ser Lys
            100                 105                 110

Lys Lys Ser His Thr Gln Ser Gln Ser Gln His Leu Gln Ala Lys Pro
        115                 120                 125

Thr Thr Leu Ser Leu Pro Leu Thr Pro Glu Ser Pro Asn Asp Pro Lys
    130                 135                 140

Gly Ser Pro Phe Glu Asn Lys Thr Ile Glu Arg Thr Leu Ser Val Glu
145                 150                 155                 160

Leu Ser Gly Thr Ala Gly Leu Thr Pro Pro Thr Thr Pro Pro His Lys
                165                 170                 175

Ala Asn Gln Asp Asn Pro Phe Arg Ala Ser Pro Lys Leu Lys Ser Ser
            180                 185                 190

Cys Lys Thr Val Val Pro Pro Pro Ser Lys Lys Pro Arg Tyr Ser Glu
        195                 200                 205

Ser Ser Gly Thr Gln Gly Asn Asn Ser Thr Lys Lys Gly Pro Glu Gln
    210                 215                 220
```

-continued

```
Ser Glu Leu Tyr Ala Gln Leu Ser Lys Ser Ser Val Leu Thr Gly Gly
225                 230                 235                 240

His Glu Glu Arg Lys Thr Lys Arg Pro Ser Leu Arg Leu Phe Gly Asp
                245                 250                 255

His Asp Tyr Cys Gln Ser Ile Asn Ser Lys Thr Glu Ile Leu Ile Asn
            260                 265                 270

Ile Ser Gln Glu Leu Gln Asp Ser Arg Gln Leu Glu Asn Lys Asp Val
        275                 280                 285

Ser Ser Asp Trp Gln Gly Gln Ile Cys Ser Ser Thr Asp Ser Asp Gln
    290                 295                 300

Cys Tyr Leu Arg Glu Thr Leu Glu Ala Ser Lys Gln Val Ser Pro Cys
305                 310                 315                 320

Ser Thr Arg Lys Gln Leu Gln Asp Gln Glu Ile Arg Ala Glu Leu Asn
                325                 330                 335

Lys His Phe Gly His Pro Ser Gln Ala Val Phe Asp Asp Glu Ala Asp
            340                 345                 350

Lys Thr Gly Glu Leu Arg Asp Ser Asp Phe Ser Asn Glu Gln Phe Ser
        355                 360                 365

Lys Leu Pro Met Phe Ile Asn Ser Gly Leu Ala Met Asp Gly Leu Phe
    370                 375                 380

Asp Asp Ser Glu Asp Glu Ser Asp Lys Leu Ser Tyr Pro Trp Asp Gly
385                 390                 395                 400

Thr Gln Ser Tyr Ser Leu Phe Asn Val Ser Pro Ser Cys Ser Ser Phe
                405                 410                 415

Asn Ser Pro Cys Arg Asp Ser Val Ser Pro Pro Lys Ser Leu Phe Ser
            420                 425                 430

Gln Arg Pro Gln Arg Met Arg Ser Arg Ser Arg Ser Phe Ser Arg His
        435                 440                 445

Arg Ser Cys Ser Arg Ser Pro Tyr Ser Arg Ser Arg Ser Arg Ser Pro
    450                 455                 460

Gly Ser Arg Ser Ser Ser Arg Ser Cys Tyr Tyr Tyr Glu Ser Ser His
465                 470                 475                 480

Tyr Arg His Arg Thr His Arg Asn Ser Pro Leu Tyr Val Arg Ser Arg
                485                 490                 495

Ser Arg Ser Pro Tyr Ser Arg Arg Pro Arg Tyr Asp Ser Tyr Glu Glu
            500                 505                 510

Tyr Gln His Glu Arg Leu Lys Arg Glu Glu Tyr Arg Arg Glu Tyr Glu
        515                 520                 525

Lys Arg Glu Ser Glu Arg Ala Lys Gln Arg Glu Arg Gln Arg Gln Lys
    530                 535                 540

Ala Ile Glu Glu Arg Arg Val Ile Tyr Val Gly Lys Ile Arg Pro Asp
545                 550                 555                 560

Thr Thr Arg Thr Glu Leu Arg Asp Arg Phe Glu Val Phe Gly Glu Ile
                565                 570                 575

Glu Glu Cys Thr Val Asn Leu Arg Asp Asp Gly Asp Ser Tyr Gly Phe
            580                 585                 590

Ile Thr Tyr Arg Tyr Thr Cys Asp Ala Phe Ala Ala Leu Glu Asn Gly
        595                 600                 605

Tyr Thr Leu Arg Arg Ser Asn Glu Thr Asp Phe Glu Leu Tyr Phe Cys
    610                 615                 620

Gly Arg Lys Gln Phe Phe Lys Ser Asn Tyr Ala Asp Leu Asp Ser Asn
625                 630                 635                 640

Ser Asp Asp Phe Asp Pro Ala Ser Thr Lys Ser Lys Tyr Asp Ser Leu
```

```
            645                 650                 655

Asp Phe Asp Ser Leu Leu Lys Glu Ala Gln Arg Ser Leu Arg Arg
        660                 665                 670
```

<210> SEQ ID NO 57
<211> LENGTH: 7667
<212> TYPE: DNA
<213> ORGANISM: Artificial Sequence
<220> FEATURE:
<223> OTHER INFORMATION: Synthetic Polymer

<400> SEQUENCE: 57

```
gtccgggttc gcttgcctcg tcagcgtccg cgtttttccc ggcccccccc aacccccccg      60
gacaggaccc ccttgagctt gtccctcagc tgccaccatg agcgaccaag atcactccat     120
ggatgaaatg acagctgtgg tgaaaattga aaaaggagtt ggtggcaata atgggggcaa     180
tggtaatggt ggtggtgcct tttcacaggc tcgaagtagc agcacaggca gtagcagcag     240
cactggagga ggagggcagg agtcccagcc atcccctttg gctctgctgg cagcaacttg     300
cagcagaatt gagtcaccca atgagaacag caacaactcc cagggcccga gtcagtcagg     360
gggaacaggt gagcttgacc tcacagccac acaactttca cagggtgcca atggctggca     420
gatcatctct tcctcctctg ggctaccccc tacctcaaag gaacagagtg gcagcagtac     480
caatggcagc aatggcagtg agtcttccaa gaatcgcaca gtctctggtg ggcagtatgt     540
tgtggctgcc gctcccaact tacagaacca gcaagttctg acaggactac ctggagtgat     600
gcctaatatt cagtatcaag taatcccaca gttccagacc gttgatgggc aacagctgca     660
gtttgctgcc actggggccc aagtgcagca ggatggttct ggtcaaatac agatcatacc     720
aggtgcaaac caacagatta tcacaaatcg aggaagtgga ggcaacatca ttgctgctat     780
gccaaaccta ctccagcagg ctgtcccccct ccaaggcctg gctaataatg tactctcagg     840
acagactcag tatgtgacca atgtaccagt ggccctgaat gggaacatca ccttgctacc     900
tgtcaacagc gtttctgcag ctaccttgac tcccagctct caggcagtca cgatcagcag     960
ctctgggtcc caggagagtg gctcacagcc tgtcacctca gggactacca tcagttctgc    1020
cagcttggta tcatcacaag ccagttccag ctcctttttc accaatgcca atagctactc    1080
aactactact accaccagca acatgggaat tatgaacttt actaccagtg gatcatcagg    1140
gaccaactct caaggccaga caccccagag ggtcagtggg ctacaggggt ctgatgctct    1200
gaacatccag caaaaccaga catctggagg ctcattgcaa gcaggccagc aaaaagaagg    1260
agagcaaaac cagcagacac agcagcaaca aattcttatc cagcctcagc tagttcaagg    1320
gggacaggcc ctccaggccc tccaagcagc accattgtca gggcagacct ttacaactca    1380
agccatctcc caggaaaccc tccagaacct ccagcttcag gctgttccaa actctggtcc    1440
catcatcatc cggacaccaa cagtggggcc caatggacag gtcagttggc agactctaca    1500
gctgcagaac ctccaagttc agaacccaca agcccaaaca atcaccttag ccccaatgca    1560
gggtgtttcc ttggggcaga ccagcagcag caacaccact ctcacaccca ttgcctcagc    1620
tgcttccatt cctgctggca cagtcactgt gaatgctgct caactctcct ccatgccagg    1680
cctccagacc attaacctca gtgcattggg tacttcagga atccaggtgc acccaattca    1740
aggcctgccg ttggctatag caaatgcccc aggtgatcat ggagctcagc ttggtctcca    1800
tggggctggt ggtgatggaa tacatgatga cacagcaggt ggagaggaag gagaaaacag    1860
cccagatgcc caaccccaag ccggtcggag gacccggcgg gaagcatgca cctgccccta    1920
```

-continued

```
ctgtaaagac agtgaaggaa ggggctcggg ggatcctggc aaaaagaaac agcatatttg   1980
ccacatccaa ggctgtggga aagtgtatgg caagacctct cacctgcggg cacacttgcg   2040
ctggcataca ggcgagaggc catttatgtg tacctggtca tactgtggga aacgcttcac   2100
acgttcggat gagctacaga ggcacaaacg tacacacaca ggtgagaaga aatttgcctg   2160
ccctgagtgt cctaagcgct tcatgaggag tgaccacctg tcaaaacata tcaagaccca   2220
ccagaataag aagggaggcc caggtgtagc tctgagtgtg ggcactttgc ccctggacag   2280
tggggcaggt tcagaaggca gtggcactgc cactccttca gcccttatta ccaccaatat   2340
ggtagccatg gaggccatct gtccagaggg cattgcccgt cttgccaaca gtggcatcaa   2400
cgtcatgcag gtggcagatc tgcagtccat taatatcagt ggcaatggct tctgagatca   2460
ggcacccggg gccagagaca tatgggccat acccccttaac cccgggatgc aaggtagcat   2520
gggtccaaga gacatggaag agagagccat gaagcattaa aatgcatggt gttgagaaga   2580
atcaggagag ggatacaaga gaggagatgg ggtcccggca cccatctgta tcatcagtgc   2640
ctctttgaag gtgggaaaca ttagtgaaaa ttctgttggt gccacgcttt gatgagcatt   2700
tgtttgaccc cagtttcttc ttacacttct taccccagcc taccccttcct gcatttctct   2760
tctcagctct tccatgatgg attccccccc ctttcctaaa gccatcatgc cttgataaat   2820
atatatgatc attgaaatac tttttaacaa aaaacagatt ctatattatt atatatatat   2880
atatatatat aaagatatat agagatgcat tcacaggggt tggctgggag gaggaagacc   2940
attctgtgac caaaatacct tggtcatttt ttttatattg ccttatttcc ctatggctga   3000
gccttgttgt gacacatcaa gcttttctgt agatgttgtc ttggcttccc accagcttaa   3060
gcgttcatat gctctgcttt tagttcatat atacatacat aatgtttttc ctttcttaat   3120
tttgtctttt tgtttgggat cagcttcttg cactccttcc ctaactcaac tgttgccgtc   3180
tcatcttctc tcatctgatc acttcatgtt ttgtttttgt tactgcctgg atgaggcact   3240
tctgtcaatt ttttcaggac cttagttcca gcagcagaat ggaaaaatcc ttgaagccca   3300
ggctgatgct tgaagtaact gtggagggag tgttcaaaat actactgacg caggcacctt   3360
cttggcgctg gagagtcaaa ggcatctccc ttcattagct gctctgagca tcaagaatta   3420
gaagtctttc agtggaattg tacaagagtc cctttgaaga taataatctt ggctcagttt   3480
gtataaactg tcaaattttc aaataatagg tagggggctt tcactaggaa aatcatgtgc   3540
tcagaagagg aaatgactcg tagtcaggtt caggagttag tggagtattt ggactttggt   3600
actgctgtct tccaaggtag ctctaagttt tgatgtgtgg gcttctgagt ttatattctg   3660
aaaggaaata cacttctttt gaacatcccc actaggttct tttccattgt caataaggag   3720
catcagccag tgaatctgtt tcaggtttcc attctgcaga actcctccaa agcatgtgct   3780
agtggcaaga cagtggttct tatgatgttt tcccttaact tttccttgta tgttcttggg   3840
tggttcctaa gggaaaggga agcacatgat catgggaatg atagcccaga acaaaaagaa   3900
atcttgtctt accacagtgt tttataggag agattgggag aaatcatcct gttttctctg   3960
tgacctgatt tcagaagaga ctgatccaaa aattataacg gcagggaacc tagtgcattt   4020
ggcactgaga tttaaatgca accagaattg tcctcaaggc ccagccataa aagcattgtc   4080
tctctcgacc ttctggtatc ttgttagaga gcttttcact gtgaggaagt gtggaaaaat   4140
agctctgtgt gtgtgtgtgt gtgtgtgtgt gtgtgtgtgt gtaatctgtt aggttgggga   4200
taggttttct gctagccaat attaaaagag acctgcaata aaaaaattac cctgatctga   4260
tagaaagcaa gtgtttttgt atgtgtgggt gaatgtgtgt tcatgcccgt atatgtctac   4320
```

```
acacagatga caaattatat ttgaaatcgt tggaaaataa attcagatca aaatgccttt   4380

caggcccatt acctagaaat ctatcttaaa acctgggtat gttcctaagg tcatttcttt   4440

gcttatgcta aattaattac aattatgaat ggaggatatt ctactgtact tttttaaaaa   4500

gaaactattt ttgtgtttga aagtgaaacc aacatccaga tctatagcag agtccttatt   4560

cttctcataa atctttttac tttggctaca aatagatgat ggtatgattc tattatatat   4620

tttatataaa atccatccaa attaagtttt gggtaagtgt gttgtttaat ctgaactata   4680

gtaacttaat actctaaaca atagttcact ccatttggtc ctttctccac agatgtaatt   4740

atgttttcaa ctcaggaact atggcaagga actttcccca gatcaaattc tattaacgct   4800

gagatacaag tcatccatgc acagccacta tcataccctt tattctcact gaaaggcaga   4860

actcagaacc tgttatttta tgtctgtaat catgtacttt ggcatctttt ggaggaaagg   4920

ggcaggataa ctcactggaa tgtacagtat tttgctagtg catttcaagg aatggaatct   4980

tctccagtat gaaattacca gatataaaat aatgtaatga tgctgaggat ataagctttt   5040

agaaggtaat ttgatggtat ttctttctcg aatgaaaagc tgctggttta ccctcaaccc   5100

tattcattag cattaccatg agtgaattta tatctaatta tttccacttg ccctgttctc   5160

ttcacaccaa ggaagctcca gatccagtat cttgtttggc ctcaaaacag aagcagcttc   5220

ttttgtctcc cagcagtagt gagccactca gtctcttcca caggaagttt ggagcctaca   5280

ttccttgagt caggagctta ttacagaaaa accccgtttc cctgaacttt tggctaacag   5340

aaattaattt aactgacatg catattgatt ctgaaatttt tttcctaagt ttttttcatt   5400

tttttgaatg agttttttaa attttttaga tgaccaaaac ttgcagggca ggggatgccc   5460

agaagagtgg tgagatagta aaacacttat tccctcatcc tttcaggttt tcaggttgcc   5520

catttatatt catttacatg tcatttgact gtctcacttt ttacccagaa cagtaacaac   5580

ccacaccgtc ttccttcagg gatttccaac tggcactctg tgggtgctac acagaatgca   5640

atttaatgga tatttctcag cctggttcag aataaattga tcctttgatc ccagaaagta   5700

tatactgaag tgtgggataa agattatgat taggggaggg ttggagacaa aagctgtaaa   5760

ttactatggc tgatttattt ctactatata catatatatt ttttgctttt gtatatccta   5820

tataggaaac taagcattgt attttttttta acaaatctaa aaaagcacta tgaactacag   5880

gtgtttgact ttcaaaatat attttgtatt gttaatatct tcacattgtg tgaatactgg   5940

aagctgcaga tctttgctag gacgcaataa atttatatac tttttgaggg gttcttctgg   6000

ggtgctaatc aggcccctgt tatgcttagg gggagccctg gtgctacttg cttgaagttt   6060

tcagtgtaag taccctgatg ccttttggac cttgggatca gatcaagagt tttggagatc   6120

aggtaccaag gaaataagga cagtctagct gcctcaagtg aggggccctt tgcatagctc   6180

tccttccccc tcactgaagc tgggtagcct attggggttg agagggaaaa tgtgaaatct   6240

cagaatttat ctcccttaga agagagccag taacttatgt acaaggatga aagaaaggtc   6300

gcagcagtag ctttggggaa agggaggaag atatggcact tctccaaccc cggaaaacat   6360

tgcttttgaa aactgctgat aaaatatgag ccggttatta cttctgtttg ggagactgtg   6420

ctctctgtgg tgcctctctt ggctctactc cacagatacc agacctcttc taagaggatg   6480

agcagaccag ctttgaggtt gacctgtttc tctttgtctg ccttcccaaa acaccagccc   6540

ccaggaagac attaagcagc cttaagctta aattcctact ccctcttcca aatttggctc   6600

acttgcctta gatccaaggc agggaaagga aaagaagggg ggtctctggc tttattactc   6660
```

```
ccctaagtct ttactctgac ttccccaaac ccagaaagat tttctccaca gtgttcattt   6720
gaaagaggag tattttgtcc cattttcccc ttcctcatta tcaaacagcc ccagtcttcc   6780
ttgtctctgc taagaaagta gaggcatgat gatctgcctc tcaactgccc taagtcctag   6840
ctaagtatca ggggaaaaaa aaaaaaaaaa agcctaacaa atgggattag actagggctg   6900
caagtagtga ggattttgtt gatacctctg ctgggatgtg tgctttccca tatcttgcct   6960
tcaggaatta cactgtgcct tttccccagg gatatgggct ctgtctaccc agtgctccag   7020
tttcccggta actgctcttg aacattgtgg acaagggcag gtcttcatat ttttgatcat   7080
ccctttctcc cagtgaaatc ccatagccct tacctagagt ctagggcaca aagacttcgg   7140
ggaagataca ctgagattga cctgaggaga catctacaca caccagtggc agctgcccca   7200
gggcctgctt ccccttccta agtctgtcat cctctggaag ggatgggtgg tgctccaatc   7260
tctggtgcct aaaaacccaa gtttatttct ctcttaacac tggcaataac cagtccacac   7320
cactgttgcc ttttaaaacc tcttaataat ctcatgctgt gtttgttttg attccaatcc   7380
aattatcacc agggctgtgt gggtaaatgc ttttaaatgc tctctcatct tgttcttccc   7440
cctcaccccc cactcttagg tatgtatgat gctaatcttg tccctaagta agtttcttcc   7500
tgctcctttt gtatcttcct ttcttgtctt tcctcctacc ttttgtctct tggtgttttg   7560
ggactttttt tttttttttt ttggcctttt gtacaaagat tagtttcaat gtagtctgta   7620
gcctcctttg taaaccaatt aaaaagtttt ttaataaaaa aaaaaaa                 7667
```

<210> SEQ ID NO 58
<211> LENGTH: 785
<212> TYPE: PRT
<213> ORGANISM: Artificial Sequence
<220> FEATURE:
<223> OTHER INFORMATION: Synthetic Polymer

<400> SEQUENCE: 58

```
Met Ser Asp Gln Asp His Ser Met Asp Glu Met Thr Ala Val Val Lys
1               5                   10                  15

Ile Glu Lys Gly Val Gly Gly Asn Asn Gly Gly Asn Gly Asn Gly Gly
            20                  25                  30

Gly Ala Phe Ser Gln Ala Arg Ser Ser Ser Thr Gly Ser Ser Ser Ser
        35                  40                  45

Thr Gly Gly Gly Gly Gln Glu Ser Gln Pro Ser Pro Leu Ala Leu Leu
    50                  55                  60

Ala Ala Thr Cys Ser Arg Ile Glu Ser Pro Asn Glu Asn Ser Asn Asn
65                  70                  75                  80

Ser Gln Gly Pro Ser Gln Ser Gly Gly Thr Gly Glu Leu Asp Leu Thr
                85                  90                  95

Ala Thr Gln Leu Ser Gln Gly Ala Asn Gly Trp Gln Ile Ile Ser Ser
            100                 105                 110

Ser Ser Gly Ala Thr Pro Thr Ser Lys Glu Gln Ser Gly Ser Ser Thr
        115                 120                 125

Asn Gly Ser Asn Gly Ser Glu Ser Ser Lys Asn Arg Thr Val Ser Gly
    130                 135                 140

Gly Gln Tyr Val Val Ala Ala Ala Pro Asn Leu Gln Asn Gln Gln Val
145                 150                 155                 160

Leu Thr Gly Leu Pro Gly Val Met Pro Asn Ile Gln Tyr Gln Val Ile
                165                 170                 175

Pro Gln Phe Gln Thr Val Asp Gly Gln Gln Leu Gln Phe Ala Ala Thr
            180                 185                 190
```

```
Gly Ala Gln Val Gln Gln Asp Gly Ser Gly Gln Ile Gln Ile Ile Pro
        195                 200                 205

Gly Ala Asn Gln Gln Ile Ile Thr Asn Arg Gly Ser Gly Gly Asn Ile
    210                 215                 220

Ile Ala Ala Met Pro Asn Leu Leu Gln Gln Ala Val Pro Leu Gln Gly
225                 230                 235                 240

Leu Ala Asn Asn Val Leu Ser Gly Gln Thr Gln Tyr Val Thr Asn Val
                245                 250                 255

Pro Val Ala Leu Asn Gly Asn Ile Thr Leu Leu Pro Val Asn Ser Val
            260                 265                 270

Ser Ala Ala Thr Leu Thr Pro Ser Ser Gln Ala Val Thr Ile Ser Ser
        275                 280                 285

Ser Gly Ser Gln Glu Ser Gly Ser Gln Pro Val Thr Ser Gly Thr Thr
    290                 295                 300

Ile Ser Ser Ala Ser Leu Val Ser Ser Gln Ala Ser Ser Ser Ser Phe
305                 310                 315                 320

Phe Thr Asn Ala Asn Ser Tyr Ser Thr Thr Thr Thr Thr Ser Asn Met
                325                 330                 335

Gly Ile Met Asn Phe Thr Thr Ser Gly Ser Ser Gly Thr Asn Ser Gln
            340                 345                 350

Gly Gln Thr Pro Gln Arg Val Ser Gly Leu Gln Gly Ser Asp Ala Leu
        355                 360                 365

Asn Ile Gln Gln Asn Gln Thr Ser Gly Gly Ser Leu Gln Ala Gly Gln
    370                 375                 380

Gln Lys Glu Gly Glu Gln Asn Gln Gln Thr Gln Gln Gln Gln Ile Leu
385                 390                 395                 400

Ile Gln Pro Gln Leu Val Gln Gly Gly Gln Ala Leu Gln Ala Leu Gln
                405                 410                 415

Ala Ala Pro Leu Ser Gly Gln Thr Phe Thr Thr Gln Ala Ile Ser Gln
            420                 425                 430

Glu Thr Leu Gln Asn Leu Gln Leu Gln Ala Val Pro Asn Ser Gly Pro
        435                 440                 445

Ile Ile Ile Arg Thr Pro Thr Val Gly Pro Asn Gly Gln Val Ser Trp
    450                 455                 460

Gln Thr Leu Gln Leu Gln Asn Leu Gln Val Gln Asn Pro Gln Ala Gln
465                 470                 475                 480

Thr Ile Thr Leu Ala Pro Met Gln Gly Val Ser Leu Gly Gln Thr Ser
                485                 490                 495

Ser Ser Asn Thr Thr Leu Thr Pro Ile Ala Ser Ala Ala Ser Ile Pro
            500                 505                 510

Ala Gly Thr Val Thr Val Asn Ala Ala Gln Leu Ser Ser Met Pro Gly
        515                 520                 525

Leu Gln Thr Ile Asn Leu Ser Ala Leu Gly Thr Ser Gly Ile Gln Val
    530                 535                 540

His Pro Ile Gln Gly Leu Pro Leu Ala Ile Ala Asn Ala Pro Gly Asp
545                 550                 555                 560

His Gly Ala Gln Leu Gly Leu His Gly Ala Gly Gly Asp Gly Ile His
                565                 570                 575

Asp Asp Thr Ala Gly Gly Glu Glu Gly Glu Asn Ser Pro Asp Ala Gln
            580                 585                 590

Pro Gln Ala Gly Arg Arg Thr Arg Arg Glu Ala Cys Thr Cys Pro Tyr
        595                 600                 605
```

```
Cys Lys Asp Ser Glu Gly Arg Gly Ser Gly Asp Pro Gly Lys Lys Lys
    610                 615                 620

Gln His Ile Cys His Ile Gln Gly Cys Gly Lys Val Tyr Gly Lys Thr
625                 630                 635                 640

Ser His Leu Arg Ala His Leu Arg Trp His Thr Gly Glu Arg Pro Phe
                645                 650                 655

Met Cys Thr Trp Ser Tyr Cys Gly Lys Arg Phe Thr Arg Ser Asp Glu
            660                 665                 670

Leu Gln Arg His Lys Arg Thr His Thr Gly Glu Lys Lys Phe Ala Cys
        675                 680                 685

Pro Glu Cys Pro Lys Arg Phe Met Arg Ser Asp His Leu Ser Lys His
    690                 695                 700

Ile Lys Thr His Gln Asn Lys Lys Gly Gly Pro Gly Val Ala Leu Ser
705                 710                 715                 720

Val Gly Thr Leu Pro Leu Asp Ser Gly Ala Gly Ser Glu Gly Ser Gly
                725                 730                 735

Thr Ala Thr Pro Ser Ala Leu Ile Thr Thr Asn Met Val Ala Met Glu
            740                 745                 750

Ala Ile Cys Pro Glu Gly Ile Ala Arg Leu Ala Asn Ser Gly Ile Asn
        755                 760                 765

Val Met Gln Val Ala Asp Leu Gln Ser Ile Asn Ile Ser Gly Asn Gly
    770                 775                 780

Phe
785


<210> SEQ ID NO 59
<211> LENGTH: 1333
<212> TYPE: DNA
<213> ORGANISM: Artificial Sequence
<220> FEATURE:
<223> OTHER INFORMATION: Synthetic Polymer

<400> SEQUENCE: 59

gaggcttcca aggcaggata cttgtgtctc agatgcggtc gcttctttca tacagcaatt     60

gccgccttgc tgaggatcaa ggaacctcag tgtcagatca cgccctcccc ccaaacttag    120

aaattcagat ggggcgcaga aatttctctt gttctgcgtg atctgcatag atggtccaag    180

aggtggtttt tccaggagcc cagcacccct cctccctccg actcagaccc aggagtctgg    240

ccctccattg aaaggacccc aggttacatc atccattcag gctgcccttg ccacgatgga    300

attctgtagc tcctgccaaa tgggtcaaat atcatggttc aggcgcaggg agggtgattg    360

ggcgggcctg tctgggtata aattctggag cttctgcatc tatcccaaaa aacaagggtg    420

ttctgtcagc tgaggatcca gccgaaagag gagccaggca ctcaggccac ctgagtctac    480

tcacctggac aactggaatc tggcaccaat tctaaaccac tcagcttctc cgagctcaca    540

ccccggagat cacctgagga cccgagccat tgatggactc ggacgagacc gggttcgagc    600

actcaggact gtgggtttct gtgctggctg gtcttctgct gggagcctgc caggcacacc    660

ccatccctga ctccagtcct ctcctgcaat tcgggggcca agtccggcag cggtacctct    720

acacagatga tgcccagcag acagaagccc acctggagat cagggaggat gggacggtgg    780

ggggcgctgc tgaccagagc cccgaaagtc tcctgcagct gaaagccttg aagccgggag    840

ttattcaaat cttgggagtc aagacatcca ggttcctgtg ccagcggcca gatggggccc    900

tgtatggatc gctccacttt gaccctgagg cctgcagctt ccgggagctg cttcttgagg    960

acggatacaa tgtttaccag tccgaagccc acggcctccc gctgcacctg ccagggaaca   1020
```

```
agtccccaca ccgggaccct gcaccccgag gaccagctcg cttcctgcca ctaccaggcc   1080

tgccccccgc actcccggag ccacccggaa tcctggcccc ccagcccccc gatgtgggct   1140

cctcggaccc tctgagcatg gtgggacctt cccagggccg aagccccagc tacgcttcct   1200

gaagccagag gctgtttact atgacatctc ctctttattt attaggttat ttatcttatt   1260

tattttttta tttttcttac ttgagataat aaagagttcc agaggaggat aaaaaaaaaa   1320

aaaaaaaaaa aaa                                                      1333
```

<210> SEQ ID NO 60
<211> LENGTH: 209
<212> TYPE: PRT
<213> ORGANISM: Artificial Sequence
<220> FEATURE:
<223> OTHER INFORMATION: Synthetic Polymer

<400> SEQUENCE: 60

```
Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser
```

<210> SEQ ID NO 61
<211> LENGTH: 1000
<212> TYPE: DNA
<213> ORGANISM: Artificial Sequence
<220> FEATURE:
<223> OTHER INFORMATION: Synthetic Polymer

<400> SEQUENCE: 61

```
agagcaaggg aaaggaactt cctccacctt cggggctgga gcccttttcc tctgcatctc     60

cagtctctga gtgaagatgg ggggcctgac agcctcggac gtacacccga ccctgggggt    120

ccagctcttc tcagctggaa tagcggcgtg cttggcggac gtgatcacct tcccgctgga    180
```

```
cacggccaaa gtccggctcc aggtccaagg tgaatgcccg acgtccagtg ttattaggta    240

taaaggtgtc ctgggaacaa tcaccgctgt ggtaaaaaca gaagggcgga tgaaactcta    300

cagcgggctg cctgcggggc ttcagcggca aatcagctcc gcctctctca ggatcggcct    360

ctacgacacg gtccaggagt tcctcaccgc agggaaagaa acagcaccta gtttaggaag    420

caagatttta gctggtctaa cgactggagg agtggcagta ttcattgggc aacccacaga    480

ggtcgtgaaa gtcagacttc aagcacagag ccatctccac ggaatcaaac ctcgctacac    540

ggggacttat aatgcgtaca gaataatagc aacaaccgaa ggcttgacgg gtctttggaa    600

agggactact cccaatctga tgagaagtgt catcatcaat tgtacagagc tagtaacata    660

tgatctaatg aaggaggcct ttgtgaaaaa caacatatta gcagatgacg tcccctgcca    720

cttggtgtcg gctcttatcg ctggattttg cgcaacagct atgtcctccc cggtggatgt    780

agtaaaaacc agatttatta attctccacc aggacagtac aaaagtgtgc ccaactgtgc    840

aatgaaagtg ttcactaacg aaggaccaac ggctttcttc aaggggttgg taccttcctt    900

cttgcgactt ggatcctgga acgtcattat gtttgtgtgc tttgaacaac tgaaacgaga    960

actgtcaaag tcaaggcaga ctatggactg tgccacataa                         1000
```

<210> SEQ ID NO 62
<211> LENGTH: 307
<212> TYPE: PRT
<213> ORGANISM: Artificial Sequence
<220> FEATURE:
<223> OTHER INFORMATION: Synthetic Polymer

<400> SEQUENCE: 62

```
Met Gly Gly Leu Thr Ala Ser Asp Val His Pro Thr Leu Gly Val Gln
1               5                   10                  15

Leu Phe Ser Ala Gly Ile Ala Ala Cys Leu Ala Asp Val Ile Thr Phe
            20                  25                  30

Pro Leu Asp Thr Ala Lys Val Arg Leu Gln Val Gln Gly Glu Cys Pro
        35                  40                  45

Thr Ser Ser Val Ile Arg Tyr Lys Gly Val Leu Gly Thr Ile Thr Ala
    50                  55                  60

Val Val Lys Thr Glu Gly Arg Met Lys Leu Tyr Ser Gly Leu Pro Ala
65                  70                  75                  80

Gly Leu Gln Arg Gln Ile Ser Ser Ala Ser Leu Arg Ile Gly Leu Tyr
                85                  90                  95

Asp Thr Val Gln Glu Phe Leu Thr Ala Gly Lys Glu Thr Ala Pro Ser
            100                 105                 110

Leu Gly Ser Lys Ile Leu Ala Gly Leu Thr Thr Gly Gly Val Ala Val
        115                 120                 125

Phe Ile Gly Gln Pro Thr Glu Val Val Lys Val Arg Leu Gln Ala Gln
    130                 135                 140

Ser His Leu His Gly Ile Lys Pro Arg Tyr Thr Gly Thr Tyr Asn Ala
145                 150                 155                 160

Tyr Arg Ile Ile Ala Thr Thr Glu Gly Leu Thr Gly Leu Trp Lys Gly
                165                 170                 175

Thr Thr Pro Asn Leu Met Arg Ser Val Ile Ile Asn Cys Thr Glu Leu
            180                 185                 190

Val Thr Tyr Asp Leu Met Lys Glu Ala Phe Val Lys Asn Asn Ile Leu
        195                 200                 205

Ala Asp Asp Val Pro Cys His Leu Val Ser Ala Leu Ile Ala Gly Phe
```

```
    210                 215                 220

Cys Ala Thr Ala Met Ser Ser Pro Val Asp Val Val Lys Thr Arg Phe
225                 230                 235                 240

Ile Asn Ser Pro Pro Gly Gln Tyr Lys Ser Val Pro Asn Cys Ala Met
                245                 250                 255

Lys Val Phe Thr Asn Glu Gly Pro Thr Ala Phe Phe Lys Gly Leu Val
            260                 265                 270

Pro Ser Phe Leu Arg Leu Gly Ser Trp Asn Val Ile Met Phe Val Cys
        275                 280                 285

Phe Glu Gln Leu Lys Arg Glu Leu Ser Lys Ser Arg Gln Thr Met Asp
    290                 295                 300

Cys Ala Thr
305
```

<210> SEQ ID NO 63
<211> LENGTH: 1766
<212> TYPE: DNA
<213> ORGANISM: Artificial Sequence
<220> FEATURE:
<223> OTHER INFORMATION: Synthetic Polymer

<400> SEQUENCE: 63

```
agggcgcagc aggccaaggg ggaggtgcga gcgtggacct gggacgggtc tgggcggctc     60

tcggtggttg gcacgggttc gcacacccat tcaagcggca ggacgcactt gtcttagcag    120

ttctcgctga ccgcgctagc tgcggcttct acgctccggc actctgagtt catcagcaaa    180

cgccctggcg tctgtcctca ccatgcctag cctttgggac cgcttctcgt cgtcgtccac    240

ctcctcttcg ccctcgtcct tgccccgaac tcccacccca gatcggccgc cgcgctcagc    300

ctgggggtcg gcgacccggg aggaggggtt tgaccgctcc acgagcctgg agagctcgga    360

ctgcgagtcc ctggacagca gcaacagtgg cttcgggccg gaggaagaca cggcttacct    420

ggatggggtg tcgttgcccg acttcgagct gctcagtgac cctgaggatg aacacttgtg    480

tgccaacctg atgcagctgc tgcaggagag cctggcccag gcgcggctgg gctctcgacg    540

ccctgcgcgc ctgctgatgc ctagccagtt ggtaagccag gtgggcaaag aactactgcg    600

cctggcctac agcgagccgt gcggcctgcg gggggcgctg ctggacgtct gcgtggagca    660

gggcaagagc tgccacagcg tgggccagct ggcactcgac cccagcctgg tgcccacctt    720

ccagctgacc ctcgtgctgc gcctggactc acgactctgg cccaagatcc aggggctgtt    780

tagctccgcc aactctccct tcctccctgg cttcagccag tccctgacgc tgagcactgg    840

cttccgagtc atcaagaaga agctgtacag ctcggaacag ctgctcattg aggagtgttg    900

aacttcaacc tgagggggcc gacagtgccc tccaagacag agacgactga acttttgggg    960

tggagactag aggcaggagc tgagggactg attcctgtgg ttggaaaact gaggcagcca   1020

cctaaggtgg aggtggggga atagtgtttc ccaggaagct cattgagttg tgtgcgggtg   1080

gctgtgcatt ggggacacat acccctcagt actgtagcat gaaacaaagg cttaggggcc   1140

aacaaggctt ccagctggat gtgtgtgtag catgtacctt attatttttg ttactgacag   1200

ttaacagtgg tgtgacatcc agagagcagc tgggctgctc ccgccccagc ccggcccagg   1260

gtgaaggaag aggcacgtgc tcctcagagc agccggaggg aggggggagg tcggaggtcg   1320

tggaggtggt ttgtgtatct tactggtctg aagggaccaa gtgtgtttgt tgtttgtttt   1380

gtatcttgtt tttctgatcg gagcatcact actgacctgt tgtaggcagc tatcttacag   1440

acgcatgaat gtaagagtag gaaggggtgg gtgtcaggga tcacttggga tctttgacac   1500
```

```
ttgaaaaatt acacctggca gctgcgttta agccttcccc catcgtgtac tgcagagttg   1560

agctggcagg ggaggggctg agagggtggg ggctggaacc cctccccggg aggagtgcca   1620

tctgggtctt ccatctagaa ctgtttacat gaagataaga tactcactgt tcatgaatac   1680

acttgatgtt caagtattaa gacctatgca atattttta cttttctaat aaacatgttt    1740

gttaaaacaa aaaaaaaaaa aaaaaa                                        1766


<210> SEQ ID NO 64
<211> LENGTH: 232
<212> TYPE: PRT
<213> ORGANISM: Artificial Sequence
<220> FEATURE:
<223> OTHER INFORMATION: Synthetic Polymer

<400> SEQUENCE: 64

Met Pro Ser Leu Trp Asp Arg Phe Ser Ser Ser Ser Thr Ser Ser Ser
1               5                   10                  15

Pro Ser Ser Leu Pro Arg Thr Pro Thr Pro Asp Arg Pro Pro Arg Ser
            20                  25                  30

Ala Trp Gly Ser Ala Thr Arg Glu Glu Gly Phe Asp Arg Ser Thr Ser
        35                  40                  45

Leu Glu Ser Ser Asp Cys Glu Ser Leu Asp Ser Ser Asn Ser Gly Phe
    50                  55                  60

Gly Pro Glu Glu Asp Thr Ala Tyr Leu Asp Gly Val Ser Leu Pro Asp
65                  70                  75                  80

Phe Glu Leu Leu Ser Asp Pro Glu Asp Glu His Leu Cys Ala Asn Leu
                85                  90                  95

Met Gln Leu Leu Gln Glu Ser Leu Ala Gln Ala Arg Leu Gly Ser Arg
            100                 105                 110

Arg Pro Ala Arg Leu Leu Met Pro Ser Gln Leu Val Ser Gln Val Gly
        115                 120                 125

Lys Glu Leu Leu Arg Leu Ala Tyr Ser Glu Pro Cys Gly Leu Arg Gly
    130                 135                 140

Ala Leu Leu Asp Val Cys Val Glu Gln Gly Lys Ser Cys His Ser Val
145                 150                 155                 160

Gly Gln Leu Ala Leu Asp Pro Ser Leu Val Pro Thr Phe Gln Leu Thr
                165                 170                 175

Leu Val Leu Arg Leu Asp Ser Arg Leu Trp Pro Lys Ile Gln Gly Leu
            180                 185                 190

Phe Ser Ser Ala Asn Ser Pro Phe Leu Pro Gly Phe Ser Gln Ser Leu
        195                 200                 205

Thr Leu Ser Thr Gly Phe Arg Val Ile Lys Lys Lys Leu Tyr Ser Ser
    210                 215                 220

Glu Gln Leu Leu Ile Glu Glu Cys
225                 230


<210> SEQ ID NO 65
<211> LENGTH: 2037
<212> TYPE: DNA
<213> ORGANISM: Artificial Sequence
<220> FEATURE:
<223> OTHER INFORMATION: Synthetic Polymer

<400> SEQUENCE: 65

aaatgacttt tctgtcttgc tcagctccag gggtcatttt ccggttagcc ttcggggtgt     60

ccgcgtgaga attggctata tcctggagcg agtgctggga ggtgctagtc cgccgcgcct    120
```

```
tattcgagag gtgtcagggc tgggagacta ggatgtcgga cacgtggagc tctatccagg    180
cccacaagaa gcagctggac tctctgcggg agaggctgca gcggaggcgg aagcaggact    240
cggggcactt ggatctacgg aatccagagg cagcattgtc tccaaccttc cgtagtgaca    300
gcccagtgcc tactgcaccc acctctggtg gccctaagcc cagcacagct tcagcagttc    360
ctgaattagc tacagatcct gagttagaga agaagttgct acaccacctc tctgatctgg    420
ccttaacatt gcccactgat gctgtgtcca tctgtcttgc catctccacg ccagatgctc    480
ctgccactca agatggggta gaaagcctcc tgcagaagtt tgcagctcag gagttgattg    540
aggtaaagcg aggtctccta caagatgatg cacatcctac tcttgtaacc tatgctgacc    600
attccaagct ctctgccatg atgggtgctg tggcagaaaa gaagggccct ggggaggtag    660
cagggactgt cacagggcag aagcggcgtg cagaacagga ctcgactaca gtagctgcct    720
ttgccagttc gttagtctct ggtctgaact cttcagcatc ggaaccagca aaggagccag    780
ccaagaaatc aaggaaacat gctgcctcag atgttgatct ggagatagag agccttctga    840
accaacagtc cactaaggaa caacagagca agaaggtcag tcaggagatc ctagagctat    900
taaatactac aacagccaag gaacaatcca ttgttgaaaa atttcgctct cgaggtcggg    960
cccaagtgca agaattctgt gactatggaa ccaaggagga gtgcatgaaa gccagtgatg   1020
ctgatcgacc ctgtcgcaag ctgcacttca gacgaattat caataaacac actgatgagt   1080
ctttaggtga ctgctctttc cttaatacat gtttccacat ggatacctgc aagtatgttc   1140
actatgaaat tgatgcttgc atggattctg aggcccctgg cagcaaagac cacacgccaa   1200
gccaggagct tgctcttaca cagagtgtcg gaggtgattc cagtgcagac cgactcttcc   1260
cacctcagtg gatctgttgt gatatccgct acctggacgt cagtatcttg ggcaagtttg   1320
cagttgtgat ggctgaccca ccctgggata ttcacatgga actgccctat gggaccctga   1380
cagatgatga gatgcgcagg ctcaacatac ccgtactaca ggatgatggc tttctcttcc   1440
tctgggtcac aggcagggcc atggagttgg ggagagaatg tctaaacctc tgggggtatg   1500
aacgggtaga tgaaattatt tgggtgaaga caaatcaact gcaacgcatc attcggacag   1560
gccgtacagg tcactggttg aaccatggga aggaacactg cttggttggt gtcaaaggaa   1620
atccccaagg cttcaaccag ggtctggatt gtgatgtgat cgtagctgag gttcgttcca   1680
ccagtcataa accagatgaa atctatggca tgattgaaag actatctcct ggcactcgca   1740
agattgagtt atttggacga ccacacaatg tgcaacccaa ctggatcacc cttggaaacc   1800
aactggatgg gatccaccta ctagacccag atgtggttgc acggttcaag caaaggtacc   1860
cagatggtat catctctaaa cctaagaatt tatagaagca cttccttaca gagctaagaa   1920
tccatagcca tggctctgta agctaaacct gaagagtgat atttgtacaa tagctttctt   1980
ctttatttaa ataaacattt gtattgtagt tgggattctg aaaaaaaaaa aaaaaaa      2037
```

```
<210> SEQ ID NO 66
<211> LENGTH: 580
<212> TYPE: PRT
<213> ORGANISM: Artificial Sequence
<220> FEATURE:
<223> OTHER INFORMATION: Synthetic Polymer

<400> SEQUENCE: 66

Met Ser Asp Thr Trp Ser Ser Ile Gln Ala His Lys Lys Gln Leu Asp
1               5                   10                  15

Ser Leu Arg Glu Arg Leu Gln Arg Arg Arg Lys Gln Asp Ser Gly His
```

-continued

```
            20                  25                  30

Leu Asp Leu Arg Asn Pro Glu Ala Ala Leu Ser Pro Thr Phe Arg Ser
        35                  40                  45

Asp Ser Pro Val Pro Thr Ala Pro Thr Ser Gly Gly Pro Lys Pro Ser
    50                  55                  60

Thr Ala Ser Ala Val Pro Glu Leu Ala Thr Asp Pro Glu Leu Glu Lys
65                  70                  75                  80

Lys Leu Leu His His Leu Ser Asp Leu Ala Leu Thr Leu Pro Thr Asp
                85                  90                  95

Ala Val Ser Ile Cys Leu Ala Ile Ser Thr Pro Asp Ala Pro Ala Thr
            100                 105                 110

Gln Asp Gly Val Glu Ser Leu Leu Gln Lys Phe Ala Ala Gln Glu Leu
        115                 120                 125

Ile Glu Val Lys Arg Gly Leu Leu Gln Asp Asp Ala His Pro Thr Leu
    130                 135                 140

Val Thr Tyr Ala Asp His Ser Lys Leu Ser Ala Met Met Gly Ala Val
145                 150                 155                 160

Ala Glu Lys Lys Gly Pro Gly Glu Val Ala Gly Thr Val Thr Gly Gln
                165                 170                 175

Lys Arg Arg Ala Glu Gln Asp Ser Thr Thr Val Ala Ala Phe Ala Ser
            180                 185                 190

Ser Leu Val Ser Gly Leu Asn Ser Ser Ala Ser Glu Pro Ala Lys Glu
        195                 200                 205

Pro Ala Lys Lys Ser Arg Lys His Ala Ala Ser Asp Val Asp Leu Glu
    210                 215                 220

Ile Glu Ser Leu Leu Asn Gln Gln Ser Thr Lys Glu Gln Gln Ser Lys
225                 230                 235                 240

Lys Val Ser Gln Glu Ile Leu Glu Leu Leu Asn Thr Thr Thr Ala Lys
                245                 250                 255

Glu Gln Ser Ile Val Glu Lys Phe Arg Ser Arg Gly Arg Ala Gln Val
            260                 265                 270

Gln Glu Phe Cys Asp Tyr Gly Thr Lys Glu Glu Cys Met Lys Ala Ser
        275                 280                 285

Asp Ala Asp Arg Pro Cys Arg Lys Leu His Phe Arg Arg Ile Ile Asn
    290                 295                 300

Lys His Thr Asp Glu Ser Leu Gly Asp Cys Ser Phe Leu Asn Thr Cys
305                 310                 315                 320

Phe His Met Asp Thr Cys Lys Tyr Val His Tyr Glu Ile Asp Ala Cys
                325                 330                 335

Met Asp Ser Glu Ala Pro Gly Ser Lys Asp His Thr Pro Ser Gln Glu
            340                 345                 350

Leu Ala Leu Thr Gln Ser Val Gly Gly Asp Ser Ser Ala Asp Arg Leu
        355                 360                 365

Phe Pro Pro Gln Trp Ile Cys Cys Asp Ile Arg Tyr Leu Asp Val Ser
    370                 375                 380

Ile Leu Gly Lys Phe Ala Val Val Met Ala Asp Pro Pro Trp Asp Ile
385                 390                 395                 400

His Met Glu Leu Pro Tyr Gly Thr Leu Thr Asp Asp Glu Met Arg Arg
                405                 410                 415

Leu Asn Ile Pro Val Leu Gln Asp Asp Gly Phe Leu Phe Leu Trp Val
            420                 425                 430

Thr Gly Arg Ala Met Glu Leu Gly Arg Glu Cys Leu Asn Leu Trp Gly
        435                 440                 445
```

```
Tyr Glu Arg Val Asp Glu Ile Ile Trp Val Lys Thr Asn Gln Leu Gln
    450                 455                 460

Arg Ile Ile Arg Thr Gly Arg Thr Gly His Trp Leu Asn His Gly Lys
465                 470                 475                 480

Glu His Cys Leu Val Gly Val Lys Gly Asn Pro Gln Gly Phe Asn Gln
                485                 490                 495

Gly Leu Asp Cys Asp Val Ile Val Ala Glu Val Arg Ser Thr Ser His
            500                 505                 510

Lys Pro Asp Glu Ile Tyr Gly Met Ile Glu Arg Leu Ser Pro Gly Thr
        515                 520                 525

Arg Lys Ile Glu Leu Phe Gly Arg Pro His Asn Val Gln Pro Asn Trp
    530                 535                 540

Ile Thr Leu Gly Asn Gln Leu Asp Gly Ile His Leu Leu Asp Pro Asp
545                 550                 555                 560

Val Val Ala Arg Phe Lys Gln Arg Tyr Pro Asp Gly Ile Ile Ser Lys
                565                 570                 575

Pro Lys Asn Leu
            580
```

<210> SEQ ID NO 67
<211> LENGTH: 4162
<212> TYPE: DNA
<213> ORGANISM: Artificial Sequence
<220> FEATURE:
<223> OTHER INFORMATION: Synthetic Polymer

<400> SEQUENCE: 67

```
agaagtccat tcggctcaca catttgcccc aagacaaacc acgttaaaat aacacccagg     60

gtagctgctg ccaccgtctt ctgtctctac ctccctcctg gctggccaat ggctctgtgt    120

tcctgggcct gctgctggct gtccagagta ggggttgctt agagctgtgt gcatccctgc    180

gggtggtgtg ggagtgggcg gttgtctaaa ggcaggtccc ctctactgat aaacaaggac    240

cggagataga cctagaggct gacattcttg gctcccccag cctacacccc ccccacctcg    300

atttcccaca gagccctagg gacgggtagc cagctctgtg gcatggtatc tggaggcagg    360

ccagcaacct gatgtgcatg ccacggcccg tccctctccc cactcagagc tgcagtagcc    420

tggaggttca gagagccggg ctactctgag aagaagacac caagtggatt ctgcttcccc    480

tgggacagca ctgagcgagt gtggagagag gtacagccct cggcctacaa gctctttagt    540

cttgaaagcg ccacaagcag cagctgctga gccatggctg aaggggaaat caccaccttc    600

acagccctga ccgagaagtt taatctgcct ccagggaatt acaagaagcc caaactcctc    660

tactgtagca acgggggcca cttcctgagg atccttccgg atggcacagt ggatgggaca    720

agggacagga gcgaccagca cattcagctg cagctcagtg cggaaagcgt gggggaggtg    780

tatataaaga gtaccgagac tggccagtac ttggccatgg acaccgacgg gcttttatac    840

ggctcacaga caccaaatga ggaatgtttg ttcctggaaa ggctggagga gaaccattac    900

aacacctata tatccaagaa gcatgcagag aagaattggt ttgttggcct caagaagaat    960

gggagctgca aacgcggtcc tcggactcac tatggccaga aagcaatctt gtttctcccc   1020

ctgccagtct cttctgatta aagagatctg ttctgggtgt tgaccactcc agagaagttt   1080

cgaggggtcc tcacctggtt gacccaaaaa tgttcccttg accattggct gcgctaaccc   1140

ccagcccaca gagcctgaat ttgtaagcaa cttgcttcta aatgcccagt tcacttcttt   1200

gcagagcctt ttacccctgc acagtttaga acagagggac caaattgctt ctaggagtca   1260
```

```
actggctggc cagtctgggt ctgggtttgg atctccaatt gcctcttgca ggctgagtcc   1320
ctccatgcaa aagtggggct aaatgaagtg tgttaagggg tcggctaagt gggacattag   1380
taactgcaca ctatttccct ctactgagta aaccctatct gtgattcccc caaacatctg   1440
gcatggctcc cttttgtcct tcctgtgccc tgcaaatatt agcaaagaag cttcatgcca   1500
ggttaggaag gcagcattcc atgaccagaa acagggacaa agaaatcccc ccttcagaac   1560
agaggcattt aaaatggaaa agagagattg gattttggtg ggtaacttag aaggatggca   1620
tctccatgta gaataaatga agaaagggag gcccagccgc aggaaggcag aataaatcct   1680
tgggagtcat taccacgcct tgaccttccc aaggttactc agcagcagag agccctgggt   1740
gacttcaggt ggagagcact agaagtggtt tcctgataac aagcaaggat atcagagctg   1800
ggaaattcat gtggatctgg ggactgagtg tgggagtgca gagaaagaaa gggaaactgg   1860
ctgaggggat accataaaaa gaggatgatt tcagaaggag aaggaaaaag aaagtaatgc   1920
cacacattgt gcttggcccc tggtaagcag aggctttggg gtcctagccc agtgcttctc   1980
caacactgaa gtgcttgcag atcatctggg gacctggttt gaatggagat tctgattcag   2040
tgggttgggg gcagagtttc tgcagttcca tcaggtcccc cccaggtgca ggtgctgaca   2100
atactgctgc cttacccgcc atacattaag gagcagggtc ctggtcctaa agagttattc   2160
aaatgaaggt ggttcgacgc cccgaacctc acctgacctc aactaaccct taaaaatgca   2220
cacctcatga gtctacctga gcattcaggc agcactgaca atagttatgc ctgtactaag   2280
gagcatgatt ttaagaggct ttggcccaat gcctataaaa tgcccatttc gaagatatac   2340
aaaaacatac ttcaaaaatg ttaaaccctt accaacagct tttcccagga gaccatttgt   2400
attaccatta cttgtataaa tacacttcct gcttaaactt gacccaggtg gctagcaaat   2460
tagaaacacc attcatctct aacatatgat actgatgcca tgtaaaggcc tttaataagt   2520
cattgaaatt tactgtgaga ctgtatgttt taattgcatt taaaaatata tagcttgaaa   2580
gcagttaaac tgattagtat tcaggcactg agaatgatag taataggata caatgtataa   2640
gctactcact tatctgatac ttatttacct ataaaatgag atttttgttt tccactgtgc   2700
tattacaaat tttcttttga aagtaggaac tcttaagcaa tggtaattgt gaataaaaat   2760
tgatgagagt gttagctcct gtttcatatg aaattgaagt aattgttaac taaaaacaat   2820
tccttagtaa ctgaactgtc atatttagaa tggaaggaaa atgacagttt gtgaaagttc   2880
aaagcaatag tgcaattgaa gaattgacct aagtaagctg acattatggt taataatagt   2940
attttagatt tgtgcagcaa aataatttca taactttttt gtttttgtta cttggataag   3000
atcaatctgt tttattttag taaatctttg caggcaagtt agagaaaatg cagtgtggct   3060
taacgtctct ttagtatgaa gatttggcca gaaaaagata cccagagagg aaatctaaga   3120
taattataat ggtccatact ttttattgta tgaatcaaac tcaagcataa cattggccaa   3180
ggaaaattaa ataccattgc taacttgtga aatggaagtc tgtgatttcg gagatgcaaa   3240
gcattgtagt aaaaacacca atgtgacctc gaccatctca gcccagatat cattcatata   3300
tctgttcaat gactattaag gtgcctactg tgtgctaggc actgtactgg atactgggga   3360
ccttgtctgt ctggtttgct gctgtatctt ctcccagggc attatattta tgatgaaaga   3420
tgctgtggat tcaattcttt cagtcaagaa taaacacaga ctttgtaggt tcctgctgaa   3480
taaagcaaat cccagaaacc cagattttgg aagaatcagc aaccccagca taaaataaac   3540
ccctatcaaa atgtcagagg acatggcaag gtaaacttag cattttcaac tttagaaccg   3600
```

```
ggtcagcttc agggggactg ctttcaaatc agccaaagag cctgtcagat cttcttagaa   3660

ggaagaggtt ggtagttccc tgctctgttt tgaacatgct ctagtttatt aacctgggga   3720

cattcccatt gctgtcttaa gtaagtctca tagccagctc ctgtcacgtg actctcatat   3780

ggattcattt tcgggccagc tctgaacaaa gcatcatgaa catatgtgct tttggtcgtt   3840

tgcaatgtga tggtggtgga ggtaggtatt ggtttccttg gaaggcatga taagaaagat   3900

tcacaatggc caacagtgtg tatgaacaaa aaactgattg gagcatcagc tagtactgaa   3960

ggtccttgct ttgtgtcaga ggcaaaggaa cccaaggcgc caagtcctca gccttgagtg   4020

tactgctgac aactaaactc acaggctgca aagcagacct ctgatgaaga tgcctgttat   4080

ttcacatcac tgtctttttg tgtatcatag tctgcacctt acaaatatta ataaatgttc   4140

caataatagg tgaaaaaaaa aa                                            4162
```

<210> SEQ ID NO 68
<211> LENGTH: 155
<212> TYPE: PRT
<213> ORGANISM: Artificial Sequence
<220> FEATURE:
<223> OTHER INFORMATION: Synthetic Polymer

<400> SEQUENCE: 68

```
Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

<210> SEQ ID NO 69
<211> LENGTH: 4833
<212> TYPE: DNA
<213> ORGANISM: Artificial Sequence
<220> FEATURE:
<223> OTHER INFORMATION: Synthetic Polymer

<400> SEQUENCE: 69

```
cccggcttta tatctatata tacacaggta tatgtgtata ttttatataa ttgttctccg     60

ttcgttgata tcaaagacag ttgaaggaaa tgaattttga aacttcacgg tgtgccaccc    120

tacagtactg ccctgaccct tacatccagc gtttcgtaga aaccccagct catttctctt    180

ggaaagaaag ttattaccga tccaccatgt cccagagcac acagacaaat gaattcctca    240

gtccagaggt tttccagcat atctgggatt ttctggaaca gcctatatgt tcagttcagc    300
```

```
ccattgactt gaactttgtg gatgaaccat cagaagatgg tgcgacaaac aagattgaga    360
ttagcatgga ctgtatccgc atgcaggact cggacctgag tgaccccatg tggccacagt    420
acacgaacct ggggctcctg aacagcatgg accagcagat tcagaacggc tcctcgtcca    480
ccagtcccta taacacagac cacgcgcaga acagcgtcac ggcgccctcg ccctacgcac    540
agcccagctc caccttcgat gctctctctc catcacccgc catcccctcc aacaccgact    600
acccaggccc gcacagtttc gacgtgtcct tccagcagtc gagcaccgcc aagtcggcca    660
cctggacgta ttccactgaa ctgaagaaac tctactgcca aattgcaaag acatgcccca    720
tccagatcaa ggtgatgacc ccacctcctc agggagctgt tatccgcgcc atgcctgtct    780
acaaaaaagc tgagcacgtc acggaggtgg tgaagcggtg ccccaaccat gagctgagcc    840
gtgaattcaa cgagggacag attgcccctc ctagtcattt gattcgagta gaggggaaca    900
gccatgccca gtatgtagaa gatcccatca caggaagaca gagtgtgctg gtaccttatg    960
agccacccca ggttggcact gaattcacga cagtcttgta caatttcatg tgtaacagca   1020
gttgtgttgg agggatgaac cgccgtccaa ttttaatcat tgttactctg gaaaccagag   1080
atgggcaagt cctgggccga cgctgctttg aggcccggat ctgtgcttgc ccaggaagag   1140
acaggaaggc ggatgaagat agcatcagaa agcagcaagt ttcggacagt acaaagaacg   1200
gtgatggtac gaagcgcccg tttcgtcaga acacacatgg tatccagatg acatccatca   1260
agaaacgaag atccccagat gatgaactgt tatacttacc agtgaggggc cgtgagactt   1320
atgaaatgct gttgaagatc aaagagtccc tggaactcat gcagtacctt cctcagcaca   1380
caattgaaac gtacaggcaa cagcaacagc agcagcacca gcacttactt cagaaacaga   1440
cctcaataca gtctccatct tcatatggta acagctcccc acctctgaac aaaatgaaca   1500
gcatgaacaa gctgccttct gtgagccagc ttatcaaccc tcagcagcgc aacgccctca   1560
ctcctacaac cattcctgat ggcatgggag ccaacattcc catgatgggc acccacatgc   1620
caatggctgg agacatgaat ggactcagcc ccacccaggc actccctccc ccactctcca   1680
tgccatccac ctcccactgc acacccccac ctccgtatcc cacagattgc agcattgtca   1740
ggatctggca agtctgaaaa tccctgagca atttcgacat gcgatctgga agggcatcct   1800
ggaccaccgg cagctccacg aattctcctc cccttctcat ctcctgcgga ccccaagcag   1860
tgcctctaca gtcagtgtgg gctccagtga gacccggggt gagcgtgtta ttgatgctgt   1920
gcgattcacc ctccgccaga ccatctcttt cccaccccga gatgagtgga atgacttcaa   1980
ctttgacatg gatgctcgcc gcaataagca acagcgcatc aaagaggagg gggagtgagc   2040
ctcaccatgt gagctcttcc tatccctctc ctaactgcca gccccctaaa agcactcctg   2100
cttaatcttc aaagccttct ccctagctcc tccccttcct cttgtctgat ttcttagggg   2160
aaggagaagt aagaggctac ctcttaccta acatctgacc tggcatctaa ttctgattct   2220
ggctttaagc cttcaaaact atagcttgca gaactgtagc tgccatggct aggtagaagt   2280
gagcaaaaaa gagttgggtg tctccttaag ctgcagagat ttctcattga cttttataaa   2340
gcatgttcac ccttatagtc taagactata tatataaatg tataaatata cagtatagat   2400
ttttgggtgg ggggcattga gtattgttta aaatgtaatt taaatgaaag aaaattgagt   2460
tgcacttatt gaccattttt taatttactt gttttggatg gcttgtctat actccttccc   2520
ttaaggggta tcatgtatgg tgataggtat ctagagctta atgctacatg tgagtgacga   2580
tgatgtacag attctttcag ttctttggat tctaaataca tgccacatca aacctttgag   2640
```

```
tagatccatt tccattgctt attatgtagg taagactgta gatatgtatt cttttctcag   2700
tgttggtata ttttatatta ctgacatttc ttctagtgat gatggttcac gttggggtga   2760
tttaatccag ttataagaag aagttcatgt ccaaacgtcc tctttagttt ttggttggga   2820
atgaggaaaa ttcttaaaag gcccatagca gccagttcaa aaacacccga cgtcatgtat   2880
ttgagcatat cagtaacccc cttaaattta ataccagata ccttatctta caatattgat   2940
tgggaaaaca tttgctgcca ttacagaggt attaaaacta aatttcacta ctagattgac   3000
taactcaaat acacatttgc tactgttgta agaattctga ttgatttgat tgggatgaat   3060
gccatctatc tagttctaac agtgaagttt tactgtctat taatattcag ggtaaatagg   3120
aatcattcag aaatgttgag tctgtactaa acagtaagat atctcaatga accataaatt   3180
caactttgta aaaatctttt gaagcataga taatattgtt tggtaaatgt ttcttttgtt   3240
tggtaaatgt ttcttttaaa gaccctccta ttctataaaa ctctgcatgt agaggcttgt   3300
ttacctttct ctctctaagg tttacaatag gagtggtgat ttgaaaaata taaaattatg   3360
agattggttt tcctgtggca taaattgcat cactgtatca ttttcttttt taaccggtaa   3420
gagtttcagt ttgttggaaa gtaactgtga gaacccagtt tcccgtccat ctcccttagg   3480
gactacccat agacatgaaa ggtccccaca gagcaagaga taagtctttc atggctgctg   3540
ttgcttaaac cacttaaacg aagagttccc ttgaaacttt gggaaaacat gttaatgaca   3600
atattccaga tctttcagaa atataacaca ttttttgca tgcatgcaaa tgagctctga   3660
aatcttccca tgcattctgg tcaagggctg tcattgcaca taagcttcca ttttaatttt   3720
aaagtgcaaa agggccagcg tggctctaaa aggtaatgtg tggattgcct ctgaaaagtg   3780
tgtatatatt ttgtgtgaaa ttgcatactt tgtattttga ttattttttt tttcttcttg   3840
ggatagtggg atttccagaa ccacacttga aaccttttt tatcgttttt gtattttcat   3900
gaaaatacca tttagtaaga ataccacatc aaataagaaa taatgctaca attttaagag   3960
gggagggaag ggaaagtttt tttttattat ttttttaaaa ttttgtatgt taaagagaat   4020
gagtccttga tttcaaagtt ttgttgtact taaatggtaa taagcactgt aaacttctgc   4080
aacaagcatg cagctttgca aacccattaa ggggaagaat gaaagctgtt ccttggtcct   4140
agtaagaaga caaactgctt cccttacttt gctgagggtt tgaataaacc taggacttcc   4200
gagctatgtc agtactattc aggtaacact agggccttgg aaattcctgt actgtgtctc   4260
atggatttgg cactagccaa agcgaggcac ccttactggc ttacctcctc atggcagcct   4320
actctccttg agtgtatgag tagccagggt aaggggtaaa aggatagtaa gcatagaaac   4380
cactagaaag tgggcttaat ggagttcttg tggcctcagc tcaatgcagt tagctgaaga   4440
attgaaaagt ttttgtttgg agacgtttat aaacagaaat ggaaagcaga gttttcatta   4500
aatcctttta cctttttttt ttcttggtaa tcccctaaaa taacagtatg tgggatattg   4560
aatgttaaag ggatattttt ttctattatt tttataattg tacaaaatta agcaaatgtt   4620
aaaagtttta tatgctttat taatgttttc aaaaggtatt atacatgtga tacatttttt   4680
aagcttcagt tgcttgtctt ctggtacttt ctgttatggg cttttgggga gccagaagcc   4740
aatctacaat ctctttttgt ttgccaggac atgcaataaa atttaaaaaa taaataaaaa   4800
ctaattaaga aattgaaaaa aaaaaaaaaa aaa                                4833
```

<210> SEQ ID NO 70
<211> LENGTH: 555
<212> TYPE: PRT
<213> ORGANISM: Artificial Sequence
<220> FEATURE:
<223> OTHER INFORMATION: Synthetic Polymer

<400> SEQUENCE: 70

```
Met Asn Phe Glu Thr Ser Arg Cys Ala Thr Leu Gln Tyr Cys Pro Asp
1               5                   10                  15

Pro Tyr Ile Gln Arg Phe Val Glu Thr Pro Ala His Phe Ser Trp Lys
            20                  25                  30

Glu Ser Tyr Tyr Arg Ser Thr Met Ser Gln Ser Thr Gln Thr Asn Glu
        35                  40                  45

Phe Leu Ser Pro Glu Val Phe Gln His Ile Trp Asp Phe Leu Glu Gln
    50                  55                  60

Pro Ile Cys Ser Val Gln Pro Ile Asp Leu Asn Phe Val Asp Glu Pro
65                  70                  75                  80

Ser Glu Asp Gly Ala Thr Asn Lys Ile Glu Ile Ser Met Asp Cys Ile
                85                  90                  95

Arg Met Gln Asp Ser Asp Leu Ser Asp Pro Met Trp Pro Gln Tyr Thr
            100                 105                 110

Asn Leu Gly Leu Leu Asn Ser Met Asp Gln Gln Ile Gln Asn Gly Ser
        115                 120                 125

Ser Ser Thr Ser Pro Tyr Asn Thr Asp His Ala Gln Asn Ser Val Thr
    130                 135                 140

Ala Pro Ser Pro Tyr Ala Gln Pro Ser Ser Thr Phe Asp Ala Leu Ser
145                 150                 155                 160

Pro Ser Pro Ala Ile Pro Ser Asn Thr Asp Tyr Pro Gly Pro His Ser
                165                 170                 175

Phe Asp Val Ser Phe Gln Gln Ser Ser Thr Ala Lys Ser Ala Thr Trp
            180                 185                 190

Thr Tyr Ser Thr Glu Leu Lys Lys Leu Tyr Cys Gln Ile Ala Lys Thr
        195                 200                 205

Cys Pro Ile Gln Ile Lys Val Met Thr Pro Pro Pro Gln Gly Ala Val
    210                 215                 220

Ile Arg Ala Met Pro Val Tyr Lys Lys Ala Glu His Val Thr Glu Val
225                 230                 235                 240

Val Lys Arg Cys Pro Asn His Glu Leu Ser Arg Glu Phe Asn Glu Gly
                245                 250                 255

Gln Ile Ala Pro Pro Ser His Leu Ile Arg Val Glu Gly Asn Ser His
            260                 265                 270

Ala Gln Tyr Val Glu Asp Pro Ile Thr Gly Arg Gln Ser Val Leu Val
        275                 280                 285

Pro Tyr Glu Pro Pro Gln Val Gly Thr Glu Phe Thr Thr Val Leu Tyr
    290                 295                 300

Asn Phe Met Cys Asn Ser Ser Cys Val Gly Gly Met Asn Arg Arg Pro
305                 310                 315                 320

Ile Leu Ile Ile Val Thr Leu Glu Thr Arg Asp Gly Gln Val Leu Gly
                325                 330                 335

Arg Arg Cys Phe Glu Ala Arg Ile Cys Ala Cys Pro Gly Arg Asp Arg
            340                 345                 350

Lys Ala Asp Glu Asp Ser Ile Arg Lys Gln Gln Val Ser Asp Ser Thr
        355                 360                 365

Lys Asn Gly Asp Gly Thr Lys Arg Pro Phe Arg Gln Asn Thr His Gly
    370                 375                 380

Ile Gln Met Thr Ser Ile Lys Lys Arg Arg Ser Pro Asp Asp Glu Leu
385                 390                 395                 400
```

```
Leu Tyr Leu Pro Val Arg Gly Arg Glu Thr Tyr Glu Met Leu Leu Lys
                405                 410                 415

Ile Lys Glu Ser Leu Glu Leu Met Gln Tyr Leu Pro Gln His Thr Ile
            420                 425                 430

Glu Thr Tyr Arg Gln Gln Gln Gln Gln Gln His Gln His Leu Leu Gln
        435                 440                 445

Lys Gln Thr Ser Ile Gln Ser Pro Ser Ser Tyr Gly Asn Ser Ser Pro
    450                 455                 460

Pro Leu Asn Lys Met Asn Ser Met Asn Lys Leu Pro Ser Val Ser Gln
465                 470                 475                 480

Leu Ile Asn Pro Gln Gln Arg Asn Ala Leu Thr Pro Thr Thr Ile Pro
                485                 490                 495

Asp Gly Met Gly Ala Asn Ile Pro Met Met Gly Thr His Met Pro Met
            500                 505                 510

Ala Gly Asp Met Asn Gly Leu Ser Pro Thr Gln Ala Leu Pro Pro Pro
        515                 520                 525

Leu Ser Met Pro Ser Thr Ser His Cys Thr Pro Pro Pro Pro Tyr Pro
    530                 535                 540

Thr Asp Cys Ser Ile Val Arg Ile Trp Gln Val
545                 550                 555
```

<210> SEQ ID NO 71
<211> LENGTH: 16
<212> TYPE: DNA
<213> ORGANISM: Artificial Sequence
<220> FEATURE:
<223> OTHER INFORMATION: Synthetic Polymer

<400> SEQUENCE: 71
tcttcaactg gcagct 16

<210> SEQ ID NO 72

<400> SEQUENCE: 72

000

<210> SEQ ID NO 73
<211> LENGTH: 15
<212> TYPE: DNA
<213> ORGANISM: Artificial Sequence
<220> FEATURE:
<223> OTHER INFORMATION: Synthetic Polymer

<400> SEQUENCE: 73
cttcaactgg cagct 15

<210> SEQ ID NO 74
<211> LENGTH: 15
<212> TYPE: DNA
<213> ORGANISM: Artificial Sequence
<220> FEATURE:
<223> OTHER INFORMATION: Synthetic Polymer

<400> SEQUENCE: 74
cttcaactgg cagct 15

<210> SEQ ID NO 75
<211> LENGTH: 16
<212> TYPE: DNA
<213> ORGANISM: Artificial Sequence
<220> FEATURE:
<223> OTHER INFORMATION: Synthetic Polymer

<400> SEQUENCE: 75
tcttcaactg gcagct 16

<210> SEQ ID NO 76
<211> LENGTH: 16
<212> TYPE: DNA
<213> ORGANISM: Artificial Sequence
<220> FEATURE:
<223> OTHER INFORMATION: Synthetic Polymer

<400> SEQUENCE: 76
tcttcaactg gcagct 16

<210> SEQ ID NO 77
<211> LENGTH: 17
<212> TYPE: DNA
<213> ORGANISM: Artificial Sequence
<220> FEATURE:
<223> OTHER INFORMATION: Synthetic Polymer

<400> SEQUENCE: 77
ttcttcaact ggcagct 17

<210> SEQ ID NO 78
<211> LENGTH: 18
<212> TYPE: DNA
<213> ORGANISM: Artificial Sequence
<220> FEATURE:
<223> OTHER INFORMATION: Synthetic Polymer

<400> SEQUENCE: 78
gttcttcaac tggcagct 18

<210> SEQ ID NO 79
<211> LENGTH: 22
<212> TYPE: RNA
<213> ORGANISM: Artificial Sequence
<220> FEATURE:
<223> OTHER INFORMATION: Synthetic Polymer

<400> SEQUENCE: 79
ugucaagaag uugaccgucg aa 22

<210> SEQ ID NO 80
<211> LENGTH: 16
<212> TYPE: DNA
<213> ORGANISM: Artificial Sequence
<220> FEATURE:
<223> OTHER INFORMATION: Synthetic Polymer

<400> SEQUENCE: 80
gatacggaag gagggt 16

<210> SEQ ID NO 81
<211> LENGTH: 16
<212> TYPE: DNA
<213> ORGANISM: Artificial Sequence
<220> FEATURE:
<223> OTHER INFORMATION: Synthetic Polymer

<400> SEQUENCE: 81
cacaatcgga caggct 16

```
<210> SEQ ID NO 82
<211> LENGTH: 16
<212> TYPE: DNA
<213> ORGANISM: Artificial Sequence
<220> FEATURE:
<223> OTHER INFORMATION: Synthetic Polymer

<400> SEQUENCE: 82

cgaatagtta gtagcg                                                    16
```